(12) United States Patent
Sampath et al.

(10) Patent No.: US 7,312,036 B2
(45) Date of Patent: Dec. 25, 2007

(54) COMPOSITIONS FOR USE IN IDENTIFICATION OF VIRAL HEMORRHAGIC FEVER VIRUSES

(75) Inventors: Rangarajan Sampath, San Diego, CA (US); Thomas A. Hall, Oceanside, CA (US); Mark W. Eshoo, Solana Beach, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 235 days.

(21) Appl. No.: 11/085,320

(22) Filed: Mar. 21, 2005

(65) Prior Publication Data

US 2006/0057605 A1 Mar. 16, 2006

Related U.S. Application Data

(60) Provisional application No. 60/555,520, filed on Mar. 22, 2004.

(51) Int. Cl.
*C12Q 1/68* (2006.01)
*C12N 15/11* (2006.01)

(52) U.S. Cl. .......................................... 435/6; 536/23.1
(58) Field of Classification Search .................... None
See application file for complete search history.

(56) References Cited

U.S. PATENT DOCUMENTS 6,300,076 B1 10/2001 Koster ........................... 435/6
2003/0104410 A1 6/2003 Mittman ........................ 435/6

OTHER PUBLICATIONS

Besselsen, D. G. et al., "Detection of Lymphocytic Choriomeningitis Virus by Use of Fluorogenic Nuclease Reverse Transcriptase-Polymerase Chain Reaction Anaylsis," *Comp. Med.* (2003) 53(1):65-69.
Boivin-Jahns, V. et al., "Bacterial Diversity in a Deep-Subsurface Clay Environment," *Appl. Environ. Microbiol.* (1996) 62(9):3405-3412.
Bronzoni, R. V. M. et al., "Duplex Reverse Transcription-PCR Followed by Nested PCR Assays for Detection and Identification of Brazilian Alphaviruses and Flaviviruses," *J. Clin. Microbiol.* (2005) 43(2):696-702.

Demby, A. H. et al., "Early Diagnosis of Lassa Fever by Reverse Transcription-PCR," *J. Clin. Microbiol.* (1994) 32(12):2898-2903.
Drosten, C. et al., "Rapid Detection and Quantification of RNA of Ebola and Marburg Viruses, Lassa Virus, Crimean-Congo Hermorrhagic Fever Virus, Rift Valley Fever Virus, Dengue Virus, and Yellow Fever Virus by Real-Time Reverse Transcription-PCR," *J. Clin. Microbiol.* (2002) 40(7):2323-2330.
Drosten, C. et al., "Molecular diagnostics of viral hemorrhagic fevers," *Antiviral Res.* (2003) 57(1-2):61-87.
Fisher-Hoch, S. P. et al., "Filovirus clearance in non-human primates," *Lancet* (1992) 340(8817):451-453.
Lozano, M. E. et al., "A simple nucleic acid amplification assay for the rapid detection of Junín virus in whole blood samples," *Virus Res.* (1993) 27(1):37-53.
Lozano, M. E. et al., "Characterization of arenaviruses using a family-specific primer set for RT-PCR amplification and RFLP analysis Its potential use for detection of uncharacterized arenaviruses," *Virus Res.* (1997) 49(1):79-89.
Lunkenheimer, K. et al., "Detection of Lassa Virus RNA in Specimens from Patients with Lassa Fever by Using the Polymerase Chain Reaction," *J. Clin. Microbiol.* (1990) 28(12):2689-2692.
Muddiman, D. C. et al., "Characterization of PCR Products from Bacilli Using Electrospray Ionization FTICR Mass Spectrometry," *Anal. Chem.* (1996) 68(21):3702-3712.
Muddiman, D. C. et al., "Length and Base Composition of PCR-Amplified Nucleic Acids Using Mass Measurements from Electrospray Ionization Mass Spectrometry," *Anal. Chem.* (1997) 69(8):1543-1549.
Niedrig, M. et al., "First International Quality Assurance Study on the Rapid Detection of Viral Agents of Bioterrorism," *J. Clin. Microbiol.* (2004) 42(4):1753-1755.
Parida, M. et al., "Rapid Detection and Differentiation of Denuge Virus Serotypes by a Real-Time Reverse Transcription-Loop-Mediated Isothermal Amplification Assay," *J. Clin. Microbiol.* (2005) 43(6):2895-2903.
Weidmann, M. et al., "Rapid detection protocol for filoviruses," *J. Clin. Virol.* (2004) 30(1):94-99.
Widjojoatmodjo, M. N. et al., "Rapid Identification of Bacteria by PCR-Single-Strand Conformation Polymorphism," *J. Clin. Microbiol.* (1994) 32(12):3002-3007.

*Primary Examiner*—James Martinell
(74) *Attorney, Agent, or Firm*—Casimir Jones, S.C.

(57) ABSTRACT

The present invention provides oligonucleotide primers, compositions, and kits containing the same for rapid identification of viruses that cause viral hemorrhagic fevers by amplification of a segment of viral nucleic acid followed by molecular mass analysis.

20 Claims, 18 Drawing Sheets

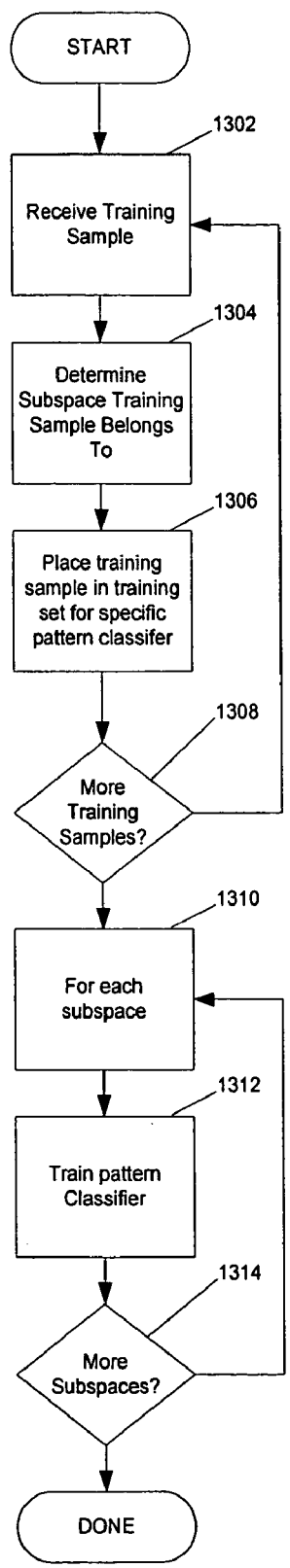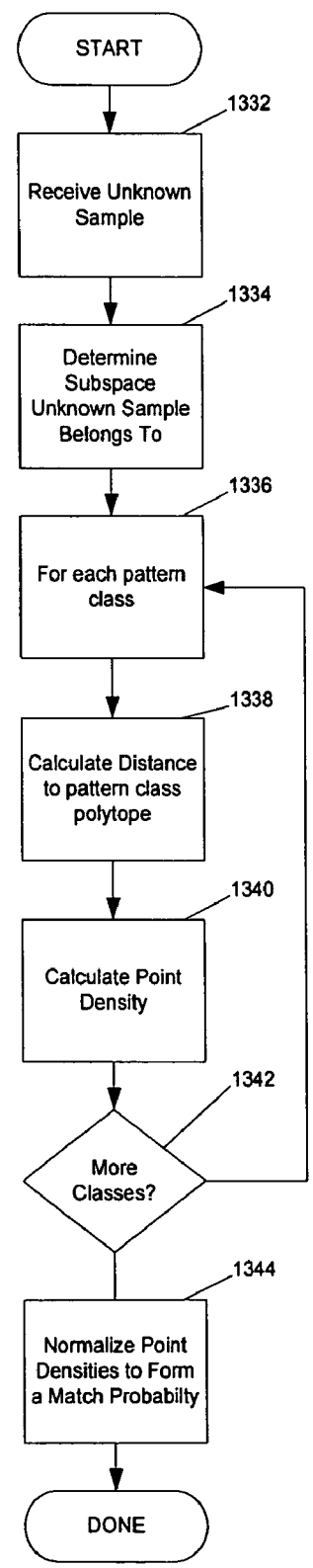
Figure 6A
Figure 6B $A+G+C+T = 56$ $15 <= A <= 17$ $16 <= G <= 18$ $13 <= C <= 16$ $7 <= T <= 11$ Volume$_{(G,C,T)} = 60$

|  | A | G | C | T |
|---|---|---|---|---|
| Neisseria gonorrhoeae B 5025 | 16 | 16 | 13 | 11 |
| Neisseria weaveri | 16 | 16 | 13 | 11 |
| Formivibrio citricus | 17 | 16 | 16 | 7 |
| Aquaspirillum delicatum | 15 | 17 | 15 | 9 |
| Aquaspirillum sinuosum | 15 | 17 | 15 | 9 |
| Aquaspirillum gracile | 15 | 17 | 16 | 8 |
| Microvirgula aerodenitrificans | 16 | 18 | 14 | 8 |

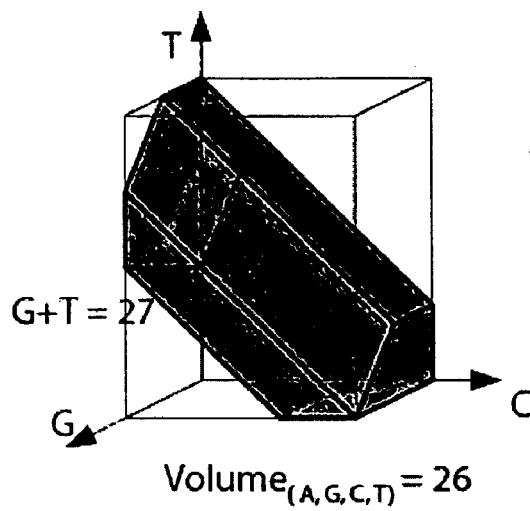

A+G+C+T = 56

$15 \leq A \leq 17$
$16 \leq G \leq 18$
$13 \leq C \leq 16$
$7 \leq T \leq 11$ $32 \leq A+G \leq 34$
$22 \leq C+T \leq 24$
$29 \leq A+C \leq 33$
$23 \leq G+T \leq 27$

G+T = 27

Volume$_{(A,G,C,T)}$ = 26

|  | A | G | C | T | C+T | G+T |
|---|---|---|---|---|---|---|
| Neisseria gonorrhoeae B 5025 | 16 | 16 | 13 | 11 | 24 | 27 |
| Neisseria weaveri | 16 | 16 | 13 | 11 | 24 | 27 |
| Formivibrio citricus | 17 | 16 | 16 | 7 | 23 | 23 |
| Aquaspirillum delicatum | 15 | 17 | 15 | 9 | 24 | 26 |
| Aquaspirillum sinuosum | 15 | 17 | 15 | 9 | 24 | 26 |
| Aquaspirillum gracile | 15 | 17 | 16 | 8 | 24 | 25 |
| Microvirgula aerodenitrificans | 16 | 18 | 14 | 8 | 22 | 26 |

Figure 9A

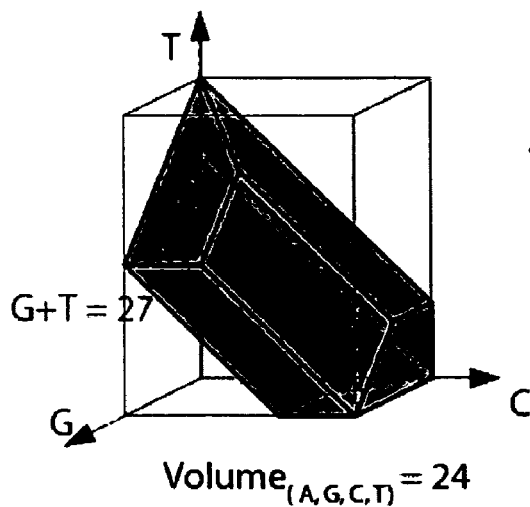

A+G+C+T = 56

$15 \leq A \leq 17$
$16 \leq G \leq 18$
$13 \leq C \leq 16$
$7 \leq T \leq 11$ $32 \leq A+G \leq 34$
$22 \leq C+T \leq 24$
$29 \leq A+C \leq 33$
$23 \leq G+T \leq 27$

G+T = 27

Volume$_{(A,G,C,T)}$ = 24

Figure 9B

| Taxon | Pop. | Vol. | Density |
|---|---|---|---|
| Neisseriales | 7 | 23 | 0.304 |

| Taxon | Pop. | Vol. | Density |
|---|---|---|---|
| Neisseriales | 7 | 23 | 0.304 |
| Nitrosomonadales | 8 | 6 | 1.333 |

| Taxon | Pop. | Vol. | Density |
|---|---|---|---|
| Neisseriales | 7 | 23 | 0.304 |
| Nitrosomonadales | 8 | 6 | 1.333 |
| Burkholderiales | 102 | 36 | 2.833 |

| Taxon | Pop. | Vol. | Density |
|---|---|---|---|
| Neisseriales | 7 | 23 | 0.304 |
| Nitrosomonadales | 8 | 6 | 1.333 |
| Burkholderiales | 102 | 36 | 2.833 |
| Hydrogenophilales | 5 | 18 | 0.278 |

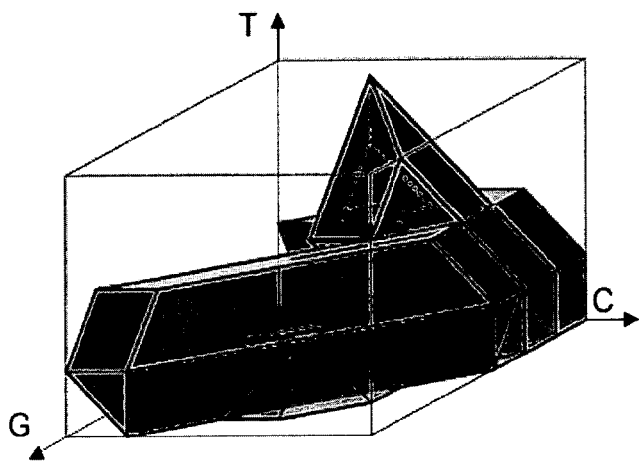

Figure 11E

| Taxon | Pop. | Vol. | Density |
|---|---|---|---|
| Neisseriales | 7 | 23 | 0.304 |
| Nitrosomonadales | 8 | 6 | 1.333 |
| Burkholderiales | 102 | 36 | 2.833 |
| Hydrogenophilales | 5 | 18 | 0.278 |
| Rhodocyclales | 14 | 25 | 0.560 |

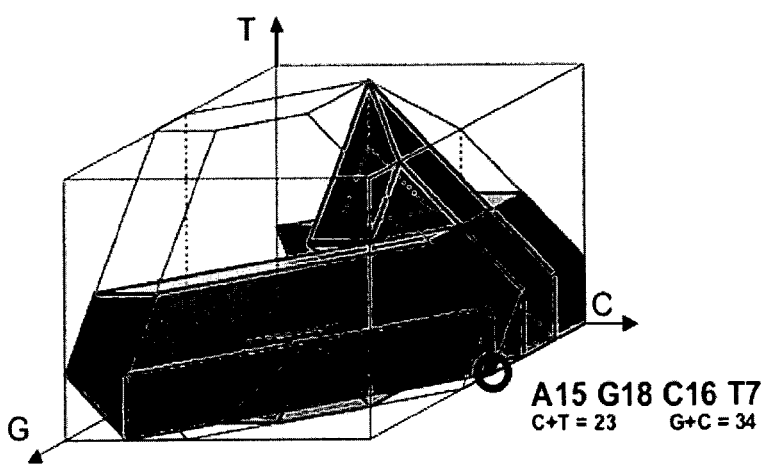

| | Polyhedron A+G+C+T=56 | | | Test base composition | | |
|---|---|---|---|---|---|---|
| Taxon | Pop. | Vol. | Density | min Distance to Polyhedron | Point Density | Match probability |
| Neisseriales | 7 | 23 | 0.304 | 1 | 0.001 | 0.03% |
| Nitrosomonadales | 8 | 6 | 1.333 | 1 | 0.005 | 0.15% |
| Burkholderiales | 102 | 36 | 2.833 | 0 | 2.833 | 83.08% |
| Hydrogenophilales | 5 | 18 | 0.278 | 1 | 0.001 | 0.03% |
| Rhodocyclales | 14 | 25 | 0.560 | 0 | 0.560 | 16.42% |
| Betaproteobacteria orders | | | | | 3.401 | 99.71% |

| Taxon | Individual primer pair match probability | | | | Assignment probability |
|---|---|---|---|---|---|
| | I | II | III | IV | |
| Rhodocyclales | 16.42% | 45.89 | 22.80% | 9.58% | 96.769% |
| Neisseriales | 0.03% | <10⁻⁶ | 1 x 10⁻⁶ | 6.40% | 0.003% |
| Burkholderiales | 83.08% | 5 x 10⁻⁶ | 1 x 10⁻⁶ | 0.04% | 0.071% |
| Hydrogenophilales | 0.03% | 7 x 10⁻⁶ | 1 x 10⁻⁶ | <10⁻⁶ | 0.000% |
| Nitrosomonadales | 0.15% | <10⁻⁶ | <10⁻⁶ | 3 x 10⁻⁶ | 0.000% |

| Phylum | Class | Order | Family | Genus |
|---|---|---|---|---|
| Betaproteobacteria 82.36% | Betaproteobacteria 82.36% | Betaproteobacteria 82.36% | Betaproteobacteria 82.36% | Betaproteobacteria 82.36% |

Figure 12

SEQUENCE LISTING

```
<160> NUMBER OF SEQ ID NOS: 275

<210> SEQ ID NO 1
<211> LENGTH: 10703
<212> TYPE: DNA
<213> ORGANISM: Dengue virus
<220> FEATURE:
<221> NAME/KEY: misc_feature
<222> LOCATION: 1, 2, 3, 4, 5, 6, 7, 8, 9, 10, 11, 12, 13, 14, 15
<223> OTHER INFORMATION: n = A,T,C or G

<400> SEQUENCE: 1
nnnnnnnnnn nnnnntggcc cgacaaagac agattctttg agggagctga gctcaacgta      60
gttctgactg ttttttgatt agagagcaga tctctgatga atgaccaacg gaaaaaggcg     120
agaaacacgc ctttcaatat gctgaaacgc gagagaaacc gcgtgtcaac tgtacaacag     180
ttgacaaaga gattctcact tggaatgctg cagggacgag gaccactaaa attgttcatg     240
gccctggtgg cattccttcg tttcctaaca atcccaccaa cagcagggat attaaaaaga     300
tggggaacaa ttaaaaaatc aaaggctatt aatgttctga gaggcttcag gaaagagatt     360
ggaaggatgc tgaatatctt aaacaggaga cgtagaactg caggcatgat catcatgctg     420
```

-continued

| | | | | | |
|---|---|---|---|---|---|
| attccaacag | tgatggcgtt | tcatctgacc | acacgcaacg | agaaccaca | catgatcgtc | 480 |
| agtagacaag | aaaaagggaa | aagccttctg | tttaagacaa | aggacggcac | gaacatgtgt | 540 |
| accctcatgg | ccatggacct | tggtgagttg | tgtgaagaca | caatcacgta | taaatgtccc | 600 |
| tttctcaagc | agaacgaacc | agaagacata | gattgttggt | gcaactccac | gtccacatgg | 660 |
| gtaacttatg | ggacatgtac | caccacagga | gagcacagaa | gagaaaaaag | atcagtggcg | 720 |
| cttgttccac | acgtgggaat | gggattggag | acacgaactg | aaacatggat | gtcatcagaa | 780 |
| ggggcctgga | acatgccca | gagaattgaa | acttggattc | tgagacatcc | aggctttacc | 840 |
| ataatggccg | caatcctggc | atacaccata | ggaacgacgc | atttccaaag | agtcctgata | 900 |
| ttcatcctac | tgacagccat | cgctccttca | atgacaatgc | gctgcatagg | aatatcaaat | 960 |
| agggactttg | tggaaggagt | gtcaggaggg | agttgggttg | acatagtttt | agaacatgga | 1020 |
| agttgtgtga | cgacgatggc | aaaaaataaa | ccaacactgg | actttgaact | gataaaaaca | 1080 |
| gaagccaaac | aacccgccac | cttaaggaag | tactgtatag | aggctaaact | gaccaacacg | 1140 |
| acaacagact | cgcgctgccc | aacacaaggg | gaacccaccc | tgaatgaaga | gcaggacaaa | 1200 |
| aggtttgtct | gcaaacattc | catggtagac | agaggatggg | gaaatggatg | tggattattt | 1260 |
| ggaaaaggag | gcatcgtgac | ctgtgccatg | ttcacatgca | aaaagaacat | ggagggaaaa | 1320 |
| attgtgcagc | cagaaaacct | ggaatacact | gtcgttataa | cacctcattc | aggggaagaa | 1380 |
| catgcagtcg | gaaatgacac | aggaaaacat | ggtaaagaag | tcaagataac | accacagagc | 1440 |
| tccatcacag | aggcggaact | gacaggctat | ggcactgtta | cgatggagtg | ctctccaaga | 1500 |
| acgggcctcg | acttcaatga | gatggtgttg | ctgcaaatga | agacaaagc | ttggctggtg | 1560 |
| cacagacaat | ggttcctaga | cctaccgttg | ccatggctgc | ccggagcaga | cacacaagga | 1620 |
| tcaaattgga | tacagaaaga | gacactggtc | accttcaaaa | atcccatgc | gaaaaaacag | 1680 |
| gatgttgttg | tcttaggatc | ccaagagggg | gccatgcata | cagcactcac | aggggctacg | 1740 |
| gaaatccaga | tgtcatcagg | aaacctgctg | ttcacaggac | atcttaagtg | caggctgaga | 1800 |
| atggacaaat | acaacttaa | agggatgtca | tactccatgt | gcacaggaaa | gtttaaagtt | 1860 |
| gtgaaggaaa | tagcagaaac | acaacatgga | acaatagtca | ttagagtaca | atatgaagga | 1920 |
| gacggctctc | catgcaagac | cccttttgag | ataatggatc | tggaaaaaag | acatgttttg | 1980 |
| ggccgcctga | ccacagtcaa | cccaattgta | acagaaaagg | acagtccagt | caacatagaa | 2040 |
| gcagaacctc | cattcggaga | cagctacatc | atcataggag | tggaaccagg | acaattgaag | 2100 |
| ctggactggt | tcaagaaagg | aagttccatc | ggccaaatgt | ttgagacaac | aatgaggga | 2160 |
| gcgaaaagaa | tggccatttt | gggcgacaca | gcctgggatt | ttggatctct | ggaggagtg | 2220 |
| ttcacatcaa | taggaaaggc | tctccaccag | gttttggag | caatctacgg | ggctgctttc | 2280 |
| agtgggtct | catggactat | gaagatcctc | ataggagtta | tcatcacatg | gataggaatg | 2340 |
| aactcacgta | gcacatcact | gtctgtgtca | ctggtattag | tgggaatcgt | gacactgtac | 2400 |
| ttgggagtta | tggtgcaggc | cgatagtggt | tgcgttgtga | gctggaagaa | caaagaacta | 2460 |
| aaatgtggca | gtggaatatt | cgtcacagat | aacgtgcata | catggacaga | acaatacaag | 2520 |
| ttccaaccag | aatcccttc | aaaactggct | cagccatcc | agaaagctca | tgaagagggc | 2580 |
| atctgtggaa | tccgctcagt | aacaagactg | gaaaatctta | tgtggaaaca | aataacatca | 2640 |
| gaattgaatc | atattctatc | agaaaatgaa | gtgaaactga | ccatcatgac | aggagacatc | 2700 |
| aaaggaatca | tgcaggtagg | aaaacgatct | ctgcggcctc | aacccactga | gttgaggtat | 2760 |

```
tcatggaaaa catggggtaa agcgaaaatg ctctccacag aactccataa tcagaccttc    2820
ctcattgatg gtcccgaaac agcagaatgc cccaacacaa acagagcttg gaattcacta    2880
gaagttgagg actacggctt tggagtattc actaccaata tatggctaag attgagagaa    2940
aagcaggatg cattttgtga ctcaaaactc atgtcagcgg ccataaagga caacagagcc    3000
gtccatgctg atatgggtta ttggatagaa agcgcactca atgatacatg gaagatagag    3060
aaagcttctt tcattgaagt caaaagttgc cactggccaa agtcacacac tctatggagt    3120
aatggagtgc tagaaagcga gatggtaatt ccaaagaatt tcgctggacc agtgtcacaa    3180
cataataaca gaccaggcta tcacacacaa acagcaggac cttggcatct aggcaagctt    3240
gagatggact ttgatttctg cgaagggact acagtggtgg taaccgagga ctgtggaaac    3300
agagggccct ctttaagaac aaccactgcc tcaggaaaac tcataacgga atggtgttgt    3360
cgatcttgca cactaccacc actaagatac agaggtgagg atggatgctg gtacgggatg    3420
gaaatcagac cattgaaaga gaagaagaa atctggtca gttctctggt cacagccgga    3480
catgggcaga ttgataattt ctcattagga atcttgggaa tggcactgtt ccttgaagaa    3540
atgctcagga ctcgagtagg aacgaaacat gcaatattac tagtcgcagt ttctttcgta    3600
acgttaatca cagggaacat gtcttttaga gacctgggaa gagtgatggt tatggtgggt    3660
gccaccatga cagatgacat aggcatgggt gtgacttatc ttgctctact agcagctttc    3720
aaagtcagac caacctttgc agctggactg ctcttgagaa aactgacctc caaggaatta    3780
atgatgacca cataggaat cgttcttctc tcccagagta gcataccaga gaccattctt    3840
gaactgaccg atgcgttagc tttaggcatg atggtcctca agatggtgag aaacatggaa    3900
aaatatcagc tggcagtgac catcatggct attttgtgcg tcccaaatgc tgtgatatta    3960
cagaacgcat ggaaagtgag ttgcacaata ttggcagtgg tgtctgtttc cccctgttc    4020 ttaacatcct cacaacagaa agcggactgg ataccattag cgttgacgat caaaggcctc    4080
aatccaacag ccattttct aacaacctc tcaagaacca gcaagaaaag gagctggcct    4140
ttaaatgagg ccatcatggc ggttgggatg gtgagtatct tggccagctc tctcttaaag    4200
aatgacaccc ccatgacagg accattagtg gctggagggc ttcttactgt gtgctacgta    4260
ctaactgggc ggtcagccga tctggaacta gagagagcta ccgatgtcaa atgggatgac    4320
caggcagaga tatcaggtag cagtccaatt ctgtcaataa caatatcaga agatggcagc    4380
atgtcaataa agaatgaaga ggaagagcaa acattgacta tactcattag aacaggattg    4440
cttgtgatct caggactctt tccggtatca ataccaatta cagcagcagc atggtacctg    4500
tgggaagtaa agaacaacg ggctggagtt ttgtgggatg tcccctcacc accacccgtg    4560
ggaaaggctg aattggaaga tggagcctac agaatcaagc aaaaaggaat ccttggatat    4620
tcccagatcg gagctggagt ttacaaagaa ggaacatttc acacaatgtg gcacgtcaca    4680
cgtggcgctc tcctaatgca taggggaag aggattgaac catcatggc ggacgtcaag    4740 aaagacttaa tatcatatgg aggaggttgg aagctagaag gagaatggaa agaaggagaa    4800
gaagtccagg tcttggcatt ggagcctggg aaaaatccaa gagccgtcca acaaaaacct    4860
ggccttttta gaaccaatac tggaaccata ggtgccgtat ctctggactt ttccccgggg    4920
acgtcaggat ctccaatcgt cgacaaaaaa ggaaaagttg taggcctcta tggcaatggt    4980
gtcgttacaa ggagtggagc atatgtgagt gccatagctc agactgaaaa aagcattgaa    5040
gacaatccag agattgaaga tgacatcttt cgaaagagaa gattgactat catggatctc    5100
cacccaggag caggaaagac aaagagatac ctcccggcca tagtcagaga ggccataaaa    5160
```

-continued

```
agaggcttga gaacactaat cctagccccc actagagtcg tggcagctga aatggaggaa      5220
gcccttagag gacttccaat aagataccaa actccagcta tcagggctga gcacaccggg      5280
cgggagattg tggacttaat gtgtcatgcc acatttacca tgaggctgct atcaccaatc      5340
agggtgccaa attacaacct gatcatcatg gacgaagccc attttacaga tccagcaagc      5400
atagcagcta ggggatacat ctcaactcga gtggagatgg gtgaggcagc tggaattttt      5460
atgacagcca ctcctccggg tagcagagat ccatttcctc agagtaatgc accaattatg      5520
gacgaagaaa gagaaatccc ggaacgttca tggaactccg ggcacgagtg ggtcacggat      5580 tttaaggaa agactgtctg gtttgttcca agcataaaaa ccggaaatga catagcagcc       5640
tgcctgagaa agaatggaaa gagggtgata caactcagta ggaagacctt tgattctgaa      5700
tatgtcaaga ctagaaccaa tgactgggat ttcgtggtta caactgacat ctcggaaatg      5760
ggtgccaact ttaaagctga gagggttata daccccagac gctgcatgaa accagttata      5820
ctgacagacg gcgaagagcg ggtgattctg gcaggaccca tgccagtgac ccactctagt      5880
gcagcacaaa aagagggag aataggaagg aatccaagga atgaaaatga tcaatatata      5940
tatatggggg aaccccctgga aaatgatgaa gactgtgcgc actggaagga agctaagatg      6000
ctcctagata acatcaacac acctgaagga atcattccca gcatgttcga gccagagcgt      6060
gaaaaggtgg atgccattga cggtgaatat cgcttgagag gagaagcacg gaaaactttt      6120
gtggacctaa tgagaagagg agacctacca gtctggttgg cttataaagt ggctgctgaa      6180
ggtatcaact acgcagacag aagatggtgt tttgacggaa ccagaaacaa tcaaatcttg      6240
gaagaaaatg tggaagtgga aatctggaca aaggaagggg aaaggaaaaa attgaaacct      6300
agatggttag atgctaggat ctactccgac ccactggcgc taaaagaatt cgcagccgga      6360
agaaagtccc taaccctgaa cctaatcaca gagatgggca gactcccaac ttttatgact      6420
cagaaggcca gagatgcact agacaacttg gcggtgctgc acacggctga agcgggtgga      6480
aaggcataca atcatgctct cagtgaacta ccggagaccc tggagacatt gcttttgctg      6540
acactgttgg ccacagtcac gggaggaatc tttctattcc tgatgagcgg aagggggtata      6600 gggaagatga cctgggaat gtgctgcata atcacggcca gcatcctctt atggtatgca      6660
caaatacaac cacattggat agcagcttca ataatattgg agttctttct catagtcttg      6720
ctcattccag aaccagaaaa gcagaggaca ccccaggata ccaattgac ttatgtcatc       6780 atagccatcc tcacagtggt ggccgcaacc atggcaaacg aaatgggttt tctgaaaaaa      6840
acaaagaaag acctcggact gggaaacatt gcaactcagc aacctgagag caacattctg      6900
gacatagatc tacgtcctgc atcagcatgg acgttatatg ccgtggccac aacatttatc      6960
acaccaatgt tgagacatag cattgaaaat tcctcagtaa atgtgtccct aacagccata      7020
gctaaccaag ccacagtgct aatgggtctc gggaaaggat ggccattgtc aaagatggac      7080
attggagttc ccctccttgc tattgggtgt tactcacaag tcaaccctat aaccctcaca      7140
gcggctcttc tttttattggt agcacattat gccatcatag accgggact tcaagccaaa      7200 gcaaccagag aagctcagaa aagagcagca gcgggcatca tgaaaaaccc aactgtggat      7260
ggaataacag tgatagatct agatccaata ccctatgatc caaagtttga aaagcagttg      7320
ggacaagtaa tgctcctagt cctctgtgtg acccaagtgc tgatgatgag gactacgtgg      7380
gctttgtgtg aagccttaac tctagcaacc ggacccgtgt ccacattgtg ggaaggaaat      7440 ccaggggagat tctggaacac aaccattgca gtgtcaatgg caaacatctt tagagggagt      7500
```

```
tacctggctg gagctggact tctcttttct atcatgaaga acacaaccag cacgagaaga    7560
ggaactggca acataggaga aacgctagga gagaaatgga aaagcaggct gaacgcattg    7620
gggaaaagtg aattccagat ctataaaaaa agtggaattc aagaagtgga cagaacctta    7680
gcaaaagaag gcattaaaag aggagaaacg gatcatcacg ctgtgtcgcg aggctcagca    7740
aaactgagat ggttcgttga agaaatttg gtcacaccag aagggaaagt agtggacctt     7800
ggttgcggca gaggggggctg gtcatactat tgtggaggat taaagaatgt aagagaagtc   7860
aaaggcttaa caaaggagg accaggacac gaagaaccta tccctatgtc aacatatggg     7920
tggaatctag tacgcttaca gagcggagtt gacgttttt ttgttccacc agagaagtgt    7980
gacacattgt tgtgtgacat agggggaatca tcaccaaatc ccacggtaga agcgggacga   8040
acactcagag tccttaacct agtggaaaat tggttgaaca ataacaccca attttgcgta    8100
aaggttctta acccgtacat gccctcagtc attgaaagaa tggaaacctt acaacggaaa    8160
tacgaggag ccttggtgag aaatccactc tcacggaatt ccacacatga gatgtactgg    8220
gtgtccaatg cttccgggaa catagtgtca tcagtgaaca tgatttcaag aatgctgatt    8280
aacagattca ccatgagaca caagaaggcc acctatgagc cagatgtcga cctcggaagc    8340
ggaacccgca atattggaat tgaaagtgag acaccgaacc tagacataat tgggaaaaga   8400
atagaaaaaa taaacaaga gcatgaaacg tcatggcact atgaccaaga ccacccatac    8460
aaaacatggg cttaccatgg cagctatgaa acaaaacaga ctggatcagc atcatccatg    8520
gtgaacggag tagtcagatt gctgacaaaa ccctgggacg ttgttccaat ggtgacacag    8580
atggcaatga cagacacaac tcctttcgga caacagcgcg tcttcaaaga aaggtggat    8640
acgagaccc aagaaccaaa agaaggcaca aaaaaactaa tgaaaatcac ggcagagtgg    8700
ctctggaaag aactaggaaa gaaaaagaca cctagaatgt gcaccagaga agaattcaca   8760
aaaaaggtga gaagcaatgc agccttgggg gccatattta ccgatgagaa caagtggaaa    8820
tcggcgcgtg aggctgttga agatagtagg ttttggggagc tggttgacaa ggaaagaaac   8880
ctccatcttg aagggaaatg tgaaacatgt gtatacaaca tgatgggaaa agagagaaa    8940
aaactaggag agtttggtaa agcaaaaggc agcagagcca tatggtacat gtggctcgga    9000
gcacgcttct tagagttcga agccctagga ttttttgaatg aagaccattg gttctccaga    9060
gagaactccc tgagtggagt agaaggagaa gggctgcata agctaggtta catcttaaga    9120
gaggtgagca agaaagaagg aggagcaatg tatgccgatg acaccgcagg ctggacaca     9180
agaatcacaa tagaggattt aaaaaatgaa gaaatgataa cgaaccacat ggcaggagaa    9240
cacaagaaac ttgccgaggc catttttaaa ttgacgtatc aaaacaaggt ggtgcgtgtg    9300
caaagaccaa caccaagagg cacagtaatg gacatcatat cgagaagaga ccaaaggggt    9360
agtggacaag ttggtaccta tggcctcaac actttcacca acatggaagc acaactaatt    9420
aggcaaatgg aggggggaagg aatcttcaaa gcatccagc acttgacagc ctcagaagaa    9480
atcgctgtgc aagattggct agcaagagta gggcgtgaaa ggttgtcaag aatggccatc    9540
agtgagatg attgtgttgt gaaacctta tgatgatagat ttgcaagagc tctaacagct    9600
ctaaatgaca tgggaaaggt taggaaggac atacagcaat gggagccctc aagaggatgg    9660
aacgactgga cacaggtacc cttctgttca caccattttc acgagttaat tatgaaagat    9720
ggtcgcacac tcgtagttcc atgcagaaac caagatgaat tgatcggcag agcccgaatt    9780
tcccaggag ctggtggtc tttacgggag acggcctgtt gggggaagtc ttacgcccaa    9840
atgtggagct tgatgtactt ccacagacgt gatctcaggc tagcggcaaa tgccatctgc    9900
```

```
tcggcagtcc cgtcacactg ggttccaaca agccggacaa cctggtccat acacgccagc    9960
catgaatgga tgacgacgga agacatgttg acagtttgga acaaagtgtg gatcctagaa   10020
aatccatgga tggaagacaa aactccagtg gaatcatggg aggaaatccc atacctggaa   10080
aaaagagaag accaatggtg cggctcactg attgggctga caagcagagc cacctgggcg   10140
aagaatatcc agacagcaat aaaccaagtc agatccctca ttggcaatga ggaatacaca   10200
gattacatgc catccatgaa aagattcaga agagaagagg aagaggcagg agttttgtgg   10260
tagaaaaaca tgaaacaaaa cagaagtcag gtcggattaa gccatagtac gggaaaaact   10320
atgctacctg tgagccccgt ccaaggacgt taaaagaagt caggccactt tgatgccata   10380
gcttgagcaa actgtgcagc ctgtagctca cctgagaagt tgtaaaaaat ccgggaggcc   10440
acaaaccatg gaagctgtac gcatggcgta gtggactagc ggttagagga gacccctccc   10500
ttacagatcg cagcaacaat gggggcccaa ggtgagatga agctgtagtc tcactggaag   10560
gactagaggt tagaggagac ccccccaaaa caaaaaacag catattgacg ctgggaaaga   10620
ccagagatcc tgctgtctcc tcagcatcat tccaggcaca ggacgccaga aaatggaatg   10680
gtgctgttga atcaacaggt tct                                            10703
```

<210> SEQ ID NO 2
<211> LENGTH: 22
<212> TYPE: DNA
<213> ORGANISM: Artificial Sequence
<220> FEATURE:
<223> OTHER INFORMATION: PCR Primer

<400> SEQUENCE: 2
tgcgagtggg ccagaactct gg                                              22

<210> SEQ ID NO 3
<211> LENGTH: 23
<212> TYPE: DNA
<213> ORGANISM: Artificial Sequence
<220> FEATURE:
<223> OTHER INFORMATION: PCR Primer

<400> SEQUENCE: 3
taggagaccg cttgggactt tgg                                             23

<210> SEQ ID NO 4
<211> LENGTH: 22
<212> TYPE: DNA
<213> ORGANISM: Artificial Sequence
<220> FEATURE:
<223> OTHER INFORMATION: PCR Primer

<400> SEQUENCE: 4
tggagagagg tctcgagtgg ta                                              22

<210> SEQ ID NO 5
<211> LENGTH: 22
<212> TYPE: DNA
<213> ORGANISM: Artificial Sequence
<220> FEATURE:
<223> OTHER INFORMATION: PCR Primer

<400> SEQUENCE: 5
tgaaattggc tggaaggcct gg                                              22

<210> SEQ ID NO 6

```
<211> LENGTH: 22
<212> TYPE: DNA
<213> ORGANISM: Artificial Sequence
<220> FEATURE:
<223> OTHER INFORMATION: PCR Primer

<400> SEQUENCE: 6
tggaatgttc cgaccactat gg                                              22

<210> SEQ ID NO 7
<211> LENGTH: 17
<212> TYPE: DNA
<213> ORGANISM: Artificial Sequence
<220> FEATURE:
<223> OTHER INFORMATION: PCR Primer

<400> SEQUENCE: 7
tgtgaccgga gtctggg                                                    17

<210> SEQ ID NO 8
<211> LENGTH: 23
<212> TYPE: DNA
<213> ORGANISM: Artificial Sequence
<220> FEATURE:
<223> OTHER INFORMATION: PCR Primer

<400> SEQUENCE: 8
tgctgactgg gttactggat aga                                             23

<210> SEQ ID NO 9
<211> LENGTH: 23
<212> TYPE: DNA
<213> ORGANISM: Artificial Sequence
<220> FEATURE:
<223> OTHER INFORMATION: PCR Primer

<400> SEQUENCE: 9
tctgtgagga gccccgagag tgg                                             23

<210> SEQ ID NO 10
<211> LENGTH: 23
<212> TYPE: DNA
<213> ORGANISM: Artificial Sequence
<220> FEATURE:
<223> OTHER INFORMATION: PCR Primer

<400> SEQUENCE: 10
tgctgtcata tgctgaaacg cgg                                             23

<210> SEQ ID NO 11
<211> LENGTH: 30
<212> TYPE: DNA
<213> ORGANISM: Artificial Sequence
<220> FEATURE:
<223> OTHER INFORMATION: PCR Primer

<400> SEQUENCE: 11
tggctgctgg tatggaatgg agattagacc                                      30

<210> SEQ ID NO 12
<211> LENGTH: 18
<212> TYPE: DNA
<213> ORGANISM: Artificial Sequence
<220> FEATURE:
<223> OTHER INFORMATION: PCR Primer

<400> SEQUENCE: 12
```

```
ttccctcta tggcccac                                                   18

<210> SEQ ID NO 13
<211> LENGTH: 23
<212> TYPE: DNA
<213> ORGANISM: Artificial Sequence
<220> FEATURE:
<223> OTHER INFORMATION: PCR Primer

<400> SEQUENCE: 13
tctggatgaa gcctttccga tcc                                            23

<210> SEQ ID NO 14
<211> LENGTH: 25
<212> TYPE: DNA
<213> ORGANISM: Artificial Sequence
<220> FEATURE:
<223> OTHER INFORMATION: PCR Primer

<400> SEQUENCE: 14
tggatgaagc tctttcccga tccgc                                          25

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
tggactgatc ccccgctagc                                                20

<210> SEQ ID NO 16
<211> LENGTH: 27
<212> TYPE: DNA
<213> ORGANISM: Artificial Sequence
<220> FEATURE:
<223> OTHER INFORMATION: PCR Primer

<400> SEQUENCE: 16
tagcgtgaaa atggggaatg agattgc                                        27

<210> SEQ ID NO 17
<211> LENGTH: 18
<212> TYPE: DNA
<213> ORGANISM: Artificial Sequence
<220> FEATURE:
<223> OTHER INFORMATION: PCR Primer

<400> SEQUENCE: 17
tccccgtggc tggctggc                                                  18

<210> SEQ ID NO 18
<211> LENGTH: 21
<212> TYPE: DNA
<213> ORGANISM: Artificial Sequence
<220> FEATURE:
<223> OTHER INFORMATION: PCR Primer

<400> SEQUENCE: 18
tgggtcttgg caaggatggc c                                              21

<210> SEQ ID NO 19
<211> LENGTH: 23
<212> TYPE: DNA
```

<213> ORGANISM: Artificial Sequence
<220> FEATURE:
<223> OTHER INFORMATION: PCR Primer

<400> SEQUENCE: 19
tgaggacact gggccttgtg tga                                    23

<210> SEQ ID NO 20
<211> LENGTH: 25
<212> TYPE: DNA
<213> ORGANISM: Artificial Sequence
<220> FEATURE:
<223> OTHER INFORMATION: PCR Primer

<400> SEQUENCE: 20
tggcggctgt tcttggttgg atgct                                  25

<210> SEQ ID NO 21
<211> LENGTH: 25
<212> TYPE: DNA
<213> ORGANISM: Artificial Sequence
<220> FEATURE:
<223> OTHER INFORMATION: PCR Primer

<400> SEQUENCE: 21
tcggctgtgg aagaggaggc tggtc                                  25

<210> SEQ ID NO 22
<211> LENGTH: 24
<212> TYPE: DNA
<213> ORGANISM: Artificial Sequence
<220> FEATURE:
<223> OTHER INFORMATION: PCR Primer

<400> SEQUENCE: 22
tagaggcggc tggtcctact atgc                                   24

<210> SEQ ID NO 23
<211> LENGTH: 22
<212> TYPE: DNA
<213> ORGANISM: Artificial Sequence
<220> FEATURE:
<223> OTHER INFORMATION: PCR Primer

<400> SEQUENCE: 23
tacgcttcac tgtctgggaa tg                                     22

<210> SEQ ID NO 24
<211> LENGTH: 21
<212> TYPE: DNA
<213> ORGANISM: Artificial Sequence
<220> FEATURE:
<223> OTHER INFORMATION: PCR Primer

<400> SEQUENCE: 24
tcctacggac tggcgtactg g                                      21

<210> SEQ ID NO 25
<211> LENGTH: 23
<212> TYPE: DNA
<213> ORGANISM: Artificial Sequence
<220> FEATURE:
<223> OTHER INFORMATION: PCR Primer

<400> SEQUENCE: 25
tacccggaag ttatgaggtg aag                                    23

```
<210> SEQ ID NO 26
<211> LENGTH: 26
<212> TYPE: DNA
<213> ORGANISM: Artificial Sequence
<220> FEATURE:
<223> OTHER INFORMATION: PCR Primer

<400> SEQUENCE: 26
tcaagagaag gttgaccgaa agctcc                                          26

<210> SEQ ID NO 27
<211> LENGTH: 25
<212> TYPE: DNA
<213> ORGANISM: Artificial Sequence
<220> FEATURE:
<223> OTHER INFORMATION: PCR Primer

<400> SEQUENCE: 27
tgtcccgtgt gtctacactg atggg                                           25

<210> SEQ ID NO 28
<211> LENGTH: 21
<212> TYPE: DNA
<213> ORGANISM: Artificial Sequence
<220> FEATURE:
<223> OTHER INFORMATION: PCR Primer

<400> SEQUENCE: 28
tccctgctct acactgatgg g                                               21

<210> SEQ ID NO 29
<211> LENGTH: 22
<212> TYPE: DNA
<213> ORGANISM: Artificial Sequence
<220> FEATURE:
<223> OTHER INFORMATION: PCR Primer

<400> SEQUENCE: 29
tccttgcgtg tacactgatg gg                                              22

<210> SEQ ID NO 30
<211> LENGTH: 22
<212> TYPE: DNA
<213> ORGANISM: Artificial Sequence
<220> FEATURE:
<223> OTHER INFORMATION: PCR Primer

<400> SEQUENCE: 30
tacttgcgtc tacactgatg gg                                              22

<210> SEQ ID NO 31
<211> LENGTH: 27
<212> TYPE: DNA
<213> ORGANISM: Artificial Sequence
<220> FEATURE:
<223> OTHER INFORMATION: PCR Primer

<400> SEQUENCE: 31
tgtgtgtaca ctgatgggga agagaga                                         27

<210> SEQ ID NO 32
<211> LENGTH: 27
<212> TYPE: DNA
<213> ORGANISM: Artificial Sequence
<220> FEATURE:
```

```
<223> OTHER INFORMATION: PCR Primer

<400> SEQUENCE: 32
tgtgtctaca ctgatgggaa agagaga                                          27

<210> SEQ ID NO 33
<211> LENGTH: 18
<212> TYPE: DNA
<213> ORGANISM: Artificial Sequence
<220> FEATURE:
<223> OTHER INFORMATION: PCR Primer

<400> SEQUENCE: 33
tgccagggaa gcgggcct                                                    18

<210> SEQ ID NO 34
<211> LENGTH: 23
<212> TYPE: DNA
<213> ORGANISM: Artificial Sequence
<220> FEATURE:
<223> OTHER INFORMATION: PCR Primer

<400> SEQUENCE: 34
tagccgagcc tctggtactg tgg                                              23

<210> SEQ ID NO 35
<211> LENGTH: 22
<212> TYPE: DNA
<213> ORGANISM: Artificial Sequence
<220> FEATURE:
<223> OTHER INFORMATION: PCR Primer

<400> SEQUENCE: 35
tgcctctggt actgtggctg gg                                               22

<210> SEQ ID NO 36
<211> LENGTH: 21
<212> TYPE: DNA
<213> ORGANISM: Artificial Sequence
<220> FEATURE:
<223> OTHER INFORMATION: PCR Primer

<400> SEQUENCE: 36
tctggttctg tggctgggag c                                                21

<210> SEQ ID NO 37
<211> LENGTH: 21
<212> TYPE: DNA
<213> ORGANISM: Artificial Sequence
<220> FEATURE:
<223> OTHER INFORMATION: PCR Primer

<400> SEQUENCE: 37
tctggtactg tggctgggag c                                                21

<210> SEQ ID NO 38
<211> LENGTH: 25
<212> TYPE: DNA
<213> ORGANISM: Artificial Sequence
<220> FEATURE:
<223> OTHER INFORMATION: PCR Primer

<400> SEQUENCE: 38
tgggattcct gaatgaagac cctgg                                            25
```

```
<210> SEQ ID NO 39
<211> LENGTH: 25
<212> TYPE: DNA
<213> ORGANISM: Artificial Sequence
<220> FEATURE:
<223> OTHER INFORMATION: PCR Primer

<400> SEQUENCE: 39
tcttgagtgg agtggaagga gaagg                                    25

<210> SEQ ID NO 40
<211> LENGTH: 26
<212> TYPE: DNA
<213> ORGANISM: Artificial Sequence
<220> FEATURE:
<223> OTHER INFORMATION: PCR Primer

<400> SEQUENCE: 40
tggaaggctt ggcttacata cctagg                                   26

<210> SEQ ID NO 41
<211> LENGTH: 27
<212> TYPE: DNA
<213> ORGANISM: Artificial Sequence
<220> FEATURE:
<223> OTHER INFORMATION: PCR Primer

<400> SEQUENCE: 41
tggagggaat cgcctgaact acctggg                                  27

<210> SEQ ID NO 42
<211> LENGTH: 26
<212> TYPE: DNA
<213> ORGANISM: Artificial Sequence
<220> FEATURE:
<223> OTHER INFORMATION: PCR Primer

<400> SEQUENCE: 42
tccgaagctg ggatactcct gcgtga                                   26

<210> SEQ ID NO 43
<211> LENGTH: 23
<212> TYPE: DNA
<213> ORGANISM: Artificial Sequence
<220> FEATURE:
<223> OTHER INFORMATION: PCR Primer

<400> SEQUENCE: 43
tctaagtcga cgagaccgag agg                                      23

<210> SEQ ID NO 44
<211> LENGTH: 21
<212> TYPE: DNA
<213> ORGANISM: Artificial Sequence
<220> FEATURE:
<223> OTHER INFORMATION: PCR Primer

<400> SEQUENCE: 44
tgaggctcgg tcggttgtga c                                        21

<210> SEQ ID NO 45
<211> LENGTH: 22
<212> TYPE: DNA
<213> ORGANISM: Artificial Sequence
<220> FEATURE:
<223> OTHER INFORMATION: PCR Primer
```

```
<400> SEQUENCE: 45
tggcggtgag tggagacgac tg                                    22

<210> SEQ ID NO 46
<211> LENGTH: 22
<212> TYPE: DNA
<213> ORGANISM: Artificial Sequence
<220> FEATURE:
<223> OTHER INFORMATION: PCR Primer

<400> SEQUENCE: 46
tctgtcgcgg agatgactgt gt                                    22

<210> SEQ ID NO 47
<211> LENGTH: 26
<212> TYPE: DNA
<213> ORGANISM: Artificial Sequence
<220> FEATURE:
<223> OTHER INFORMATION: PCR Primer

<400> SEQUENCE: 47 tgcccttttac ttcctgaatg actggc                               26

<210> SEQ ID NO 48
<211> LENGTH: 23
<212> TYPE: DNA
<213> ORGANISM: Artificial Sequence
<220> FEATURE:
<223> OTHER INFORMATION: PCR Primer

<400> SEQUENCE: 48
taaggcctac ggacgatgtg gct                                   23

<210> SEQ ID NO 49
<211> LENGTH: 21
<212> TYPE: DNA
<213> ORGANISM: Artificial Sequence
<220> FEATURE:
<223> OTHER INFORMATION: PCR Primer

<400> SEQUENCE: 49
tgtggctgct gctgtacttc c                                     21

<210> SEQ ID NO 50
<211> LENGTH: 22
<212> TYPE: DNA
<213> ORGANISM: Artificial Sequence
<220> FEATURE:
<223> OTHER INFORMATION: PCR Primer

<400> SEQUENCE: 50
tcccacagcc gaacacctgg tc                                    22

<210> SEQ ID NO 51
<211> LENGTH: 20
<212> TYPE: DNA
<213> ORGANISM: Artificial Sequence
<220> FEATURE:
<223> OTHER INFORMATION: PCR Primer

<400> SEQUENCE: 51
tggatgacga cggaagactg                                       20

<210> SEQ ID NO 52
<211> LENGTH: 28
```

```
<212> TYPE: DNA
<213> ORGANISM: Artificial Sequence
<220> FEATURE:
<223> OTHER INFORMATION: PCR Primer

<400> SEQUENCE: 52
tgtctggatt gaggagaatg aatggatg                                28

<210> SEQ ID NO 53
<211> LENGTH: 15
<212> TYPE: DNA
<213> ORGANISM: Artificial Sequence
<220> FEATURE:
<223> OTHER INFORMATION: PCR Primer

<400> SEQUENCE: 53
tgatgtgtca tgccc                                              15

<210> SEQ ID NO 54
<211> LENGTH: 18
<212> TYPE: DNA
<213> ORGANISM: Artificial Sequence
<220> FEATURE:
<223> OTHER INFORMATION: PCR Primer

<400> SEQUENCE: 54
tgtatgtaca ctgatggg                                           18

<210> SEQ ID NO 55
<211> LENGTH: 12
<212> TYPE: DNA
<213> ORGANISM: Artificial Sequence
<220> FEATURE:
<223> OTHER INFORMATION: PCR Primer

<400> SEQUENCE: 55
tacactgatg gg                                                 12

<210> SEQ ID NO 56
<211> LENGTH: 22
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: 18, 20
<223> OTHER INFORMATION: n = inosine

<400> SEQUENCE: 56
tacacatgat ggggaagngn ga                                      22

<210> SEQ ID NO 57
<211> LENGTH: 22
<212> TYPE: DNA
<213> ORGANISM: Artificial Sequence
<220> FEATURE:
<223> OTHER INFORMATION: PCR Primer

<400> SEQUENCE: 57
tacacatgat gggaaagaga ga                                      22

<210> SEQ ID NO 58
<211> LENGTH: 16
<212> TYPE: DNA
<213> ORGANISM: Artificial Sequence
<220> FEATURE:
```

<223> OTHER INFORMATION: PCR Primer

<400> SEQUENCE: 58
tggtactgtg gctggg                                                    16

<210> SEQ ID NO 59
<211> LENGTH: 17
<212> TYPE: DNA
<213> ORGANISM: Artificial Sequence
<220> FEATURE:
<223> OTHER INFORMATION: PCR Primer

<400> SEQUENCE: 59
tgaatgaaga tcactgg                                                   17

<210> SEQ ID NO 60
<211> LENGTH: 17
<212> TYPE: DNA
<213> ORGANISM: Artificial Sequence
<220> FEATURE:
<223> OTHER INFORMATION: PCR Primer

<400> SEQUENCE: 60
tgaatgaaga ccattgg                                                   17

<210> SEQ ID NO 61
<211> LENGTH: 14
<212> TYPE: DNA
<213> ORGANISM: Artificial Sequence
<220> FEATURE:
<223> OTHER INFORMATION: PCR Primer

<400> SEQUENCE: 61
tacgcgcgat gtgg                                                      14

<210> SEQ ID NO 62
<211> LENGTH: 23
<212> TYPE: DNA
<213> ORGANISM: Artificial Sequence
<220> FEATURE:
<223> OTHER INFORMATION: PCR Primer

<400> SEQUENCE: 62
tgctctccgt ttgagctccc gtg                                            23

<210> SEQ ID NO 63
<211> LENGTH: 22
<212> TYPE: DNA
<213> ORGANISM: Artificial Sequence
<220> FEATURE:
<223> OTHER INFORMATION: PCR Primer

<400> SEQUENCE: 63
ttgcgtgatc cggacttcct cc                                             22

<210> SEQ ID NO 64
<211> LENGTH: 16
<212> TYPE: DNA
<213> ORGANISM: Artificial Sequence
<220> FEATURE:
<223> OTHER INFORMATION: PCR Primer

<400> SEQUENCE: 64
tgctcctccc tggcct                                                    16

```
<210> SEQ ID NO 65
<211> LENGTH: 22
<212> TYPE: DNA
<213> ORGANISM: Artificial Sequence
<220> FEATURE:
<223> OTHER INFORMATION: PCR Primer

<400> SEQUENCE: 65
tcttccttgg tctccggtcc tc                                              22

<210> SEQ ID NO 66
<211> LENGTH: 22
<212> TYPE: DNA
<213> ORGANISM: Artificial Sequence
<220> FEATURE:
<223> OTHER INFORMATION: PCR Primer

<400> SEQUENCE: 66
tctctctatc cgtaaccctg tc                                              22

<210> SEQ ID NO 67
<211> LENGTH: 23
<212> TYPE: DNA
<213> ORGANISM: Artificial Sequence
<220> FEATURE:
<223> OTHER INFORMATION: PCR Primer

<400> SEQUENCE: 67
tctccgagac tctgatctgt gtg                                             23

<210> SEQ ID NO 68
<211> LENGTH: 16
<212> TYPE: DNA
<213> ORGANISM: Artificial Sequence
<220> FEATURE:
<223> OTHER INFORMATION: PCR Primer

<400> SEQUENCE: 68
tccgcctcct tgctcc                                                     16

<210> SEQ ID NO 69
<211> LENGTH: 24
<212> TYPE: DNA
<213> ORGANISM: Artificial Sequence
<220> FEATURE:
<223> OTHER INFORMATION: PCR Primer

<400> SEQUENCE: 69
taccggcctt atttcctggc tacc                                            24

<210> SEQ ID NO 70
<211> LENGTH: 23
<212> TYPE: DNA
<213> ORGANISM: Artificial Sequence
<220> FEATURE:
<223> OTHER INFORMATION: PCR Primer

<400> SEQUENCE: 70
tcctgaagaa cgcgaaaaga gcc                                             23

<210> SEQ ID NO 71
<211> LENGTH: 22
<212> TYPE: DNA
<213> ORGANISM: Artificial Sequence
<220> FEATURE:
<223> OTHER INFORMATION: PCR Primer
```

-continued

```
<400> SEQUENCE: 71
tggccggaac tgaccgaagg cc                                              22

<210> SEQ ID NO 72
<211> LENGTH: 20
<212> TYPE: DNA
<213> ORGANISM: Artificial Sequence
<220> FEATURE:
<223> OTHER INFORMATION: PCR Primer

<400> SEQUENCE: 72
tcctctttcc ctgccccgta                                                 20

<210> SEQ ID NO 73
<211> LENGTH: 23
<212> TYPE: DNA
<213> ORGANISM: Artificial Sequence
<220> FEATURE:
<223> OTHER INFORMATION: PCR Primer

<400> SEQUENCE: 73
tgaagatcgc gctgcctctc cct                                             23

<210> SEQ ID NO 74
<211> LENGTH: 20
<212> TYPE: DNA
<213> ORGANISM: Artificial Sequence
<220> FEATURE:
<223> OTHER INFORMATION: PCR Primer

<400> SEQUENCE: 74
tcccggcggg gtggctgtct                                                 20

<210> SEQ ID NO 75
<211> LENGTH: 21
<212> TYPE: DNA
<213> ORGANISM: Artificial Sequence
<220> FEATURE:
<223> OTHER INFORMATION: PCR Primer

<400> SEQUENCE: 75
tatggctccg ttggactccg g                                               21

<210> SEQ ID NO 76
<211> LENGTH: 22
<212> TYPE: DNA
<213> ORGANISM: Artificial Sequence
<220> FEATURE:
<223> OTHER INFORMATION: PCR Primer

<400> SEQUENCE: 76
tgtcgttgtg atgacaagtc cc                                              22

<210> SEQ ID NO 77
<211> LENGTH: 21
<212> TYPE: DNA
<213> ORGANISM: Artificial Sequence
<220> FEATURE:
<223> OTHER INFORMATION: PCR Primer

<400> SEQUENCE: 77
tcctctgggc cttccctgtc c                                               21

<210> SEQ ID NO 78
<211> LENGTH: 23
```

<212> TYPE: DNA
<213> ORGANISM: Artificial Sequence
<220> FEATURE:
<223> OTHER INFORMATION: PCR Primer

<400> SEQUENCE: 78
tcctgggcct attatggcta atg                                              23

<210> SEQ ID NO 79
<211> LENGTH: 23
<212> TYPE: DNA
<213> ORGANISM: Artificial Sequence
<220> FEATURE:
<223> OTHER INFORMATION: PCR Primer

<400> SEQUENCE: 79
tggaccggct atggtggtgt tcc                                              23

<210> SEQ ID NO 80
<211> LENGTH: 25
<212> TYPE: DNA
<213> ORGANISM: Artificial Sequence
<220> FEATURE:
<223> OTHER INFORMATION: PCR Primer

<400> SEQUENCE: 80
tgctcttccc ggcgttaaag ctgta                                            25

<210> SEQ ID NO 81
<211> LENGTH: 26
<212> TYPE: DNA
<213> ORGANISM: Artificial Sequence
<220> FEATURE:
<223> OTHER INFORMATION: PCR Primer

<400> SEQUENCE: 81
tggttcttct gtcctggtcc tccttt                                           26

<210> SEQ ID NO 82
<211> LENGTH: 22
<212> TYPE: DNA
<213> ORGANISM: Artificial Sequence
<220> FEATURE:
<223> OTHER INFORMATION: PCR Primer

<400> SEQUENCE: 82
tgttccaccg aggcttgtta cc                                               22

<210> SEQ ID NO 83
<211> LENGTH: 19
<212> TYPE: DNA
<213> ORGANISM: Artificial Sequence
<220> FEATURE:
<223> OTHER INFORMATION: PCR Primer

<400> SEQUENCE: 83
tcaatccccc agtggctcc                                                   19

<210> SEQ ID NO 84
<211> LENGTH: 20
<212> TYPE: DNA
<213> ORGANISM: Artificial Sequence
<220> FEATURE:
<223> OTHER INFORMATION: PCR Primer

<400> SEQUENCE: 84
tcttcccgtg cttcctggcc                                                    20

<210> SEQ ID NO 85
<211> LENGTH: 17
<212> TYPE: DNA
<213> ORGANISM: Artificial Sequence
<220> FEATURE:
<223> OTHER INFORMATION: PCR Primer

<400> SEQUENCE: 85
tcgtctggcc tggtggt                                                       17

<210> SEQ ID NO 86
<211> LENGTH: 20
<212> TYPE: DNA
<213> ORGANISM: Artificial Sequence
<220> FEATURE:
<223> OTHER INFORMATION: PCR Primer

<400> SEQUENCE: 86
taggccccac cgttggtggt                                                    20

<210> SEQ ID NO 87
<211> LENGTH: 17
<212> TYPE: DNA
<213> ORGANISM: Artificial Sequence
<220> FEATURE:
<223> OTHER INFORMATION: PCR Primer

<400> SEQUENCE: 87
tgctcccgcc ctgtacc                                                       17

<210> SEQ ID NO 88
<211> LENGTH: 24
<212> TYPE: DNA
<213> ORGANISM: Artificial Sequence
<220> FEATURE:
<223> OTHER INFORMATION: PCR Primer

<400> SEQUENCE: 88
tggtcttctt gaggaatccc gagc                                               24

<210> SEQ ID NO 89
<211> LENGTH: 18
<212> TYPE: DNA
<213> ORGANISM: Artificial Sequence
<220> FEATURE:
<223> OTHER INFORMATION: PCR Primer

<400> SEQUENCE: 89 tactcccgc cctgtacc                                                       18

<210> SEQ ID NO 90
<211> LENGTH: 21
<212> TYPE: DNA
<213> ORGANISM: Artificial Sequence
<220> FEATURE:
<223> OTHER INFORMATION: PCR Primer

<400> SEQUENCE: 90
tgcccgccct gtaccgatgg c                                                  21

<210> SEQ ID NO 91
<211> LENGTH: 24
<212> TYPE: DNA
<213> ORGANISM: Artificial Sequence

```
-continued

<220> FEATURE:
<223> OTHER INFORMATION: PCR Primer

<400> SEQUENCE: 91
tctctggaaa gccgtggtct tctt                                          24

<210> SEQ ID NO 92
<211> LENGTH: 19
<212> TYPE: DNA
<213> ORGANISM: Artificial Sequence
<220> FEATURE:
<223> OTHER INFORMATION: PCR Primer

<400> SEQUENCE: 92
ttccctcact ccgctccct                                                19

<210> SEQ ID NO 93
<211> LENGTH: 21
<212> TYPE: DNA
<213> ORGANISM: Artificial Sequence
<220> FEATURE:
<223> OTHER INFORMATION: PCR Primer

<400> SEQUENCE: 93
tctgcccgcc gtggtcttct t                                             21

<210> SEQ ID NO 94
<211> LENGTH: 23
<212> TYPE: DNA
<213> ORGANISM: Artificial Sequence
<220> FEATURE:
<223> OTHER INFORMATION: PCR Primer

<400> SEQUENCE: 94
tgcgaccttc tccttccctc cct                                           23

<210> SEQ ID NO 95
<211> LENGTH: 22
<212> TYPE: DNA
<213> ORGANISM: Artificial Sequence
<220> FEATURE:
<223> OTHER INFORMATION: PCR Primer

<400> SEQUENCE: 95
tgtgtcccgc cggctgtgtc tc                                            22

<210> SEQ ID NO 96
<211> LENGTH: 18
<212> TYPE: DNA
<213> ORGANISM: Artificial Sequence
<220> FEATURE:
<223> OTHER INFORMATION: PCR Primer

<400> SEQUENCE: 96
tcccgccggc tgtgtctc                                                 18

<210> SEQ ID NO 97
<211> LENGTH: 17
<212> TYPE: DNA
<213> ORGANISM: Artificial Sequence
<220> FEATURE:
<223> OTHER INFORMATION: PCR Primer

<400> SEQUENCE: 97
tccctccgcg gtgtctc                                                  17
```

-continued

<210> SEQ ID NO 98
<211> LENGTH: 20
<212> TYPE: DNA
<213> ORGANISM: Artificial Sequence
<220> FEATURE:
<223> OTHER INFORMATION: PCR Primer

<400> SEQUENCE: 98
tcgtgtcccg ccgctgtgtc                                              20

<210> SEQ ID NO 99
<211> LENGTH: 21
<212> TYPE: DNA
<213> ORGANISM: Artificial Sequence
<220> FEATURE:
<223> OTHER INFORMATION: PCR Primer

<400> SEQUENCE: 99
tagcactccg cccttagctt c                                            21

<210> SEQ ID NO 100
<211> LENGTH: 25
<212> TYPE: DNA
<213> ORGANISM: Artificial Sequence
<220> FEATURE:
<223> OTHER INFORMATION: PCR Primer

<400> SEQUENCE: 100
tgcttctgcc ttctgatcat tggac                                        25

<210> SEQ ID NO 101
<211> LENGTH: 21
<212> TYPE: DNA
<213> ORGANISM: Artificial Sequence
<220> FEATURE:
<223> OTHER INFORMATION: PCR Primer

<400> SEQUENCE: 101
tatgacccct cccctcctc t                                             21

<210> SEQ ID NO 102
<211> LENGTH: 25
<212> TYPE: DNA
<213> ORGANISM: Artificial Sequence
<220> FEATURE:
<223> OTHER INFORMATION: PCR Primer

<400> SEQUENCE: 102
taaccttgga ctggcgttga gatgg                                        25

<210> SEQ ID NO 103
<211> LENGTH: 25
<212> TYPE: DNA
<213> ORGANISM: Artificial Sequence
<220> FEATURE:
<223> OTHER INFORMATION: PCR Primer

<400> SEQUENCE: 103
tggatgtctt ttcggacctt tgact                                        25

<210> SEQ ID NO 104
<211> LENGTH: 24
<212> TYPE: DNA
<213> ORGANISM: Artificial Sequence
<220> FEATURE:
<223> OTHER INFORMATION: PCR Primer

<400> SEQUENCE: 104
tgtgagcgaa ggggacctct tccc  24

<210> SEQ ID NO 105
<211> LENGTH: 20
<212> TYPE: DNA
<213> ORGANISM: Artificial Sequence
<220> FEATURE:
<223> OTHER INFORMATION: PCR Primer

<400> SEQUENCE: 105
tgcccctggc tggatgctcc  20

<210> SEQ ID NO 106
<211> LENGTH: 24
<212> TYPE: DNA
<213> ORGANISM: Artificial Sequence
<220> FEATURE:
<223> OTHER INFORMATION: PCR Primer

<400> SEQUENCE: 106
tgtcttctgt tgtctccctc tcct  24

<210> SEQ ID NO 107
<211> LENGTH: 21
<212> TYPE: DNA
<213> ORGANISM: Artificial Sequence
<220> FEATURE:
<223> OTHER INFORMATION: PCR Primer

<400> SEQUENCE: 107
tagctgtctt ccgtggtctc c  21

<210> SEQ ID NO 108
<211> LENGTH: 20
<212> TYPE: DNA
<213> ORGANISM: Artificial Sequence
<220> FEATURE:
<223> OTHER INFORMATION: PCR Primer

<400> SEQUENCE: 108
tcctcatccg accctgttcc  20

<210> SEQ ID NO 109
<211> LENGTH: 19
<212> TYPE: DNA
<213> ORGANISM: Artificial Sequence
<220> FEATURE:
<223> OTHER INFORMATION: PCR Primer

<400> SEQUENCE: 109
tgaggcttcc cccgatgtc  19

<210> SEQ ID NO 110
<211> LENGTH: 17
<212> TYPE: DNA
<213> ORGANISM: Artificial Sequence
<220> FEATURE:
<223> OTHER INFORMATION: PCR Primer

<400> SEQUENCE: 110
taatgggctt catccat  17

<210> SEQ ID NO 111

```
<211> LENGTH: 15
<212> TYPE: DNA
<213> ORGANISM: Artificial Sequence
<220> FEATURE:
<223> OTHER INFORMATION: PCR Primer

<400> SEQUENCE: 111
tcccgccctg tacca                                                      15

<210> SEQ ID NO 112
<211> LENGTH: 13
<212> TYPE: DNA
<213> ORGANISM: Artificial Sequence
<220> FEATURE:
<223> OTHER INFORMATION: PCR Primer

<400> SEQUENCE: 112
tagccctgta cca                                                        13

<210> SEQ ID NO 113
<211> LENGTH: 16
<212> TYPE: DNA
<213> ORGANISM: Artificial Sequence
<220> FEATURE:
<223> OTHER INFORMATION: PCR Primer

<400> SEQUENCE: 113
tccagtggtc ttcatt                                                     16

<210> SEQ ID NO 114
<211> LENGTH: 20
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: 6, 9, 12, 18
<223> OTHER INFORMATION: n = inosine

<400> SEQUENCE: 114
tcccanccng cngtgtcntc                                                 20

<210> SEQ ID NO 115
<211> LENGTH: 19
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: 6, 9, 12
<223> OTHER INFORMATION: n = inosine

<400> SEQUENCE: 115
tcccanccng cngtgtctc                                                  19

<210> SEQ ID NO 116
<211> LENGTH: 18
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: 5, 8, 11
<223> OTHER INFORMATION: n = inosine

<400> SEQUENCE: 116
```
tcccnccngc ngtgtctc                                                18

<210> SEQ ID NO 117
<211> LENGTH: 19
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: 5, 8, 11, 17
<223> OTHER INFORMATION: n = inosine

<400> SEQUENCE: 117
tcccnccngc ngtgtcntc                                               19

<210> SEQ ID NO 118
<211> LENGTH: 18
<212> TYPE: DNA
<213> ORGANISM: Artificial Sequence
<220> FEATURE:
<223> OTHER INFORMATION: PCR Primer

<400> SEQUENCE: 118
tgtcttctgt tgtctcca                                                18

<210> SEQ ID NO 119
<211> LENGTH: 23
<212> TYPE: DNA
<213> ORGANISM: Artificial Sequence
<220> FEATURE:
<223> OTHER INFORMATION: PCR Primer

<400> SEQUENCE: 119
tggacacaua gatggtaatt ttc                                          23

<210> SEQ ID NO 120
<211> LENGTH: 22
<212> TYPE: DNA
<213> ORGANISM: Artificial Sequence
<220> FEATURE:
<223> OTHER INFORMATION: PCR Primer

<400> SEQUENCE: 120
tggacacatg atggtaatttt tc                                          22

<210> SEQ ID NO 121
<211> LENGTH: 23
<212> TYPE: DNA
<213> ORGANISM: Artificial Sequence
<220> FEATURE:
<223> OTHER INFORMATION: PCR Primer

<400> SEQUENCE: 121
tgtgaagctc tgttagcaga tgg                                          23

<210> SEQ ID NO 122
<211> LENGTH: 21
<212> TYPE: DNA
<213> ORGANISM: Artificial Sequence
<220> FEATURE:
<223> OTHER INFORMATION: PCR Primer

<400> SEQUENCE: 122
tgaagctctg ttagcagatg g                                            21

<210> SEQ ID NO 123
<211> LENGTH: 22
<212> TYPE: DNA
<213> ORGANISM: Artificial Sequence
<220> FEATURE:
<223> OTHER INFORMATION: PCR Primer

<400> SEQUENCE: 123
tgcatcaggc atcttggcac ca                                          22

<210> SEQ ID NO 124
<211> LENGTH: 22
<212> TYPE: DNA
<213> ORGANISM: Artificial Sequence
<220> FEATURE:
<223> OTHER INFORMATION: PCR Primer

<400> SEQUENCE: 124
ttcatcaggc atcatggcac ca                                          22

<210> SEQ ID NO 125
<211> LENGTH: 20
<212> TYPE: DNA
<213> ORGANISM: Artificial Sequence
<220> FEATURE:
<223> OTHER INFORMATION: PCR Primer

<400> SEQUENCE: 125
tcaggcatca tggcaccaca                                             20

<210> SEQ ID NO 126
<211> LENGTH: 20
<212> TYPE: DNA
<213> ORGANISM: Artificial Sequence
<220> FEATURE:
<223> OTHER INFORMATION: PCR Primer

<400> SEQUENCE: 126
tcaggcttca tggcaccaca                                             20

<210> SEQ ID NO 127
<211> LENGTH: 30
<212> TYPE: DNA
<213> ORGANISM: Artificial Sequence
<220> FEATURE:
<223> OTHER INFORMATION: PCR Primer

<400> SEQUENCE: 127
tagccctgtc actgatctag agaaatacaa                                  30

<210> SEQ ID NO 128
<211> LENGTH: 32
<212> TYPE: DNA
<213> ORGANISM: Artificial Sequence
<220> FEATURE:
<223> OTHER INFORMATION: PCR Primer

<400> SEQUENCE: 128
tatggtgtga ggaatgtctt tgattggatg ca                               32

<210> SEQ ID NO 129
<211> LENGTH: 32
<212> TYPE: DNA
<213> ORGANISM: Artificial Sequence
<220> FEATURE:
<223> OTHER INFORMATION: PCR Primer

```
<220> FEATURE:
<221> NAME/KEY: misc_feature
<222> LOCATION: 9, 10, 11, 12
<223> OTHER INFORMATION: n = inosine

<400> SEQUENCE: 129
tatggtgtnn nnaatgtctt tgattggatg ca                                     32

<210> SEQ ID NO 130
<211> LENGTH: 27
<212> TYPE: DNA
<213> ORGANISM: Artificial Sequence
<220> FEATURE:
<223> OTHER INFORMATION: PCR Primer

<400> SEQUENCE: 130
tgtgcggaat gtctttgatt ggatgca                                            27

<210> SEQ ID NO 131
<211> LENGTH: 23
<212> TYPE: DNA
<213> ORGANISM: Artificial Sequence
<220> FEATURE:
<223> OTHER INFORMATION: PCR Primer

<400> SEQUENCE: 131
taatgtcttt gattggatgc att                                                23

<210> SEQ ID NO 132
<211> LENGTH: 31
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: 2, 3
<223> OTHER INFORMATION: n = inosine

<400> SEQUENCE: 132
tnncgttaca tgcatgtcag tgactattat a                                       31

<210> SEQ ID NO 133
<211> LENGTH: 20
<212> TYPE: DNA
<213> ORGANISM: Artificial Sequence
<220> FEATURE:
<223> OTHER INFORMATION: PCR Primer

<400> SEQUENCE: 133
tgttacatgc atgtcagtga                                                    20

<210> SEQ ID NO 134
<211> LENGTH: 28
<212> TYPE: DNA
<213> ORGANISM: Artificial Sequence
<220> FEATURE:
<223> OTHER INFORMATION: PCR Primer

<400> SEQUENCE: 134
tgccgcatgc atgtcagtga ttattata                                           28

<210> SEQ ID NO 135
<211> LENGTH: 24
<212> TYPE: DNA
<213> ORGANISM: Artificial Sequence
<220> FEATURE:
```

<223> OTHER INFORMATION: PCR Primer

<400> SEQUENCE: 135
tctgtggaca agtatatcat gtgc                                    24

<210> SEQ ID NO 136
<211> LENGTH: 30
<212> TYPE: DNA
<213> ORGANISM: Artificial Sequence
<220> FEATURE:
<223> OTHER INFORMATION: PCR Primer

<400> SEQUENCE: 136
tccgtggaca agtatatcat gtgctcaaat                              30

<210> SEQ ID NO 137
<211> LENGTH: 20
<212> TYPE: DNA
<213> ORGANISM: Artificial Sequence
<220> FEATURE:
<223> OTHER INFORMATION: PCR Primer

<400> SEQUENCE: 137
tggacaagta tatcatgtgc                                         20

<210> SEQ ID NO 138
<211> LENGTH: 26
<212> TYPE: DNA
<213> ORGANISM: Artificial Sequence
<220> FEATURE:
<223> OTHER INFORMATION: PCR Primer

<400> SEQUENCE: 138
tggacaagta tatcatgtgc tcaaat                                  26

<210> SEQ ID NO 139
<211> LENGTH: 18
<212> TYPE: DNA
<213> ORGANISM: Artificial Sequence
<220> FEATURE:
<223> OTHER INFORMATION: PCR Primer

<400> SEQUENCE: 139
tggagtggcc acagcaca                                           18

<210> SEQ ID NO 140
<211> LENGTH: 23
<212> TYPE: DNA
<213> ORGANISM: Artificial Sequence
<220> FEATURE:
<223> OTHER INFORMATION: PCR Primer

<400> SEQUENCE: 140
tcatcaaatc ctgttatgag tcg                                     23

<210> SEQ ID NO 141
<211> LENGTH: 21
<212> TYPE: DNA
<213> ORGANISM: Artificial Sequence
<220> FEATURE:
<223> OTHER INFORMATION: PCR Primer

<400> SEQUENCE: 141
tcctgtaatg agtcgctttg c                                       21

```
<210> SEQ ID NO 142
<211> LENGTH: 20
<212> TYPE: DNA
<213> ORGANISM: Artificial Sequence
<220> FEATURE:
<223> OTHER INFORMATION: PCR Primer

<400> SEQUENCE: 142
gagacaacgg aagctaatgc                                              20

<210> SEQ ID NO 143
<211> LENGTH: 20
<212> TYPE: DNA
<213> ORGANISM: Artificial Sequence
<220> FEATURE:
<223> OTHER INFORMATION: PCR Primer

<400> SEQUENCE: 143
ggtcagtttc tatcctttgc                                              20

<210> SEQ ID NO 144
<211> LENGTH: 26
<212> TYPE: DNA
<213> ORGANISM: Artificial Sequence
<220> FEATURE:
<223> OTHER INFORMATION: PCR Primer

<400> SEQUENCE: 144
tttctaccca aacttgtcgt tgggga                                       26

<210> SEQ ID NO 145
<211> LENGTH: 26
<212> TYPE: DNA
<213> ORGANISM: Artificial Sequence
<220> FEATURE:
<223> OTHER INFORMATION: PCR Primer

<400> SEQUENCE: 145
ttccttccca aactggtcgt tggaga                                       26

<210> SEQ ID NO 146
<211> LENGTH: 22
<212> TYPE: DNA
<213> ORGANISM: Artificial Sequence
<220> FEATURE:
<223> OTHER INFORMATION: PCR Primer

<400> SEQUENCE: 146
tcccaaaact tgtcgtcgga ga                                           22

<210> SEQ ID NO 147
<211> LENGTH: 21
<212> TYPE: DNA
<213> ORGANISM: Artificial Sequence
<220> FEATURE:
<223> OTHER INFORMATION: PCR Primer

<400> SEQUENCE: 147
tccgaaactg gtcgtgggag a                                            21

<210> SEQ ID NO 148
<211> LENGTH: 21
<212> TYPE: DNA
<213> ORGANISM: Artificial Sequence
<220> FEATURE:
<223> OTHER INFORMATION: PCR Primer
```

-continued

```
<400> SEQUENCE: 148
tccgaaactg gttgtcggag a                                              21

<210> SEQ ID NO 149
<211> LENGTH: 21
<212> TYPE: DNA
<213> ORGANISM: Artificial Sequence
<220> FEATURE:
<223> OTHER INFORMATION: PCR Primer

<400> SEQUENCE: 149
tccgaaactg gtagtgggag a                                              21

<210> SEQ ID NO 150
<211> LENGTH: 21
<212> TYPE: DNA
<213> ORGANISM: Artificial Sequence
<220> FEATURE:
<223> OTHER INFORMATION: PCR Primer

<400> SEQUENCE: 150
tccgaaactg gtcgtaggag a                                              21

<210> SEQ ID NO 151
<211> LENGTH: 28
<212> TYPE: DNA
<213> ORGANISM: Artificial Sequence
<220> FEATURE:
<223> OTHER INFORMATION: PCR Primer

<400> SEQUENCE: 151
ttcagaggca aattcaggta catgcaga                                       28

<210> SEQ ID NO 152
<211> LENGTH: 21
<212> TYPE: DNA
<213> ORGANISM: Artificial Sequence
<220> FEATURE:
<223> OTHER INFORMATION: PCR Primer

<400> SEQUENCE: 152
tggcatcatg accagccacc a                                              21

<210> SEQ ID NO 153
<211> LENGTH: 21
<212> TYPE: DNA
<213> ORGANISM: Artificial Sequence
<220> FEATURE:
<223> OTHER INFORMATION: PCR Primer

<400> SEQUENCE: 153
tggcatcatg gccggccacc a                                              21

<210> SEQ ID NO 154
<211> LENGTH: 20
<212> TYPE: DNA
<213> ORGANISM: Artificial Sequence
<220> FEATURE:
<223> OTHER INFORMATION: PCR Primer

<400> SEQUENCE: 154
tggtgccatg atgcctgatg                                                20

<210> SEQ ID NO 155
<211> LENGTH: 24
```

```
<212> TYPE: DNA
<213> ORGANISM: Artificial Sequence
<220> FEATURE:
<223> OTHER INFORMATION: PCR Primer

<400> SEQUENCE: 155
ttcagtgact accatcatat tgct                                            24

<210> SEQ ID NO 156
<211> LENGTH: 24
<212> TYPE: DNA
<213> ORGANISM: Artificial Sequence
<220> FEATURE:
<223> OTHER INFORMATION: PCR Primer

<400> SEQUENCE: 156
ttcagtgact accatcatgt tact                                            24

<210> SEQ ID NO 157
<211> LENGTH: 21
<212> TYPE: DNA
<213> ORGANISM: Artificial Sequence
<220> FEATURE:
<223> OTHER INFORMATION: PCR Primer

<400> SEQUENCE: 157
tcgttcagtg actaccatca t                                               21

<210> SEQ ID NO 158
<211> LENGTH: 34
<212> TYPE: DNA
<213> ORGANISM: Artificial Sequence
<220> FEATURE:
<223> OTHER INFORMATION: PCR Primer

<400> SEQUENCE: 158
tggcgagatt gtatttctct agatcagtga caaa                                 34

<210> SEQ ID NO 159
<211> LENGTH: 29
<212> TYPE: DNA
<213> ORGANISM: Artificial Sequence
<220> FEATURE:
<223> OTHER INFORMATION: PCR Primer

<400> SEQUENCE: 159
tcggcgaggt tgtatttctc tagatcagt                                       29

<210> SEQ ID NO 160
<211> LENGTH: 27
<212> TYPE: DNA
<213> ORGANISM: Artificial Sequence
<220> FEATURE:
<223> OTHER INFORMATION: PCR Primer

<400> SEQUENCE: 160
tgcaaggttg tatttctcta gatcagt                                         27

<210> SEQ ID NO 161
<211> LENGTH: 24
<212> TYPE: DNA
<213> ORGANISM: Artificial Sequence
<220> FEATURE:
<223> OTHER INFORMATION: PCR Primer

<400> SEQUENCE: 161
```
tagattgtat ttctctagat cagt                                             24

<210> SEQ ID NO 162
<211> LENGTH: 28
<212> TYPE: DNA
<213> ORGANISM: Artificial Sequence
<220> FEATURE:
<223> OTHER INFORMATION: PCR Primer

<400> SEQUENCE: 162
tgcggtaatc actgacatgc atataaca                                         28

<210> SEQ ID NO 163
<211> LENGTH: 28
<212> TYPE: DNA
<213> ORGANISM: Artificial Sequence
<220> FEATURE:
<223> OTHER INFORMATION: PCR Primer

<400> SEQUENCE: 163
tgcaaaaatc actgacatgc atgtaaca                                         28

<210> SEQ ID NO 164
<211> LENGTH: 31
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: 9, 10, 11
<223> OTHER INFORMATION: n = inosine

<400> SEQUENCE: 164
tgctataann ntcactgaca tgcatgtaac a                                     31

<210> SEQ ID NO 165
<211> LENGTH: 28
<212> TYPE: DNA
<213> ORGANISM: Artificial Sequence
<220> FEATURE:
<223> OTHER INFORMATION: PCR Primer

<400> SEQUENCE: 165
tatgccaatc actgacatgc atgtaaca                                         28

<210> SEQ ID NO 166
<211> LENGTH: 21
<212> TYPE: DNA
<213> ORGANISM: Artificial Sequence
<220> FEATURE:
<223> OTHER INFORMATION: PCR Primer

<400> SEQUENCE: 166
ttcactgaca tgcatataac a                                                21

<210> SEQ ID NO 167
<211> LENGTH: 25
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: 5, 14
<223> OTHER INFORMATION: n = inosine

<400> SEQUENCE: 167

```
tttgngcaca gganatgctt gtcca                                    25

<210> SEQ ID NO 168
<211> LENGTH: 20
<212> TYPE: DNA
<213> ORGANISM: Artificial Sequence
<220> FEATURE:
<223> OTHER INFORMATION: PCR Primer

<400> SEQUENCE: 168
tgtagtccct ctatccctcc                                          20

<210> SEQ ID NO 169
<211> LENGTH: 25
<212> TYPE: DNA
<213> ORGANISM: Artificial Sequence
<220> FEATURE:
<223> OTHER INFORMATION: PCR Primer

<400> SEQUENCE: 169
tttgagcaca ggatatgctt gtcca                                    25

<210> SEQ ID NO 170
<211> LENGTH: 22
<212> TYPE: DNA
<213> ORGANISM: Artificial Sequence
<220> FEATURE:
<223> OTHER INFORMATION: PCR Primer

<400> SEQUENCE: 170
tacactgatt gtcacccatg ac                                       22

<210> SEQ ID NO 171
<211> LENGTH: 22
<212> TYPE: DNA
<213> ORGANISM: Artificial Sequence
<220> FEATURE:
<223> OTHER INFORMATION: PCR Primer

<400> SEQUENCE: 171
tacactgatt gtcacccatc ac                                       22

<210> SEQ ID NO 172
<211> LENGTH: 29
<212> TYPE: DNA
<213> ORGANISM: Artificial Sequence
<220> FEATURE:
<223> OTHER INFORMATION: PCR Primer

<400> SEQUENCE: 172
tctgtgatac actgattgtc acccatgac                                29

<210> SEQ ID NO 173
<211> LENGTH: 19
<212> TYPE: DNA
<213> ORGANISM: Artificial Sequence
<220> FEATURE:
<223> OTHER INFORMATION: PCR Primer

<400> SEQUENCE: 173
ttacactgat tgtcaccca                                           19

<210> SEQ ID NO 174
<211> LENGTH: 26
<212> TYPE: DNA
```

```
<213> ORGANISM: Artificial Sequence
<220> FEATURE:
<223> OTHER INFORMATION: PCR Primer

<400> SEQUENCE: 174
tctgtgatac actgattgtc acccat                                              26

<210> SEQ ID NO 175
<211> LENGTH: 22
<212> TYPE: DNA
<213> ORGANISM: Artificial Sequence
<220> FEATURE:
<223> OTHER INFORMATION: PCR Primer

<400> SEQUENCE: 175
tctgttctcc aacattgact cc                                                  22

<210> SEQ ID NO 176
<211> LENGTH: 21
<212> TYPE: DNA
<213> ORGANISM: Artificial Sequence
<220> FEATURE:
<223> OTHER INFORMATION: PCR Primer

<400> SEQUENCE: 176
ttgatactgt tctccaacat t                                                   21

<210> SEQ ID NO 177
<211> LENGTH: 17
<212> TYPE: DNA
<213> ORGANISM: Artificial Sequence
<220> FEATURE:
<223> OTHER INFORMATION: PCR Primer

<400> SEQUENCE: 177
tccttcaagg tatccta                                                        17

<210> SEQ ID NO 178
<211> LENGTH: 20
<212> TYPE: DNA
<213> ORGANISM: Artificial Sequence
<220> FEATURE:
<223> OTHER INFORMATION: PCR Primer

<400> SEQUENCE: 178
tgttccttca agatatccta                                                     20

<210> SEQ ID NO 179
<211> LENGTH: 20
<212> TYPE: DNA
<213> ORGANISM: Artificial Sequence
<220> FEATURE:
<223> OTHER INFORMATION: PCR Primer

<400> SEQUENCE: 179
aacggaagat caccatcatg                                                     20

<210> SEQ ID NO 180
<211> LENGTH: 20
<212> TYPE: DNA
<213> ORGANISM: Artificial Sequence
<220> FEATURE:
<223> OTHER INFORMATION: PCR Primer

<400> SEQUENCE: 180
catgtgtcca actgattgcc                                                     20
```

```
<210> SEQ ID NO 181
<211> LENGTH: 26
<212> TYPE: DNA
<213> ORGANISM: Artificial Sequence
<220> FEATURE:
<223> OTHER INFORMATION: PCR Primer

<400> SEQUENCE: 181
ttcaaacgga agatcaccat catgtg                                              26

<210> SEQ ID NO 182
<211> LENGTH: 27
<212> TYPE: DNA
<213> ORGANISM: Artificial Sequence
<220> FEATURE:
<223> OTHER INFORMATION: PCR Primer

<400> SEQUENCE: 182
taggcggaaa attaccatca tgtgtcc                                             27

<210> SEQ ID NO 183
<211> LENGTH: 26
<212> TYPE: DNA
<213> ORGANISM: Artificial Sequence
<220> FEATURE:
<223> OTHER INFORMATION: PCR Primer

<400> SEQUENCE: 183
tgcaaccgga aaattaccat catgtg                                              26

<210> SEQ ID NO 184
<211> LENGTH: 23
<212> TYPE: DNA
<213> ORGANISM: Artificial Sequence
<220> FEATURE:
<223> OTHER INFORMATION: PCR Primer

<400> SEQUENCE: 184
ttcatgtggc ctgtggtaag cca                                                 23

<210> SEQ ID NO 185
<211> LENGTH: 22
<212> TYPE: DNA
<213> ORGANISM: Artificial Sequence
<220> FEATURE:
<223> OTHER INFORMATION: PCR Primer

<400> SEQUENCE: 185
tgaaaattac cttcatgtgt cc                                                  22

<210> SEQ ID NO 186
<211> LENGTH: 22
<212> TYPE: DNA
<213> ORGANISM: Artificial Sequence
<220> FEATURE:
<223> OTHER INFORMATION: PCR Primer

<400> SEQUENCE: 186
tgaaaattac tttcatgtgt cc                                                  22

<210> SEQ ID NO 187
<211> LENGTH: 22
<212> TYPE: DNA
<213> ORGANISM: Artificial Sequence
<220> FEATURE:
```

```
<223> OTHER INFORMATION: PCR Primer

<400> SEQUENCE: 187
tcatgtgtcc tactgattgc ca                                              22

<210> SEQ ID NO 188
<211> LENGTH: 22
<212> TYPE: DNA
<213> ORGANISM: Artificial Sequence
<220> FEATURE:
<223> OTHER INFORMATION: PCR Primer

<400> SEQUENCE: 188
tgaaaattac catcatgtgt cc                                              22

<210> SEQ ID NO 189
<211> LENGTH: 27
<212> TYPE: DNA
<213> ORGANISM: Artificial Sequence
<220> FEATURE:
<223> OTHER INFORMATION: PCR Primer

<400> SEQUENCE: 189
taccatcatg tgtcctactg attgcca                                         27

<210> SEQ ID NO 190
<211> LENGTH: 21
<212> TYPE: DNA
<213> ORGANISM: Artificial Sequence
<220> FEATURE:
<223> OTHER INFORMATION: PCR Primer

<400> SEQUENCE: 190
tacagccaca tggttccaat a                                               21

<210> SEQ ID NO 191
<211> LENGTH: 22
<212> TYPE: DNA
<213> ORGANISM: Artificial Sequence
<220> FEATURE:
<223> OTHER INFORMATION: PCR Primer

<400> SEQUENCE: 191
tggagaaata tagagagatt ca                                              22

<210> SEQ ID NO 192
<211> LENGTH: 20
<212> TYPE: DNA
<213> ORGANISM: Artificial Sequence
<220> FEATURE:
<223> OTHER INFORMATION: PCR Primer

<400> SEQUENCE: 192
tcaactgtcg gtgcaagtgg                                                 20

<210> SEQ ID NO 193
<211> LENGTH: 21
<212> TYPE: DNA
<213> ORGANISM: Artificial Sequence
<220> FEATURE:
<223> OTHER INFORMATION: PCR Primer

<400> SEQUENCE: 193
taaggcactc agatgggcat c                                               21
```

```
<210> SEQ ID NO 194
<211> LENGTH: 22
<212> TYPE: DNA
<213> ORGANISM: Artificial Sequence
<220> FEATURE:
<223> OTHER INFORMATION: PCR Primer

<400> SEQUENCE: 194
tcatgtatgt tagtgctgat gc                                              22

<210> SEQ ID NO 195
<211> LENGTH: 21
<212> TYPE: DNA
<213> ORGANISM: Artificial Sequence
<220> FEATURE:
<223> OTHER INFORMATION: PCR Primer

<400> SEQUENCE: 195
tgctcatcat tcagatgatg c                                               21

<210> SEQ ID NO 196
<211> LENGTH: 22
<212> TYPE: DNA
<213> ORGANISM: Artificial Sequence
<220> FEATURE:
<223> OTHER INFORMATION: PCR Primer

<400> SEQUENCE: 196
tagatgatgg aactgactgg tt                                              22

<210> SEQ ID NO 197
<211> LENGTH: 23
<212> TYPE: DNA
<213> ORGANISM: Artificial Sequence
<220> FEATURE:
<223> OTHER INFORMATION: PCR Primer

<400> SEQUENCE: 197
tgagatgtgg aaaagcatgt tta                                             23

<210> SEQ ID NO 198
<211> LENGTH: 23
<212> TYPE: DNA
<213> ORGANISM: Artificial Sequence
<220> FEATURE:
<223> OTHER INFORMATION: PCR Primer

<400> SEQUENCE: 198
tattgtaaca gctatgacca tgc                                             23

<210> SEQ ID NO 199
<211> LENGTH: 21
<212> TYPE: DNA
<213> ORGANISM: Artificial Sequence
<220> FEATURE:
<223> OTHER INFORMATION: PCR Primer

<400> SEQUENCE: 199
tgctatgaca atgcagtcac c                                               21

<210> SEQ ID NO 200
<211> LENGTH: 20
<212> TYPE: DNA
<213> ORGANISM: Artificial Sequence
<220> FEATURE:
<223> OTHER INFORMATION: PCR Primer
```

<400> SEQUENCE: 200
tgtgggatga gatttaaaac                                                    20

<210> SEQ ID NO 201
<211> LENGTH: 21
<212> TYPE: DNA
<213> ORGANISM: Artificial Sequence
<220> FEATURE:
<223> OTHER INFORMATION: PCR Primer

<400> SEQUENCE: 201
tatgcggaat accatcatgg c                                                  21

<210> SEQ ID NO 202
<211> LENGTH: 21
<212> TYPE: DNA
<213> ORGANISM: Artificial Sequence
<220> FEATURE:
<223> OTHER INFORMATION: PCR Primer

<400> SEQUENCE: 202
tacacaatcg atgggaatac a                                                  21

<210> SEQ ID NO 203
<211> LENGTH: 19
<212> TYPE: DNA
<213> ORGANISM: Artificial Sequence
<220> FEATURE:
<223> OTHER INFORMATION: PCR Primer

<400> SEQUENCE: 203
tggctctaca tgcaccctg                                                     19

<210> SEQ ID NO 204
<211> LENGTH: 18
<212> TYPE: DNA
<213> ORGANISM: Artificial Sequence
<220> FEATURE:
<223> OTHER INFORMATION: PCR Primer

<400> SEQUENCE: 204
tacgtgccgc tttcgccc                                                      18

<210> SEQ ID NO 205
<211> LENGTH: 18
<212> TYPE: DNA
<213> ORGANISM: Artificial Sequence
<220> FEATURE:
<223> OTHER INFORMATION: PCR Primer

<400> SEQUENCE: 205
tcaaagacac acgtgccg                                                      18

<210> SEQ ID NO 206
<211> LENGTH: 19
<212> TYPE: DNA
<213> ORGANISM: Artificial Sequence
<220> FEATURE:
<223> OTHER INFORMATION: PCR Primer

<400> SEQUENCE: 206
tggctgccct aaagtggag                                                     19

<210> SEQ ID NO 207
<211> LENGTH: 18

```
<212> TYPE: DNA
<213> ORGANISM: Artificial Sequence
<220> FEATURE:
<223> OTHER INFORMATION: PCR Primer

<400> SEQUENCE: 207
tgagtacaaa gtccctgg                                                      18

<210> SEQ ID NO 208
<211> LENGTH: 21
<212> TYPE: DNA
<213> ORGANISM: Artificial Sequence
<220> FEATURE:
<223> OTHER INFORMATION: PCR Primer

<400> SEQUENCE: 208
tgacatgatt aggagcagga a                                                  21

<210> SEQ ID NO 209
<211> LENGTH: 21
<212> TYPE: DNA
<213> ORGANISM: Artificial Sequence
<220> FEATURE:
<223> OTHER INFORMATION: PCR Primer

<400> SEQUENCE: 209
tggtctgaga gagatctatg t                                                  21

<210> SEQ ID NO 210
<211> LENGTH: 22
<212> TYPE: DNA
<213> ORGANISM: Artificial Sequence
<220> FEATURE:
<223> OTHER INFORMATION: PCR Primer

<400> SEQUENCE: 210
tgacgattcc tgaaacacat gg                                                 22

<210> SEQ ID NO 211
<211> LENGTH: 18
<212> TYPE: DNA
<213> ORGANISM: Artificial Sequence
<220> FEATURE:
<223> OTHER INFORMATION: PCR Primer

<400> SEQUENCE: 211
tgcgacatca gatgatgc                                                      18

<210> SEQ ID NO 212
<211> LENGTH: 21
<212> TYPE: DNA
<213> ORGANISM: Artificial Sequence
<220> FEATURE:
<223> OTHER INFORMATION: PCR Primer

<400> SEQUENCE: 212
tcagatgatg ctagcaagtg g                                                  21

<210> SEQ ID NO 213
<211> LENGTH: 18
<212> TYPE: DNA
<213> ORGANISM: Artificial Sequence
<220> FEATURE:
<223> OTHER INFORMATION: PCR Primer

<400> SEQUENCE: 213
```

| tactgggatg atgcaggg | 18 |

<210> SEQ ID NO 214
<211> LENGTH: 16
<212> TYPE: DNA
<213> ORGANISM: Artificial Sequence
<220> FEATURE:
<223> OTHER INFORMATION: PCR Primer

<400> SEQUENCE: 214

| ttcacaccct gcacca | 16 |

<210> SEQ ID NO 215
<211> LENGTH: 16
<212> TYPE: DNA
<213> ORGANISM: Artificial Sequence
<220> FEATURE:
<223> OTHER INFORMATION: PCR Primer

<400> SEQUENCE: 215

| tgcaaggctc agatga | 16 |

<210> SEQ ID NO 216
<211> LENGTH: 20
<212> TYPE: DNA
<213> ORGANISM: Artificial Sequence
<220> FEATURE:
<223> OTHER INFORMATION: PCR Primer

<400> SEQUENCE: 216

| tgaacatacc agagaactgg | 20 |

<210> SEQ ID NO 217
<211> LENGTH: 23
<212> TYPE: DNA
<213> ORGANISM: Artificial Sequence
<220> FEATURE:
<223> OTHER INFORMATION: PCR Primer

<400> SEQUENCE: 217

| tcaaagattg cacatagttt cat | 23 |

<210> SEQ ID NO 218
<211> LENGTH: 20
<212> TYPE: DNA
<213> ORGANISM: Artificial Sequence
<220> FEATURE:
<223> OTHER INFORMATION: PCR Primer

<400> SEQUENCE: 218

| tgaccagtca tgctttatca | 20 |

<210> SEQ ID NO 219
<211> LENGTH: 20
<212> TYPE: DNA
<213> ORGANISM: Artificial Sequence
<220> FEATURE:
<223> OTHER INFORMATION: PCR Primer

<400> SEQUENCE: 219

| ttcccatgca gacccttttc | 20 |

<210> SEQ ID NO 220
<211> LENGTH: 22
<212> TYPE: DNA
<213> ORGANISM: Artificial Sequence

```
<220> FEATURE:
<223> OTHER INFORMATION: PCR Primer

<400> SEQUENCE: 220
tggcatctgc actaacatac at                                            22

<210> SEQ ID NO 221
<211> LENGTH: 21
<212> TYPE: DNA
<213> ORGANISM: Artificial Sequence
<220> FEATURE:
<223> OTHER INFORMATION: PCR Primer

<400> SEQUENCE: 221
tgaattatct cctggtgacc a                                             21

<210> SEQ ID NO 222
<211> LENGTH: 22
<212> TYPE: DNA
<213> ORGANISM: Artificial Sequence
<220> FEATURE:
<223> OTHER INFORMATION: PCR Primer

<400> SEQUENCE: 222
tgctgaatta tctcctggtg ac                                            22

<210> SEQ ID NO 223
<211> LENGTH: 21
<212> TYPE: DNA
<213> ORGANISM: Artificial Sequence
<220> FEATURE:
<223> OTHER INFORMATION: PCR Primer

<400> SEQUENCE: 223
taaccaatca gttccatcat c                                             21

<210> SEQ ID NO 224
<211> LENGTH: 20
<212> TYPE: DNA
<213> ORGANISM: Artificial Sequence
<220> FEATURE:
<223> OTHER INFORMATION: PCR Primer

<400> SEQUENCE: 224
ttaaacatgc tcttccacat                                               20

<210> SEQ ID NO 225
<211> LENGTH: 24
<212> TYPE: DNA
<213> ORGANISM: Artificial Sequence
<220> FEATURE:
<223> OTHER INFORMATION: PCR Primer

<400> SEQUENCE: 225
tagattaaac atgcttttcc acat                                          24

<210> SEQ ID NO 226
<211> LENGTH: 24
<212> TYPE: DNA
<213> ORGANISM: Artificial Sequence
<220> FEATURE:
<223> OTHER INFORMATION: PCR Primer

<400> SEQUENCE: 226
tattgataca gcacaacctt caaa                                          24
```

<210> SEQ ID NO 227
<211> LENGTH: 21
<212> TYPE: DNA
<213> ORGANISM: Artificial Sequence
<220> FEATURE:
<223> OTHER INFORMATION: PCR Primer

<400> SEQUENCE: 227
ttcatgtgtt gctttgcttg c                                          21

<210> SEQ ID NO 228
<211> LENGTH: 21
<212> TYPE: DNA
<213> ORGANISM: Artificial Sequence
<220> FEATURE:
<223> OTHER INFORMATION: PCR Primer

<400> SEQUENCE: 228
tacctccctg aatgttaccc a                                          21

<210> SEQ ID NO 229
<211> LENGTH: 20
<212> TYPE: DNA
<213> ORGANISM: Artificial Sequence
<220> FEATURE:
<223> OTHER INFORMATION: PCR Primer

<400> SEQUENCE: 229
ttaggctttc cccattcaaa                                            20

<210> SEQ ID NO 230
<211> LENGTH: 20
<212> TYPE: DNA
<213> ORGANISM: Artificial Sequence
<220> FEATURE:
<223> OTHER INFORMATION: PCR Primer

<400> SEQUENCE: 230
tggtccagtt gtattcccat                                            20

<210> SEQ ID NO 231
<211> LENGTH: 20
<212> TYPE: DNA
<213> ORGANISM: Artificial Sequence
<220> FEATURE:
<223> OTHER INFORMATION: PCR Primer

<400> SEQUENCE: 231
tcaggatcca tatcatcacc                                            20

<210> SEQ ID NO 232
<211> LENGTH: 21
<212> TYPE: DNA
<213> ORGANISM: Artificial Sequence
<220> FEATURE:
<223> OTHER INFORMATION: PCR Primer

<400> SEQUENCE: 232
tacagggata gtcccaaagc a                                          21

<210> SEQ ID NO 233
<211> LENGTH: 23
<212> TYPE: DNA
<213> ORGANISM: Artificial Sequence
<220> FEATURE:
<223> OTHER INFORMATION: PCR Primer

<400> SEQUENCE: 233
tcacagaagg aggcggagtt tgt                                    23

<210> SEQ ID NO 234
<211> LENGTH: 21
<212> TYPE: DNA
<213> ORGANISM: Artificial Sequence
<220> FEATURE:
<223> OTHER INFORMATION: PCR Primer

<400> SEQUENCE: 234
tgcctcgatt tggttctcca t                                      21

<210> SEQ ID NO 235
<211> LENGTH: 20
<212> TYPE: DNA
<213> ORGANISM: Artificial Sequence
<220> FEATURE:
<223> OTHER INFORMATION: PCR Primer

<400> SEQUENCE: 235
tcgccaggga ctttgtactc                                        20

<210> SEQ ID NO 236
<211> LENGTH: 20
<212> TYPE: DNA
<213> ORGANISM: Artificial Sequence
<220> FEATURE:
<223> OTHER INFORMATION: PCR Primer

<400> SEQUENCE: 236
ttcctgctcc taatcatgtc                                        20

<210> SEQ ID NO 237
<211> LENGTH: 17
<212> TYPE: DNA
<213> ORGANISM: Artificial Sequence
<220> FEATURE:
<223> OTHER INFORMATION: PCR Primer

<400> SEQUENCE: 237
tcccaaggag ggttgaa                                           17

<210> SEQ ID NO 238
<211> LENGTH: 19
<212> TYPE: DNA
<213> ORGANISM: Artificial Sequence
<220> FEATURE:
<223> OTHER INFORMATION: PCR Primer

<400> SEQUENCE: 238
tgccgtgtgt ttcaggaat                                         19

<210> SEQ ID NO 239
<211> LENGTH: 22
<212> TYPE: DNA
<213> ORGANISM: Artificial Sequence
<220> FEATURE:
<223> OTHER INFORMATION: PCR Primer

<400> SEQUENCE: 239
tccacttgct agcatcatct ga                                     22

<210> SEQ ID NO 240

```
<211> LENGTH: 19
<212> TYPE: DNA
<213> ORGANISM: Artificial Sequence
<220> FEATURE:
<223> OTHER INFORMATION: PCR Primer

<400> SEQUENCE: 240
tcgagcatcc tctaatgat                                                   19

<210> SEQ ID NO 241
<211> LENGTH: 23
<212> TYPE: DNA
<213> ORGANISM: Artificial Sequence
<220> FEATURE:
<223> OTHER INFORMATION: PCR Primer

<400> SEQUENCE: 241
tacatcgagc atcctctaat gat                                              23

<210> SEQ ID NO 242
<211> LENGTH: 18
<212> TYPE: DNA
<213> ORGANISM: Artificial Sequence
<220> FEATURE:
<223> OTHER INFORMATION: PCR Primer

<400> SEQUENCE: 242
tatcatctga gccctgca                                                    18

<210> SEQ ID NO 243
<211> LENGTH: 17
<212> TYPE: DNA
<213> ORGANISM: Artificial Sequence
<220> FEATURE:
<223> OTHER INFORMATION: PCR Primer

<400> SEQUENCE: 243
tgatgggtaa atgccaa                                                     17

<210> SEQ ID NO 244
<211> LENGTH: 21
<212> TYPE: DNA
<213> ORGANISM: Artificial Sequence
<220> FEATURE:
<223> OTHER INFORMATION: PCR Primer

<400> SEQUENCE: 244
tcctggacta tggaccttct c                                                21

<210> SEQ ID NO 245
<211> LENGTH: 19
<212> TYPE: DNA
<213> ORGANISM: Artificial Sequence
<220> FEATURE:
<223> OTHER INFORMATION: PCR Primer

<400> SEQUENCE: 245
ttcttgacat gggtcaggg                                                   19

<210> SEQ ID NO 246
<211> LENGTH: 19
<212> TYPE: DNA
<213> ORGANISM: Artificial Sequence
<220> FEATURE:
<223> OTHER INFORMATION: PCR Primer

<400> SEQUENCE: 246
```

```
ttcttgatat gggccaggg                                           19

<210> SEQ ID NO 247
<211> LENGTH: 16
<212> TYPE: DNA
<213> ORGANISM: Artificial Sequence
<220> FEATURE:
<223> OTHER INFORMATION: PCR Primer

<400> SEQUENCE: 247
ttgacatggg tcaggg                                              16

<210> SEQ ID NO 248
<211> LENGTH: 16
<212> TYPE: DNA
<213> ORGANISM: Artificial Sequence
<220> FEATURE:
<223> OTHER INFORMATION: PCR Primer

<400> SEQUENCE: 248
ttgatatggg ccaggg                                              16

<210> SEQ ID NO 249
<211> LENGTH: 20
<212> TYPE: DNA
<213> ORGANISM: Artificial Sequence
<220> FEATURE:
<223> OTHER INFORMATION: PCR Primer

<400> SEQUENCE: 249
tcttacacct caagtgatga                                          20

<210> SEQ ID NO 250
<211> LENGTH: 23
<212> TYPE: DNA
<213> ORGANISM: Artificial Sequence
<220> FEATURE:
<223> OTHER INFORMATION: PCR Primer

<400> SEQUENCE: 250
tacacttcta gtgatgatca gat                                      23

<210> SEQ ID NO 251
<211> LENGTH: 20
<212> TYPE: DNA
<213> ORGANISM: Artificial Sequence
<220> FEATURE:
<223> OTHER INFORMATION: PCR Primer

<400> SEQUENCE: 251
tttgtcagcc ctaaaagtgt                                          20

<210> SEQ ID NO 252
<211> LENGTH: 18
<212> TYPE: DNA
<213> ORGANISM: Artificial Sequence
<220> FEATURE:
<223> OTHER INFORMATION: PCR Primer

<400> SEQUENCE: 252
taacaaatca gcattcca                                            18

<210> SEQ ID NO 253
<211> LENGTH: 21
<212> TYPE: DNA
```

```
<213> ORGANISM: Artificial Sequence
<220> FEATURE:
<223> OTHER INFORMATION: PCR Primer

<400> SEQUENCE: 253
tggtgttgtg agagtctggg a                                              21

<210> SEQ ID NO 254
<211> LENGTH: 21
<212> TYPE: DNA
<213> ORGANISM: Artificial Sequence
<220> FEATURE:
<223> OTHER INFORMATION: PCR Primer

<400> SEQUENCE: 254
tggtgttgtg aaggtctggg a                                              21

<210> SEQ ID NO 255
<211> LENGTH: 17
<212> TYPE: DNA
<213> ORGANISM: Artificial Sequence
<220> FEATURE:
<223> OTHER INFORMATION: PCR Primer

<400> SEQUENCE: 255
tcaggtgaag gttggcc                                                   17

<210> SEQ ID NO 256
<211> LENGTH: 17
<212> TYPE: DNA
<213> ORGANISM: Artificial Sequence
<220> FEATURE:
<223> OTHER INFORMATION: PCR Primer

<400> SEQUENCE: 256
tcaggtgatg gatggcc                                                   17

<210> SEQ ID NO 257
<211> LENGTH: 22
<212> TYPE: DNA
<213> ORGANISM: Artificial Sequence
<220> FEATURE:
<223> OTHER INFORMATION: PCR Primer

<400> SEQUENCE: 257
tctggtcatc actagaggta ta                                             22

<210> SEQ ID NO 258
<211> LENGTH: 22
<212> TYPE: DNA
<213> ORGANISM: Artificial Sequence
<220> FEATURE:
<223> OTHER INFORMATION: PCR Primer

<400> SEQUENCE: 258
tctggtcatc actagaagtg ta                                             22

<210> SEQ ID NO 259
<211> LENGTH: 18
<212> TYPE: DNA
<213> ORGANISM: Artificial Sequence
<220> FEATURE:
<223> OTHER INFORMATION: PCR Primer

<400> SEQUENCE: 259
tgagatctgg tcatcact                                                  18
```

-continued

<210> SEQ ID NO 260
<211> LENGTH: 20
<212> TYPE: DNA
<213> ORGANISM: Artificial Sequence
<220> FEATURE:
<223> OTHER INFORMATION: PCR Primer

<400> SEQUENCE: 260
ttagggctga caaacttgtt                                              20

<210> SEQ ID NO 261
<211> LENGTH: 20
<212> TYPE: DNA
<213> ORGANISM: Artificial Sequence
<220> FEATURE:
<223> OTHER INFORMATION: PCR Primer

<400> SEQUENCE: 261
tctttgcact ttacattgtg                                              20

<210> SEQ ID NO 262
<211> LENGTH: 19
<212> TYPE: DNA
<213> ORGANISM: Artificial Sequence
<220> FEATURE:
<223> OTHER INFORMATION: PCR Primer

<400> SEQUENCE: 262
tgtgtagcgc tgcagcaac                                               19

<210> SEQ ID NO 263
<211> LENGTH: 17
<212> TYPE: DNA
<213> ORGANISM: Artificial Sequence
<220> FEATURE:
<223> OTHER INFORMATION: PCR Primer

<400> SEQUENCE: 263
tcctataaag ccagatg                                                 17

<210> SEQ ID NO 264
<211> LENGTH: 21
<212> TYPE: DNA
<213> ORGANISM: Artificial Sequence
<220> FEATURE:
<223> OTHER INFORMATION: PCR Primer

<400> SEQUENCE: 264
tggcattgac ccaaactggt t                                            21

<210> SEQ ID NO 265
<211> LENGTH: 21
<212> TYPE: DNA
<213> ORGANISM: Artificial Sequence
<220> FEATURE:
<223> OTHER INFORMATION: PCR Primer

<400> SEQUENCE: 265
tggcattgac ccgaactgat t                                            21

<210> SEQ ID NO 266
<211> LENGTH: 21
<212> TYPE: DNA
<213> ORGANISM: Artificial Sequence
<220> FEATURE:

<223> OTHER INFORMATION: PCR Primer

<400> SEQUENCE: 266
tgtgttgtcc caagcccttc c                                              21

<210> SEQ ID NO 267
<211> LENGTH: 21
<212> TYPE: DNA
<213> ORGANISM: Artificial Sequence
<220> FEATURE:
<223> OTHER INFORMATION: PCR Primer

<400> SEQUENCE: 267
tgtgttgtcc caagctctcc c                                              21

<210> SEQ ID NO 268
<211> LENGTH: 18959
<212> TYPE: DNA
<213> ORGANISM: Ebola Zaire virus
<220> FEATURE:

<400> SEQUENCE: 268

| | |
|---|---|
| cggacacaca aaagaaaga agaatttta ggatcttttg tgtgcgaata actatgagga | 60 |
| agattaataa ttttcctctc attgaaattt atatcggaat ttaaattgaa attgttactg | 120 |
| taatcacacc tggtttgttt cagagccaca tcacaaagat agagaacaac ctaggtctcc | 180 |
| gaagggagca agggcatcag tgtgctcagt tgaaaatccc ttgtcaacac ctaggtctta | 240 |
| tcacatcaca agttccacct cagactctgc agggtgatcc aacaacctta atagaaacat | 300 |
| tattgttaaa ggacagcatt agttcacagt caaacaagca agattgagaa ttaaccttgg | 360 |
| ttttgaactt gaacacttag gggattgaag attcaacaac cctaaagctt ggggtaaaac | 420 |
| attggaaata gttaaaagac aaattgctcg gaatcacaaa attccgagta tggattctcg | 480 |
| tcctcagaaa atctggatgg cgccgagtct cactgaatct gacatggatt accacaagat | 540 |
| cttgacagca ggtctgtccg ttcaacaggg gattgttcgg caaagagtca tcccagtgta | 600 |
| tcaagtaaac aatcttgaag aaatttgcca acttatcata caggcctttg aagcaggtgt | 660 |
| tgattttcaa gagagtgcgg acagtttcct tctcatgctt tgtcttcatc atgcgtacca | 720 |
| gggagattac aaacttttct tggaaagtgg cgcagtcaag tatttggaag ggcacgggtt | 780 |
| ccgttttgaa gtcaagaagc gtgatggagt gaagcgcctt gaggaattgc tgccagcagt | 840 |
| atctagtgga aaaacatta agagaacact tgctgccatg ccggaagagg agacaactga | 900 |
| agctaatgcc ggtcagtttc tctcctttgc aagtctattc cttccgaaat tggtagtagg | 960 |
| agaaaaggct tgccttgaga aggttcaaag gcaaattcaa gtacatgcag agcaaggact | 1020 |
| gatacaatat cccaacagctt ggcaatcagt aggacacatg atggtgattt ccgtttgat | 1080 |
| gcgaacaaat tttctgatca aatttctcct aatacaccaa gggatgcaca tggttgccgg | 1140 |
| gcatgatgcc aacgatgctg tgatttcaaa ttcagtggct caagctcgtt tttcaggctt | 1200 |
| attgattgtc aaaacagtac ttgatcatat cctacaaaag acagaacgag gagttcgtct | 1260 |
| ccatcctctt gcaaggaccg ccaaggtaaa aaatgaggtg aactccttta aggctgcact | 1320 |
| cagctccctg gccaagcatg gagagtatgc tcctttcgcc cgactttga acctttctgg | 1380 |
| agtaaataat cttgagcatg gtcttttccc tcaactatcg gcaattgcac tcggagtcgc | 1440 |
| cacagcacac gggagtaccc tcgcaggagt aaatgttgga gaacagtatc aacaactcag | 1500 |
| agaggctgcc actgaggctg agaagcaact ccaacaatat gcagagtctc gcgaacttga | 1560 |

-continued

```
ccatcttgga cttgatgatc aggaaaagaa aattcttatg aacttccatc agaaaagaa   1620 cgaaatcagc ttccagcaaa caaacgctat ggtaactcta agaaaagagc gcctggccaa   1680
gctgacagaa gctatcactg ctgcgtcact gcccaaaaca agtggacatt acgatgatga   1740
tgacgacatt ccctttccag gacccatcaa tgatgacgac aatcctggcc atcaagatga   1800
tgatccgact gactcacagg atacgaccat tcccgatgtg gtggttgatc ccgatgatgg   1860
aagctacggc gaataccaga gttactcgga aaacggcatg aatgcaccag atgacttggt   1920
cctattcgat ctagacgagg acgacgagga cactaagcca gtgcctaata gatcgaccaa   1980
gggtggacaa cagaagaaca gtcaaaaggg ccagcatata gagggcagac agacacaatc   2040
caggccaatt caaaatgtcc caggccctca cagaacaatc caccacgcca gtgcgccact   2100
cacggacaat gacagaagaa atgaaccctc cggctcaacc agccctcgca tgctgacacc   2160
aattaacgaa gaggcagacc cactggacga tgccgacgac gagacgtcta gccttccgcc   2220
cttggagtca gatgatgaag agcaggacag ggacggaact tccaaccgca cacccactgt   2280
cgccccaccg gctcccgtat acagagatca ctctgaaaag aaagaactcc gcaagacga   2340 gcaacaagat caggaccaca ctcaagaggc caggaaccag gacagtgaca cacccagtc   2400 agaacactct tttgaggaga tgtatcgcca cattctaaga tcacaggggc catttgatgc   2460
tgttttgtat tatcatatga tgaaggatga gcctgtagtt ttcagtacca gtgatggcaa   2520
agagtacacg tatccagact cccttgaaga ggaatatcca ccatggctca ctgaaaaga   2580 ggctatgaat gaagagaata gatttgttac attggatggt caacaatttt attggccggt   2640
gatgaatcac aagaataaat tcatggcaat cctgcaacat catcagtgaa tgagcatgga   2700
acaatgggat gattcaaccg acaaatagct aacattaagt agtcaaggaa cgaaaacagg   2760
aagaattttt gatgtctaag gtgtgaatta ttatcacaat aaaagtgatt cttatttttg   2820
aatttaaagc tagcttatta ttactagccg ttttttcaaag ttcaatttga gtcttaatgc   2880
aaataggcgt taagccacag ttatagccat aattgtaact caatattcta actagcgatt   2940
tatctaaatt aaattacatt atgctttat aacttaccta ctagcctgcc caacatttac   3000
acgatcgttt tataattaag aaaaaactaa tgatgaagat taaaaccttc atcatcctta   3060
cgtcaattga attctctagc actcgaagct tattgtcttc aatgtaaaag aaaagctggt   3120
ctaacaagat gacaactaga acaaagggca ggggccatac tgcggccacg actcaaaacg   3180
acagaatgcc aggccctgag cttttcgggct ggatctctga gcagctaatg accggaagaa   3240
ttcctgtaag cgacatcttc tgtgatattg agaacaatcc aggattatgc tacgcatccc   3300 aaaatgcaaca aacgaagcca aacccgaaga cgcgcaacag tcaaacccaa acggacccaa   3360
tttgcaatca tagttttgag gaggtagtac aaacattggc ttcattggct actgttgtgc   3420
aacaacaaac catcgcatca gaatcattag aacaacgcat tacgagtctt gagaatggtc   3480
taaagccagt ttatgatatg gcaaaaacaa tctcctcatt gaacagggtt tgtgctgaga   3540
tggttgcaaa atatgatctt ctggtgatga caaccggtcg ggcaacagca accgctgcgg   3600
caactgaggc ttattgggcc gaacatggtc aaccaccacc tggaccatca ctttatgaag   3660
aaagtgcgat tcggggtaag attgaatcta gagatgagac cgtccctcaa agtgttaggg   3720
aggcattcaa caatctaaac agtaccactt cactaactga ggaaaatttt gggaaacctg   3780
acatttcggc aaaggatttg agaaacatta tgtatgatca cttgcctggt tttggaactg   3840 cttttccacca attagtacaa gtgatttgta aattgggaaa agatagcaac tcattggaca   3900
tcattcatgc tgagttccag gccagcctgg ctgaaggaga ctctcctcaa tgtgccctaa   3960
```

-continued

```
ttcaaattac aaaaagagtt ccaatcttcc aagatgctgc tccacctgtc atccacatcc    4020
gctctcgagg tgacattccc cgagcttgcc agaaaagctt gcgtccagtc ccaccatcgc    4080
ccaagattga tcgaggttgg gtatgtgttt ttcagcttca agatggtaaa acacttggac    4140
tcaaaatttg agccaatctc ccttccctcc gaaagaggcg aataatagca gaggcttcaa    4200
ctgctgaact atagggtacg ttacattaat gatacacttg tgagtatcag ccctggataa    4260
tataagtcaa ttaaacgacc aagataaaat tgttcatatc tcgctagcag cttaaaatat    4320
aaatgtaata ggagctatat ctctgacagt attataatca attgttatta gtaacccaa    4380
accaaaagtg atgaagatta agaaaaacct acctcggctg agagagtgtt ttttcattaa    4440
ccttcatctt gtaaacgttg agcaaaattg ttaaaaatat gaggcgggtt atattgccta    4500
ctgctcctcc tgaatatatg gaggccatat accctgtcag gtcaaattca acaattgcta    4560
gaggtggcaa cagcaataca ggcttcctga caccggagtc agtcaatggg gacactccat    4620
cgaatccact caggccaatt gccgatgaca ccatcgacca tgccagccac acaccaggca    4680
gtgtgtcatc agcattcatc cttgaagcta tggtgaatgt catatcgggc cccaaagtgc    4740
taatgaagca aattccaatt tggcttcctc taggtgtcgc tgatcaaaag acctacagct    4800
ttgactcaac tacggccgcc atcatgcttg cttcatacac tatcacccat ttcggcaagg    4860
caaccaatcc acttgtcaga gtcaatcggc tgggtcctgg aatcccggat catcccctca    4920
ggctcctgcg aattggaaac caggctttcc tccaggagtt cgttcttccg ccagtccaac    4980
taccccagta tttcaccttt gatttgacag cactcaaact gatcacccaa ccactgcctg    5040
ctgcaacatg gaccgatgac actccaacag gatcaaatgg agcgttgcgt ccaggaattt    5100
catttcatcc aaaacttcgc cccattcttt tacccaacaa agtgggaag aagggagaaca    5160
gtgccgatct aacatctccg gagaaaatcc aagcaataat gacttcactc caggacttta    5220
agatcgttcc aattgatcca accaaaaata tcatgggaat cgaagtgcca gaaactctgg    5280
tccacaagct gaccggtaag aaggtgactt ctaaaaatgg acaaccaatc atccctgttc    5340
ttttgccaaa gtacattggg ttggacccgg tggctccagg agacctcacc atggtaatca    5400
cacaggattg tgacacgtgt cattctcctg caagtcttcc agctgtgatt gagaagtaat    5460
tgcaataatt gactcagatc cagttttata gaatcttctc agggatagtg ataacatcta    5520
tttagtaatc cgtccattag aggagacact tttaattgat caatatacta aaggtgcttt    5580
acaccattgt ctttttttctc tcctaaatgt agaacttaac aaaagactca taatatactt    5640
gtttttaaag gattgattga tgaaagatca taactaataa cattacaaat aatcctacta    5700
taatcaatac ggtgattcaa atgttaatct ttctcattgc atatactttt tgcccttatc    5760
ctcaaattgc ctgcatgctt acatctgagg atagccagtg tgacttggat tggaaatgtg    5820
gagaaaaaat cgggacccat ttctaggttg ttcacaatcc aagtacagac attgcccttc    5880
taattaagaa aaaatcggcg atgaagatta agccgacagt gagcgtaatc ttcatctctc    5940
ttagattatt tgttttccag agtaggggtc gtcaggtcct tttcaatcgt gtaaccaaaa    6000
taaactccac tagaaggata ttgtggggca acaacacaat gggcgttaca ggaatattgc    6060
agttacctcg tgatcgattc aagaggacat cattctttct ttgggtaatt atcctttccc    6120
aaagaacatt ttccatccca cttggagtca tccacaataag cacattacag gttagtgatg    6180
tcgacaaact agtttgtcgt gacaaactgt catccacaaa tcaattgaga tcagttggac    6240
tgaatctcga agggaatgga gtggcaactg acgtgccatc tgcaactaaa agatggggct    6300
```

```
tcaggtccgg tgtcccacca aaggtggtca attatgaagc tggtgaatgg gctgaaaact    6360
gctacaatct tgaaatcaaa aaacctgacg ggagtgagtg tctaccagca gcgccagacg    6420
ggattcgggg cttcccccgg tgccggtatg tgcacaaagt atcaggaacg ggaccgtgtg    6480
ccggagactt tgccttccat aaagagggtg ctttcttcct gtatgatcga cttgcttcca    6540
cagttatcta ccgaggaacg actttcgctg aaggtgtcgt tgcatttctg atactgcccc    6600
aagctaagaa ggacttcttc agctcacacc ccttgagaga gccggtcaat gcaacggagg    6660
acccgtctag tggctactat tctaccacaa ttagatatca ggctaccggt tttggaacca    6720
atgagacaga gtacttgttc gaggttgaca atttgaccta cgtccaactt gaatcaagat    6780
tcacaccaca gtttctgctc cagctgaatg agacaatata caagtggg aaaaggagca    6840 ataccacggg aaaactaatt tggaaggtca accccgaaat tgatacaaca atcggggagt    6900
gggccttctg ggaaactaaa aaaacctcac tagaaaaatt cgcagtgaag agttgtcttt    6960
cacagttgta tcaaacggag ccaaaaacat cagtggtcag agtccggcgc gaacttcttc    7020
cgacccaggg accaacacaa caactgaaga ccacaaaatc atggcttcag aaaattcctc    7080
tgcaatggtt caagtgcaca gtcaaggaag ggaagctgca gtgtcgcatc taacaaccct    7140
tgccacaatc tccacgagtc cccaatccct cacaaccaaa ccaggtccgg acaacagcac    7200
ccataataca cccgtgtata aacttgacat ctctgaggca actcaagttg aacaacatca    7260
ccgcagaaca gacaacgaca gcacagcctc cgacactccc tctgccacga ccgcagccgg    7320 accccccaaaa gcagagaaca ccaacacgag caagagcact gacttcctgg accccgccac    7380
cacaacaagt ccccaaaacc acagcgagac cgctggcaac aacaacactc atcaccaaga    7440
taccggagaa gagagtgcca gcagcgggaa gctaggctta attaccaata ctattgctgg    7500
agtcgcagga ctgatcacag gcgggagaag aactcgaaga gaagcaattg tcaatgctca    7560
acccaaatgc aacccctaatt tacattactg gactactcag gatgaaggtg ctgcaatcgg    7620
actggcctgg ataccatatt tcgggccagc agccgaggga atttacatag aggggctaat    7680
gcacaatcaa gatggtttaa tctgtgggtt gagacagctg gccaacgaga cgactcaagc    7740
tcttcaactg ttcctgagag ccacaactga gctacgcacc ttttcaatcc tcaaccgtaa    7800
ggcaattgat ttcttgctgc agcgatgggg cggcacatgc cacattctgg gaccggactg    7860
ctgtatcgaa ccacatgatt ggaccaagaa cataacagac aaaattgatc agattattca    7920 tgatttttgtt gataaaaccc ttccggacca gggggacaat gacaattggt ggacaggatg    7980
gagacaatgg ataccggcag gtattggagt tacaggcgtt ataattgcag ttatcgcttt    8040
attctgtata tgcaaatttg tctttttagtt tttcttcaga ttgcttcatg aaaagctca    8100 gcctcaaatc aatgaaacca ggatttaatt atatggatta cttgaatcta agattacttg    8160
acaaatgata atataataca ctggagcttt aaacatagcc aatgtgattc taactccttt    8220
aaactcacag ttaatcataa acaaggtttg acatcaatct agttatctct ttgagaatga    8280
taaacttgat gaagattaag aaaaaggtaa tctttcgatt atctttaatc ttcatccttg    8340
attctacaat catgacagtt gtctttagtg acaagggaaa gaagcctttt tattaagttg    8400
taataatcag atctgcgaac cggtagagtt tagttgcaac ctaacacaca taaagcattg    8460
gtcaaaaagt caatagaaat ttaaacagtg agtgggacaa cttttaaat ggaagcttca    8520 tatgagagag gacgcccacg agctgccaga cagcattcaa gggatggaca cgaccaccat    8580
gttcgagcac gatcatcatc cagagagaat tatcgaggtg agtaccgtca atcaaggagc    8640
gcctcacaag tgcgcgttcc tactgtattt cataagaaga gagttgaacc attaacagtt    8700
```

-continued

```
cctccagcac ctaaagacat atgtccgacc ttgaaaaaag gattttttgtg tgacagtagt      8760 ttttgcaaaa aagatcacca gttggagagt ttaactgata gggaattact cctactaatc      8820
gcccgtaaga cttgtggatc agtagaacaa caattaaata taactgcacc caaggactcg      8880
cgcttagcaa atccaacggc tgatgatttc cagcaagagg aaggtccaaa aattaccttg      8940
ttgacactga tcaagacggc agaacactgg gcgagacaag acatcagaac catagaggat      9000
tcaaaattaa gagcattgtt gactctatgt gctgtgatga cgaggaaatt ctcaaaatcc      9060
cagctgagtc ttttatgtga gacacaccta aggcgcgagg ggcttgggca agatcaggca      9120
gaacccgttc tcgaagtata tcaacgatta cacagtgata aaggaggcag ttttgaagct      9180
gcactatggc aacaatggga ccgacaatcc ctaattatgt ttatcactgc attcttgaat      9240
attgctctcc agttaccgtg tgaaagttct gctgtcgttg tttcagggtt aagaacattg      9300
gttcctcaat cagataatga ggaagcttca accaacccgg ggacatgctc atggtctgat      9360
gagggtaccc cttaataagg ctgactaaaa cactatataa ccttctactt gatcacaata      9420
ctccgtatac ctatcatcat atatttaatc aagacgatat cctttaaaac ttattcagta      9480
ctataatcac tctcgtttca aattaataag atgtgcatga ttgccctaat atatgaagag      9540
gtatgataca accctaacag tgatcaaaga aaatcataat ctcgtatcgc tcgtaatata      9600
acctgccaag catacctctt gcacaaagtg attcttgtac acaataatg ttttactcta       9660 caggaggtag caacgatcca tcccatcaaa aaataagtat ttcatgactt actaatgatc      9720
tcttaaaata ttaagaaaaa ctgacggaac ataaattctt tatgcttcaa gctgtggagg      9780
aggtgtttgg tattggctat tgttatatta caatcaataa caagcttgta aaaatattgt      9840
tcttgtttca agaggtagat tgtgaccgga atgctaaac taatgatgaa gattaatgcg       9900
gaggtctgat aagaataaac cttattattc agattaggcc ccaagaggca ttcttcatct      9960 cctttttagca aagtactatt tcagggtagt ccaattagtg gcacgtcttt tagctgtata    10020
tcagtcgccc ctgagatacg ccacaaaagt gtctctaagc taaattggtc tgtacacatc    10080
ccatacattg tattaggggc aataatatct aattgaactt agccgtttaa aatttagtgc    10140
ataaatctgg gctaacacca ccaggtcaac tccattggct gaaaagaagc ttacctacaa    10200
cgaacatcac tttgagcgcc ctcacaatta aaaaatagga acgtcgttcc aacaatcgag    10260
cgcaaggttt caaggttgaa ctgagagtgt ctagacaaca aaatattgat actccagaca    10320
ccaagcaaga cctgagaaaa aaccatggct aaagctacgg gacgatacaa tctaatatcg    10380
cccaaaaagg acctggagaa aggggttgtc ttaagcgacc tctgtaactt cttagttagc    10440
caaactattc agggggtggaa ggtttattgg gctggtattg agtttgatgt gactcacaaa    10500
ggaatggccc tattgcatag actgaaaact aatgactttg cccctgcatg gtcaatgaca    10560
aggaatctct ttcctcattt atttcaaaat ccgaattcca caattgaatc accgctgtgg    10620
gcattgagag tcatccttgc agcagggata caggaccagc tgattgacca gtctttgatt    10680 gaaccettag caggagccct tggtctgatc tctgattggc tgctaacaac caacactaac    10740
catttcaaca tgcgaacaca acgtgtcaag gaacaattga gcctaaaaat gctgtcgttg    10800
attcgatcca atattctcaa gtttattaac aaattggatg ctctacatgt cgtgaactac    10860
aacggattgt tgagcagtat tgaaattgga actcaaaatc atacaatcat cataactcga    10920
actaacatgg gttttctggt ggagctccaa gaacccgaca atcggcaat gaaccgcatg     10980 aagcctgggc cggcgaaatt ttccctcctt catgagtcca cactgaaagc atttacacaa    11040
```

```
ggatcctcga cacgaatgca aagtttgatt cttgaattta atagctctct tgctatctaa    11100
ctaaggtaga atacttcata ttgagctaac tcatatatgc tgactcaata gttatcttga    11160
catctctgct ttcataatca gatatataag cataataaat aaatactcat atttcttgat    11220
aatttgttta accacagata aatcctcact gtaagccagc ttccaagttg acacccttac    11280
aaaaaccagg actcagaatc cctcaaacaa gagattccaa gacaacatca tagaattgct    11340
ttattatatg aataagcatt ttatcaccag aaatcctata tactaaatgg ttaattgtaa    11400
ctgaacccgc aggtcacatg tgttaggttt cacagattct atatattact aactctatac    11460
tcgtaattaa cattagataa gtagattaag aaaaaagcct gaggaagatt aagaaaaact    11520
gcttattggg tctttccgtg ttttagatga agcagttgaa attcttcctc ttgatattaa    11580
atggctacac aacatacccca ataccccagac gctaggttat catcaccaat tgtattggac    11640
caatgtgacc tagtcactag agcttgcggg ttatattcat catactccct taatccgcaa    11700
ctacgcaact gtaaactccc gaaacatatc taccgtttga aatacgatgt aactgttacc    11760
aagttcttga gtgatgtacc agtggcgaca ttgcccatag atttcatagt cccagttctt    11820
ctcaaggcac tgtcaggcaa tggattctgt cctgttgagc cgcggtgcca acagttctta    11880
gatgaaatca ttaagtacac aatgcaagat gctctcttct tgaaatatta tctcaaaaat    11940
gtgggtgctc aagaagactg tgttgatgaa cactttcaag agaaaatctt atcttcaatt    12000
cagggcaatg aattttttaca tcaaatgttt ttctggtatg atctggctat tttaactcga    12060
aggggtagat aaatcgagg aaactctaga tcaacatggt ttgttcatga tgatttaata    12120
gacatcttag gctatgggga ctatgttttt tggaagatcc caatttcaat gttaccactg    12180
aacacacaag gaatccccca tgctgctatg gactggtatc aggcatcagt attcaaagaa    12240
gcggttcaag ggcatacaca cattgttcct gtttctactg ccgacgtctt gataatgtgc    12300
aaagatttaa ttcatgtcg attcaacaca actctaatct caaaaatagc agagattgag    12360
gatccagttt gttctgatta tcccaatttt aagattgtgt ctatgcttta ccagagcgga    12420
gattacttac tctccatatt agggtctgat gggtataaaa ttattaagtt cctcgaacca    12480
ttgtgcttgg ccaaaattca attatgctca agtacactg agaggaaggg ccgattctta    12540
acacaaatgc atttagctgt aaatcacacc ctagaagaaa ttacagaaat gcgtgcacta    12600
aagccttcac aggctcaaaa gatccgtgaa ttccatagaa cattgataag gctggagatg    12660
acgccacaac aactttgtga gctatttttcc attcaaaaac actgggggca tcctgtgcta    12720
catagtgaaa cagcaatcca aaaagttaaa aaacatgcta cggtgctaaa agcattacgc    12780
cctatagtga ttttcgagac atactgtgtt tttaaatata gtattgccaa acattatttt    12840
gatagtcaag gatcttggta cagtgttact tcagatagga atctaacacc gggtcttaat    12900
tcttatatca aaagaaatca attccctccg ttgccaatga ttaaagaact actatgggaa    12960
ttttaccacc ttgaccaccc tccacttttc tcaaccaaaa ttattagtga cttaagtatt    13020
tttataaaag acagagctac cgcagtagaa aggacatgct gggatgcagt attcgagcct    13080
aatgttctag gatataatcc acctcacaaa tttagtacta acgtgtacc ggaacaattt    13140 ttagagcaag aaaacttttc tattgagaat gttctttcct acgcacaaaa actcgagtat    13200
ctactaccac aatatcggaa cttttctttc tcattgaaag agaaagagtt gaatgtaggt    13260
agaaccttcg gaaaattgcc ttatccgact cgcaatgttc aaacactttg tgaagctctg    13320
ttagctgatg gtcttgctaa agcatttcct agcaatatga tggtagttac ggaacgtgag    13380
caaaaagaaa gcttattgca tcaagcatca tggcaccaca caagtgatga ttttggtgaa    13440
```

```
catgccacag ttagagggag tagctttgta actgatttag agaaatacaa tcttgcattt    13500
agatatgagt ttacagcacc ttttatagaa tattgcaacc gttgctatgg tgttaagaat    13560
gtttttaatt ggatgcatta tacaatccca cagtgttata tgcatgtcag tgattattat    13620
aatccaccac ataacctcac actggagaat cgagacaacc cccccgaagg gcctagttca    13680
tacaggggtc atatgggagg gattgaagga ctgcaacaaa aactctggac aagtatttca    13740
tgtgctcaaa tttctttagt tgaaattaag actggtttta agttacgctc agctgtgatg    13800
ggtgacaatc agtgcattac tgttttatca gtcttcccct tagagactga cgcagacgag    13860
caggaacaga gcgccgaaga caatgcagcg agggtggccg ccagcctagc aaaagttaca    13920
agtgcctgtg gaatcttttt aaaacctgat gaaacatttg tacattcagg ttttatctat    13980
tttggaaaaa aacaatattt gaatgggggtc caattgcctc agtcccttaa aacggctaca    14040
agaatggcac cattgtctga tgcaattttt gatgatcttc aagggaccct ggctagtata    14100
ggcactgctt ttgagcgatc catctctgag acacgacata tctttccttg caggataacc    14160
gcagctttcc atacgttttt ttcggtgaga atcttgcaat atcatcatct cgggttcaat    14220
aaaggttttg accttggaca gttaacactc ggcaaacctc tggatttcgg aacaatatca    14280
ttggcactag cggtaccgca ggtgcttgga gggttatcct tcttgaatcc tgagaaatgt    14340
ttctaccgga atctaggaga tccagttacc tcaggcttat tccagttaaa aacttatctc    14400
cgaatgattg agatggatga tttattctta cctttaattg cgaagaaccc tgggaactgc    14460
actgccattg actttgtgct aaatcctagc ggattaaatg tccctgggtc gcaagactta    14520
acttcatttc tgcgccagat tgtacgcagg accatcaccc taagtgcgaa aaacaaactt    14580
attaatacct tatttcatgc gtcagctgac ttcgaagacg aaatggtttg taaatggcta    14640
ttatcatcaa ctcctgttat gagtcgtttt gcggccgata tcttttcacg cacgccgagc    14700
gggaagcgat tgcaaattct aggatacctg gaaggaacac gcacattatt agcctctaag    14760
atcatcaaca ataatacaga gacaccggtt ttggacagac tgaggaaaat aacattgcaa    14820
aggtggagcc tatggtttag ttatcttgat cattgtgata atatcctggc ggaggcttta    14880
acccaaataa cttgcacagt tgatttagca cagattctga gggaatattc atgggctcat    14940
attttagagg gaagacctct tattggagcc acactcccat gtatgattga gcaattcaaa    15000
gtgttttggc tgaaacccta cgaacaatgt ccgcagtgtt caaatgcaaa gcaaccaggt    15060
gggaaaccat tcgtgtcagt ggcagtcaag aaacatattg ttagtgcatg gccgaacgca    15120
tcccgaataa gctggactat cggggatgga atcccataca ttggatcaag gacagaagat    15180
aagataggac aacctgctat taaaccaaaa tgtccttccg cagccttaag agaggccatt    15240
gaattggcgt cccgtttaac atgggtaact caaggcagtt cgaacagtga cttgctaata    15300
aaaccatttt tggaagcacg agtaaattta agtgttcaag aaatacttca aatgaccccct    15360
tcacattact caggaaatat tgttcacagg tacaacgatc aatacagtcc tcattctttc    15420
atggccaatc gtatgagtaa ttcagcaacg cgattgattg tttctacaaa cactttaggt    15480
gagttttcag gaggtggcca gtctgcacgc gacagcaata ttattttcca gaatgttata    15540
aattatgcag ttgcactgtt cgatattaaa tttagaaaca ctgaggctac agatatccaa    15600
tataatcgtg ctcaccttca tctaactaag tgttgcaccc gggaagtacc agctcagtat    15660
ttaacataca catctacatt ggatttagat ttaacaagat accgagaaaa cgaattgatt    15720
tatgacagta atcctctaaa aggaggactc aattgcaata tctcattcga taatccatttt   15780
```

```
ttccaaggta aacggctgaa cattatagaa gatgatctta ttcgactgcc tcacttatct    15840
ggatgggagc tagccaagac catcatgcaa tcaattattt cagatagcaa caattcatct    15900
acagacccaa ttagcagtgg agaaacaaga tcattcacta cccatttctt aacttatccc    15960
aagataggac ttctgtacag ttttggggcc tttgtaagtt attatcttgg caatacaatt    16020
cttcggacta agaaattaac acttgacaat ttttatatt acttaactac tcaaattcat     16080
aatctaccac atcgctcatt gcgaatactt aagccaacat tcaaacatgc aagcgttatg    16140
tcacggttaa tgagtattga tcctcatttt tctatttaca taggcggtgc tgcaggtgac    16200
agaggactct cagatgcggc caggttattt ttgagaacgt ccatttcatc ttttcttaca    16260
tttgtaaaag aatggataat taatcgcgga acaattgtcc ctttatggat agtatatccg    16320
ctagagggtc aaaacccaac acctgtgaat aattttctct atcagatcgt agaactgctg    16380
gtgcatgatt catcaagaca acaggctttt aaaactacca taagtgatca tgtacatcct    16440
cacgacaatc ttgtttacac atgtaagagt acagccagca atttcttcca tgcatcattg    16500
gcgtactgga ggagcagaca cagaaacagc aaccgaaaat acttggcaag agactcttca    16560
actggatcaa gcacaaacaa cagtgatggt catattgaga gaagtcaaga acaaaccacc    16620
agagatccac atgatggcac tgaacggaat ctagtcctac aaatgagcca tgaaataaaa    16680
agaacgacaa ttccacaaga aaacacgcac cagggtccgt cgttccagtc ctttctaagt    16740
gactctgctt gtggtacagc aaatccaaaa ctaaatttcg atcgatcgag acacaatgtg    16800
aaatttcagg atcataactc ggcatccaag agggaaggtc atcaaataat ctcacaccgt    16860
ctagtcctac cttctttac attatctcaa gggacacgcc aattaacgtc atccaatgag    16920
tcacaaaccc aagacgagat atcaaagtac ttacggcaat tgagatccgt cattgatacc    16980
acagtttatt gtagatttac cggtatagtc tcgtccatgc attacaaact tgatgaggtc    17040
ctttgggaaa tagagagttt caagtcggct gtgacgctag cagagggaga aggtgctggt    17100
gccttactat tgattcagaa ataccaagtt aagacttat ttttcaacac gctagctact     17160
gagtccagta tagagtcaga aatagtatca ggaatgacta ctcctaggat gcttctacct    17220
gttatgtcaa aattccataa tgaccaaatt gagattattc ttaacaactc agcaagccaa    17280
ataacagaca taacaaatcc tacttggttt aaagaccaaa gagcaaggct acctaagcaa    17340
gtcgaggtta taaccatgga tgcagagaca acagagaata taaacagatc gaaattgtac    17400
gaagctgtat ataaattgat cttacaccat attgatccta gcgtattgaa agcagtggtc    17460
cttaaagtct ttctaagtga tactgagggt atgttatggc taaatgataa tttagccccg    17520
ttttttgcca ctggttattt aattaagcca ataacgtcaa gtgctagatc tagtgagtgg    17580
tatctttgtc tgacgaactt cttatcaact acacgtaaga tgccacacca aaaccatctc    17640
agttgtaaac aggtaatact tacggcattg caactgcaaa ttcaacgaag cccatactgg    17700
ctaagtcatt taactcagta tgctgactgt gagttacatt taagttatat ccgccttggt    17760
tttccatcat tagagaaagt actataccac aggtataacc tcgtcgattc aaaaagaggt    17820
ccactagtct ctatcactca gcacttagca catcttagag cagagattcg agaattaact    17880
aatgattata tcaacagcg acaaagtcgg actcaaacat atcactttat tcgtactgca    17940
aaaggacgaa tcacaaaact agtcaatgat tatttaaaat tctttcttat tgtgcaagca    18000
ttaaaacata tgggacatg gcaagctgag tttaagaaat taccagagtt gattagtgtg    18060
tgcaataggt tctaccatat tagagattgc aattgtgaag aacgtttctt agttcaaacc    18120
ttatatttac atagaatgca ggattctgaa gttaagctta tcgaaaggct gacagggctt    18180
```

```
ctgagtttat tccggatgg tctctacagg tttgattgaa ttaccgtgca tagtatcctg    18240
atacttgcaa aggttggtta ttaacataca gattataaaa aactcataaa ttgctctcat    18300
acatcatatt gatctaatct caataaacaa ctatttaaat aacgaaagga gtccctatat    18360
tatatactat atttagcctc tctccctgcg tgataatcaa aaaattcaca atgcagcatg    18420
tgtgacatat tactgccgca atgaatttaa cgcaacataa taaactctgc actctttata    18480
attaagcttt aacgaaaggt ctgggctcat attgttattg atataataat gttgtatcaa    18540
tatcctgtca gatggaatag tgttttggtt gataacacaa cttcttaaaa caaaattgat    18600
ctttaagatt aagttttta taattatcat tactttaatt tgtcgttta aaaacggtga    18660 tagccttaat ctttgtgtaa aataagagat taggtgtaat aaccttaaca tttttgtcta    18720
gtaagctact atttcataca gaatgataaa attaaaagaa aaggcaggac tgtaaaatca    18780 gaaataccttt ctttacaata tagcagacta gataataatc ttcgtgttaa tgataattaa    18840
gacattgacc acgctcatca gaaggctcgc cagaataaac gttgcaaaaa ggattcctgg    18900
aaaaatggtc gcacacaaaa atttaaaaat aaatctatt cttcttttt gtgtgtcca     18959
```

<210> SEQ ID NO 269
<211> LENGTH: 6533
<212> TYPE: DNA
<213> ORGANISM: Hantaan virus
<220> FEATURE:

<400> SEQUENCE: 269

```
tagtagtaga ctccctaaat aacaaactct gaaaagaatg gataaatata gagaaattca      60
caataagttg aaggagtttt ctcctggtac attaactgca gtagagtgta tagattatct     120
tgatagactt tacgccgtga gacatgacat tgtagaccaa atgattaagc atgactggtc     180
tgataataag gattcagaag aagcaatagg gaaagtacta ttatttgcag gggtcccttc     240
aaacattata acagcactag agaagaaaat aataccaaat catcctacag gaaagagtct     300 aaaggcctttc ttcaagatga cacctgataa ttataaaatt agtggaacaa caattgagtt     360
tgttgaggtt actgtcacgg cagatgttga caagggaata agagagaaga gcttaaaata     420
tgaggcaggc ttaacctata ttgaacaaga gttgcataag ttcttcctaa agggtgagat     480
cccacaaccc tataaaataa catttaatgt agttgcagtt cgcacagatg gctccaatat     540
tactacacaa tggcctagta gaagaaatga tggtgttgtc cagtatatga ggctagttca     600
agctgagata agttatgtta gagagcactt gatcaaaact gaggagagag ctgcactaga     660
agccatgttt aatttaaaat tcaacataag tacacacaaa agccagccct attacatacc     720
agattataag gggatggaac caataggagc aaatattgaa gacttagtgg actattcgaa     780
agactggttg tctagagcta gaaatttttc attttttgaa gttaaaggta cagcagtgtt     840
cgagtgcttt aattcaaatg aggccaatca ttgtcaaaga tatcctatgt cccgaaagcc     900
tagaaatttc ctactcatac aatgttcttt aatcacatct tataaacctg ctaccacatt     960
gtcagatcaa attgatagta gaagggcctg ttcatacatt ctaaacttaa ttccagatac    1020
accagcatcc tatctgatcc atgatatggc atatagatac ataaacctaa caagagaaga    1080
tatgattaat tattatgccc cgcggataca gtttaaacag acacaaaatg taagagagcc    1140
aggaacgttt aagttgacat caagtatgtt gagagcagaa tcaaaagcaa tgctagattt    1200
acttaataat cataaaagtg gtgaaaagca tggtgcacaa atagagagcc taaatattgc    1260
tagtcatatt gtacagtctg aatctgttag cctgattaca aaaatattat ctgatttaga    1320
```

-continued

```
attgaatata actgagccat caactcaaga atattccaca actaagcata cttatgtcga    1380
tacagtgtta gacaagtttt ttcaaaatga acccagaag tacctgatag atgtgttgaa     1440
aaaaacaaca gcatggcaca taggtcatct cataagggat ataacagaaa gtttaattgc    1500
tcattcagga ttaaaaagat caaagtattg gtccttacac tcatacaata acggcaatgt    1560
catattattt attctcccat caaagtcgct tgaagtagca ggttccttta ttaggttcat    1620
tacagttttc agaataggac ctggtttagt agataaagat aacttggata caatattaat    1680
tgatggtgac tctcagtggg gggtatccaa agttatgagc attgatttaa ataggctgct    1740
agcattaaat atagcttttg aaaaggcttt aattgcaaca gccacatggt tccaatacta    1800
tacagaagac caagggcaat tcccattaca atatgcaatt agatctgtgt ttgcaaatca    1860
ttttctgtta gctatatgcc aaaagatgaa actctgtgcc atctttgaca atttacgtta    1920
tcttatacct gcagtaacat cattatactc tgggtttcca tcactgatag aaaaattatt    1980
tgaacgtcca tttaagtctt cattagaggt atatatatat taatatatta agagcctgtt    2040
agttgcactt gctcaaaata ataaagccag attctattct aaggtaaagt tactaggctt    2100
aacagttgac caatcaactg ttggtgcaag tggagtttat ccttcattca tgtcacgtat    2160
agtatacaaa cattcagga gcttaatatc tgaagtaaca acctgtttct ttttatttga     2220
aaagggtctt catggaaata tgaatgaaga agcaaaaatt catcttgaga cagttgaatg    2280
ggcacttaaa ttcagagaga aggaagaaaa gtatggggaa tctctagtag aaaatggata    2340
tatgatgtgg gagctgcgag caaatgcaga gttggcagaa caacaattgt actgtcaaga    2400
tgctattgag ttggcagcaa tagaattaaa taaagtcttg gctacaaagt ctagtgttgt    2460
tgctaatagt atattgagta agaactggga agaaccatat tttagtcaaa caagaaatat    2520
cagcctgaaa ggcatgtcag ggcaggttca ggaagatggc catttatcat catctgtaac    2580
aattatagag gccatccgct atttatcaaa ttcaagacat aatcctagcc tcctaaaatt    2640
atatgaggaa acaagggagc agaaagcaat ggcaagaatt gtgagaaaat atcaaaggac    2700
agaggcagat aggggctttt ttatcacaac acttcctact agatgcaggc ttgaaattat    2760
tgaggactac tatgatgcca ttgccaagaa tatttctgaa gagtacatat catatggagg    2820
tgaaaaaaag attcttgcaa ttcaaggggc acttgagaag gccttgagat gggcatcagg    2880
tgaaagcttt atcgaactta gtaaccacaa atttattagg atgaagcgta aactcatgta    2940
tgttagtgca gatgctacaa agtggtcacc aggagataat tcagcaaagt tccgtaggtt    3000
cacctccatg ctacataacg gacttcccaa taataagcta aaaaactgtg taattgatgc    3060
acttaaacaa gttataagaa cagattttt tatgtcaagg aaactaagga attatattga    3120
cagcatggaa agccttgacc cacacatcaa acagttttta gattttttcc ctgatgggca    3180
ccatggggaa gtgaagggaa actggctgca gggtaacttg aacaagtgtt cttcactttt    3240
cggtgttgca atgtcattac tatttaaaca ggtatggact aacttattcc ctgagcttga    3300
ttgtttcttt gagtttgcac atcactctga tgatgcatta ttcatttatg gatacttgga    3360
accagtagat gatgggactg actggttttt gtttgtctca caacagattc aagcaggcca    3420
tttgcactgg tttagtgtaa atacagagat gtggaagagt atgtttaatc tacatgagca    3480
tatacttctt ctaggctcca tcaagatctc accaaagaaa actacagtgt ccccgacaaa    3540
tgctgaattt ttatcaacat tttttgaagg ttgtgctgta tcaataccat tgttaaaat    3600 actcttaggt tctctatcag acttaccagg attaggttat tttgacgatt tagcagccgc    3660
```

```
acaaagtagg tgtgttaagg ctctggacct tggagcatca cctcaggttg cacaactagc    3720
tgtagcattg tgcaccagta aagttgaaag attatatggt acagcgccag gcatggtaaa    3780 ccacccctgca gcatacttgc aggttaagca tactgataca ccaattccat tgggaggaaa    3840
tggtgcaatg tcaataatgg agttagcaac agctgggatt gggatgtcag ataaaaatct    3900
attaaagcgc gcacttctgg gatactcaca caagagacaa aaatcaatgc tatatatatt    3960
aggtctattc aagtttctga tgaagttatc tgatgaaaca tttcaacatg agaggttagg    4020
gcaattttct tttatcggga aagtacagtg gaagatcttc actccaaaat ctgaattcga    4080
gtttgctgat atgtacacat caaaatttt agagttatgg agtagtcaac atgtaactta    4140
tgattatatt attccgaagg gcagagacaa tcttctcatt tatttagtcc gaaagctcaa    4200
tgatccaagt attgttacag caatgaccat gcagtcacct ttgcagctcc gatttagaat    4260
gcaagctaag cagcacatga aggtgtgtag attggatgga gaatgggtta ctttcaggga    4320
agttctggca gctgcaaaca gttttgcgga gaattatagt gctactagcc aagatatgga    4380
tctatttcaa acgttaacaa gttgtacatt ttctaaagag tatgcttgga agatttcct    4440 gaatggaatt cactgtgatg ttatcccgac aaaacaggtt caagggcca agttgcacg    4500 aacattcaca gtcagagaaa aggatcagat catacaaaat agtattcctg ctgtcattgg    4560
gtacaaattt gctgtaactg tagaggaaat gtcagatgta ctggacacag ccaagttccc    4620
agactctcta tctgttgacc taaagacaat gaaagacgga gtttatcgtg agttagggtt    4680
ggacatatcc ttacctgatg ttatgaaaag aattgcacct atgctctata aatcttctaa    4740
atcaagggta gtcattgtcc aagggaatgt tgaagggaca gctgaggcta tatgtcgcta    4800
ctggctaaaa tcaatgtcat tggtaaagac tataagagtg aagcctcata agaagtcct    4860 tcaagcagtt tctattttta atcgcaaaga agatatagga caacagaaag acttagctgc    4920
tcttaaactg tgcatagaag tttggagatg gtgtaaagca aatagtgctc catatagaga    4980
ttggttccag gctctatggt tcgaggataa aaccttttca gagtggttag ataggttttg    5040
tagggttgga gttccaccaa ttgatccaga gatccagtgt gcagcattaa tgatagctga    5100
tataaagggt gattactcag tcttgcagtt acaagcgaat aggcgagcat attcaggtaa    5160
gcaatatgat gcatattgtg tacaaacata taatgaagtg acaaagcttt atgagggaga    5220
cctaagggta acatttaatt ttggtcttga ctgtgcaagg cttgagatct tttgggataa    5280
aaaggcatat atattagaaa catcgattac acaaaagcat gtattgaaga tcatgatgga    5340
tgaggtttcg aaagagttga ttaagtgtgg gatgagattt aatacagaac aggtccaagg    5400
agtacggcac atggtgttat ttaagacaga gtctggattt gaatgtgggaa accaaaatat    5460 tccatgtatt gttataaga actgtgtcct aaggacaagc cttaggacta cgcaagcaat    5520
taaccataaa tttatgatta caataaagga tgatgggctt cgtgctattg cacaacatga    5580
tgaagatagc ccaagattcc tattagctca tgcatttcac acaataagag atattaggta    5640
tcaagcggta gatgctgtaa gtaatgtatg gttcatccac aaaggagtaa aactgtattt    5700
aaatcccatc atttcatctg gtttacttga gaattttatg aagaatcttc cagctgcaat    5760
ccctcctgct gcatattcac tgatcatgaa ccgtgcaaaa atatctgttg acctctttat    5820
gtttaacgat ttacttaagc taattaaccc taggaataca ttggatctat caggccttga    5880
aacaacaggg gatgaattca gtactgtaag ttcaatgtca agccgattat ggtctgaaga    5940
aatgagctta gtagatgatg atgaagagct tgatgatgag ttcacaattg acttgcaaga    6000
tgtggatttt gagaatatag atatagaagc agacattgaa catttcctgc aggatgaaag    6060
```

-continued

```
ttcatacaca ggagacctat taatcagcac agaggaaact gaatcaaaga aaatgagggg      6120
catagtgaaa atacttgagc ctgttagatt gattaaaagc tgggtatcac gtgggttatc      6180
tattgagaaa gtatatagtc ctgttaatat tatcttaatg tcacggtata tctccaaaac      6240
atttaatttg agtaccaaac aggtctcatt attagatcca tatgatttaa cagaattaga      6300
gagcattgtc cgaggatggg gagaatgtgt tattgaccag ttcgaaagtc tcgatagaga      6360
ggctcagaat atggttgtta ataaaggaat atgccctgag gatgttattc ctgattcatt      6420
attttcattt aggcacacca tggtactgtt gaggaggtta ttcccgcagg attctatttc      6480
ctctttctat taggctttct ttcttttttca ttttccggag catactacta cta             6533
```

<210> SEQ ID NO 270
<211> LENGTH: 1871
<212> TYPE: DNA
<213> ORGANISM: Andes virus
<220> FEATURE:

<400> SEQUENCE: 270

```
tagtagtaga ctccttgaga agctactgct gcgaaagctg gaatgagcac cctccaagaa       60
ttgcaggaaa acatcacagc acacgaacaa cagctcgtga ctgctcggca aaagcttaag     120
gatgccgaga aggcagtgga ggtggacccg atgacgttaa acaagagcac actacaaagt     180
agacgggcag ctgtgtctac attggagacc aaactcggag aacttaagag gcaacttgca     240
gatttggtgg cagctcaaaa attggctaca aaaccagttg atccaacagg gcttgagcct     300
gatgatcatc taaaggaaaa atcatctctg agatatggga atgtcctgga tgttaattca     360
attgatttgg aagaaccgag tggacagact gctgattgga aggctatagg agcatacatc     420
ttagggtttg caattccgat catcctaaag gccttataca tgctgtcaac ccgtgggaga     480
caaactgtga agacaacaa agggaccagg ataaggttta aggatgattc ttcctttgaa     540
gaagtcaatg ggatacgtaa accaaaacac ctttacgtct caatgccaac tgcacagtcc     600
actatgaagg ctgaagaaat cacgccagga cgatttagga caattgcttg tggcctttt      660 ccagcacagg tcaaagcccg aaatataata agtcctgtaa tgggagtaat tggatttggc     720
ttctttgtaa aggattggat ggatcggata gaagagtttc tggctgcaga gtgtccattc     780
ttacctaagc caaaggtcgc ctcagaagcc ttcatgtcta ccaataagat gtattttctg     840
aacagacaga gacaagtcaa tgaatctaag gttcaagata ttatcgattt gatagaccat     900
gctgagaccg agtctgctac cttgtttaca gagattgcaa caccccattc agtctgggtg     960
tttgcatgtg cacctgaccg gtgccctcca actgcattgt atgttgcagg ggtaccggaa    1020
cttggtgcat tttttttctat ccttcaggac atgcgtaata ccatcatggc atctaaatct    1080
gtagggactg cagaagagaa gctaaagaaa aaatctgcct tctaccaatc atacctaaga    1140
aggacacaat ctatgggaat ccaactggac cagaagatca taatccttta catgctatca    1200 tgggtaaag aagctgtgaa tcacttccat cttggtgatg atatggaccc tgaactcagg    1260
cagctagcac aatctctgat cgatactaag gtgaaggaga tctccaacca agagccactt    1320
aagttgtagg tgcttaatga aatcatgatt gaagaaagac tttccgggct tgtgccacat    1380
attaatcatc tcaggaccta tccttaatgt gattaatagg gttttattat aagggcagtt    1440 aatgggggttg gttactaact atgggtaagg gttcattacc attttttgcac tagggttaaa    1500 gggccactac attgtatttg cactaaggga aatgggaggt gggttagttt gtatttagtt    1560 gttaagttt ttataatcat atgttaatga ggaattagct atatgatatc actgattgat    1620
```

-continued

```
tggctatttt taggttaagt aattgtagtt aaatagttgt gttaagttag tatgttaagg      1680
tttataggtt aagatttact aacaatcata ttatgtcatt agatgtaaat ttcattcctg      1740
gcttgcttct gctttcgcat tgctaaccta caacaagact acctcaccca ctaccctcc       1800 cctattctac ctcaacacat actacctcac atttgatttt tcttgattgc ttttcaagga     1860
gcatactact a                                                           1871
```

<210> SEQ ID NO 271
<211> LENGTH: 1672
<212> TYPE: DNA
<213> ORGANISM: Crimean-Congo hemorrhagic fever virus
<220> FEATURE:

<400> SEQUENCE: 271

```
tctcaaagaa acacgtgccg cttacgccca cagtgttctc ttgagtgtta gcagaatgga      60
aaacaagatc gaggtgaata acaaagatga gatgaacagg tggtttgaag agttcaaaaa     120
aggaaatgga cttgtggaca ccttcacaaa ctcctattcc ttttgcgaga gtgttcccaa     180
tttggacagg tttgtgtttc agatggccag tgccaccgat gatgcacaga aggactccat     240
ctacgcatct gctctggtgg aggcaacaaa gttttgtgca cctatatatg agtgcgcatg     300
ggttagctcc actggcattg taaaaaaggg acttgaatgg ttcgagaaaa atgcaggaac     360
cattaagtcc tgggatgaaa gttatactga gctaaaggtc gacgtcccga aaatagagca     420
gcttaccggt taccaacaag ctgccttgaa gtggagaaaa gacataggtt ccgtgtcaa      480 tgccaacaca gcagctctga gcaacaaagt cctcgcagaa tacaaagtcc ctggtgagat     540
tgtgatgtct gtcaaagaga tgctgtcaga catgattagg agaaggaacc tgattctaaa     600 cagggtggt gatgagaacc cacgtggccc agtgagccat gagcatgtag actggtgcag      660
ggagtttgtc aaaggcaaat acatcatggc cttcaaccca ccatgggggg acatcaacaa     720
gtcaggccgt tcaggaatag cacttgttgc aacaggcctt gctaagcttg cagagactga     780
aggaaaggga atatttgatg aagccaaaaa gactgtggag gccctcaacg ggtatctgga     840
caagcataag gacgaagttg atagagcaag cgccgacagc atgataacaa accttcttaa     900
gcatattgcc aaggcacagg agctctataa aaattcatct gcacttcgtg cacaaagcgc     960
acagattgac actgctttca gctcatacta ttggctttac aaggctggcg tgactcctga    1020
aaccttcccg acggtgtcac agttcctctt tgagctaggg aaacagccaa gaggtaccaa    1080
gaaaatgaag aaggctcttc tgagcacccc aatgaagtgg gggaagaagc tttatgagct    1140
ctttgccgat gattctttcc agcagaacag gattacatg catcctgccg tgcttacagc     1200
tggtagaatc agtgaaatgg gagtctgctt tgggacaatc cctgtggcca atcctgatga    1260
tgctgcccaa ggatctggac acactaagtc tattctcaac ctccgtacca acactgagac    1320
caataatccg tgtgccaaaa ccatcgtcaa gctatttgaa gttcaaaaaa cagggttcaa    1380
cattcaggac atggacatag tggcctctga gcacttgcta caccaatccc ttgttggcaa    1440
gcaatcccca ttccagaacg cctacaacgt caagggcaat gccaccagtg ctaacatcat    1500
ttaaaataca aactgctctg tactcaactt ccttccttct gaaccgccat ccataattgc    1560
aatacttaat catgcttttt tacttgctta tgtaaccttg ttttattaac ctttctctat    1620
tttctcttgt tttaaacact taagggctg tgcggcaacg gtatctttga ga               1672
```

<210> SEQ ID NO 272
<211> LENGTH: 6606

<212> TYPE: DNA
<213> ORGANISM: Rift Valley fever virus
<220> FEATURE:

<400> SEQUENCE: 272

| | | | | | |
|---|---|---|---|---|---|
| acacaaaggc | gcccaatcat | ggattctata | ttatcaaaac | agctggttga | caagactggt | 60 |
| tttgttagag | tgccaatcaa | gcattttgac | tgtacaatgc | taactctggc | acttccaaca | 120 |
| tttgatgttt | ccaagatggt | agatagaatt | accatagact | tcaatctgga | tgatatacaa | 180 |
| ggagcatctg | aaataggctc | aactttgcta | ccctccatgt | cgatagatgt | ggaagatatg | 240 |
| gccaattttg | ttcacgattt | cacctttggc | cacttagctg | acaagactga | cagactgtta | 300 |
| atgcgtgagt | tcccatgat | gaatgacggg | tttgatcatt | tgagccctga | tatgatcatt | 360 |
| aaaactacat | ctggcgtata | caacatcgtt | gagttcacca | actttagggg | agatgaaaga | 420 |
| ggtgcattcc | aggctgccat | gatcaaactc | gctaagtatg | aggttccttg | tgagaacaga | 480 |
| tctcagggca | ggactgttgt | tctttacgtt | gttagtgctt | atcgggcatg | gtgcatggtc | 540 |
| tatctggagc | tagagcggac | tctgaagcag | agggagatgg | tttataggta | cagacttgct | 600 |
| cttagtgtga | tggatgagct | aaggaccttg | ttcccagaac | tgtcatccac | agatgaggaa | 660 |
| ctagggaaga | ctgagagaga | gttgccagcc | atggtgtcct | ccatccaaat | aaattggtca | 720 |
| gtcactgaat | ctgtgtttcc | acccttcagc | agagaaatgt | tgacaggtt | tagatcctcc | 780 |
| cctcccgatt | cagagtatat | cacgaggata | gtgagcagat | gcctaataaa | ttctcaagag | 840 |
| aaactcatca | atagttcctt | ctttgctgaa | gggaatgata | aggctctgag | attttcaaaa | 900 |
| aacgctgaag | agtgttcctt | ggcagtagag | agagccttaa | atcagtatag | agcagaagac | 960 |
| aaccttaggg | acctcaatga | ccacaagtca | actattcagc | tgcctccctg | gctgtcctat | 1020 |
| catgatgtcg | atggcaaaga | tctgtgccct | cttcagggac | tagatgtgag | aggggaccat | 1080 |
| cccatgtgca | acttgtggag | ggaagtggtc | acctctgcaa | acctagagga | gattgagagg | 1140 |
| atgcacgatg | atgcagcagc | agaacttgag | tttgctttcg | ggagtaaagg | acaggccaga | 1200 |
| gagagaaaca | gataccatag | agtccaccta | aatatgggct | cagatgtatt | agtctacata | 1260 |
| gctgctttag | gagttaatgg | aaagaagcat | aaagcagaca | ctttagtgca | acaaatgaga | 1320 |
| gacaggagta | aacagccttt | ctccccagac | cacgatgtga | tcacatatct | gaatttctct | 1380 |
| ctgcatgctc | tagtgacttg | tgggcaacag | atgaggacct | gtacagccct | ctctcttgtg | 1440 |
| ataagagatt | cagttggcag | cccagaggat | tcatcagcca | tccttgtcag | aaagggtttt | 1500 |
| catgagatca | taacagagca | ctacaaattc | atgggaagta | ggataggtca | tggttgccaa | 1560 |
| atggtcagct | tgataggagc | tgagctatca | gcttctgtta | aacaacatgt | caagcctaac | 1620 |
| tactttgtga | ttaaacgact | actaggttct | gggatttttct | tgctaatcaa | gcccacttcc | 1680 |
| agcaaaagcc | atatatttgt | gtcttttgca | ttaagcgctc | ttgctgggcc | tttgatctct | 1740 |
| ccacttccag | ggttttcaag | ccctactaag | atgctgggga | ttctgttagt | tactgacttt | 1800 |
| gtttcttata | agctaagcaa | gcttaccaac | ctctgcaagt | gcgtttcatt | aatggagtcc | 1860 |
| tccttctcat | tctgggcaga | agcatttgga | attcaagctg | gaactttggt | tggtgacttt | 1920 |
| gttccaaggt | cttcagactc | tgcagcaatg | gatgcctcat | acatgggcaa | actttcttta | 1980 |
| ttaaccctt | tggaagacaa | agcagcaact | gaagagttac | agactattgc | aagatatata | 2040 |
| atcatggagg | gctttgtctc | gcccccagaa | atcccaaaac | tcacaagat | gacctctaag | 2100 |
| tttcctaagg | ttctcaggtc | agagctgcaa | gtttacttat | aaactgctt | atgcagaact | 2160 |
| atccagagaa | tagcaggtga | gcccttcatt | cttaagaaga | aggatgggtc | tatatcctgg | 2220 |

-continued

```
ggtggcatgt tcaatccttt ttcagggcgt ccactgcttg atatgcaacc actcatcagc    2280
tgttgttaca atggttactt taaaaataaa gaagaagaga ctgagccttc gtccctttct    2340
gggatgtata agaaaatcat agaacttgag caccttagac cacagtcaga tgccttcttg    2400
ggttacaaag atccagaact tcccagaatg catgagttca gtgtttccta cttgaaggag    2460
gcttgcaatc atgctaagct agtcttgagg agcctctatg gacagaattt catggagcag    2520
atagacaacc agattattcg agagctcagt gggttgactc tagaaaggtt ggccacgctt    2580
aaggccacaa gcaactttaa tgagaattgg tatgtctata aggatgtagc agacaaaaac    2640
tacacaaggg ataaattatt agtgaagatg tcaaaatatg cctctgaggg aaagagccta    2700
gctatccaga gtttgagga ttgtatgagg cagatagagt cacaaggatg catgcatatt    2760
tgtttgttta agaaacaaca gcatggaggt ctgagagaga tctatgtgat gggtgcagag    2820
gaaagaattg ttcaatcggt ggtggagaca atagccaggt ccatagggaa gttctttgct    2880
tctgataccc tctgtaaccc ccccaataaa gtgaaaattc ctgaaacaca tggcatcagg    2940
gcccggaagc aatgtaaggg gcctgtgtgg acttgtgcaa catcagatga tgcaaggaag    3000
tggaaccaag gccattttgt tacaaagttt gccctcatgc tgtgtgagtt cacctctcct    3060
aaatggtggc cgctgatcat taggggatgc tcaatgttta ccaagaaaag gatgatgatg    3120
aatttgaatt atcttaagat cctggatggt catcgggagc ttgatattag agatgacttt    3180
gtgatggatc tcttcaaggc ttatcatggc gaggcagaag ttccatgggc ctttaaaggc    3240
aaaacatatt tggaaaccac aacagggatg atgcaggaa tactgcatta tacttcctca    3300
ctattacaca ccattcacca agaatacatc cggtccttgt cctttaagat attcaacctg    3360
aaggttgctc ctgagatgag caagagcctg gtttgtgaca tgatgcaagg atcagatgat    3420
agtagtatgc taatcagctt cccagctgat gatgagaagg ttcttaccag atgcaaagtg    3480
gccgcagcta tatgcttccg catgaagaag gagctgggga tgtaccttgc catttacccc    3540
tcagagaagt ccacagcaaa cacagatttt gtgatggagt acaattctga attttatttc    3600
cacacccagc atgttagacc aacgatcagg tggattgcag cttgttgcag cctgccagaa    3660
gtggaaacac tagtagcccg ccaggaagag gcctctaacc taatgacttc agttactgag    3720
ggaggtgggt cattctcctt agctgcaata attcagcaag ctcagtgtac tctccattac    3780
atgctgatgg gcatgggagt gtctgagcta ttcttagagt ataagaaggc agtgctgaag    3840
tggaatgacc ctggcctggg tttcttcctg cttgacaatc cttatgcgtg cggattggga    3900
ggtttcagat ttaatctctt caaagctatc accagaactg atttgcagaa gctatatgct    3960
ttcttcatga agaaggtcaa gggctcagct gctagggact gggcagatga agatgtcacc    4020
atcccagaaa cgtgtagcgt gagcccaggt ggcgctctaa ttcttagctc ctctctaaag    4080
tggggatcta ggaagaagtt tcagaaattg agagaccgtt tgaacatacc agagaactgg    4140
attgaactaa taaatgagaa tccagaggtg ctctatcggg ctcccagaac aggcccagaa    4200
atattgttgc gcattgcaga gaaagtccat agcccaggtg ttgtgtcatc attgtcttct    4260
ggcaatgcag tttgtaaagt catggcctca gctgtatact tcttatcagc aacaattttt    4320
gaggacactg gacgtcctga gttcaacttc ttggaggatt ctaagtatag cttgctacaa    4380
aagatggctg catattctgg cttttcatggt ttcaatgata tggagccaga agatatatta    4440 ttccttattcc cgaatattga ggaattagaa tcactggatt ctatagttta caacaaggga    4500
gaaatagaca tcatcccaag agtcaacatc agggatgcaa cccaaaccag ggtcactatc    4560
```

-continued

```
tttaatgagc agaagaacct ccggacatct ccagagaagt tggtgtcaga caagtggttt    4620
gggactcaga agagtaggat aggcaaaaca accttcctgg ctgaatggga aaagctaaag    4680
aaaattgtaa agtggttgga agacgctcca gaagcaactc tagctcacac cccactgaat    4740
aaccatattc aagttaggaa tttctttgct agaatggaaa gcaagcctag aacagtcaga    4800
ataacaggag ctccagtaaa gaagaggtca ggggttagta agatagctat ggttatccgt    4860
gaccatttct cccggatggg ccatcttcga ggtgtagaag accttgctgg tttcactcgt    4920
agtgtgtcag ctgaaattct caagcacttt ctattctgta tactacaagg tccatacagt    4980
gagagctata agctacagct aatctacaga gtcctaagct cagtgtcaaa cgttgagata    5040
aaggaatcag atggtaagac aaaaaccaac ttgattggaa tccttcagag atttctagat    5100
ggtgatcacg ttgtccccat aattgaagag atgggagccg aacagtggg tggattcatc    5160 aagagacaac aatctaaagt tgtgcagaac aaagtggtct attatggggt tgggatttgg    5220
agaggcttca tggatggata tcaggtccat ctagagatag aaaatgacat aggacagccc    5280
ccaaggctta ggaatgtcac aactaactgt cagagcagcc catgggacct gagtattcca    5340
ataaggcaat gggcagaaga catggggtc acaaacaacc aggattattc ctctaaatct    5400
agcagggggg ccagatattg gatgcattca ttcaggatgc aaggacctag caagccattt    5460
ggatgcccag tttatattat taaggtgat atgtcagatg tcatcagact gagaaaggag    5520
gaggtggaga tgaaagtacg gggctctact ctcaacttgt acaccaagca ccattctcat    5580
caggacctac acattctatc ttacactgca tcagacaatg atctcagtcc aggcattttc    5640
aagtcaatat cagatgaggg ggtggctcaa gccctgcaat tatttgagag ggagccaagc    5700
aactgctggg tgagatgtga gtctgtagcc ccaaaattta tatcagccat ccttgagata    5760
tgtgagggga agagacagat aaagggaatt aacagaacca gactctcaga gattgtgaga    5820
atttgttctg aatcttccct aagatcaaaa gtcggatcta tgttctcatt tgtcgccaat    5880
gtcgaggagg cccatgatgt tgattatgat gcgttaatgg atctaatgat agaggatgcc    5940
aagaacaatg cattcagtca tgttgttgac tgcatagagt tggatgttag tggcccttac    6000
gagatggagt cttttcatgg taggtctact ctaacttgta caccaagcac cattctcatc    6060
aggacctaca cattctatct tacactgcat cagacaatga tctcagtcca ggcatttcaa    6120
gtcatattag atgagggggt gctcttaata gccctagtta acaattattt gagagggagc    6180
aaagcaaact gctgggtgag atgtgagtct gtagccccaa aatttatatc agccatcctt    6240
gagatatgtg aggggaagag acagataaag ggaattaaca gaaccagact ctcagagatt    6300
gtagaatttg ttctgaatct tcctaagatc aaaagtcgga tctatgttct catttgtcgc    6360
caatgtcatg gcgcaaattt tcctccgata tctgtcagaa ggctgatgct ggaagacatc    6420
gcatcagtcg cacgaaggct gatcattgtc gcatcgttcg gtagctaaaa ctgaccgcta    6480
gcaaatccta gcctagttca aacatcgagc catattctct tgccaatcg actgatctcg    6540 acctttacg acttccgcga catcttgttc tgcgccatat agatccatga ttgggcgcct    6600
ttgtgt                                                              6606
```

<210> SEQ ID NO 273
<211> LENGTH: 7279
<212> TYPE: DNA
<213> ORGANISM: Lassa virus
<220> FEATURE:

<400> SEQUENCE: 273

-continued

```
cgcaccgggg atcctaggca atttggttgt ctttttttga ggccttgtgc gctgtacttc      60
tccaaatggg aaacaagcaa gccaaagccc cagaatcaaa agacagtccg agagccagcc     120
tgatcccaga tgccacacat ctagggccac agttctgtaa gagctgctgg ttcgaaaaca     180
agggcctggt tgagtgcaac aaccactatc tgtgtctcaa ctgcctcacc ttacttctaa     240
gtgtcagcaa caggtgtccc atttgcaaga tgcctctccc cacaaaactg agaccatcag     300
ccgctccaac agcacctcca accggagcag cggacagcat cagaccccca ccctacagtc     360
cctgaatctc ccaccgaccc ccaccactcc catcctcccc ccgacacccc cggggggac     420 ccccccgccgg gggccccccc gggggagcca accatcacca aaaaactact caatgtcttc     480
gatgcattca tccttcctag tcagctcctc acatgttctg cccttcaatc tcaatttacc     540
accacttgat tgtaccatca cctttcccct tgacttacta taacagagag cataaccctt     600
gaactccacc cagttgtcca ctgcctcaag aaccgcactc aagatcccct cacaactcgg     660
cgctgcagcc ctaagtgtgg agacaatgtc caccctgac cactgcatcc ttaaccccag      720
cctgtctatc atcatatcac tcaatgcccc aatcagcagg tcagacgaag tgtccccaac     780
ctctctcaca aatatctcaa gatcctggtc ttgtataaca ggtgtaaagg atgccaattt     840 cttttccacat tcccacaagc ctcccctatg cacaaccagg ggggttggtt cagtgcaagg     900
acccaccaat acaaagtcat actccgtaaa ctgcaacctt ccatatcaa caacaatctc      960 aacagggggtc acatgcccta gttgatttgt gtcaattaaa aactcattaa tgatctcggt    1020
gtcaacatac catgctgatt tgcccttgaa agtaggtcct gacaaaacca gtctccaaca    1080
gtctgacaag acacacggac tcactgcacc tgagtacata acggttacat catgtactag    1140
atacttggcc tgttgattca ttgagccagt atactcaagg tggatggcaa agctttcctt    1200
aaaactagca tcttgacttt taacacggaa cctcactgtc tgactcagtt ttgcagaccc    1260
tggaggtagt gaagctacgg catcaaagaa atcctccaat gagtcaaaact taggatcaac    1320 taaacctgat gcgatcaatt gatttttgatt gaatctagct ggctcaatat caaagtctat    1380
ccaagcataa cccatcatca gatcatgctt aaacattggc cttttcaacac ctttgtgaat    1440 aactttctct acaaatgaag aaaatggacc cattctatgc aacccttcac cctctggaac    1500
tgatgtcttg tgtggaaacc acgtgaagga ccccaatgtt cttgtagtcg caacaaatgg    1560
tctcacgtaa gactcaaaat aaatttgcct catgaaattg tcaacagcat cactagtgct    1620
cactactctt tcttccacca tgggttcatg tgtcctactg tgagacaacc tcaattcaga    1680
tgataacaca atgtaatgtt cctctctttt ccattttact atgtgtgaga caagagacaa    1740
ggcttcacag ttaacatcca acgctacaca gagatctaga aatttttattc tgggtgacca    1800 cttcattttg gttgacgcta atcgctcat gaatggtaat atgtgtttct caaacactga    1860
tgggtacagc cttcttaaag aatgaatgat gtgattcaaa ccaaccctat cctccaatag    1920
ttttgatgca gttggcttta agggaaaata gtcacaaggg ttatgtttga aaaaatcaaa    1980
caccttaact gtcttaggtt cccctaagac ccatgcaccc agttctattg cagttgataa    2040
ggagatgcac atataatccc ataacaaggg tctgaaataa ctgaccacac tttcacctcc    2100
acttccattt ctaagttcta gcggaacttg ccaatattga atgccattag aatttgtcaa    2160
caatttgatt ccctttgacat cagaaatcag agactgaatg gacttaatat acagattctc    2220
tttatttggt ccccgaacac atttgctacc caatgttctg cacaatccta caaagccaga    2280
tgcaatggaa ctttggaatg cagatttgtt gatagcttca gacagcaatt tttgcgcacc    2340
tcgagtgaaa gtggaagaca acttattttg gattgttttg acaatggtag gaatcttctc    2400
```

```
atcatctagg ttcacagcac ctgaatatat tatcttttgt ctcaacacca ttcttaaagg    2460
atgatgcgca gccaagttta gccaagaata ctcaaggtca gactcagatg ggggctcaac    2520
atccaacagc tcacaaagat tcttagtga tgagaggtgc tcactagaca aatagtttgt    2580
tgtgaactct tcatggagtt gcccagtctt caacctattg tacagttttc ttaacataga    2640
tctaatcttg ctgcaagcat taggaatcaa tccctctatt tgcctcataa tcctataact    2700
acggttgcca tctacccagt ctctaacatc tgtctcgcaa ttcaataaga atgggtcaat    2760
agggtatctt gcatattgca aaggatttaa ggttcttttc tgtattagat tacataagtg    2820
aacagggaca ccattcgcaa ccgactgatc aatgattgtg tcaattgttt ctgccagttg    2880
gtgtggctct ttacacttta tattgtgaag agctgctgca acgaactttg tcaataatgg    2940
cacttcatct ccccaaacaa aaaatctaga tttaaactct gcaacaaacc tgccaatgac    3000
acttttaggg ctcacaaact tattgagttg atcactcata taatagtgga actctattag    3060
agtcctaaat tcttctgggt ctctttgcaa aagctctgtg agagattgat caaagagaga    3120
aatctgatca tcactagagg tataagcatc tatcgtacca ccgcatatac aactgatagc    3180
ataattaatg aacctctctg aaatgagggc ataaaaatct gatgtgttgt gtaatattcc    3240
ttgacccatg tcaagtattg aactgatgtg agaaggcact acaccagctt ggaaattaga    3300
gtaaagaaaa tcttctgtta ttgactgttt agttttcttc cttaacccta gttgggcttt    3360
aatgaaagac ttcatcatgg ctgtcaccac attaaaaggt atttccacca tttttgtgcat   3420 atgccacata agtagggttg agagatagtc cctccctttt atgtcagctt gcaagtcctt    3480
tgagaggaaa attaaattct gtaagacagt caagaacaaa aatggacaca tcattgggcc    3540
ccacttacta tgatccatgc tataagacac atgtgccaat gaaacattca atttcatgga    3600
aaggatagca ttttcaaatt ccttctcgtt gttcaggcaa ctccctgata actgtaggct    3660
tatagcttca aagtaatctt ctataagtct agtaaacatc tttgttctaa gatcaccaat    3720
atataattct ctgttaccac ccacttgttc tttatatgac aaagaaaact taagccttcc    3780
tgtatcaggt cccactgagt cataagattg tggcgactct tggctataaa aacacaaatt    3840 cttaacatt gctgtggtac agtttgtcag tgacagagcc ttactaagtg cctctgaatt     3900
gctctccctt tcactaattc ttacatcatc agagagttta cccatatcaa acttgaaatt    3960
aaggttcctt gacttataat gagtgtacct ccccataagt gtattcgcat tcatgatcaa    4020
gagtatggac ttaaaacact gaaagtattc atggttaaag tatgtccttg ttgacactgc    4080
ctttgtcaac tctccaatag gacactgtga catatgtcca cagtaaaaat acttctgctt    4140
caatctacta ttctcataga cagcattaca gaattcttca taaaatttac ctggtaagat    4200
atcatgatca aactcctcaa ccatgtgatt ggataattca cccttgatca acctaatgta    4260
aaacttattt gagacaatct catctagatc atttattgat ggttggccat caccattagg    4320
gcctgagcct agcttgacag gttccctata ctgatcaaca attttttcaa cagtctcctt    4380
tagctgatca aaataatcgc ttgcacctcc atcgagcaaa atttcgtcta ggtcagcccc    4440
atcagcatca cttttgagct gcccagatcc tagaaccaaa ttgctcattg cctgctgaac    4500
tttgtactca tagtcctgct tgttgagaag gtactttcct ttccttgaga agacttcagt    4560
gagctgcgac acggccagtg ctgtgagctt attgaagtca tagtttaata ttctagaacc    4620
atctgtgtat ttattaacaa caacactttt cttgctggct aaatccaagg ctgcactgcc    4680
actggtgatg agaggatctt tgatttccct ttttacttcc ctctccttaa atagtgaacc    4740
```

```
attgttaaaa gaggatgtaa gaagagataa atacttcttt gaaacaccag gcctttata    4800 atctggtccc tcgatagttg tgcatccatc tttacttaaa aactttttg cattgtagac    4860 catgtcatcc aattcttcct cagtggctgt gtctgcagga ttagtgctca catgaccaaa   4920 tctcacctt ggttccagaa acttctcaaa acatttatc tgatctgtca atctatctgg    4980
tgtttctttc gtaatgaagt ggcacatgta ggaaacattc aaaatgaact tgaacctatt   5040
agtcatcatg ctcttcacat cctcagataa aaccagattc attaatgtcc ttattaacct   5100
atagagcagg aactcaacat cagtgattaa ttcttcctt attttgtcaa tgaggtcctt    5160
atgatgataa tctgatagat aagccattac aaagtaccta agattttgga ggagcttttg   5220
agaacgttta ctgggtgag ctaaaattaa aaccaggatc atctttgtca gagacctgat    5280
attgttcaac tgcccttcca gctcattgca atcttctatc caagaaatca tagtgcttat   5340
tgttgtttgt aaaacctcag ctgaaaatat tgctggaaaa tatcttttag gatcagcata   5400
aaatgagcac acctcaccaa cttttgttatc attaatagca tagcacttcg agcactcccc  5460
tgtcttttga taaatcagtt gtaattcagt gttacccaat gaaaactctt gacaatatgc   5520
ttctttgcat ctgaccactt gataccttgc gggtccaaat tcattctgtc tcagctttac   5580
ggtagaagaa gttttcatag agttcaccaa agcgaggctc aatgaggaaa gtctctctaa   5640
gtcagtggtt cccagtagtt ccacatcccc catcacataa gggaatgttt cttcctctgt   5700
tctctgataa ctgattgttg ggacaactcc ggagacatca aagtccataa tcaaatcata   5760
gctgttaagg cagatcacct ccatatcaat tttatagtgg tccacactga tcccaacatc   5820 cttaaagca gtggtggcct tcaaaatggt tttctggaat attgaattga ggatttgatt   5880
cttactcaaa cactgggagg actgtgtgat tctagatctt agcctgttgc ctcgctctcc   5940
ccatttctcg agatccctct ttgttgcctc caaagaaact agtctatctt taactcttaa   6000
gaagcaagac cccaaccacc cttttaaaca cttttgtttc atcaggtcat gcttacttgc   6060
aaggagaatt agtgcatcaa aaattaatag aagtttcctc cttgtgttca atatcctcaa   6120
agattttact ttatttagga atgatctcca gcattgaacc tgacattctc caatagtttg   6180 gtttccccctt ttttcattcc cctcatcaac atttgcatac aaaaatctca atattggtga   6240
tgctctcttg aactggtaaa ttaagtgttc gatattgtct tctgcaacta ccttatcagc   6300
gtacaaattg ttaagctcat taagtaactg gctcttatca acctttaaaa actgaccttc   6360
tatctctcct ttcctcaatc tgttcctaaa cacttgatac tcctcttcga tctgcagctt   6420
tacctcatga gctgttaatt tattattgat gccctggtgg catgaggcaa tcacttcctc   6480
ataatgatta gagcgattgt ccatcagaac atttaaactc tccacccctg ataatctacc   6540
cgaagtcatg aataaagatt cacagagtct gctatactct gactcttcaa aaagtgaatt   6600
actctcctgt gcatacttta aaagtgagaa gagcgtatcc ctcaacttat cattgaccca   6660
gtcaggtatt tgttcattgt agaatgatgt tctcccgtct ataagtggta ttaaattgat   6720
gtcgacactc ttcaggtctt ctttcagctg ctctaatttt ttgaagtcct caatgtactt   6780
ctgctcaaag ttagcaggag atgatctaac aaaacactcc agcagtatta gaacattgcc   6840
cgtcagtttg taaccgtccg ggtaccacaa acatagtgaa ggtgtcaaga ttccatggtc   6900
atggagaatt ctttccacag atttgtcctc actgttatgc tcgcaaccat ttgcgttgca   6960
agaatcaacc tcaatacaga gggacaagag tttcaaccct tccattaata gcatcctagg   7020
ctctgtctgc acaagaaatg ctaacttctg tcttgacaat ctctcgttgt ccactaggta   7080
ttttgatact aagtctttga cacaggctat gtcttcctcc atgtttagct gcaggtatga   7140
```

```
tgttcagaac cctcagaaca tgtggtctgc tagagcaaca gttcgctatg ggatagggtc   7200
ccgtaggggc acagaagaca caagaggcaa ttaaagacaa ttaaataaga tagccttaat   7260
gcctaggatc ctcggtgcg                                                7279

<210> SEQ ID NO 274
<211> LENGTH: 3402
<212> TYPE: DNA
<213> ORGANISM: Lassa virus
<220> FEATURE:

<400> SEQUENCE: 274
cgcacagtgg atcctaggct attggattgc gctttgcttt tgtcattttg gcagatagtc     60
tcagttcttt gttgcgtgca tacaacacaa caatctggcg atgagtgcct caaaggaaat   120
aaaatccttt ttgtggacac aatctttgag gagggaatta tctggttact gctccaacat   180
caaactacag gtggtgaaag atgcccaggc tcttttacat ggacttgact ctccgaagt    240 cagtaatgtt caacggttga tgcgcaagga gagaagggat gacaatgatt gaaacggtt    300 gagggaccta aatcaagcgg tcaacaatct tgttgaatta aaatcaactc aacaaaagag   360
tatactgaga gttgggactc taacctcaga tgacttatta atcttagccg ctgatctaga   420
gaagttaaag tcaaaggtga tcagaacaga aaggccatta agtgcaggtg tctatatggg   480
caacctaagc tcacagcaac ttgaccaaag aagagctctc ctgaatatga taggaatgag   540
tggtggtaat caaggggctc gggctgggag agatggagtg tgagagtttt gggatgtgaa   600
aaatgcagag ttgctcaata atcagttcgg gaccatgcca agtctgacac tggcatgtct   660
gacaaaacag gggcaggttg acttgaatga tgcagtacaa gcattgacag atttgggttt   720
gatctacaca gcaaagtatc ccaacacttc agacttagac aggctgactc aaagtcatcc   780
catcctaaat atgattgaca ccaagaaaag ctcttttgaat atctcaggtt ataattttag   840
cttgggtgca gctgtgaagg caggagcttg catgctggat ggtggcaata tgttggagac   900
aatcaaggtg tcacctcaga caatggatgg tatcctcaaa tccatttttaa aggtcaagaa   960 ggctcttgga atgttcattt cagacacccc tggtgaaagg aatccttatg aaaacatact   1020
ctacaagatt tgtttgtcag agatggatg ccatatatt gcatcaagaa cctcaataac   1080
aggaagggcc tgggaaaaca ctgtcgttga tctggaatca gatgggaagc cacagaaagc   1140
tgacagcaac aattccagta atccctgca gtcggcaggg tttaccgctg ggcttaccta   1200
ttctcagctg atgaccctca aggatgcaat gctgcaactt gacccaaatg ctaagacctg   1260
gatggacatt gaaggaagac ctgaagatcc agtggaaatt gccctctatc aaccaagttc   1320
aggctgctac atacacttct tccgtgaacc tactgattta aagcagttca gcaggatgc   1380 taagtactca catgggattg atgtcacaga cctcttcgct acacaaccgg gcttgaccag   1440
tgctgtcatt gatgcactcc cccggaatat ggtcattacc tgtcaggggt ccgatgacat   1500
aaggaaactc cttgaatcac aaggaagaaa agacattaaa ctaattgata ttgccctcag   1560
caaaactgat tccaggaagt atgaaaatgc agtctgggac cagtataaag acttatgcca   1620
catgcacaca ggtgtcgttg ttgaaaagaa gaaagagagc ggtaaagagg aaataacccc   1680
tcactgtgca ctaatggact gcatcatgtt tgatgcagca gtgtcaggag actgaacac    1740 atcggttttg agagcagtgc tgcccagaga tatggtgttc agaacatcga cacctagagt   1800
cgttctgtaa atggacgccc ccgtgaccca ccgccaatag gcggtgggtc acggggccc    1860 tgacaagggt ctcatctctt ccatttcaca ggcacaccag gctgtttgta gagtccacag   1920
```

```
gaacaaatgc ccatatgatt caatctgtga ggtttgggac acgacttgcc tacaatatgc   1980
ctatgagttg gtattttgac taggtgaagg aagatgctaa taagatagaa acttgtactg   2040
aacacaaaga ggtcaactag acccaatggt gtcttcccct gcctctccat atactccttc   2100
tgtaacatct cagtgatcat attgtcagct tgttgttcaa tatcatcaga aaagtgggtc   2160
tcgttcaagt atgaaccatt tgatacaagc caacatttgg gcagtgatgt tctcccagta   2220
gttgtgtggt tgaggtacca atacttgctg taattacagt atggaattcc catgatgtcc   2280
cgtagatggt tcttcattat aagttggtca tttatcaaag catttactgc tttgttgatc   2340
aactgaatgc tcatttgtgc ttcagctttc aacctttgaa tggcttgttt gttgaagtca   2400
aacagcctca gcatgtcaca aaattcctca tcatgcttct cattacattt tgccacagct   2460
gtgttcccga agcattttag ttcagcctca attagcatcc acctggtcag acaatatccc   2520
cctggtgtgt ctttaccttc agaatctgac agtgtccatg tgaatgtgcc tagcaatctt   2580
ctactaatat aaatatctct agtcctttgt gagaggagcc cgagataacc gatgggagat   2640
ggtctcgaga attggcagtg atcttcccag gttgtatttt ggattatcag atattgataa   2700
ctagtcataa tacagtccca gttgccacgg cctgagtcaa gagcaatgta gctcccaccc   2760
caagccatcc tcataaaagt ctgtaacaca ccatttgcaa cagtaccaca atggttggct   2820
gcatccccag catagctgtg actcaggttg tactgcacac taatctttcc cccattaaaa   2880
tcgcagctca ttgcctcata ctgattgaag ttggggatgg acaagtggaa agttgagatt   2940
atgctcataa gagcgtggtc atagaggttc tttttgtggg catcagacag attgcaaaat   3000
ttgtgattaa taatgctcgt gttggtcaag gtcagttcta gtcctgtctc attgcccacc   3060
attatataat gatgactgtt gttctttgtg caggagagag gcatggtcat attgagtgtc   3120
tccatgttta gttccagagt ctgaagctca taaaccccctt tataaagact ggttgtgcaa   3180
gacctaccac acaacaggag gaaagtgacc aaaccaacaa ggccacacgt tgcaaaattg   3240
tacagacctt tcagcactgc tagtacagac agtgcaatga gaacaatgtt catcacctct   3300
tctattacat gaggcacttc ctggaagaat gtcactattt gtcccatttt aaataggaca   3360
cttgaattgc gcaaccaaaa atgcctagga tccccggtgc gc                      3402

<210> SEQ ID NO 275
<211> LENGTH: 510
<212> TYPE: DNA
<213> ORGANISM: Artificial Sequence
<220> FEATURE:
<223> OTHER INFORMATION: Calibration sequence

<400> SEQUENCE: 275
aatgttcaaa cactttgtga agctctgtta gctgatggtc ttgccatttc ctagcaatat     60
gatggtagtt acggaacgtg agcaaaaaga aagcttattg catcaagcat catggcacca    120
cacaagtgat gattttggtg accacagtta gagggagtag ctttgtaact gatttagaga    180
aatacaatct tgcatttaga tatgagttta cagcaccttt tatagaatat tgcaaccgtt    240
gctatggtgt taagaatgtt tttaattgga tgcattatcc cacagtgtta tatgcatgtc    300
agtgattatt ataatccacc acataacctc agagaatcga dacaaccccc ccgaagggcc    360
tagttcatac agggtcata tgggagggat tgaaggactg caacaaaaac tctggacaag    420
tatttcatgt gctcaaattt ctttagttga aattaagttt taagttacgc tcagctgtga    480
tgggtgacaa tcagtgcatt actgtttat                                       510
```

COMPOSITIONS FOR USE IN IDENTIFICATION OF VIRAL HEMORRHAGIC FEVER VIRUSES

CROSS REFERENCE TO RELATED APPLICATIONS

This application claims the benefit of priority to U.S. Provisional Application Ser. No. 60/555,520 filed Mar. 22, 2004, which is incorporated herein by reference in its entirety.

STATEMENT OF GOVERNMENT SUPPORT

This invention was made with United States Government support under DARPA/SPO contract BAA00-09. The United States Government may have certain rights in the invention.

FIELD OF THE INVENTION

The present invention relates generally to the field of genetic identification and quantification of viruses in the Filoviridae, Flaviviridae, Bunyaviridae and Arenaviridae families and provides methods, compositions and kits useful for this purpose, as well as others, when combined with molecular mass analysis.

BACKGROUND OF THE INVENTION

A. Viral Hemorrhagic Fever

Viral hemorrhagic fevers (VHFs) are a group of febrile illnesses caused by RNA viruses from several viral families. These highly infectious viruses lead to a potentially lethal disease syndrome characterized by fever, malaise, vomiting, mucosal and gastrointestinal (GI) bleeding, edema and hypotension. The four viral families known to cause VHF disease in humans include Arenaviridae, Bunyaviridae, Filoviridae and Flaviviridae.

In acute VHF, patients are extremely viremic, and mRNA evidence of multiple events cytokine activation exists. In vitro studies reveal these cytokines lead to shock and increased vascular permeability, the basic pathophysiologic processes most often seen with VHF. Multi-system organ failure affecting the hematopoietic, neurologic and pulmonary systems often accompanies the vascular involvement. Another prominent pathologic feature is pronounced macrophage involvement. Inadequate or delayed immune response to these novel viral antigens may lead to rapid development of overwhelming viremia. Extensive infection and necrosis of affected organs also are described. Hemorrhagic complications are multifactorial and are related to hepatic damage, consumptive coagulopathy and primary marrow injury to megakaryocytes. Aerosol transmission of some VHF viruses is reported among nonhuman primates and likely is a mode of transmission in patients with severe infection. Specific symptoms of VHF and modes of transmission vary depending on the particular viral pathogen.

B. Filoviruses

Filoviruses are enveloped viruses with a genome consisting of one linear single-stranded RNA segment of negative polarity. The viral genome encodes 7 proteins. Nucleoprotein (NP), virion protein 35 kDa (VP35) and virion protein 30 kDa (VP30) are associated with the viral ribonucleoprotein complex. VP35 is known to be required for virus replication and is thought to function as a polymerase cofactor. The viral RNA-dependent RNA polymerase is termed L (for large protein). The matrix protein (VP40) is the major protein of the viral capsid. The remaining proteins include virion glycoprotein (GP) and membrane-associated protein (VP24), which is thought to form ion channels. The Ebola viruses have one additional protein, small secreted glycoprotein (SGP).

Members of the filovirus genus include Zaire Ebola virus, Sudan Ebola virus, Reston Ebola virus, Cote d'Ivoire Ebola virus and Marburg virus. Ebola and Marburg viruses can cause severe hemorrhagic fever and have a high mortality rate. Ebola virus (Zaire and Sudan species) was first described in 1976 after outbreaks of a febrile, rapidly fatal hemorrhagic illness were reported along the Ebola River in Zaire (now the Democratic Republic of the Congo) and Sudan. Sporadic outbreaks have continued since that time, usually in isolated areas of central Africa. In 1995, eighteen years after the first outbreak was reported, Zaire Ebola reemerged in Kikwit, Zaire with 317 confirmed cases and an 81% mortality rate. The natural host for Ebola viruses is still unknown. Marburg virus, named after the German town where it was first reported in 1967, is primarily found in equatorial Africa. The host range of Marburg virus includes non-human and human primates. Marburg made its first appearance in Zimbabwe in 1975 and was later identified in other African countries, including Kenya (1980 & 1987) and Democratic Republic of the Congo (1999). Marburg hemorrhagic fever is characterized by fever, abdominal pain, hemorrhage, shock and a mortality rate of 25% or greater ("The Springer Index of Viruses," pgs. 296-303, Tidona and Darai eds., 2001, Springer, N.Y.).

C. Flaviviruses

Flaviviridae is a family of viruses that includes the genera flavivirus, hepacivirus and pestivirus. Viruses in the genus flavivirus are known to cause VHFs. Flaviviruses are enveloped viruses with a genome consisting of one linear single-stranded RNA segment of positive polarity. The RNA genome has a single open reading frame and is translated as a polyprotein. The polyprotein is co- and post-transcriptionally cleaved by cell signal peptidase and the viral protease to generate individual viral proteins. Viral structural proteins include capsid (C), precursor to M (prM), minor envelope (M) and major envelope (E). Flavivirus non-structural proteins include NS1, NS2A, NS2B, NS3, NS4A, NS4B and NS5. NS1, NS2A, NS3 and NS4A are found in the viral replicase complex. In addition, NS3 is known to function as the viral protease, helicase and NTPase. NS2B is a co-factor for the protease function of NS3. NS5 is the viral RNA-dependent RNA polymerase and also has methyltransferase activity.

Members of the flavivirus genus include yellow fever virus, Apoi virus, Aroa virus, Bagaza virus, Banzi virus, Bouboui virus, Bukalasa bat virus, Cacipacore virus, Carey Island virus, Cowbone Ridge virus, Dakar bat virus, dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Sal Vieja virus, San Perlita virus, Saumarez Reef virus, Sepik virus, St. Louis encephalitis virus, Tembusu virus, tick-borne encephalitis virus, Tyuleniy virus, Uganda S virus, Usutu virus, Wesselsbron virus, West Nile virus, Yaounde virus, Yokose virus, Zika virus, cell fusing agent virus and Tamana bat virus.

A number of flaviviruses cause human disease, particularly hemorrhagic fevers and encephalitis. Each species of flavivirus has a unique geographic distribution; however, taken together, flaviviruses, and flavivirus-induced disease, can be found world-wide. One of the more commonly known diseases is dengue fever, or dengue hemorrhagic fever/shock, which was first described as a virus-induced illness in 1960. Dengue fever occurs in tropical and temperate climates-and is spread by Aedes mosquitoes. The mortality rate is 1-10% and symptoms include febrile headache, joint pain, rash, capillary leakage, hemorrhage and shock. Another common flavivirus-induced disease is yellow fever. Yellow fever is found in tropical Africa and America and is transmitted by mosquitoes. The mortality rate is approximately 30% and symptoms include febrile headache, myalgia (muscle pain), vomiting and jaundice. Examples of some of the other diseases caused by flavivirus species include Japanese encephalitis, Kyasanur Forest disease, Murray Valley encephalitis, Omsk hemorrhagic fever, St. Louis encephalitis and West Nile fever. The mortality rate of these diseases ranges from 0-20%. These diseases share many of the same symptoms, which may include headache, myalgia, fever, hemorrhage, encephalitis, paralysis and rash ("The Springer Index of Viruses," pgs. 306-319, Tidona and Darai eds., 2001, Springer, N.Y).

D. Bunyaviridae

Bunyaviridae is a family of viruses that includes the genera bunyavirus, phlebovirus, nairovirus, hantavirus and tospovirus. Viruses in three of these genera, hantavirus, phlebovirus and nairovirus, are known to cause VHFs. Members of the Bunyaviridae family are enveloped viruses with a genome that consists of 3 single-stranded RNA segments of negative polarity. The genome segments are designated S (small), M (medium) and L (large). The S segment encodes the nucleocapsid protein (N). The two viral glycoproteins (G1 and G2) are encoded by the M segment and the L segment encodes the viral RNA-dependent RNA polymerase (L). For some Bunyaviridae species, additional viral non-structural proteins are encoded by the S and/or M segment ("The Springer Index of Viruses," pgs. 141-174, Tidona and Darai eds., 2001, Springer, N.Y.).

Members of the hantavirus genus include, Hantaan virus, Seoul virus, Dobrava-Belgrade virus, Thailand virus, Puumala virus, Prospect Hill virus, Tula virus, Khabarovsk virus, Topografov virus, Isla Vista virus, Sin Nombre virus, New York virus, Black Creek virus, Bayou virus, Caño Delgadito virus, Rio Mamore virus, Laguna Negra virus, Muleshoe virus, El Moro Canyon virus, Rio Segundo virus, Andes virus and Thottapalayam virus. Hantaviruses have a wide geographic distribution and typically cause either hemorrhagic fever with renal syndrome (HFRS) or hantavirus pulmonary syndrome (HPS). Symptoms of HFRS include fever, hemorrhage and renal damage, with a mortality rate up to 15%, depending on the hantavirus species. The first documented case of HFRS occurred in 1934 with a notable epidemic among United Nations soldiers during the Korean War (1951). However, the causative agent of HFRS, Hantaan virus, was not isolated until 1978 (Lee et al. J. Inf. Dis., 1978, 137, 298-308). Symptoms of HPS include fever, pulmonary edema, shock and interstitial pneumonitis (a type of pneumonia involving connective tissue). Sin Nombre virus and Andes virus are two of the hantaviruses that cause a severe form HPS, with an approximately 40% mortality rate. A significant outbreak of pulmonary syndrome occurred in the Southwestern United States in 1993. The etiologic agent of the outbreak was later identified as a hantavirus (Sin Nombre) (Nichol et al. Science, 1993, 262, 914-917). The typical route of transmission for hantaviruses is through rodent excreta aerosols, however, Andes virus has been associated with person-to-person transmission ("The Springer Index of Viruses," pgs. 141-174, Tidona and Darai eds., 2001, Springer, N.Y.; Wells et al. Emerg. Infect. Dis., 1997, 3, 171-174).

Members of the phlebovirus genus include Bujaru virus, Chandiru virus, Chilibre virus, Frijoles virus, Punta Toro virus, Rift Valley Fever virus, Salehebad virus, Sandfly fever Naples virus, Uukuniemi virus, Aguacate virus, Anhanga virus, Arboledas virus, Arumowot virus, Caimito virus, Chagres virus, Corfou virus, Gabek Forest virus, Gordil virus, Itaporanga virus, Odrenisrou virus, Pacui virus, Rio Grande virus, Sandfly fever Sicilian virus, Saint-Floris virus and Urucuri virus. Several phleboviruses (e.g., Sandfly fever Naples virus, Sandfly fever Sicilian virus, Chandiru virus and Chagres virus) cause phlebotomus fever, which is typically found in America and the Mediterranean region. Phlebotomus fever, a non-fatal disease, is transmitted by phlebotomines (sand flies) and induces fever, myalgia (muscle pain) and other flu-like symptoms. Rift Valley fever virus, transmitted by mosquitoes, causes a disease of the same name in Africa. Rift Valley fever is characterized by hemorrhagic fever, hepatitis and encephalitis.

Members of the nairovirus genus include Crimean-Congo hemorrhagic fever virus, Dera Ghazi Khan virus, Dugbe virus, Hughes virus, Nairobi sheep disease virus, Qalyub virus, Sakhalin virus and Thiafora virus. Nairoviruses are primarily found in Africa, Asia, Europe and the Middle East. In humans, nairoviruses can cause hemorrhagic fever (Crimean-Congo hemorrhagic fever), Nairobi sheep disease and Dugbe disease. Nairoviruses are typically transmitted to humans by ticks. The first recognized description of Crimean-Congo hemorrhagic fever dates back to the year 1110. This disease is characterized by sudden onset of fever, nausea, severe headache, myalgia and hemorrhage. The mortality rate is approximately 30%. Nairobi sheep disease symptoms include fever, joint pains and general malaise, while Dugbe disease results in fever and prolonged thrombocytopenia (abnormal reduction in platelets) ("The Springer Index of Viruses," pgs. 141-174, Tidona and Darai eds., 2001, Springer, N.Y.).

E. Arenaviruses

Arenavirus is the sole genus of the family Arenaviridae. Arenaviruses are enveloped viruses with a genome that consists of 2 single-stranded RNA segments of negative polarity. The negative-sense RNA of the arenavirus genome serves as both a template for transcription of complementary RNA as well as a template for protein synthesis (ambisense RNA). The genome segments are designated S, which encodes the nucleocapsid protein (NP) and the precursor glycoprotein (GPC), and L, which encodes the zinc-binding protein (Z) and the RNA-dependent RNA polymerase (L).

Members of the arenavirus genus include lymphocytic choriomeningitis virus (LCMV), Lassa virus, Ippy virus, Mobala virus, Mopeia virus, Amapari virus, Flexal virus, Guanarito virus, Junin virus, Latino virus, Machupo virus, Parana virus, Pichinde virus, Pirital virus, Oliveros virus, Sabia virus, Tacaribe virus, Tamiami virus, Whitewater Arroyo virus and Pampa virus. A number of arenaviruses are known to cause disease in humans, including LCMV, Lassa virus, Junin virus, Machupo virus, Guanarito virus and Sabia virus. LCMV has a world-wide geographic distribution and infection with LCMV leads to fever, malaise, weakness, myalgia and severe headache. The remaining disease-causing arenaviruses are more limited in their distribution. Lassa fever is found in West Africa and is characterized by fever, headache, dry cough, exudative pharyngitis and hemorrhage. Sabia fever is found is Brazil with symptoms including fever, headache, myalgia (muscle pain), nausea, vomiting and hemorrhage. Junin virus, Machupo virus and Guanarito virus are the causative agents of Argentinean hemorrhagic fever, Bolivian hemorrhagic fever and Venezuelan hemorrhagic fever, respectively, and as their names suggest, are found only in Argentina, Bolivia and Venezuela. Symptoms of these hemorrhagic fevers include malaise, fever, headache, arthralgia (joint pain), nausea, vomiting, hemorrhage and CNS involvement ("The Springer Index of Viruses," pgs. 36-42, Tidona and Darai eds., 2001, Springer, N.Y).

F. Bioagent Detection

A problem in determining the cause of a natural infectious outbreak or a bioterrorist attack is the sheer variety of organisms that can cause human disease. There are over 1400 organisms infectious to humans; many of these have the potential to emerge suddenly in a natural epidemic or to be used in a malicious attack by bioterrorists (Taylor et al., Philos. Trans. R. Soc. London B. Biol. Sci., 2001, 356, 983-989). This number does not include numerous strain variants, bioengineered versions, or pathogens that infect plants or animals.

Much of the new technology being developed for detection of biological weapons incorporates a polymerase chain reaction (PCR) step based upon the use of highly specific primers and probes designed to selectively detect individual pathogenic organisms. Although this approach is appropriate for the most obvious bioterrorist organisms, like smallpox and anthrax, experience has shown that it is very difficult to predict which of hundreds of possible pathogenic organisms might be employed in a terrorist attack. Likewise, naturally emerging human disease that has caused devastating consequence in public health has come from unexpected families of bacteria, viruses, fungi, or protozoa. Plants and animals also have their natural burden of infectious disease agents and there are equally important biosafety and security concerns for agriculture.

An alternative to single-agent tests is to do broad-range consensus priming of a gene target conserved across groups of bioagents. Broad-range priming has the potential to generate amplification products across entire genera, families, or, as with bacteria, an entire domain of life. This strategy has been successfully employed using consensus 16S ribosomal RNA primers for determining bacterial diversity, both in environmental samples (Schmidt et al., J. Bact., 1991, 173, 4371-4378) and in natural human flora (Kroes et al., Proc Nat Acad Sci (USA), 1999, 96, 14547-14552). The drawback of this approach for unknown bioagent detection and epidemiology is that analysis of the PCR products requires the cloning and sequencing of hundreds to thousands of colonies per sample, which is impractical to perform rapidly or on a large number of samples.

Conservation of sequence is not as universal for viruses, however, large groups of viral species share conserved protein-coding regions, such as regions encoding viral polymerases or helicases. Like bacteria, consensus priming has also been described for detection of several viral families, including coronaviruses (Stephensen et al., Vir. Res., 1999, 60, 181-189), enteroviruses (Oberste et al., J. Virol., 2002, 76, 1244-51); Oberste et al., J. Clin. Virol., 2003, 26, 375-7); Oberste et al., Virus Res., 2003, 91, 241-8), retroid viruses (Mack et al., Proc. Natl. Acad. Sci. U.S.A., 1988, 85, 6977-81); Seifarth et al., AIDS Res. Hum. Retroviruses, 2000, 16, 721-729); Donehower et al., J. Vir. Methods, 1990, 28, 33-46), and adenoviruses (Echavarria et al., J. Clin. Micro., 1998, 36, 3323-3326). However, as with bacteria, there is no adequate analytical method other than sequencing to identify the viral bioagent present.

In contrast to PCR-based methods, mass spectrometry provides detailed information about the molecules being analyzed, including high mass accuracy. It is also a process that can be easily automated. DNA chips with specific probes can only determine the presence or absence of specifically anticipated organisms. Because there are hundreds of thousands of species of benign pathogens, some very similar in sequence to threat organisms, even arrays with 10,000 probes lack the breadth needed to identify a particular organism.

There is a need for a method for identification of bioagents which is both specific and rapid, and in which no culture or nucleic acid sequencing is required. Disclosed in U.S. Patent Application Publication Nos. 2003-0027135, 2003-0082539, 2003-0228571, 2004-0209260, 2004-0219517 and 2004-0180328, and in U.S. application Ser. Nos. 10/660, 997, 10/728,486, 10/754,415 and 10/829,826, all of which are commonly owned and incorporated herein by reference in their entirety, are methods for identification of bioagents (any organism, cell, or virus, living or dead, or a nucleic acid derived from such an organism, cell or virus) in an unbiased manner by molecular mass and base composition analysis of "bioagent identifying amplicons" which are obtained by amplification of segments of essential and conserved genes which are involved in, for example, translation, replication, recombination and repair, transcription, nucleotide metabolism, amino acid metabolism, lipid metabolism, energy generation, uptake, secretion and the like. Examples of these proteins include, but are not limited to, ribosomal RNAs, ribosomal proteins, DNA and RNA polymerases, RNA-dependent RNA polymerases, RNA capping and methylation enzymes, elongation factors, tRNA synthetases, protein chain initiation factors, heat shock protein groEL, phosphoglycerate kinase, NADH dehydrogenase, DNA ligases, DNA gyrases and DNA topoisomerases, helicases, metabolic enzymes, and the like.

To obtain bioagent identifying amplicons, primers are selected to hybridize to conserved sequence regions which bracket variable sequence regions to yield a segment of nucleic acid which can be amplified and which is amenable to methods of molecular mass analysis. The variable sequence regions provide the variability of molecular mass which is used for bioagent identification. Upon amplification by PCR or other amplification methods with the specifically chosen primers, an amplification product that represents a bioagent identifying amplicon is obtained. The molecular mass of the amplification product, obtained by mass spectrometry for example, provides the means to uniquely identify the bioagent without a requirement for prior knowledge of the possible identity of the bioagent. The molecular mass of the amplification product or the corresponding base composition (which can be calculated from the molecular mass of the amplification product) is compared with a database of molecular masses or base compositions and a match indicates the identity of the bioagent. Furthermore, the method can be applied to rapid parallel analyses (for example, in a multi-well plate format) the results of which can be employed in a triangulation identification strategy which is amenable to rapid throughput and does not require nucleic acid sequencing of the amplified target sequence for bioagent identification.

The result of determination of a previously unknown base composition of a previously unknown bioagent (for example, a newly evolved and heretofore unobserved virus) has downstream utility by providing new bioagent indexing information with which to populate base composition databases. The process of subsequent bioagent identification analyses is thus greatly improved as more base composition data for bioagent identifying amplicons becomes available.

The present invention provides, inter alia, methods of identifying unknown viruses, including viruses of the Filoviridae, Flaviviridae, Bunyaviridae and Arenaviridae families. Also provided are oligonucleotide primers, compositions and kits containing the oligonucleotide primers, which define viral bioagent identifying amplicons and, upon amplification, produce corresponding amplification products whose molecular masses provide the means to identify viruses of the Filoviridae, Flaviviridae, Bunyaviridae and Arenaviridae families at the sub-species level.

SUMMARY OF THE INVENTION

The present invention provides primers and compositions comprising pairs of primers, and kits containing the same, and methods for use in identification of viruses in the Filoviridae, Flaviviridae, Bunyaviridae and Arenaviridae families. The primers are designed to produce viral bioagent identifying amplicons of DNA encoding genes essential to virus replication. The invention further provides compositions comprising pairs of primers and kits containing the same, which are designed to provide species and sub-species characterization of members of the Filoviridae, Flaviviridae, Bunyaviridae and Arenaviridae families.

In some embodiments, an oligonucleotide primer 23 to 35 nucleobases in length comprising at least 70% sequence identity with SEQ ID NO: 129, or a composition comprising the same is provided. In other embodiments, an oligonucleotide primer 22 to 35 nucleobases in length comprising at least 70% sequence identity with SEQ ID NO: 164 is provided. In some embodiments, a composition comprising both primers is provided. In some embodiments, either or both of the primers comprises at least one modified nucleobase, such as a 5-propynyluracil or 5-propynylcytosine. In some embodiments, either or both of the primers comprises at least one universal nucleobase, such as inosine. In some embodiments, either or both of the primers further comprises a non-templated T residue on the 5'-end. In some embodiments, either or both of the primers comprises at least one non-template tag. In some embodiments, either or both of the primers comprises at least one molecular mass modifying tag. In some embodiments, the forgoing composition(s) are present within a kit. The kit may also comprise at least one calibration polynucleotide, and/or at least one ion exchange resin linked to magnetic beads.

In some embodiments, methods for identification of an unknown filovirus are provided. In some embodiments, nucleic acid from the filovirus is amplified using the composition described above to obtain an amplification product. The molecular mass of the amplification product is measured. Optionally, the base composition of the amplification product is determined from the molecular mass. The molecular mass or base composition is compared with a plurality of molecular masses or base compositions of known filoviral bioagent identifying amplicons, wherein a match between the molecular mass or base composition and a member of the plurality of molecular masses or base compositions identifies the unknown filovirus. In some embodiments, the molecular mass is measured by mass spectrometry.

In some embodiments, methods of determining the presence or absence of a filovirus in a sample are provided. Nucleic acid from the sample is amplified using the composition described above to obtain an amplification product. The molecular mass of the amplification product is determined. Optionally, the base composition of the amplification product is determined from the molecular mass. The molecular mass or base composition of the amplification product is compared with the known molecular masses or base compositions of one or more known filoviral bioagent identifying amplicons, wherein a match between the molecular mass or base composition of the amplification product and the molecular mass or base composition of one or more known filoviral bioagent identifying amplicons indicates the presence of the filovirus in the sample. In some embodiments, the molecular mass is measured by mass spectrometry.

In some embodiments, methods for determination of the quantity of an unknown filovirus in a sample are provided. The sample is contacted with the composition described above and a known quantity of a calibration polynucleotide comprising a calibration sequence. Nucleic acid from the unknown filovirus in the sample is concurrently amplified with the composition described above and nucleic acid from the calibration polynucleotide in the sample is concurrently amplified with the composition described above to obtain a first amplification product comprising a filoviral bioagent identifying amplicon and a second amplification product comprising a calibration amplicon. The molecular mass and abundance for the filoviral bioagent identifying amplicon and the calibration amplicon is determined. The filoviral bioagent identifying amplicon is distinguished from the calibration amplicon based on molecular mass, wherein comparison of filoviral bioagent identifying amplicon abundance and calibration amplicon abundance indicates the quantity of filovirus in the sample. In some embodiments, the base composition of the filoviral bioagent identifying amplicon is determined.

BRIEF DESCRIPTION OF THE DRAWINGS

The foregoing summary of the invention, as well as the following detailed description of the invention, is better understood when read in conjunction with the accompanying drawings which are included by way of example and not by way of limitation.

FIG. 6A is a flow chart illustrating a method of training an embodiment of a polytope pattern classifier of a lower dimension when the sample space is reduced in dimension by imposing a constraint. FIG. 6B and FIG. 6C are flow charts illustrating the method of identifying a unknown bioagent using different embodiments of a trained polytope pattern classifier.

FIG. 9A and FIG. 9B are three dimensional representations of polytopes defined by applying the G+T (keto/amino preference) binary inequality.

FIG. 11E shows the addition of the three dimensional representation of the Rhodocyclales polytope along with its population, volume and density to the polytope of FIG. 11D; FIG. 11F outlines the polytope for betaproteobacteria order in relationship to the five exemplary taxons.

FIG. 12 is a comparison of the individual probabilities of detecting a bioagent using individual amplicons as compared to the overall probability of classifying the bioagent using multiple amplicons.

DETAILED DESCRIPTION OF EMBODIMENTS

Figure 1:
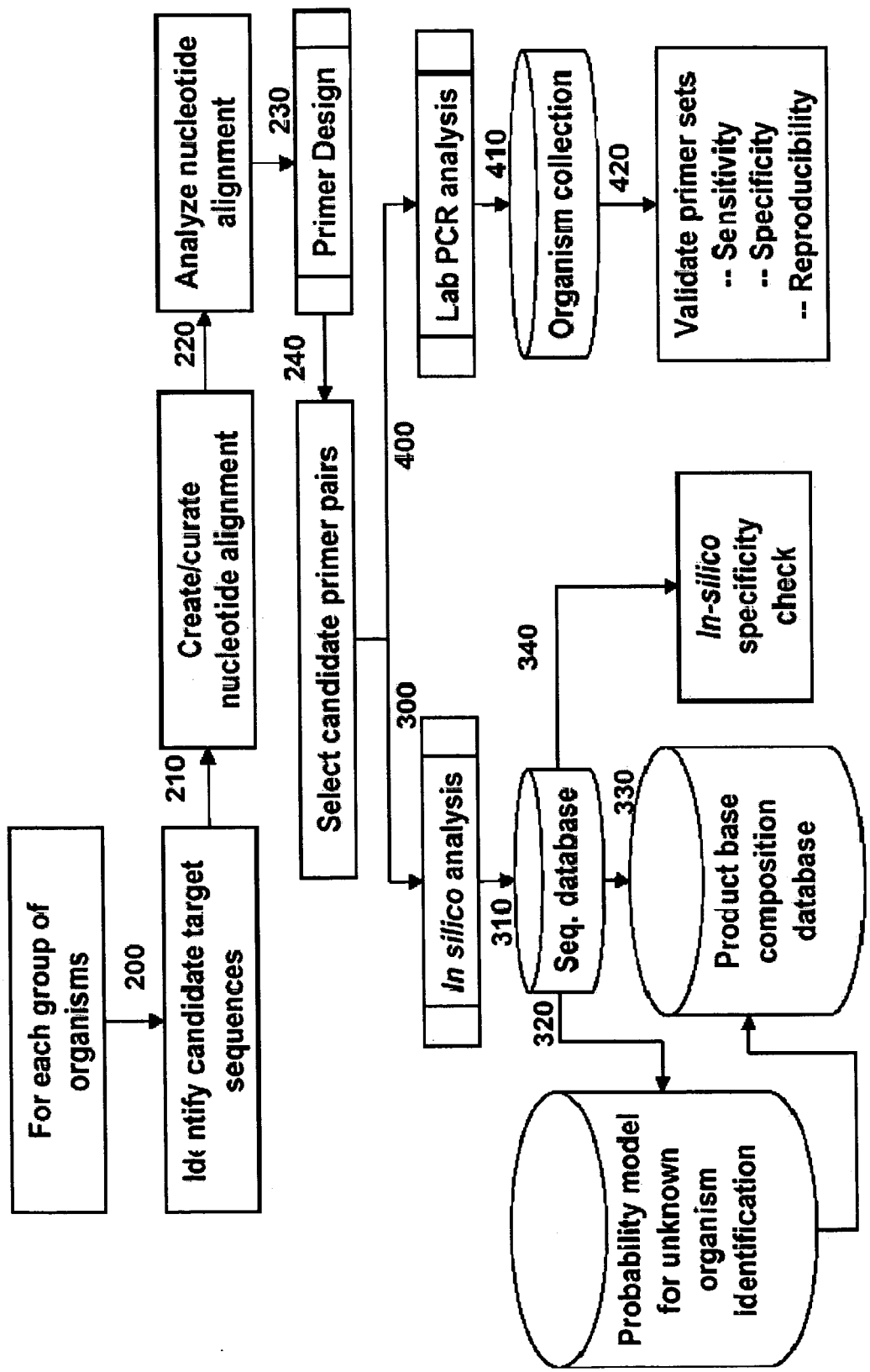
FIG. 1 is a process diagram illustrating a representative primer selection process.
Figure 2:
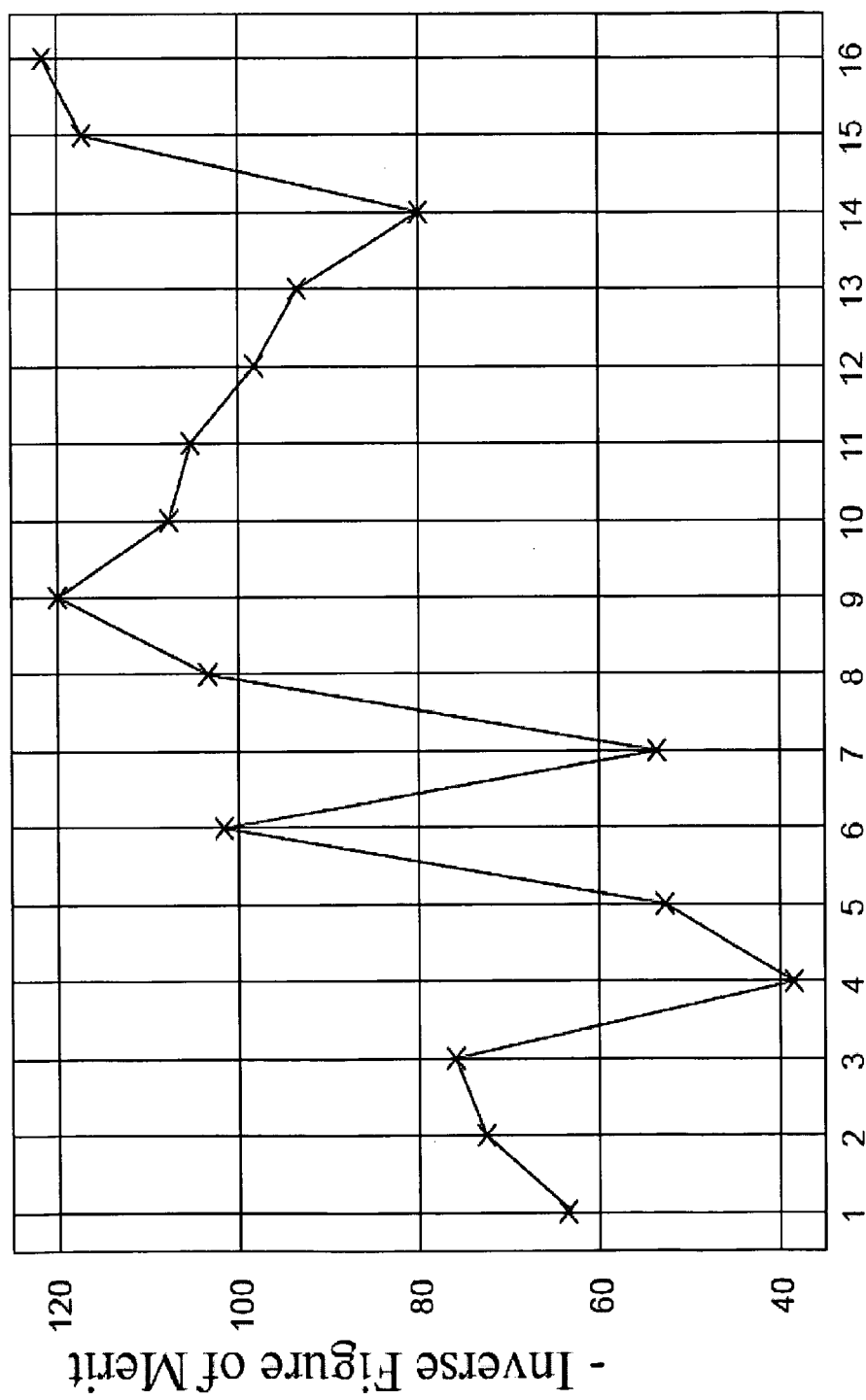
FIG. 2 is a graph of the inverse figure of merit φ plotted for a master list of 16 primer sets in a *Yersinia pestis* target biocluster.

In the context of the present invention, a "bioagent" is any organism, cell, or virus, living or dead, or a nucleic acid derived from such an organism, cell or virus. Examples of bioagents include, but are not limited, to cells, including but not limited to human clinical samples, cell cultures, bacterial cells and other pathogens), viruses, viroids, fungi, protists, parasites, and pathogenicity markers (including, but not limited to: pathogenicity islands, antibiotic resistance genes, virulence factors, toxin genes and other bioregulating compounds). Samples may be alive or dead or in a vegetative state (for example, vegetative bacteria or spores) and may be encapsulated or bioengineered. In the context of this invention, a "pathogen" is a bioagent which causes a disease or disorder.

As used herein, "intelligent primers" are primers that are designed to bind to highly conserved sequence regions of a bioagent identifying amplicon that flank an intervening variable region and yield amplification products which ide-ally provide enough variability to distinguish each individual bioagent, and which are amenable to molecular mass analysis. By the term "highly conserved," it is meant that the sequence regions exhibit between about 80-100%, or between about 90-100%, or between about 95-100% identity among all or at least 70%, at least 80%, at least 90%, at least 95%, or at least 99% of species or strains.

As used herein, "broad range survey primers" are intelligent primers designed to identify an unknown bioagent as a member of a particular division (e.g., an order, family, class, lade, genus or other such grouping of bioagents above the species level of bioagents). In some cases, broad range survey primers are able to identify unknown bioagents at the species or sub-species level. As used herein, "division-wide primers" are intelligent primers designed to identify a bioagent at the species level and "drill-down" primers are intelligent primers designed to identify a bioagent at the sub-species level. As used herein, the "sub-species" level of identification includes, but is not limited to, strains, subtypes, variants, and isolates.

As used herein, a "bioagent division" is defined as group of bioagents above the species level and includes but is not limited to, orders, families, classes, clades, genera or other such groupings of bioagents above the species level.

As used herein, a "sub-species characteristic" is a genetic characteristic that provides the means to distinguish two members of the same bioagent species. For example, one viral strain could be distinguished from another viral strain of the same species by possessing a genetic change (e.g., for example, a nucleotide deletion, addition or substitution) in one of the viral genes, such as the RNA-dependent RNA polymerase. In this case, the sub-species characteristic that can be identified using the methods of the present invention, is the genetic change in the viral polymerase.

As used herein, the term "bioagent identifying amplicon" refers to a polynucleotide that is amplified from a bioagent in an amplification reaction and which 1) provides enough variability to distinguish each individual bioagent and 2) whose molecular mass is amenable to molecular mass determination.

As used herein, a "base composition" is the exact number of each nucleobase (A, T, C and G) in a given sequence.

As used herein, a "base composition signature" (BCS) is the exact base composition (i.e., the number of A, T, G and C nucleobases) determined from the molecular mass of a bioagent identifying amplicon.

As used herein, a "base composition probability cloud" is a representation of the diversity in base composition resulting from a variation in sequence that occurs among different isolates of a given species. The "base composition probability cloud" represents the base composition constraints for each species and is typically visualized using a pseudo four-dimensional plot.

As used herein, a "wobble base" is a variation in a codon found at the third nucleotide position of a DNA triplet. Variations in conserved regions of sequence are often found at the third nucleotide position due to redundancy in the amino acid code.

In the context of the present invention, the term "unknown bioagent" may mean either: (i) a bioagent whose existence is known (such as the well known bacterial species *Staphylococcus aureus* for example) but which is not known to be in a sample to be analyzed, or (ii) a bioagent whose existence is not known (for example, the SARS coronavirus was unknown prior to April 2003). For example, if the method for identification of coronaviruses disclosed in commonly owned U.S. patent Ser. No. 10/829,826 (incorporated herein by reference in its entirety) was to be employed prior to April 2003 to identify the SARS coronavirus in a clinical sample, both meanings of "unknown" bioagent are applicable since the SARS coronavirus was unknown to science prior to April, 2003 and since it was not known what bioagent (in this case a coronavirus) was present in the sample. On the other hand, if the method of U.S. patent Ser. No. 10/829,826 was to be employed subsequent to April 2003 to identify the SARS coronavirus in a clinical sample, only the first meaning (i) of "unknown" bioagent would apply since the SARS coronavirus became known to science subsequent to April 2003 and since it was not known what bioagent was present in the sample.

As used herein, "triangulation identification" means the employment of more than one bioagent identifying amplicons for identification of a bioagent.

In the context of the present invention, "viral nucleic acid" includes, but is not limited to, DNA, RNA, or DNA that has been obtained from viral RNA, such as, for example, by performing a reverse transcription reaction. Viral RNA can either be single-stranded (of positive or negative polarity) or double-stranded.

As used herein, the term "etiology" refers to the causes or origins, of diseases or abnormal physiological conditions.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

The present invention provides methods for detection and identification of bioagents in an unbiased manner using bioagent identifying amplicons. Intelligent primers are selected to hybridize to conserved sequence regions of nucleic acids derived from a bioagent and which bracket variable sequence regions to yield a bioagent identifying amplicon which can be amplified and which is amenable to molecular mass determination. The molecular mass then provides a means to uniquely identify the bioagent without a requirement for prior knowledge of the possible identity of the bioagent. The molecular mass or corresponding base composition signature (BCS) of the amplification product is then matched against a database of molecular masses or base composition signatures. Furthermore, the method can be applied to rapid parallel multiplex analyses, the results of which can be employed in a triangulation identification strategy. The present method provides rapid throughput and does not require nucleic acid sequencing of the amplified target sequence for bioagent detection and identification.

Despite enormous biological diversity, all forms of life on earth share sets of essential, common features in their genomes. Since genetic data provide the underlying basis for identification of bioagents by the methods of the present invention, it is necessary to select segments of nucleic acids which ideally provide enough variability to distinguish each individual bioagent and whose molecular mass is amenable to molecular mass determination.

Unlike bacterial genomes, which exhibit conversation of numerous genes (i.e. housekeeping genes) across all organisms, viruses do not share a gene that is essential and conserved among all virus families. Therefore, viral identification is achieved within smaller groups of related viruses, such as members of a particular virus family or genus. For example, RNA-dependent RNA polymerase is present in all single-stranded RNA viruses and can be used for broad priming as well as resolution within the virus family.

In some embodiments of the present invention, at least one viral nucleic acid segment is amplified in the process of identifying the bioagent. Thus, the nucleic acid segments that can be amplified by the primers disclosed herein and that provide enough variability to distinguish each individual bioagent and whose molecular masses are amenable to molecular mass determination are herein described as bioagent identifying amplicons.

In some embodiments of the present invention, bioagent identifying amplicons comprise from about 45 to about 200 nucleobases (i.e. from about 45 to about 200 linked nucleosides). One of ordinary skill in the art will appreciate that the invention embodies compounds of 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 nucleobases in length, or any range therewithin.

It is the combination of the portions of the bioagent nucleic acid segment to which the primers hybridize (hybridization sites) and the variable region between the primer hybridization sites that comprises the bioagent identifying amplicon. In some embodiments, bioagent identifying amplicons amenable to molecular mass determination which are produced by the primers described herein are either of a length, size or mass compatible with the particular mode of molecular mass determination or compatible with a means of providing a predictable fragmentation pattern in order to obtain predictable fragments of a length compatible with the particular mode of molecular mass determination. Such means of providing a predictable fragmentation pattern of an amplification product include, but are not limited to, cleavage with restriction enzymes or cleavage primers, for example. Thus, in some embodiments, bioagent identifying amplicons are larger than 200 nucleobases and are amenable to molecular mass determination following restriction digestion. Methods of using restriction enzymes and cleavage primers are well known to those with ordinary skill in the art.

In some embodiments, amplification products corresponding to bioagent identifying amplicons are obtained using the polymerase chain reaction (PCR) which is a routine method to those with ordinary skill in the molecular biology arts. Other amplification methods may be used such as ligase chain reaction (LCR), low-stringency single primer PCR, and multiple strand displacement amplification (MDA) which are also well known to those with ordinary skill.

Intelligent primers are designed to bind to highly conserved sequence regions of a bioagent identifying amplicon that flank an intervening variable region and yield amplification products which ideally provide enough variability to distinguish each individual bioagent, and which are amenable to molecular mass analysis. In some embodiments, the highly conserved sequence regions exhibit between about 80-100%, or between about 90-100%, or between about 95-100% identity, or between about 99-100% identity. The molecular mass of a given amplification product provides a means of identifying the bioagent from which it was obtained, due to the variability of the variable region. Thus design of intelligent primers requires selection of a variable region with appropriate variability to resolve the identity of a given bioagent. Bioagent identifying amplicons are ideally specific to the identity of the bioagent.

Identification of bioagents can be accomplished at different levels using intelligent primers suited to resolution of each individual level of identification. Broad range survey intelligent primers are designed with the objective of identifying a bioagent as a member of a particular division (e.g., an order, family, class, clade, genus or other such grouping of bioagents above the species level of bioagents). As a non-limiting example, members of the filovirus genus may be identified as such by employing broad range survey intelligent primers such as primers which target the viral RNA-dependent RNA polymerase. As another non-limiting example, members of the hantavirus genus may be identified as such by employing broad range survey intelligent primers such as primers which target the viral RNA-dependent RNA polymerase. In some embodiments, broad range survey intelligent primers are capable of identification of bioagents at the species or sub-species level.

Division-wide intelligent primers are designed with an objective of identifying a bioagent at the species level. As a non-limiting example, Zaire Ebola virus, Sudan Ebola virus and Marburg virus, species of the filovirus genus, can be distinguished from each other using division-wide intelligent primers. As another non-limiting example, Hantaan, Sin Nombre and Andes virus, species of the hantavirus genus, can be distinguished from each other using division-wide intelligent primers. Division-wide intelligent primers are not always required for identification at the species level because broad range survey intelligent primers may provide sufficient identification resolution to accomplishing this identification objective.

Drill-down intelligent primers are designed with the objective of identifying a bioagent at the sub-species level (including strains, subtypes, variants and isolates) based on sub-species characteristics. As one non-limiting example, the Mayinga, Zaire and Eckron isolates of Zaire Ebola can be distinguished from each other using drill-down primers. As another non-limiting example, the NMR11, NMH10 and CC107 isolates of Sin Nombre virus can be-distinguished from each other using drill-down primers. Drill-down intelligent primers are not always required for identification at the sub-species level because broad range survey intelligent primers may provide sufficient identification resolution to accomplishing this identification objective.

A representative process flow diagram used for primer selection and validation process is outlined in FIG. 1. For each group of organisms, candidate target sequences are identified (200) from which nucleotide alignments are created (210) and analyzed (220). Primers are then designed by selecting appropriate priming regions (230) which then makes possible the selection of candidate primer pairs (240). The primer pairs are then subjected to in silico analysis by electronic PCR (ePCR) (300) wherein bioagent identifying amplicons are obtained from sequence databases such as GenBank or other sequence collections (310), compared to a probability model for unknown organism identification (320), and checked for specificity in silico (340). Bioagent identifying amplicons obtained from GenBank sequences (310) can also be analyzed by a probability model which predicts the capability of a given amplicon to identify unknown bioagents such that the base compositions of amplicons with favorable probability scores are then stored in a base composition database (325). Alternatively, base compositions of the bioagent identifying amplicons obtained from the primers and GenBank sequences can be directly entered into the base composition database (330). Candidate primer pairs (240) are validated by in vitro amplification by a method such as PCR analysis (400) of nucleic acid from a collection of organisms (410). Amplification products thus obtained are analyzed to confirm the sensitivity, specificity and reproducibility of the primers used to obtain the amplification products (420).

Many of the important pathogens, including the organisms of greatest concern as biological weapons agents, have been completely sequenced. This effort has greatly facilitated the design of primers and probes for the detection of unknown bioagents. The combination of broad-range priming with division-wide and drill-down priming has been used very successfully in several applications of the technology, including environmental surveillance for biowarfare threat agents and clinical sample analysis for medically important pathogens.

Synthesis of primers is well known and routine in the art. The primers may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

The primers are employed as compositions for use in methods for identification of viral bioagents as follows: a primer pair composition is contacted with nucleic acid (such as, for example, DNA from a DNA virus, or DNA reverse transcribed from the RNA of an RNA virus) of an unknown viral bioagent. The nucleic acid is then amplified by a nucleic acid amplification technique, such as PCR for example, to obtain an amplification product that represents a bioagent identifying amplicon. The molecular mass of each strand of the double-stranded amplification product is determined by a molecular mass measurement technique such as mass spectrometry for example, wherein the two strands of the double-stranded amplification product are separated during the ionization process. In some embodiments, the mass spectrometry is electrospray Fourier transform ion cyclotron resonance mass spectrometry (ESI-FTICR-MS) or electrospray time of flight mass spectrometry (ESI-TOF-MS). A list of possible base compositions can be generated for the molecular mass value obtained for each strand and the choice of the correct base composition from the list is facilitated by matching the base composition of one strand with a complementary base composition of the other strand. The molecular mass or base composition thus determined is then compared with a database of molecular masses or base compositions of analogous bioagent identifying amplicons for known viral bioagents. A match between the molecular mass or base composition of the amplification product and the molecular mass or base composition of an analogous bioagent identifying amplicon for a known viral bioagent indicates the identity of the unknown bioagent. In some embodiments, the primer pair used is one of the primer pairs of Tables 4-7. In some embodiments, the method is repeated using a different primer pair to resolve possible ambiguities in the identification process or to improve the confidence level for the identification assignment.

In some embodiments, a bioagent identifying amplicon may be produced using only a single primer (either the forward or reverse primer of any given primer pair), provided an appropriate amplification method is chosen, such as, for example, low stringency single primer PCR (LSSP-PCR). Adaptation of this amplification method in order to produce bioagent identifying amplicons can be accomplished by one with ordinary skill in the art without undue experimentation.

In some embodiments, the oligonucleotide primers are broad range survey primers which hybridize to conserved regions of nucleic acid encoding the RNA-dependent RNA polymerase of all (or between 80% and 100%, between 85% and 100%, between 90% and 100% or between 95% and 100%) known filoviruses and produce bioagent identifying amplicons. In some embodiments, the oligonucleotide primers are broad range survey primers which hybridize to conserved regions of nucleic acid encoding nucleocapsid of all (or between 80% and 100%, between 85% and 100%, between 90% and 100% or between 95% and 100%) known filoviruses and produce bioagent identifying amplicons.

In some embodiments, the oligonucleotide primers are broad range survey primers which hybridize to conserved regions of nucleic acid encoding the RNA-dependent RNA polymerase (NS5) of all (or between 80% and 100%, between 85% and 100%, between 90% and 100% or between 95% and 100%) known flaviviruses and produce bioagent identifying amplicons. In some embodiments, the oligonucleotide primers are broad range survey primers which hybridize to conserved regions of nucleic acid encoding the protease/helicase (NS3) of all (or between 80% and 100%, between 85% and 100%, between 90% and 100% or between 95% and 100%) known flaviviruses and produce bioagent identifying amplicons.

In some embodiments, the oligonucleotide primers are broad range survey primers which hybridize to conserved regions of nucleic acid encoding the RNA-dependent RNA polymerase of all (or between 80% and 100%, between 85% and 100%, between 90% and 100% or between 95% and 100%) known hantaviruses and produce bioagent identifying amplicons. In some embodiments, the oligonucleotide primers are broad range survey primers which hybridize to conserved regions of nucleic acid encoding nucleocapsid of all (or between 80% and 100%, between 85% and 100%, between 90% and 100% or between 95% and 100%) known hantaviruses and produce bioagent identifying amplicons.

In some embodiments, the oligonucleotide primers are broad range survey primers which hybridize to conserved regions of nucleic acid encoding the RNA-dependent RNA polymerase of all (or between 80% and 100%, between 85% and 100%, between 90% and 100% or between 95% and 100%) known phleboviruses and produce bioagent identifying amplicons.

In some embodiments, the oligonucleotide primers are broad range survey primers which hybridize to conserved regions of nucleic acid encoding nucleocapsid of all (or between 80% and 100%, between 85% and 100%, between 90% and 100% or between 95% and 100%) known nairoviruses and produce bioagent identifying amplicons.

In some embodiments, the oligonucleotide primers are broad range survey primers which hybridize to conserved regions of nucleic acid encoding the RNA-dependent RNA polymerase (L) of all (or between 80% and 100%, between 85% and 100%, between 90% and 100% or between 95% and 100%) known arenaviruses and produce bioagent identifying amplicons. In some embodiments, the oligonucleotide primers are broad range survey primers which hybridize to conserved regions of nucleic acid encoding nucleocapsid (NP) of all (or between 80% and 100%, between 85% and 100%, between 90% and 100% or between 95% and 100%) known arenaviruses and produce bioagent identifying amplicons.

As used herein, the term broad range survey primers refers to primers that bind to nucleic acid encoding genes essential to filovirus, flavivirus, hantavirus, phlebovirus, nairovirus or arenavirus replication (e.g., for example, RNA-dependent RNA polymerase or nucleocapsid) of all (or between 80% and 100%, between 85% and 100%, between 90% and 100% or between 95% and 100%) known species of filovirus, flavivirus, hantavirus, phlebovirus, nairovirus or arenavirus.

In some embodiments, the broad range survey primer pairs comprise oligonucleotides ranging in length from 13-35 nucleobases, each of which have from 70% to 100% sequence identity with primer pair number 853, which corresponds to SEQ ID NOs: 129:164. In some embodiments, the broad range survey primer pairs comprise oligonucleotides ranging in length from 13-35 nucleobases, each of which have from 70% to 100% sequence identity with primer pair number 858, which corresponds to SEQ ID NOs: 124:159. In some embodiments, the broad range survey primer pairs comprise oligonucleotides ranging in length from 13-35 nucleobases, each of which have from 70% to 100% sequence identity with primer pair number 856, which corresponds to SEQ ID NOs: 134:169. In some embodiments, the broad range survey primer pairs comprise oligonucleotides ranging in length from 13-35 nucleobases, each of which have from 70% to 100% sequence identity with primer pair number 864, which corresponds to SEQ ID NOs: 138:174.

In some cases, the molecular mass or base composition of a viral bioagent identifying amplicon defined by a broad range survey primer pair does not provide enough resolution to unambiguously identify a viral bioagent at the species level. These cases benefit from further analysis of one or more viral bioagent identifying amplicons generated from at least one additional broad range survey primer pair or from at least one additional division-wide primer pair. The employment of more than one bioagent identifying amplicon for identification of a bioagent is herein referred to as triangulation identification.

In other embodiments, the oligonucleotide primers are division-wide primers which hybridize to nucleic acid encoding genes of species within a genus of viruses. In other embodiments, the oligonucleotide primers are drill-down primers which enable the identification of sub-species characteristics. Drill down primers provide the functionality of producing bioagent identifying amplicons for drill-down analyses such as strain typing when contacted with nucleic acid under amplification conditions. Identification of such sub-species characteristics is often critical for determining proper clinical treatment of viral infections. In some embodiments, sub-species characteristics are identified using only broad range survey primers and division-wide and drill-down primers are not used.

In some embodiments, the primers used for amplification hybridize to and amplify genomic DNA, DNA of bacterial plasmids, DNA of DNA viruses or DNA reverse transcribed from RNA of an RNA virus.

In some embodiments, the primers used for amplification hybridize directly to viral RNA and act as reverse transcription primers for obtaining DNA from direct amplification of viral RNA. Methods of amplifying RNA using reverse transcriptase are well known to those with ordinary skill in the art and can be routinely established without undue experimentation.

One with ordinary skill in the art of design of amplification primers will recognize that a given primer need not hybridize with 100% complementarity in order to effectively prime the synthesis of a complementary nucleic acid strand in an amplification reaction. Moreover, a primer may hybridize over one or more segments such that intervening or adjacent segments are not involved in the hybridization event. (e.g., for example, a loop structure or a hairpin structure). The primers of the present invention may comprise at least 70%, at least 75%, at least 80%, at least 85%, at least 90%, at least 95% or at least 99% sequence identity with any of the primers listed in Tables 4-7. Thus, in some embodiments of the present invention, an extent of variation of 70% to 100%, or any range therewithin, of the sequence identity is possible relative to the specific primer sequences disclosed herein. Determination of sequence identity is described in the following example: a primer 20 nucleobases in length which is identical to another 20 nucleobase primer having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer.

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, complementarity, of primers with respect to the conserved priming regions of viral nucleic acid, is between about 70% and about 80%. In other embodiments, homology, sequence identity or complementarity, is between about 80% and about 90%. In yet other embodiments, homology, sequence identity or complementarity, is at least 90%, at least 92%, at least 94%, at least 95%, at least 96%, at least 97%, at least 98%, at least 99% or is 100%.

In some embodiments, the primers described herein comprise at least 70%, at least 75%, at least 80%, at least 85%, at least 90%, at least 92%, at least 94%, at least 95%, at least 96%, at least 98%, or at least 99%, or 100% (or any range therewithin) sequence identity with the primer sequences specifically disclosed herein. Thus, for example, a primer may have between 70% and 100%, between 75% and 100%, between 80% and 100%, and between 95% and 100% sequence identity with SEQ ID NO: 129. Likewise, a primer may have similar sequence identity with any other primer whose nucleotide sequence is disclosed herein.

One with ordinary skill is able to calculate percent sequence identity or percent sequence homology and able to determine, without undue experimentation, the effects of variation of primer sequence identity on the function of the primer in its role in priming synthesis of a complementary strand of nucleic acid for production of an amplification product of a corresponding bioagent identifying amplicon.

In some embodiments of the present invention, the oligonucleotide primers are 13 to 35 nucleobases in length (13 to 35 linked nucleotide residues). These embodiments comprise oligonucleotide primers 13, 14, 15, 16, 17, 18, 19, 20, 21, 22, 23, 24, 25, 26, 27, 28, 29, 30, 31, 32, 33, 34 or 35 nucleobases in length, or any range therewithin.

In some embodiments, any given primer comprises a modification comprising the addition of a non-templated T residue to the 5' end of the primer (i.e., the added T residue does not necessarily hybridize to the nucleic acid being amplified). The addition of a non-templated T residue has an effect of minimizing the addition of non-templated A residues as a result of the non-specific enzyme activity of Taq polymerase (Magnuson et al., Biotechniques, 1996, 21, 700-709), an occurrence which may lead to ambiguous results arising from molecular mass analysis.

In some embodiments of the present invention, primers may contain one or more universal bases. Because any variation (due to codon wobble in the $3^{rd}$ position) in the conserved regions among species is likely to occur in the third position of a DNA (or RNA) triplet, oligonucleotide primers can be designed such that the nucleotide corresponding to this position is a base which can bind to more than one nucleotide, referred to herein as a "universal nucleobase." For example, under this "wobble" pairing, inosine (I) binds to U, C or A; guanine (G) binds to U or C, and uridine (U) binds to U or C. Other examples of universal nucleobases include nitroindoles such as 5-nitroindole or 3-nitropyrrole (Loakes et al., Nucleosides and Nucleotides, 1995, 14, 1001-1003), the degenerate nucleotides dP or dK (Hill et al.), an acyclic nucleoside analog containing 5-nitroindazole (Van Aerschot et al., Nucleosides and Nucleotides, 1995, 14, 1053-1056) or the purine analog 1-(2-deoxy-β-D-ribofuranosyl)-imidazole-4-carboxamide (Sala et al., Nucl. Acids Res., 1996, 24, 3302-3306).

In some embodiments, to compensate for the somewhat weaker binding by the wobble base, the oligonucleotide primers are designed such that the first and second positions of each triplet are occupied by nucleotide analogs which bind with greater affinity than the unmodified nucleotide. Examples of these analogs include, but are not limited to, 2,6-diaminopurine which binds to thymine, 5-propynyluracil which binds to adenine and 5-propynylcytosine and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are described in U.S Pre-Grant Publication No. 2003-0170682, which is also commonly owned and incorporated herein by reference in its entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

In some embodiments, to enable broad priming of rapidly evolving RNA viruses, primer hybridization is enhanced using primers and probes containing 5-propynyl deoxycytidine and deoxy-thymidine nucleotides. These modified primers and probes offer increased affinity and base pairing selectivity.

In some embodiments, non-template primer tags are used to increase the melting temperature ($T_m$) of a primer-template duplex in order to improve amplification efficiency. A non-template tag is at least three consecutive A or T nucleotide residues on a primer which are not complementary to the template. In any given non-template tag, A can be replaced by C or G and T can also be replaced by C or G. Although Watson-Crick hybridization is not expected to occur for a non-template tag relative to the template, the extra hydrogen bond in a G-C pair relative to an A-T pair confers increased stability of the primer-template duplex and improves amplification efficiency for subsequent cycles of amplification when the primers hybridize to strands synthesized in previous cycles.

In other embodiments, propynylated tags may be used in a manner similar to that of the non-template tag, wherein two or more 5-propynylcytidine or 5-propynyluridine residues replace template matching residues on a primer. In other embodiments, a primer contains a modified internucleoside linkage such as a phosphorothioate linkage, for example.

In some embodiments, the primers contain mass-modifying tags. Reducing the total number of possible base compositions of a nucleic acid of specific molecular weight provides a means of avoiding a persistent source of ambiguity in determination of base composition of amplification products. Addition of mass-modifying tags to certain nucleobases of a given primer will result in simplification of de novo determination of base composition of a given bioagent identifying amplicon from its molecular mass.

In some embodiments of the present invention, the mass modified nucleobase comprises one or more of the following: for example, 7-deaza-2'-deoxyadenosine-5-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $^{15}N$ or $^{13}C$ or both $^{15}N$ and $^{13}C$.

In some cases, a molecular mass of a given bioagent identifying amplicon alone does not provide enough resolution to unambiguously identify a given bioagent. The employment of more than one bioagent identifying amplicon for identification of a bioagent is herein referred to as triangulation identification. Triangulation identification is pursued by analyzing a plurality of bioagent identifying amplicons selected within multiple core genes. This process is used to reduce false negative and false positive signals, and enable reconstruction of the origin of hybrid or otherwise engineered bioagents. For example, identification of the three part toxin genes typical of *B. anthracis* (Bowen et al., J. Appl. Microbiol., 1999, 87, 270-278) in the absence of the expected signatures from the *B. anthracis* genome would suggest a genetic engineering event.

In some embodiments, the triangulation identification process can be pursued by characterization of bioagent identifying amplicons in a massively parallel fashion using the polymerase chain reaction (PCR), such as multiplex PCR where multiple primers are employed in the same amplification reaction mixture, or PCR in multi-well plate format wherein a different and unique pair of primers is used in multiple wells containing otherwise identical reaction mixtures. Such multiplex and multi-well PCR methods are well known to those with ordinary skill in the arts of rapid throughput amplification of nucleic acids.

In some embodiments, the molecular mass of a given bioagent identifying amplicon is determined by mass spectrometry. Mass spectrometry has several advantages, not the least of which is high bandwidth characterized by the ability to separate (and isolate) many molecular peaks across a broad range of mass to charge ratio (m/z). Thus mass spectrometry is intrinsically a parallel detection scheme without the need for radioactive or fluorescent labels, since every amplification product is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons.

In some embodiments, intact molecular ions are generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). Upon ionization, several peaks are observed from one sample due to the formation of ions with different charges. Averaging the multiple readings of molecular mass obtained from a single mass spectrum affords an estimate of molecular mass of the bioagent identifying amplicon. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods of the present invention include, but are not limited to, Fourier transform ion cyclotron resonance mass spectrometry (FT-ICR-MS), time of flight (TOF), ion trap, quadrupole, magnetic sector, Q-TOF, and triple quadrupole.

Although the molecular mass of amplification products obtained using intelligent primers provides a means for identification of bioagents, conversion of molecular mass data to a base composition signature is useful for certain analyses. As used herein, a base composition signature (BCS) is the exact base composition determined from the molecular mass of a bioagent identifying amplicon. In one embodiment, a BCS provides an index of a specific gene in a specific organism.

In some embodiments, conversion of molecular mass data to a base composition is useful for certain analyses. As used herein, a base composition is the exact number of each nucleobase (A, T, C and G).

RNA viruses depend on error-prone polymerases for replication and therefore their nucleotide sequences (and resultant base compositions) drift over time within the functional constraints allowed by selection pressure. Base composition probability distribution of a viral species or group represents a probabilistic distribution of the above variation in the A, C, G and T base composition space and can be derived by analyzing base compositions of all known isolates of that particular species.

In some embodiments, assignment of base compositions to experimentally determined molecular masses is accomplished using base composition probability clouds. Base compositions, like sequences, vary slightly from isolate to isolate within species. It is possible to manage this diversity by building base composition probability clouds around the composition constraints for each species. This permits identification of organisms in a fashion similar to sequence analysis. A pseudo four-dimensional plot can be used to visualize the concept of base composition probability clouds. Optimal primer design requires optimal choice of bioagent identifying amplicons and maximizes the separation between the base composition signatures of individual bioagents. Areas where clouds overlap indicate regions that may result in a misclassification, a problem which is overcome by a triangulation identification process using bioagent identifying amplicons not affected by overlap of base composition probability clouds.

In some embodiments, base composition probability clouds provide the means for screening potential primer pairs in order to avoid potential misclassifications of base compositions. In other embodiments, base composition probability clouds provide the means for predicting the identity of a bioagent whose assigned base composition was not previously observed and/or indexed in a bioagent identifying amplicon base composition database due to evolutionary transitions in its nucleic acid sequence. Thus, in contrast to probe-based techniques, mass spectrometry determination of base composition does not require prior knowledge of the composition or sequence in order to make the measurement.

The present invention provides bioagent classifying information similar to DNA sequencing and phylogenetic analysis at a level sufficient to identify a given bioagent. Furthermore, the process of determination of a previously unknown base composition for a given bioagent (for example, in a case where sequence information is unavailable) has downstream utility by providing additional bioagent indexing information with which to populate base composition databases. The process of future bioagent identification is thus greatly improved as more base composition indexes become available in base composition databases.

Existing nucleic acid-based tests for bioagent detection are primarily based upon amplification methods using primer and probes designed to detect specific organisms. Because prior knowledge of nucleic acid sequence information is required to develop these probe-based tests they cannot be used to identify unanticipated, newly emergent, or previously unknown infections organisms. Thus, the discovery of new bioagents still relies largely on traditional culture methods and microscopy.

Methods of the present invention, however, allow rapid identification of new bioagent species without the need for prior knowledge of nucleotide sequence. This is achieved by applying a mathematical and/or probabilistic model for sequence variation developed based on known bioagent amplicon base composition (the "training set" of data) and matching the unknown bioagent data ("test data") to the model.

For unambiguous detection and identification of bioagents, it would be ideal if every isolate of a given species of bioagent (*E. coli*, for example) had exactly the same base count in any particular amplified region. However, due to naturally occurring mutations and/or deliberately engineered changes, isolates of any species might have some variation in the base count of a particular region. Because of naturally occurring variation and because engineered threat bioagents may differ slightly in particular regions from their naturally occurring counterparts, it is useful to "blur" the expected base count for a given species to allow for this variation so that the system does not miss detections. The more the expected base count is blurred, the less likely it is that a particular species will escape detection; however, such blurring will cause more overlap between the expected base counts of different species, contributing to misclassifications.

To solve this problem, expected base counts can be blurred according to the natural principles of biological mutations, customizing the specific blurring to the biological constraints of each amplified region. Each amplified region of a particular bioagent is constrained in some fashion by its biological purpose (i.e., RNA structure, protein coding, etc.). For example, protein coding regions are constrained by amino acid coding considerations, whereas a ribosome is mostly constrained by base pairing in stems and sequence constraints in unpaired loop regions. Moreover, different regions of the ribosome might have significant preferences that differ from each other.

One embodiment of application of the cloud algorithm is described in Example 1. By collecting all likely species amplicons from a primer set and enlarging the set to include all biologically likely variant amplicons using the cloud algorithm, a suitable cluster region of base count space is defined for a particular species of bioagent. The regions of base count space in which groups of related species are clustered are referred to as "bioclusters."

When a biocluster is constructed, every base count in the biocluster region is assigned a percentage probability that a species variant will occur at that base count. To form a probability density distribution of the species over the biocluster region, the entire biocluster probability values are normalized to one. Thus, if a particular species is present in a sample, the probability of the species biocluster integrated over all of base count space is equal to one.

At this point in the ranking procedure, proposed target species to be detected are taken into account. These generally are the bioagents that are of primary importance in a particular detection scenario. For example, if *Yersinia pestis* (the causative agent of bubonic and pneumonic plague) were the target, the *Yersinia pestis* species biocluster identified as described above, would be the "target biocluster." To complete the example, assume that all other database species serve as the scenario background. The discrimination metric in this case is defined as the sum total of all the biocluster overlap from other species into the *Yersinia pestis* biocluster.

In this example, the *Yersinia pestis* biocluster overlap is calculated as follows. A probability of detection of 99% ($P_D$=0.99) is defined, although this value can be altered as needed. The "detection range" is defined as the set of biocluster base counts, of minimal number, that encloses 99% of the entire target biocluster. For each additional bacterial species in the database, the amount of biocluster probability density that resides in the base counts in the defined detection range is calculated and is the effective biocluster overlap between that background species and the target species. The sum of the biocluster overlap over all background species serves as the metric for measuring the discrimination ability of a defined target by a proposed primer set. Mathematically, because the most discriminating primer sets will have minimal biocluster overlap, an inverse figure of merit $\phi$ is defined, 1=i=all bioclusters i where the sum is taken over the individual biocluster overlap values [$\theta_i$ from all N background species bioclusters (i=1, . . . , N ). For example, FIG. 2 shows the inverse figure of merit $\phi$ plotted for a master list of 16 primer sets using *Yersinia pestis* as the target biocluster. Using the inverse figure of merit minimization criteria defined above, the result is that primer set number 4 provides the best discrimination of any of the individual primer sets in the master list.

This set of discrimination criteria also can be applied to combinations of primer sets. The respective four-dimensional base count spaces from each primer set can be dimensionally concatenated to form a (4×N)-dimensional base count space for N primer sets. Nowhere in the biocluster definition is it necessary that the biocluster reside in a four-dimensional space, thus the biocluster analysis seamlessly adapts to any arbitrary dimensionality. As a result, a master list of primer sets can be searched and ranked according to the discrimination of any combination of primer sets with any arbitrary number of primer sets making up the combination.

Using again the example of *Yersinia pestis* as the target, improved discrimination is achieved through use of an increasing number of primers. For each number of primers value on the x-axis, the plotted inverse figure of merit value is that obtained from the most discriminating group (that group with the minimum figure of merit for that number of primer sets simultaneously used for discrimination). The result is that after the best groups of 3 and 4 primer sets are found, the inverse figure of merit approaches one and goes no further. That means that there is the equivalent of one background species biocluster overlapping into the target biocluster. In this example it is the *Yersinia pseudotuberculosis* species biocluster, which cannot be discriminated from *Yersinia pestis* by any combination of the 16 primer sets in the example. Thus, using the "best" 3 or 4 primer sets in the master list, *Yersinia pestis* is essentially discriminated from all other species bioclusters.

Thus, one the one hand, probability clouds can be used to detect variants of known bioagents. On the other hand, this method of the present invention can be used to unambiguously determine that an unknown bioagent is not a likely variant of a known bioagent and at the same time, classify the bioagent in terms of similarity to the known bioagents in the database.

RNA viruses depend on an error-prone polymerase for replication and therefore their nucleotide sequences (and the resultant base compositions) drift over time within the different regions within the genome of 120 nucleotide (nt) average length, were picked based on priming considerations and a maximum amplicon length criterion of ~150 nt. Base composition probability distributions for a species were determined in two steps. In the first step, mutation probabilities, i.e., the probabilities of occurrence of each type of substitution, insertion, or deletion, were derived by pairwise comparisons of all known HCV isolates in each target region, and an estimate of the maximum number of mutations that a sequence may undergo were calculated. In the second step, the mutation probabilities and maxima derived from the model organism were used to estimate variations in base compositions for each test species and to calculate mutation probability distances ($\Delta_m$) between the species in base composition space, which is calculated as the negative base 10 logarithm ($-\log_{10} P$) of the cumulative probabilities of all possible mutations of the A, G C, and T base counts of one species that would lead to the other.

There are several approaches to classifying an unknown organism based on the base composition of certain amplicons. To illustrate these approaches, the classification technique for exemplary primer pairs is shown. The method can be applied to other primer pairs.

TABLE 1

Position Independent, Nucleotide Mutation Probabilities Over 6 Training Sequences For HCV-1b

| Mutation | Seq. 1 | Seq. 2 | Seq. 3 | Seq. 4 | Seq. 5 | Seq. 6 | All Seq. |
| --- | --- | --- | --- | --- | --- | --- | --- |
| A -> A | 91.82% | 88.42% | 91.98% | 92.51% | 91.08% | 89.89% | 93.30% |
| A -> C | 1.54% | 1.22% | 0.56% | 2.25% | 0.14% | 0.61% | 0.80% |
| A -> G | 6.28% | 9.57% | 7.16% | 5.08% | 8.52% | 8.61% | 5.59% |
| A -> T/U | 0.36% | 0.79% | 0.30% | 0.15% | 0.26% | 0.90% | 0.30% |
| A -> | 0.00% | 0.00% | 0.00% | 0.00% | 0.00% | 0.00% | 0.00% |
| C -> A | 1.00% | 0.64% | 0.40% | 1.29% | 0.10% | 0.22% | 0.46% |
| C -> C | 89.91% | 93.27% | 89.89% | 93.87% | 93.84% | 93.87% | 94.68% |
| C -> G | 1.26% | 0.61% | 0.76% | 0.13% | 0.00% | 0.71% | 0.37% |
| C -> T/U | 7.83% | 5.48% | 8.95% | 4.71% | 6.06% | 5.20% | 4.49% |
| C -> | 0.00% | 0.00% | 0.00% | 0.00% | 0.00% | 0.00% | 0.00% |
| G -> A | 3.97% | 6.93% | 3.96% | 4.29% | 7.10% | 2.52% | 3.47% |
| G -> C | 1.22% | 0.85% | 0.60% | 0.19% | 0.00% | 0.57% | 0.41% |
| G -> G | 94.41% | 91.93% | 95.29% | 94.96% | 92.72% | 96.77% | 95.93% |
| G -> T/U | 0.41% | 0.29% | 0.15% | 0.56% | 0.18% | 0.13% | 0.19% |
| G -> | 0.00% | 0.00% | 0.00% | 0.00% | 0.00% | 0.00% | 0.00% |
| T -> A | 0.49% | 0.77% | 0.22% | 0.21% | 0.22% | 0.58% | 0.29% |
| T -> C | 16.21% | 10.23% | 9.61% | 11.40% | 7.68% | 9.17% | 7.67% |
| T -> G | 0.88% | 0.39% | 0.20% | 0.93% | 0.18% | 0.30% | 0.30% |
| T -> T/U | 82.42% | 88.61% | 89.96% | 87.46% | 91.92% | 89.95% | 91.75% |
| T -> | 0.00% | 0.00% | 0.00% | 0.00% | 0.00% | 0.00% | 0.00% |
| -> A | 0.00% | 0.00% | 0.00% | 0.00% | 0.00% | 0.00% | 0.00% |
| -> C | 0.00% | 0.00% | 0.00% | 0.00% | 0.00% | 0.00% | 0.00% |
| -> G | 0.00% | 0.00% | 0.00% | 0.00% | 0.00% | 0.00% | 0.00% |
| -> T/U | 0.00% | 0.00% | 0.00% | 0.00% | 0.00% | 0.00% | 0.00% |
| Total -> | 100.00% | 0.00% | 0.00% | 0.00% | 0.00% | 0.00% | 0.00% | functional constraints allowed by selection pressure. Base composition probability distribution of a viral species or group represents a probabilistic distribution of the above variations in the {A, G, C, and T} base composition space and can be derived by analyzing base compositions of all known isolates of that particular species.

In one embodiment of the invention, a model organism, such as the positive strand RNA virus, hepatitis C virus (HCV), can be used to model these sequence variations. Mutation probabilities can be derived from the observed variations among, e.g., a number of HCV sequences. Table 1 below, lists mutation probabilities that were derived from the observed variations among 50 HCV-1 b sequences. Six There are several approaches to classifying an unknown organism based on the base composition of certain amplicons. To illustrate these approaches, the classification technique for exemplary primer pairs is shown. The method can be applied to other primer pairs.

To develop a pattern classifier, the known base composition counts of amplicons of known organisms are used to construct the pattern classifier as a training set. In one embodiment of the pattern classifier, for each pattern class a base organism serves as a central point. For that pattern class, a distance is calculated from each organism in the training set to the base organism. The maximum distance found in this manner defines the class within the pattern classifier; all organisms less than the maximum distance to the base organism fall within the class.

Once the pattern classifier has been trained the unknown organism can be classified by determining the distance between the unknown organism and the base organism for each pattern. If the unknown organism falls within the maximum distance determined in the training process, the organism is classified as belonging to the same pattern class as the base organism. If the unknown organism falls outside the maximum distance, a probability that the organism belongs to the class can be derived as a function of the distance from the unknown organism to the base organism.

In an alternate embodiment of the pattern classifier, rather than identifying a base organism, a pattern is defined by selecting a centroid, which may not correspond to an actual organism, but serves as a center for the pattern class. During the training process, the centroid and the maximum distance is determined. Once trained, the classification of an unknown organism follows much the same as described above.

Several criteria for measuring the distance between organisms can be employed. For a particular primer-pair, the distance between the base compositions can be used. That is, if the base counts are treated as a mathematical vector, the distance between the vectors is the measure of distance.

As an example, the 229 E Human Coronavirus has a base count in the RdRp target region of A25,G24,C11,T28 and the SARS Coronavirus has a base count of A27,G19,C14, T28. Using the first example of distance (a Euclidean distance), the distance between them is 6.164.

An alternative measure of distance is to use the probability of mutation to derive distance. There are a number of mutation pathways between two polynucleotide sequences, which comprises a series of one or more mutation events. Based on empirical finding, the probability of individual mutations is known. Table 1 shows a list of typical individual mutations with their associated probabilities. The probability of a specific mutation pathway is the product of the probabilities of the individual mutations. One method of defining distance is to take the sum of all probabilities of all mutations pathways, P. The mutational distance between the two polynucleotide sequences can be defined as $-\log_{10} P$. In the above example, the distance between the 229E Human Coronavirus and the SARS coronavirus is 8.8. It should be noted that since longer mutation pathways are less likely, only certain mutations are needed to get from 229E to SARS, and thus the longer pathways can be discarded.

Figure 3:
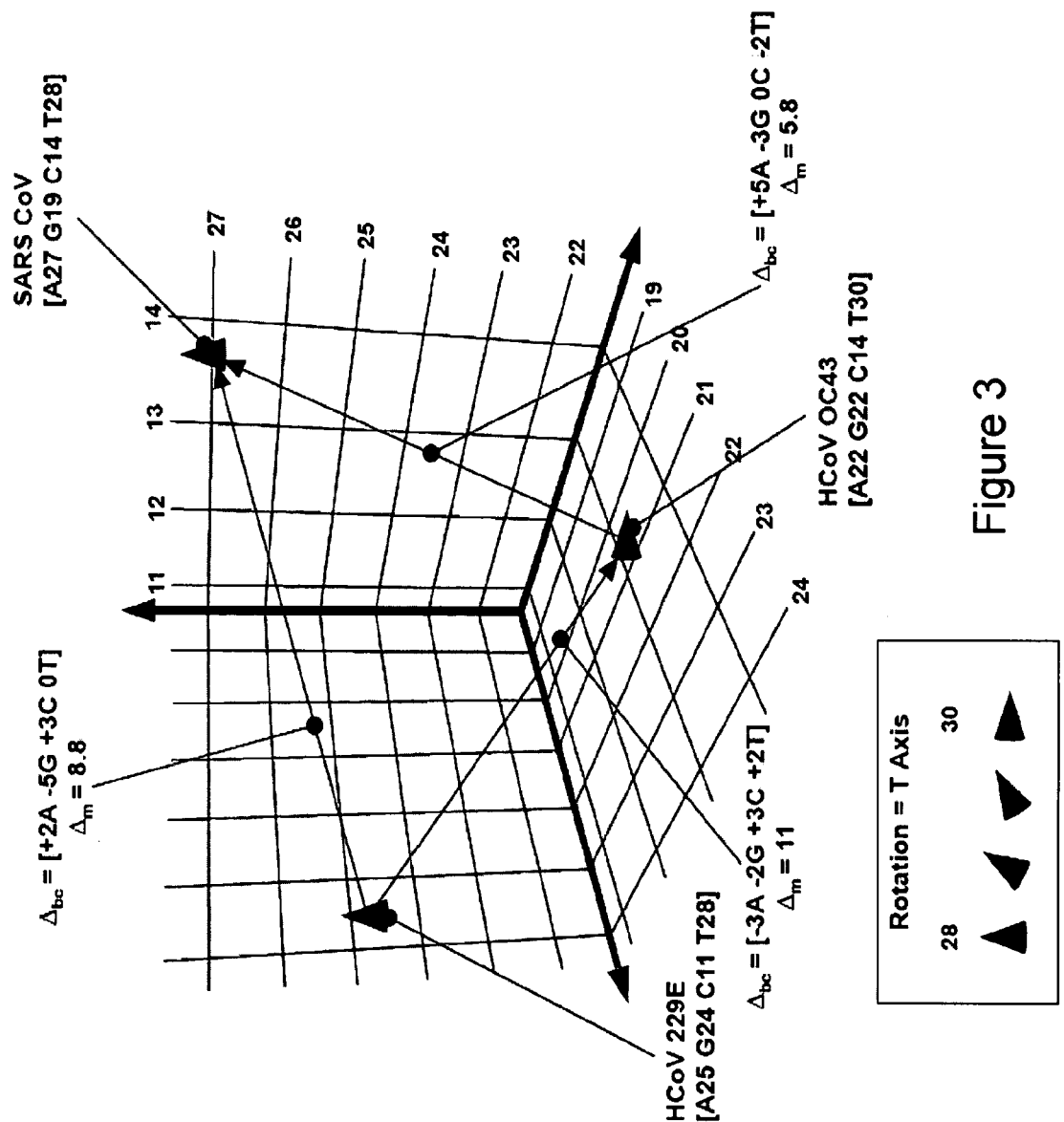
FIG. 3 is a graph showing the base compositions of the 229E Human Coronavirus, OC43 Human Coronavirus and the SARS Coronavirus.

FIG. 3 is a graph showing the base compositions of the 229E Human Coronavirus, OC43 Human Coronavirus and the SARS Coronavirus. In this graph, the A, G, and C base counts are plotted on the axes and the T base count is represented by using rotation.

Figure 4:
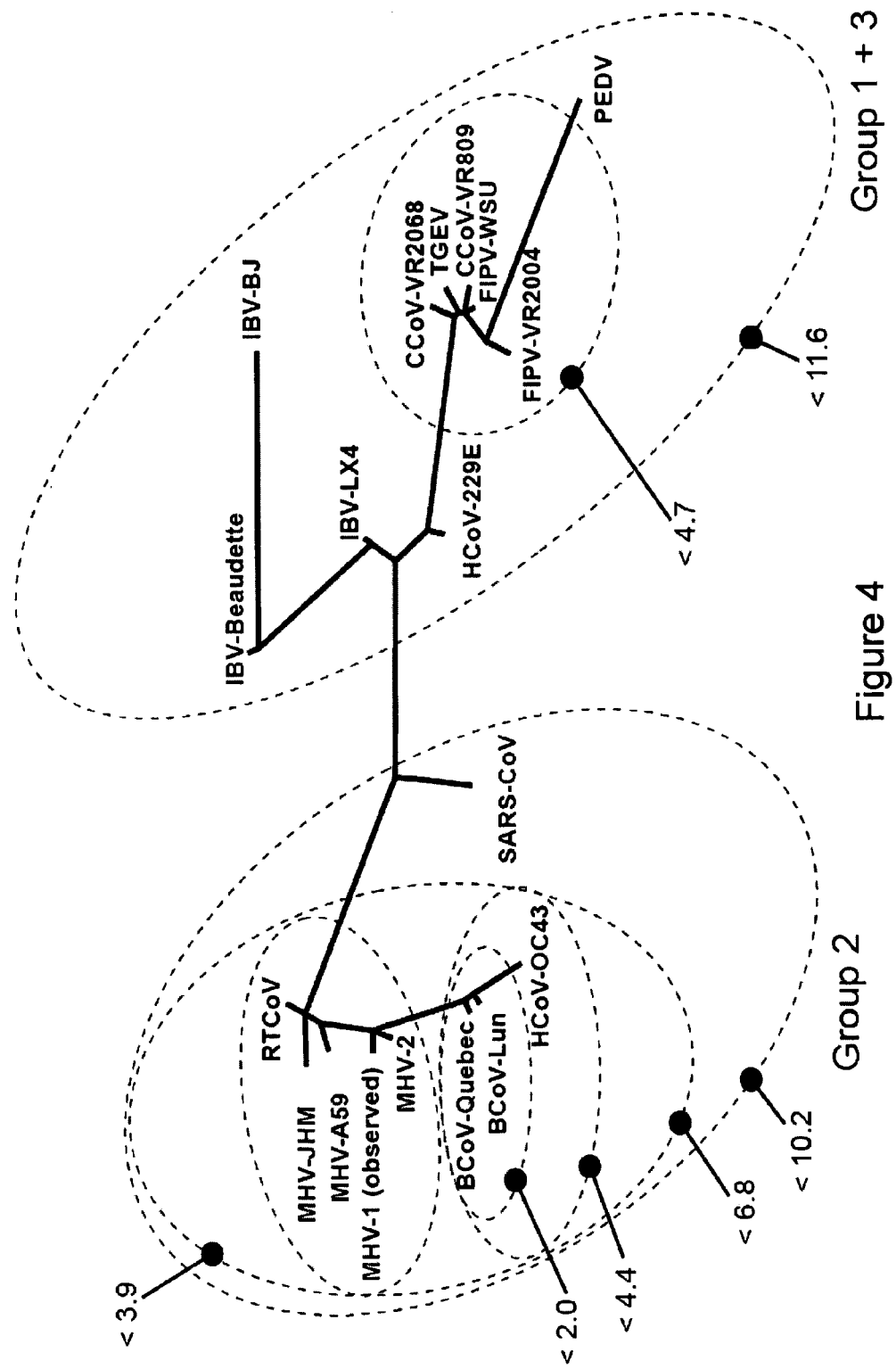
FIG. 4 shows the phylogenetic relationship between a number of animal coronavirus species.

FIG. 4 shows a number of animal coronavirus species. The branches on the tree represent the phylogenetic relationship between the various taxons. For each taxonomic grouping, an oval represents the maximal distance between any two members of the group represented by $\Delta_m$ next to the oval. For example, the bovine isolates (BCoV-Quebec and BCov-Lun) are clustered together ($\Delta_m<2.0$), and are closer to each other than to their nearest neighbor on the phylogenetic tree, HCoV-OC43. The bovine and the OC43 species form a closely related cluster with a relatively high probability of misclassification (($\Delta_m<4.5$). Similarly, the murine and rat coronavirus isolates are closely related species that can not be distinguished from each other using just two target regions ($\Delta_m<0.9$), yet the rodent viruses are easily distinguished from the bovine/OC43 group ($\Delta_m<6.8$). Similarly, many of the group 1 animal coronaviruses (CCoV, FCoV, TGEV) clustered together and were very close to each other in mutation and base composition distance. These, therefore, could potentially be misclassified at the species level ($\Delta_m<4.7$). This is consistent with previous reports that suggest that CCoV are serologically and genetically related to other group 1 animal coronaviruses. However, this group was clearly resolved from other members of group 1 coronaviruses such as 229E and PEDV ($\Delta_m<11.6$). In contrast to the group 1 and group 2 species clusters, the two target regions chosen here did not cluster the group 3 species together. The three known isolates of avian coronaviruses were as far away from each other as they were from members of group 1 coronaviruses. Overall, the mutation-distance analysis suggests that the previously known members of group 2 coronaviruses represent a clearly delineated group, well resolved from groups 1 and 3. In contrast, no clear delineation between groups 1 and 3 was observed.

Further refinement to the classification can be made by assigning a match probability of an unknown for each pattern class by calculating the distance to each pattern class. By applying additional pattern classifiers based on other primer pairs, the ability to resolve unknowns is enhanced. In the example described above, it would be difficult to distinguish an unknown in group 1 from group 3 for the given primer pair. Applying the pattern classifier with other primer pairs may yield a greater distance between group 1 and group 3 coronaviruses. This triangulation approach is described further below.

In alternate embodiments of the mutational probability model, a centroid is not chosen and restrictions among strains were compared to one another. Using best estimates of the phylogenetic tree, only descendants were compared to their direct forebears, for a direct estimate of a mutational probability. This comparison had the effect of reducing the magnitude of the mutation probabilities.

Because it is known that DNA triplets code for a single amino acid, in some embodiments, for primer regions that are in a protein-coding region of the sequence, the mutational probabilities are determined in a position-dependent way, so that the 20 types of mutations (12 substitutions, 4 deletions, and 4 insertions) are now expanded to a set of 60 (20 types×3 positions). It is well known that the first position of a triplet is highly conserved, while the third position is the least conserved (and it is referred to as a wobble position because of this) and this is reflected in the different mutation probabilities per position.

In other embodiments, the mutational probability model incorporates both the restrictions among strains and position dependence of a given nucleobase within a triplet. In one embodiment of the invention, a polytope pattern classifier is used to classify test or unknown organism according to its amplicon base composition. The polytope pattern classifier of the present invention defines the bounds of a pattern class by a convex polytope. The polytope pattern classifier is trained by defining a minimal polytope which contains all the samples in the training set.

Generally, a polytope can be expressed by a system of linear inequalities. Data supplied to the pattern classifier are typically expressed as an n-dimensional vector. Accordingly, an n-dimensional polytope can be expressed as a system of inequalities of the form:

$$a_1x_1+a_2x_2+a_3x_3+\ldots+a_nx_n \leq C$$

and of the form, $$D \leq b_1x_1+b_2x_2+b_3x_3+\ldots+b_nx_n.$$

According to one embodiment of the present invention, the components of the data vectors are integers. Thus, the polytopes can be reduced to a system of linear inequalities of the following form, $$D \leq a_1 x_1 + a_2 x_2 + a_3 x_3 + \ldots + a_n x_n \leq C, \text{ where each } a_i \text{ is either 0 or 1.}$$

To define a minimal polytope, all inequalities of the form equation shown above can be used for all combinations of $a_i$. During the training process the constants C and D are determined for each inequality.

In certain aspects of the invention, a density is defined for each polytope by taking the total number of samples in the training set residing in the polytope and dividing by the total volume of the polytope. Once the polytopes are calculated for each pattern class identified in the training set, the polytope pattern classifier is trained and can be applied to test or unknown data. In classifying an unknown represented by a data vector, the distance to each pattern class is calculated. A point density of the data vector to a polytope is defined to be the density of the polytope multiplied by a decay factor which is a function of distance of the data vector to the polytope. A match probability to each of the classes is calculated based on the point density. In one embodiment of the invention, for example, the match probability can be the normalized average of all point densities for that particular data sample.

It should be noted that the measure of volume and distance described in the density and point density calculations need not be standard Euclidean-based measures of distance and volume. For example, if the data vectors have integer components, the volume of a polytope can be defined as a lattice volume that is the number of integer lattice points within a given polytope. Similarly, the distance from a point to a polytope can be defined as a lattice distance that is the minimum number of lattice points traversed between a point and any point within the polytope.

Figure 5A:
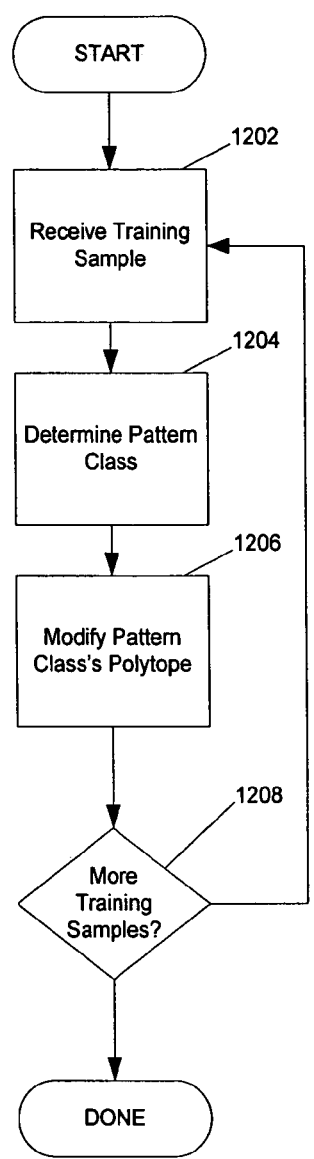
FIG. 5A is a flow chart illustrating a method of training an embodiment of a polytope pattern classifier.

FIG. 5A is a flow chart illustrating a method of training an embodiment of a polytope pattern classifier. At step 1202, a training sample is received from a training set. Associated with each training sample is the pattern class it is a member of. At step 1204, the pattern class is determined. At step 1206, if necessary that pattern class' polytope is modified so as to incorporate the training sample. If the training sample lies within the current version of the pattern class' polytope, no modification is required. This modification typically takes the form of comparing the training sample to the existing inequalities that defined the polytope. If the training sample falls outside an inequality, the inequality is modified to incorporated the training sample. In the modification process, the inequality is modified to expand the polytope as little as possible. At step 1208, the process iterates to the next training sample, if any remain. Otherwise, the training is complete.

One should note that though the flowchart describes an iteration through the training samples and in polytope modification, an iteration through the inequalities which defined the polytope, the order of iteration could be equivalently transposed. That is, rather than considering each training sample first, each inequality is considered. For each inequality, the training sample is compared against the inequality and the inequality is modified to accommodate the training sample if necessary. Then the iteration can continue to the next inequality.

Figure 5B:
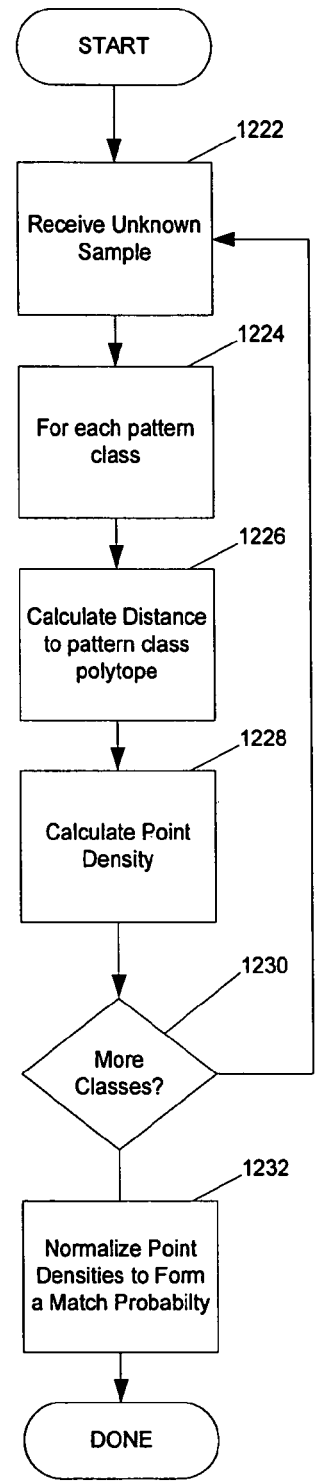
FIG. 5B is a flow chart illustrating a method of identifying an unknown sample using an embodiment of a trained polytope pattern classifier.

FIG. 5B is a flow chart illustrating the method of identifying an unknown sample using an embodiment of a trained polytope pattern classifier. At step 1222, an unknown sample is received by the polytope pattern classifier. At step 1224, a pattern class is selected. At step 1226, the distance between the pattern class' polytope and the unknown sample is calculated. Based on the distance, at step 1228, the point density of the unknown sample with respect to the pattern class is calculated. At step 1230, the process repeats for the next pattern class. When all point densities with respect to all the pattern classes are calculated, a match probability is generated by normalizing the point densities at step 1232.

To simplify the complexity of higher dimensional polytope pattern classifiers, a plurality of lower dimensional polytope pattern classifiers can be used. According to this embodiment of the invention, all data including unknowns and the data in the training set, are divided into a plurality of subspaces having the lower dimension. A polytope pattern classifier is associated with each subspace. Each polytope pattern classifier is trained on the subset of the training set that resides within the associated subspace. Once trained, the one of the plurality of subspaces to which an unknown belongs is first applied, then the polytope pattern classifier associated with that subspace is applied to the data.

In certain aspects of the invention, subspaces are defined by the length of the data, e.g. the amplicon length. When the components of the data vectors are integers, the subspaces determined in this manner can yield a finite if not small number of subspaces.

In an alternative embodiment of the polytope pattern classifier, contributions from all polytopes are considered, regardless of which subspace the unknown data belongs to. For example, the point density of an unknown to a given pattern class can be a function of the distance of the unknown data vector to every polytope associated with a given pattern class. In order to simplify this calculation, the distance can be broken into two components, the distance between the unknown data vector to the subspace containing the polytope, and the distance between a projected data vector, i.e., the data vector when projected onto the subspace containing the polytope, and the polytope. These two components of the data vector can be into different decay factors.

FIG. 6A is a flow chart illustrating the method of training an embodiment of a polytope pattern classifier of a lower dimension when the sample space is reduced in dimension by imposing a constraint. At step 1302, a training sample is received from the training set. The constraint is applied to determine which subspace the training sample belongs to at step 1304. The training sample is placed into a training subset corresponding to that subspace, at step 1306. At step 1308, the process is made to repeat, until all training samples have been grouped into corresponding subspaces. Then at step 1310, a subspace is selected along with the corresponding subset of the training samples. At step 1312 the pattern classifier corresponding to that subspace is trained. It can be trained using a method like that described in FIG. 6A. At step 1314, the process is made to repeat, until all subspaces derived from the constraint have fully trained pattern classifiers. It should be noted that in another method of training the order can be changed. For example, after the subspace of a training sample is identified, it can be used to train the corresponding pattern classifier immediately rather than waiting until all training samples are sorted. The flow chart is intended to clearly describe an example of a training method.

FIG. 6B is a flow chart illustrating a method of identifying a unknown sample in a manner similar to that of FIG. 5B. At step 1332, an unknown sample is received by the pattern classification system. At step 1334, the constraint is applied and the subspace to which the sample belongs is determined. Steps 1336, 1338, 1340, 1342, and 1344 apply a similar same pattern identification algorithm to that described in steps 1224, 1226, 1228, 1230, and 1232 respectively, where the polytope associated with each pattern class used is the polytope contained in the subspace to which the sample belongs. It should be noted that depending on the members of the various pattern classes, a pattern class can have more than one polytope, but in different subspaces.

Figure 6C:
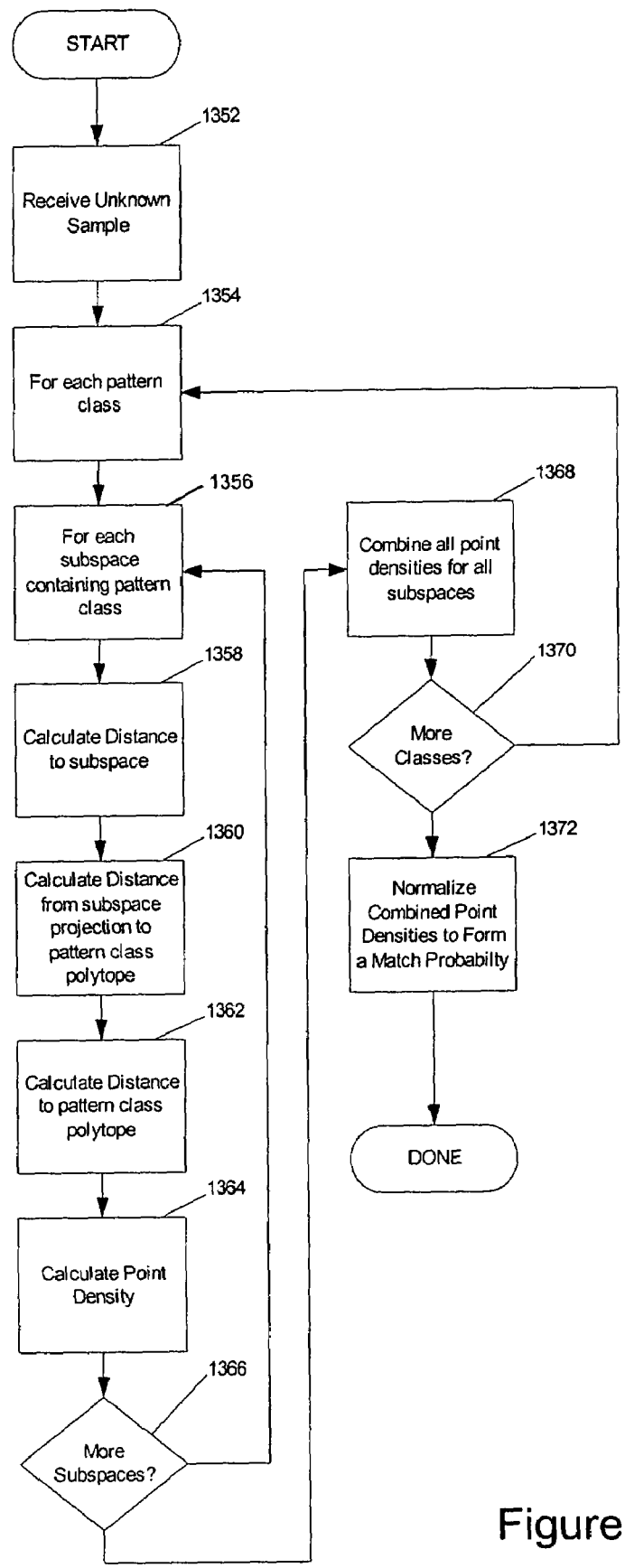

The method described in FIG. 6B does not account for the polytopes for a given class in subspaces other than that to which the sample belongs. FIG. 6C is a flow chart illustrating an alternative method of identifying an unknown sample using polytope classifiers trained by a process such as that described in FIG. 6A. At step 1352, an unknown sample is received by the pattern classification system. At step 1354, a pattern class is selected. At step 1356, a subspace is selected which contains one of the pattern class' polytopes. If no polytope for that pattern class exists in that subspace, another subspace can be selected. At step 1358, a gap distance is calculated, i.e. the distance between the unknown sample and the selected subspace. At step 1360, the mutation distance is calculated, i.e. the distance between a "projection" of the unknown sample and the pattern class' polytopes. In practice, the distance is actually the minimum distance between all possible minimal insertions (or deletions) sufficient to mutate the sample to the given subspace. At step 1362, the point density of the unknown sample with respect to the pattern class' polytope is calculated as a function of either the gap distance, the mutation distance or both. At step 1364, the process is made to repeat until all subspaces with the specific pattern class' polytopes have be selected. Once all the point densities have been calculated, at step 1366, the point probabilities are all combined to produce a composite point probability for the unknown sample with respect to the entire pattern class. At step 1368, the process is made to repeat until all pattern classes have been selected. When all point densities with respect to all the pattern classes are calculated, a match probability is generated by normalizing the point densities at step 1370.

Specifically, as applied to the classification of an unknown organism, the polytope pattern classifier is applied to data vectors representing the amplicon base composition of organisms. The polytope pattern classifiers are trained on the amplicon base compositions of known organisms using a database of known organism amplicon mass spectra that has been indexed for key parameters of amplicon DNA sequence, including amplicon length, base composition and ratios of key nucleotides (e.g., C+T, G+T, G+C). In one aspect of the invention, the amplicon database is organized according to taxonomic identification of the known organisms. In certain aspects of the invention, the database includes amplicon data for all known organisms in a given genus, order, class, phyla, or kingdom.

In one embodiment of the present invention, each amplicon is analyzed separately. For each amplicon, a taxon is associated with at least one pattern class. When considering a given amplicon, the data used in classification lies within the theoretical maximum base composition space defined by the content of A, G, C and T bases. Thus, the data used in classification can be represented by a four dimensional vector. Furthermore, these base counts result in integer values.

To further simplify the classifier models, the data are subdivided into potential pattern subclasses based on amplicon length. By applying a constraint to the length of the data vectors, three dimensional pattern classifiers can be employed.

Figure 7A:
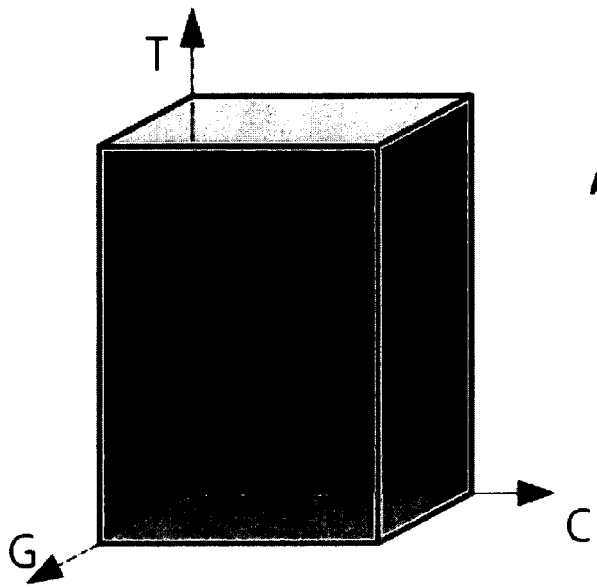
FIG. 7A is a three dimensional representation of a polytope defined by applying the three unary inequality constraints.
Figure 7B:
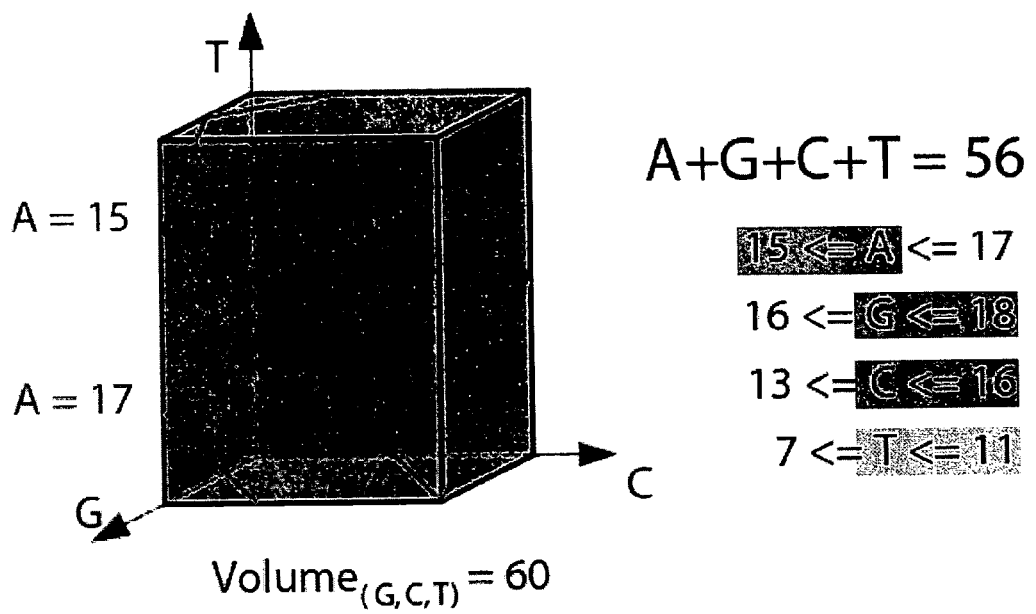
FIG. 7B and FIG. 7C are three dimensional representations of polytopes defined by additionally applying a unary inequality on A, equivalent to a trinary inequality on the three dimensions shown.
Figure 7C:
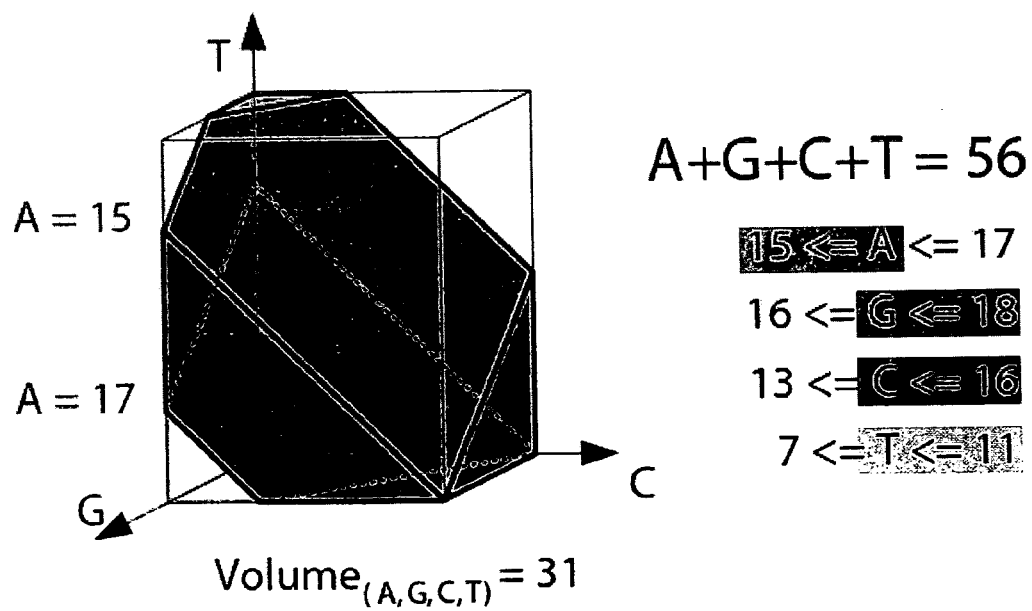

For example, Table 2 (below) represents a set of known organisms belonging to the Neisseriales taxon. The base compositions for bioagent identifying amplicons obtained with a broad range bacterial primer pair are shown. Within the known taxons of Neisseriales, for example, the amplicons are either 55 or 56 nucleotides in length. In accordance with the use of three dimensional polytope classification, the data are broken into two groups where each member has the same amplicon length. For illustrative purposes, the training of a three-dimensional classifier on a training set comprising data of amplicon length 56 is considered. In the figures, the polyhedra (3-dimensional polytopes) are shown in the G, C, and T axis. First unary inequalities are applied to first define the polyhedron, these inequalities are derived selecting a smallest unary inequality ranges for which the data in the training sets still reside within the polyhedron. For the given example, these inequalities are $16 \leq G \leq 18$, $13 \leq C \leq 16$, and $7 \leq T \leq 11$. As illustrated in FIG. 7A, these inequalities define a polyhedron of volume 60. It should be noted that the A composition value was not used since the value of A is governed by the amplicon length. However, it should be noted that from the training set, a minimal unary inequality of $15 \leq A \leq 17$ can be derived. Because of the constraint on amplicon length, this is equivalent to the trinary inequality of $39 \leq G+C+T \leq 41$. FIG. 7B shows the result of boundaries of this inequality and FIG. 7C shows the resultant polyhedron when the inequality is applied, resulting in a polyhedron with the volume of 31.

TABLE 2

Neisseriales Base Compositions for a Representative Broad Range Bacterial Survey Primer Pair

| Bioagent | Base Composition | | | | |
|---|---|---|---|---|---|
| | A | G | C | T | A+G+C+T |
| *Neisseria gonorrhoeae* FA1090 | 16 | 16 | 13 | 10 | 55 |
| *Neisseria meningitidis* A | 16 | 16 | 15 | 8 | 55 |
| *Neisseria meningitidis* B | 16 | 16 | 15 | 8 | 55 |
| *Neisseria meningitidis* C | 16 | 16 | 15 | 8 | 55 |
| *Chromobacterium violaceum* | 16 | 18 | 15 | 6 | 55 |
| *Neisseria gonorrhoeae* B 5025 | 16 | 16 | 13 | 11 | 56 |
| *Neisseria weaveri* | 16 | 16 | 13 | 11 | 56 |
| *Formivibrio citricus* | 17 | 16 | 16 | 7 | 56 |
| *Aquaspirillum delicatum* | 15 | 17 | 15 | 9 | 56 |
| *Aquaspirilium sinuosum* | 15 | 17 | 15 | 9 | 56 |
| *Aquaspirillum gracile* | 15 | 17 | 16 | 8 | 56 |
| *Microvigula aerodenitrificans* | 16 | 18 | 14 | 8 | 56 |

In addition, individual binary inequalities can be applied. While within the A, G, C, T space, there are six possible binary inequalities, there are only three in the G, C, T space as the binary inequalities involving A are accounted for because of the constraint on amplicon length.

Figure 8A:
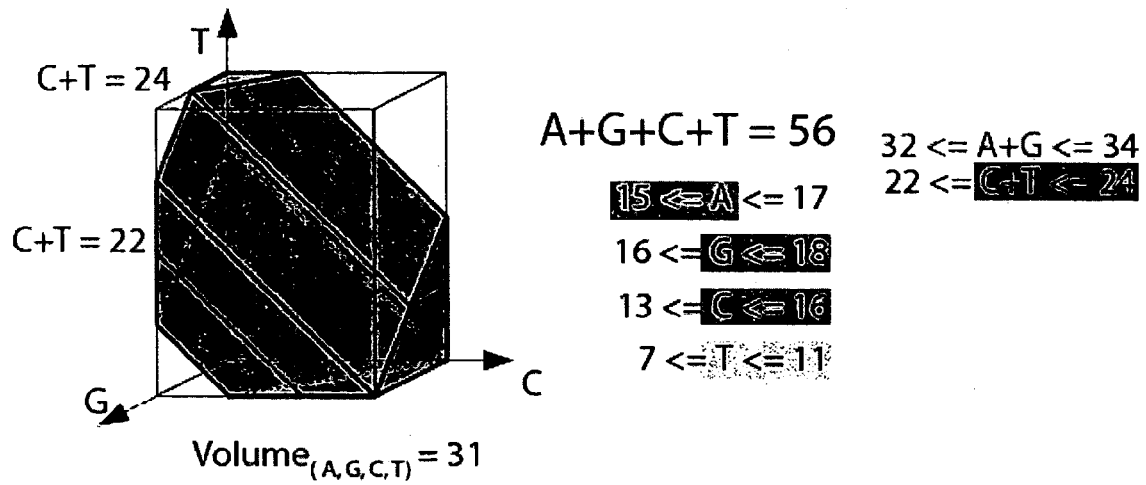
FIG. 8A and FIG. 8B are three dimensional representations of polytopes defined by applying the C+T (pyrimidine/purine) binary inequality.
Figure 8B:
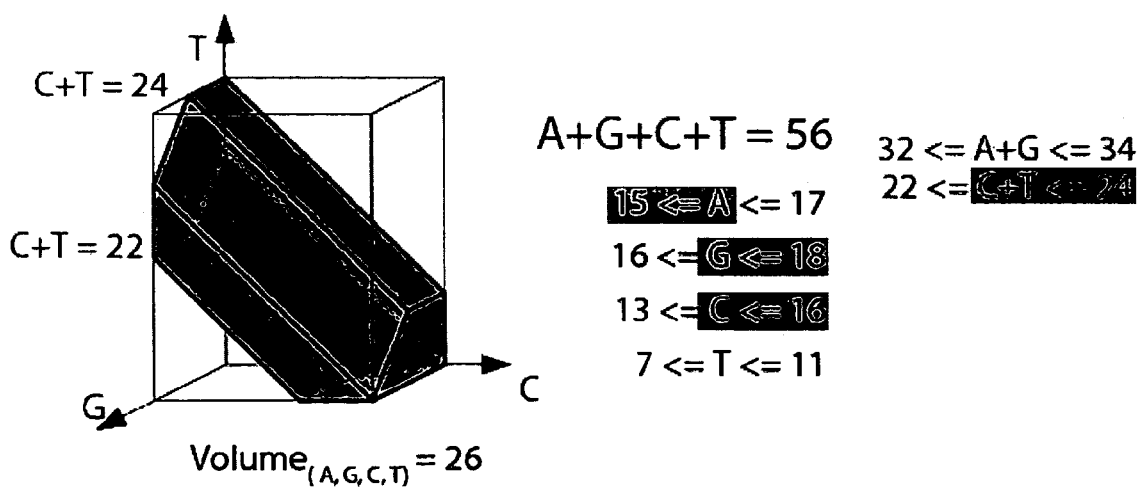

FIG. 8A illustrates the application of the $22 \leq C+T \leq 24$ binary inequality and shows the boundaries imposed by the inequality to the existing polyhedron. FIG. 8B shows the resultant polyhedron, which has a volume of 26. This inequality is a constraint on the composition of purines (C+T) in the amplicons determined. As will be apparent to the skilled artisan, constraining the polyhedron according to pyrimidine composition can be considered complementary to the purine constraint, because of the constraints on amplicon length. FIGS. 9A and 9B show the result of applying the keto/amino preference (G+T binary inequality).

Figure 10:
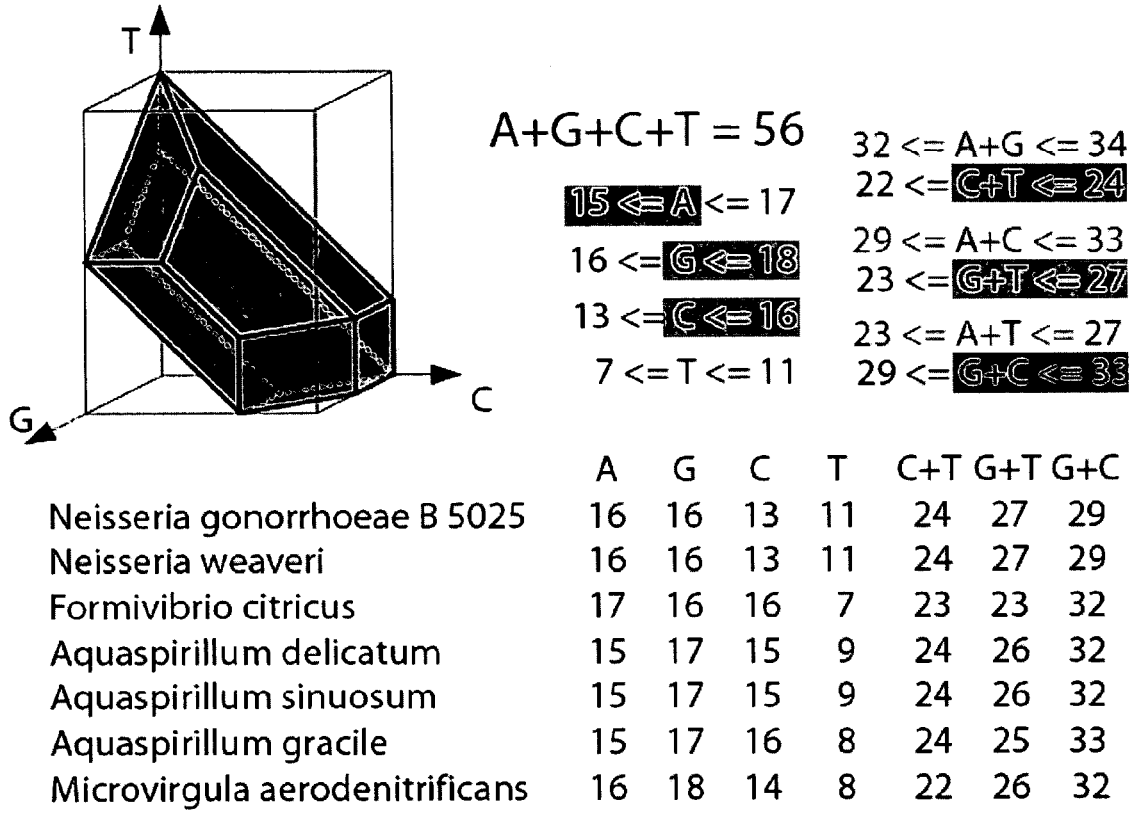
FIG. 10 is a three dimensional representation of polytopes defined by applying the G+C (strong/weak base paring constraints).

FIG. 10 shows the result of applying the strong/weak base pairing constraints (G+C binary inequality). In this example, the resulting polyhedral pattern class is reduced to a minimum volume of 23.

A density calculation can also be performed based on the number of amplicons that occupy the taxon. For this example, the 7 amplicons occupy a volume of 23 in base compositional space giving a density of 0.304.

Though not shown, similar classification training results a pattern classifier where the amplicons of length 55 generate a polyhedron of volume 9. With 5 exemplars in the training set, a density of 0.556 can be calculated.

The skilled artisan will recognize that the polytopes thus generated can be generated or represented in various forms, including but not limited to, 4 dimensions rather than 3, and the minimum volume of base compositions space-may be observed by varying the parameters used to constrain the polyhedrons.

Figure 11A:
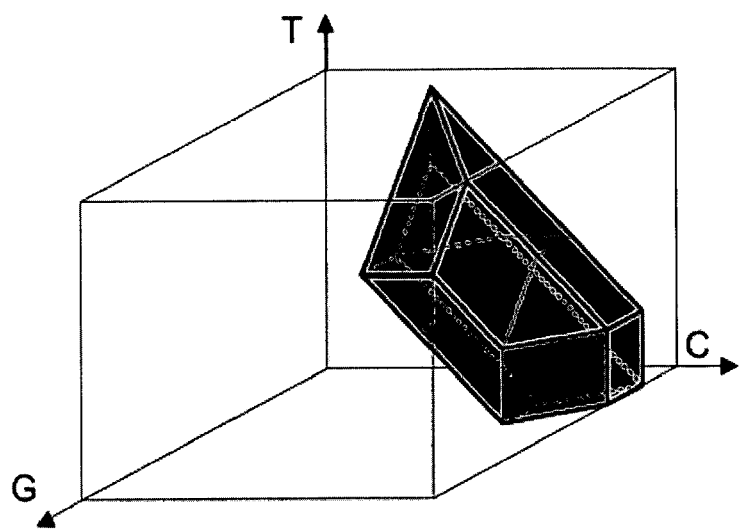
FIG. 11A shows the three dimensional representation of the *Neisseriales* polytope along with its population, volume and density.
Figure 11B:
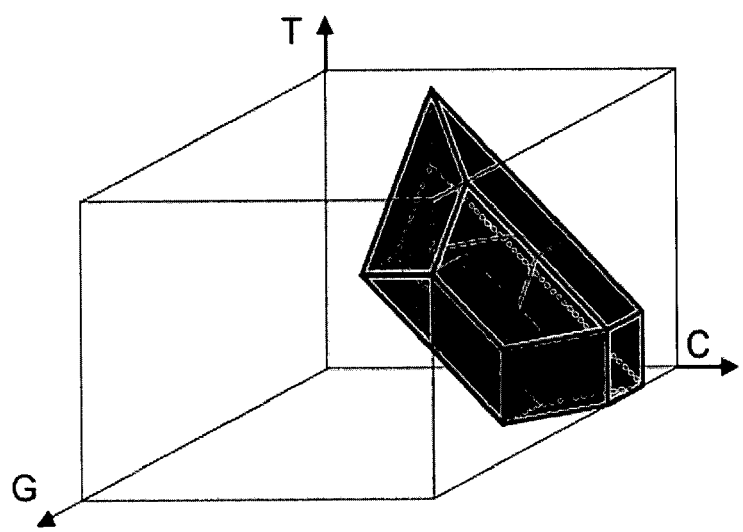
FIG. 11B shows the addition of the three dimensional representation of the Nitrosomonades polytope along with its population, volume and density to the polytope of FIG. 11A.
Figure 11C:
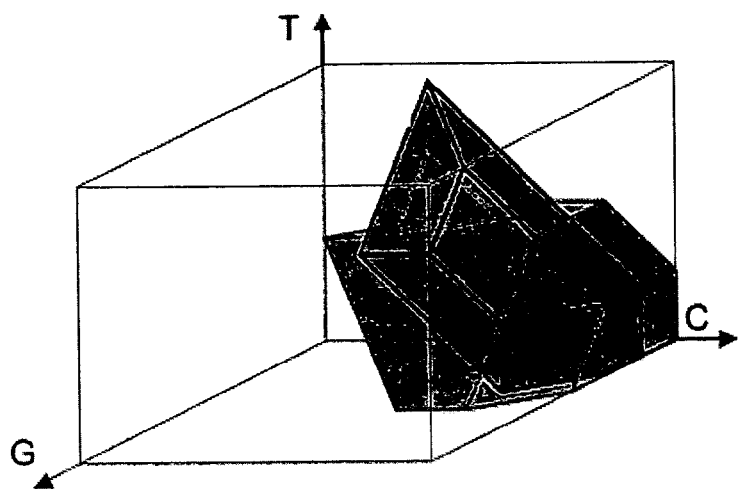
FIG. 11C shows the addition of the three dimensional representation of the Burkholderiales polytope along with its population, volume and density to the polytope of FIG. 11B.
Figure 11D:
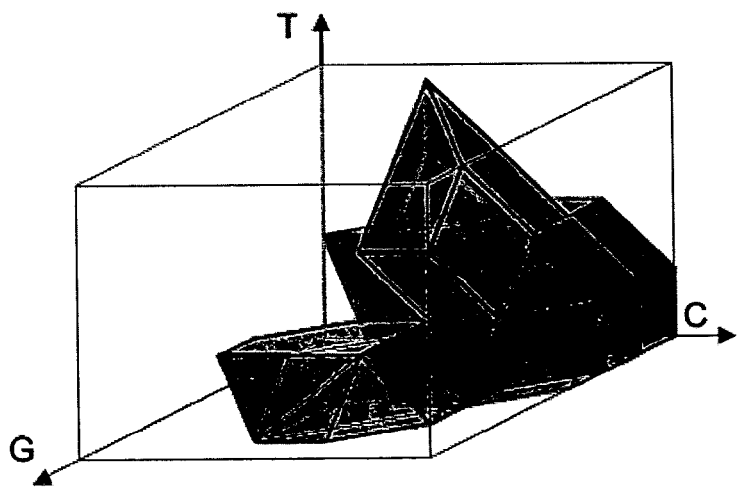
FIG. 11D shows the addition of the three dimensional representation of the Hydrogenophilales polytope along with its population, volume and density; to the polytope of FIG. 11C.

For a given amplicon length, in one embodiment of the invention, the multidimensional polyhedron space and the density thereof can be determined for all taxonomic groups. As shown in FIGS. 11A-E, the polyhedrons for each individual taxon can be superimposed, while the constraints imposed by the sum of all the taxons in, for example, a given class can be independently applied to define the overall base compositional space occupied. It will be apparent to the skilled artisan that the polyhedrons for each taxon may overlap, while the overall base compositional space of the larger class taxon may occupy space for which no model organism has been observed (FIG. 11F).

Shown in FIG. 11F, an unknown bioagent is determined to have a 346 base composition of A=15, G=18, C=16, T=7, which has a total length of 56. Accordingly, the polytope pattern classifier trained on amplicons of length 56 is used. As shown in FIG. 11F, the base composition resides in the polytope for the Birkholderiales Taxon and Hydrogenophilales Taxon and has a distance of 1 (determined by lattice hops) to the remain taxons. The point densities for each taxon are determined by applying a decay factor of 1/256 raised to the power of the distance. The resultant match probabilities are then calculated by normalizing the point densities. In the example only 5 bacteriological orders are shown, but the results are normalized to all 71 bacteriological orders, but most are not shown for clarity.

In an alternate embodiment of the pattern classifier, the point densities can be calculated by combining the density values derived from polytopes all representing a specific taxon. In the example shown above, the Neisseriales pattern class comprises amplicons of both length 55 and length 56, as a result in the training of the pattern classifier there is a polytope in the "55 length subspace" associated with the Neisseriales pattern class (henceforth the Neisserales-55 polytope) and a polytope in the "56 length subspace" also associated with the Neisseriales pattern class (henceforth the Niesseriales-56 polytope). The alternate pattern classifier uses both polytopes for identification of the unknown sample. In the preceding example, there is a distance of 1 between the unknown sample and the Neisseriales-56. In deriving the distance between the unknown sample and the Niesseriales-55 polytope, the distance measure can be broken into two distance components, the distance between the sample and the "55 length subspace" which is 1 and the distance between the sample projected onto the 55 length subspace to the Neisseriales-55 polytope is 1. The first component of distance is referred to as the "gap distance" and the second component of the distance is referred to as the "mutation distance." In this case, the projection is the point in the 55 length subspace which lies closest to the Neisseriales-55 polytope with only one change in A, C, or T. If the gap distance were 2, the projection would be the point in the subspace which lies closest to the polytope have at most two changes in A, G, C, or T. It should be noted that since the unknown sample resides in the 56 length subspace, the gap distance between the unknown sample and the *Neisseriales*-56 polytope is 0.

However, the match probability based on a single primer pair may not provide accurate results. According to the present invention, the assignment of an unknown bioagent to a taxon can be further refined by comparing the base compositional space occupied by additional amplicons (FIG. 12). Using this "triangulation" approach, the normalized product of the individual primer pair probabilities yields a global assignment probability for each taxon. Thus, in certain embodiments of the invention, an unknown bioagent is matched in base compositional space to the 1, 2, 3, 4 or more polyhedrons representing the base compositional space of different amplicons from known bioagents (the "training set").

Probability calculations can be applied to determine reliability of the method, as summarized in Table 3 below, wherein the primer pair numbers refer to primer pairs disclosed in commonly owned U.S. application Ser. No. 11/060,135 which is incorporated herein by reference in entirety.

TABLE 3

Reliability of Taxonomic Assignment of Bacteria using the Polytope Pattern Model.

| Assignment Threshold | Primer Pair Comb. | % of assignment above threshold | | | | | % of correct assignment | | | | |
|---|---|---|---|---|---|---|---|---|---|---|---|
| | | Phy. | Cl. | Ord. | Fam. | Gen. | Phy. | Cl. | Ord. | Fam. | Gen. |
| 50% | 346 | 48.6% | 32.8% | 32.4% | 33.1% | 31.7% | 70.6% | 70.0% | 67.6% | 60.4% | 57.1% |
| | 347 | 86.2% | 79.8% | 65.2% | 61.7% | 56.6% | 84.8% | 73.0% | 74.3% | 70.7% | 71.3% |
| | 348 | 92.4% | 71.6% | 66.4% | 62.4% | 65.3% | 79.9% | 82.4% | 78.2% | 73.8% | 76.0% |
| | 361 | 97.1% | 97.4% | 97.4% | 97.9% | 95.9% | 87.7% | 94.7% | 87.3% | 83.6% | 75.2% |
| | 346 + 347 | 85.7% | 77.4% | 79.3% | 80.9% | 80.3% | 87.1% | 91.1% | 83.9% | 88.3% | 85.2% |
| | 346 + 348 | 96.4% | 82.8% | 86.4% | 88.1% | 85.3% | 83.5% | 91.0% | 82.8% | 83.0% | 83.8% |
| | 346 + 361 | 87.6% | 64.5% | 71.4% | 73.3% | 75.5% | 81.1% | 87.4% | 85.5% | 80.9% | 84.0% |
| | 347 + 348 | 97.2% | 94.7% | 93.6% | 91.7% | 91.0% | 90.4% | 92.2% | 89.7% | 89.1% | 86.9% |

TABLE 3-continued

Reliability of Taxonomic Assignment of Bacteria using the Polytope Pattern Model.

| Assignment Threshold | Primer Pair Comb. | % of assignment above threshold | | | | | % of correct assignment | | | | |
|---|---|---|---|---|---|---|---|---|---|---|---|
| | | Phy. | Cl. | Ord. | Fam. | Gen. | Phy. | Cl. | Ord. | Fam. | Gen. |
| | 347 + 361 | 92.8% | 89.3% | 90.7% | 84.7% | 86.0% | 91.1% | 91.9% | 87.1% | 87.8% | 83.0% |
| | 348 + 361 | 96.9% | 86.7% | 84.5% | 82.9% | 87.9% | 85.1% | 94.6% | 87.8% | 85.4% | 85.7% |
| | 346 + 347 + 348 | 94.1% | 92.9% | 92.9% | 95.0% | 92.9% | 89.6% | 95.2% | 91.3% | 90.9% | 86.6% |
| | 346 + 347 + 361 | 90.5% | 87.9% | 89.0% | 90.5% | 89.3% | 90.9% | 94.5% | 90.1% | 92.8% | 89.6% |
| | 346 + 348 + 361 | 95.7% | 87.4% | 87.4% | 91.9% | 89.7% | 87.0% | 95.7% | 91.9% | 88.9% | 89.2% |
| | 347 + 348 + 361 | 97.8% | 94.7% | 92.8% | 95.9% | 94.0% | 93.5% | 96.5% | 92.8% | 91.7% | 90.8% |
| | 346 + 347 + 348 + 361 | 95.9% | 95.5% | 93.3% | 96.0% | 92.8% | 89.4% | 96.6% | 93.2% | 94.3% | 91.4% |
| 60% | | 88.4% | 88.8% | 88.1% | 91.6% | 88.6% | 94.3% | 97.5% | 96.3% | 95.5% | 93.2% |
| 70% | | 81.7% | 81.9% | 82.1% | 86.2% | 84.5% | 96.8% | 97.9% | 96.8% | 95.8% | 94.1% |
| 80% | 346 + 347 + 348 + 361 | 66.9% | 72.2% | 76.0% | 81.6% | 77.4% | 97.9% | 98.6% | 98.0% | 96.8% | 96.0% |
| 90% | | 55.3% | 61.2% | 66.6% | 69.1% | 70.7% | 99.1% | 99.2% | 98.7% | 98.0% | 96.1% |

Phy = phylum; Cl. = Class; Ord. = Order; Fam. = Family; Gen. = Genus

Figure 13:
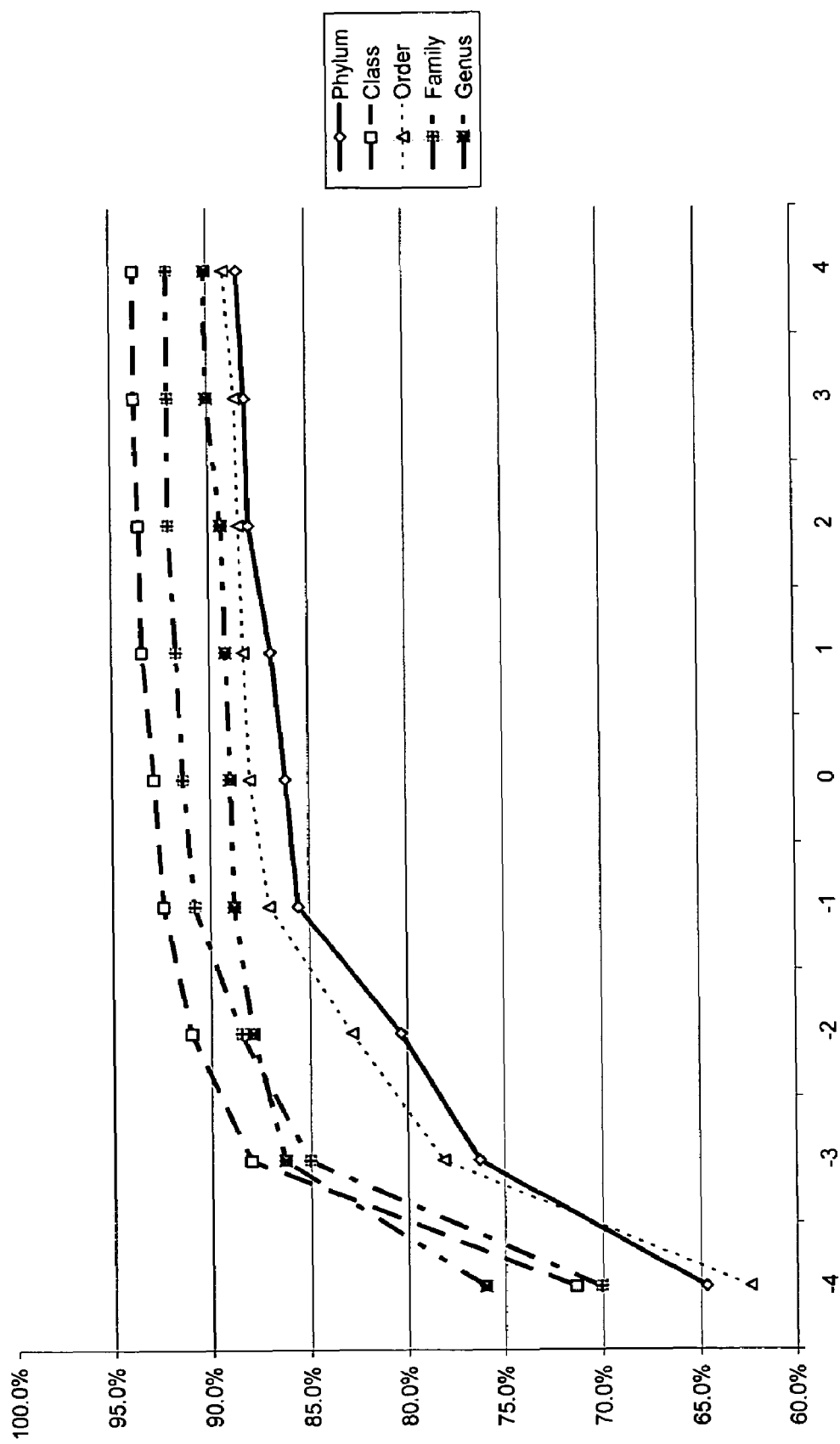
FIG. 13 is an graph illustrating the reliability of phylogenetic assignment made using one embodiment of the polytope pattern classifier.

Table 3 provides a summary of the polytope analysis of 580 test bioagents (sample set) compared to 3413 individual known species in the training set. To date, 14/19 Phyla, 22/28 Classes, 56/71 Orders, 119/170 Families, 229/466 Genera have been analyzed. FIG. 13 illustrates that reliable phylogenetic assignment can be made using the polytope pattern model. In certain embodiments of the invention alternate compatible assignments may be suggested. The present invention contemplates that in some circumstances the present invention will generate multiple possible phylogenetic assignments in parallel at different levels, allowing at least a partial assignment of unknown bioagents.

Figure 14:
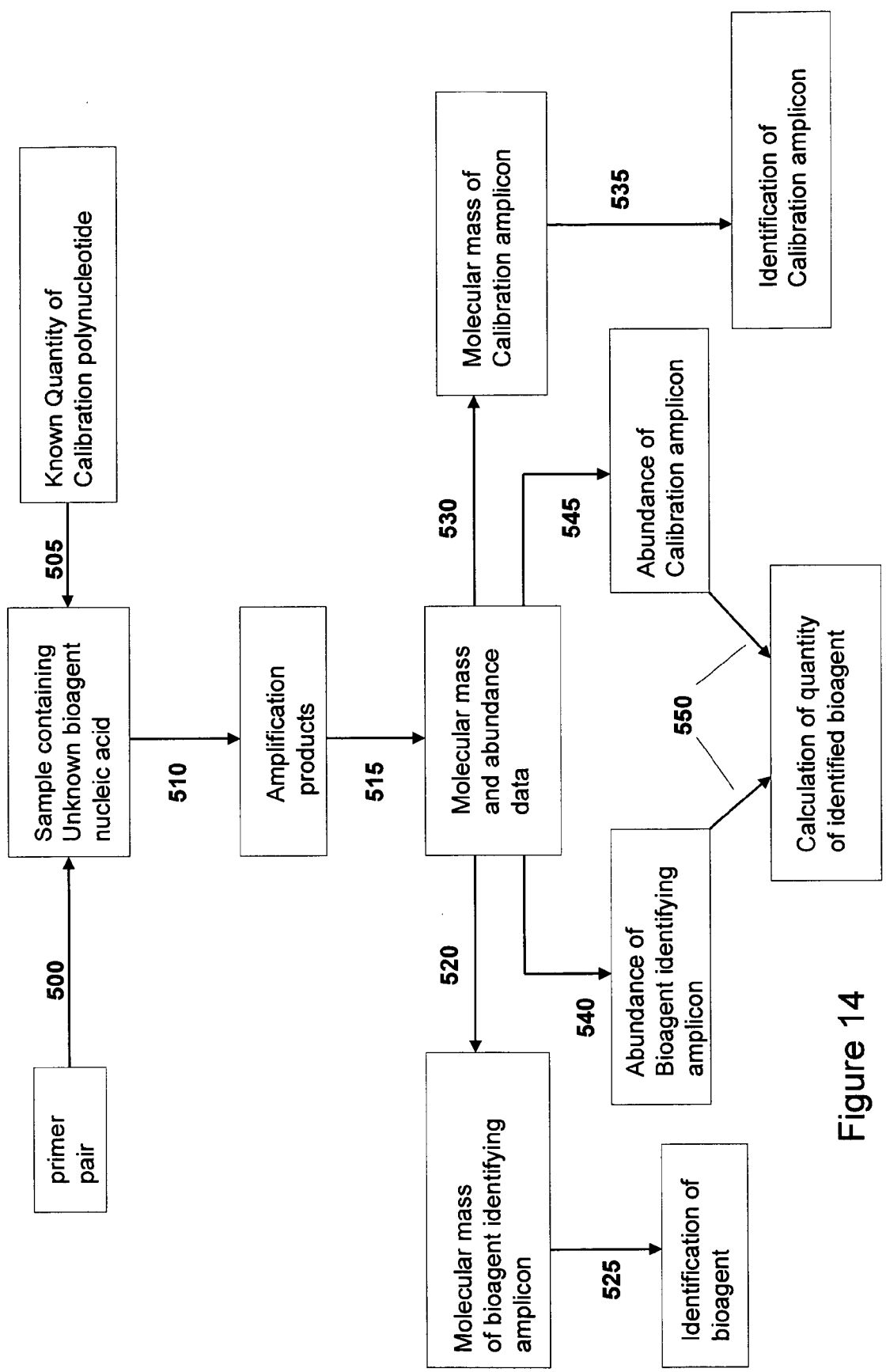
FIG. 14 is a process diagram illustrating an embodiment of the calibration method.

In some embodiments, the identity and quantity of an unknown bioagent can be determined using the process illustrated in FIG. 14. Primers (500) and a known quantity of a calibration polynucleotide (505) are added to a sample containing nucleic acid of an unknown bioagent. The total nucleic acid in the sample is then subjected to an amplification reaction (510) to obtain amplification products. The molecular masses of amplification products are determined (515) from which are obtained molecular mass and abundance data. The molecular mass of the bioagent identifying amplicon (520) provides the means for its identification (525) and the molecular mass of the calibration amplicon obtained from the calibration polynucleotide (530) provides the means for its identification (535). The abundance data of the bioagent identifying amplicon is recorded (540) and the abundance data for the calibration data is recorded (545), both of which are used in a calculation (550) which determines the quantity of unknown bioagent in the sample.

A sample comprising an unknown bioagent is contacted with a pair of primers which provide the means for amplification of nucleic acid from the bioagent, and a known quantity of a polynucleotide that comprises a calibration sequence. The nucleic acids of the bioagent and of the calibration sequence are amplified and the rate of amplification is reasonably assumed to be similar for the nucleic acid of the bioagent and of the calibration sequence. The amplification reaction then produces two amplification products: a bioagent identifying amplicon and a calibration amplicon. The bioagent identifying amplicon and the calibration amplicon should be distinguishable by molecular mass while being amplified at essentially the same rate. Effecting differential molecular masses can be accomplished by choosing as a calibration sequence, a representative bioagent identifying amplicon (from a specific species of bioagent) and performing, for example, a 2-8 nucleobase deletion or insertion within the variable region between the two priming sites. The amplified sample containing the bioagent identifying amplicon and the calibration amplicon is then subjected to molecular mass analysis by mass spectrometry, for example. The resulting molecular mass analysis of the nucleic acid of the bioagent and of the calibration sequence provides molecular mass data and abundance data for the nucleic acid of the bioagent and of the calibration sequence. The molecular mass data obtained for the nucleic acid of the bioagent enables identification of the unknown bioagent and the abundance data enables calculation of the quantity of the bioagent, based on the knowledge of the quantity of calibration polynucleotide contacted with the sample.

In some embodiments, construction of a standard curve where the amount of calibration polynucleotide spiked into the sample is varied, provides additional resolution and improved confidence for the determination of the quantity of bioagent in the sample. The use of standard curves for analytical determination of molecular quantities is well known to one with ordinary skill and can be performed without undue experimentation.

In some embodiments, multiplex amplification is performed where multiple bioagent identifying amplicons are amplified with multiple primer pairs which also amplify the corresponding standard calibration sequences. In this or other embodiments, the standard calibration sequences are optionally included within a single vector which functions as the calibration polynucleotide. Multiplex amplification methods are well known to those with ordinary skill and can be performed without undue experimentation.

In some embodiments, the calibrant polynucleotide is used as an internal positive control to confirm that amplification conditions and subsequent analysis steps are successful in producing a measurable amplicon. Even in the absence of copies of the genome of a bioagent, the calibration polynucleotide should give rise to a calibration amplicon. Failure to produce a measurable calibration amplicon indicates a failure of amplification or subsequent analysis step such as amplicon purification or molecular mass determination. Reaching a conclusion that such failures have occurred is in itself, a useful event.

In some embodiments, the calibration sequence is comprised of DNA. In some embodiments, the calibration sequence is comprised of RNA.

In some embodiments, the calibration sequence is inserted into a vector which then itself functions as the calibration polynucleotide. In some embodiments, more than one calibration sequence is inserted into the vector that functions as the calibration polynucleotide. Such a calibration polynucleotide is herein termed a "combination calibration polynucleotide." The process of inserting polynucleotides into vectors is routine to those skilled in the art and can be accomplished without undue experimentation. Thus, it should be recognized that the calibration method should not be limited to the embodiments described herein. The calibration method can be applied for determination of the quantity of any bioagent identifying amplicon when an appropriate standard calibrant polynucleotide sequence is designed and used. The process of choosing an appropriate vector for insertion of a calibrant is also a routine operation that can be accomplished by one with ordinary skill without undue experimentation.

Bioagents that can be identified by the methods of the present invention include RNA viruses. The genomes of RNA viruses can be positive-sense single-stranded RNA, negative-sense single-stranded RNA or double-stranded RNA. Examples of RNA viruses with positive-sense single-stranded genomes include, but are not limited to members of the Caliciviridae, Picornaviridae, Flaviviridae, Togaviridae, Retroviridae and Coronaviridae families. Examples of RNA viruses with negative-sense single-stranded RNA genomes include, but are not limited to, members of the Filoviridae, Rhabdoviridae, Bunyaviridae, Orthomyxoviridae, Paramyxoviridae and Arenaviridae families. Examples of RNA viruses with double-stranded RNA genomes include, but are not limited to, members of the Reoviridae and Bimaviridae families.

In some embodiments of the present invention, RNA viruses are identified by first obtaining RNA from an RNA virus, or a sample containing or suspected of containing an RNA virus, obtaining corresponding DNA from the RNA by reverse transcription, amplifying the DNA to obtain one or more amplification products using one or more pairs of oligonucleotide primers that bind to conserved regions of the RNA viral genome, which flank a variable region of the genome, determining the molecular mass or base composition of the one or more amplification products and comparing the molecular masses or base compositions with calculated or experimentally determined molecular masses or base compositions of known RNA viruses, wherein at least one match identifies the RNA virus. Methods of isolating RNA from RNA viruses and/or samples containing RNA viruses, and reverse transcribing RNA to DNA are well known to those of skill in the art.

Members of the Filoviridae, Flaviviridae, Bunyaviridae and Arenaviridae families represent RNA virus examples of bioagents which can be identified by the methods of the present invention. Filoviruses, flaviviruses, arenaviruses and three genera of the Bunyaviridae family (hantavirus, phlebovirus and nairovirus) are known to cause to VHF.

In one embodiment of the present invention, the target gene is filovirus RNA-dependent RNA polymerase. In another embodiment, the target gene is filovirus nucleocapsid.

In one embodiment of the present invention, the target gene is flavivirus NS5, the viral RNA-dependent RNA polymerase. In another embodiment, the target gene is flavivirus NS3, the viral protease, helicase and NTPase.

In one embodiment of the present invention, the target gene is hantavirus RNA-dependent RNA polymerase. In another embodiment, the target gene is hantavirus nucleocapsid. In another embodiment, the target gene is phlebovirus RNA-dependent RNA polymerase. In another embodiment, the target gene is nairovirus nucleocapsid.

In one embodiment of the present invention, the target gene is the arenavirus gene L, which is the viral RNA-dependent RNA polymerase. In another embodiment, the target gene is arenavirus NP, the viral nucleocapsid.

In other embodiments of the present invention, the intelligent primers produce bioagent identifying amplicons within stable and highly conserved regions of hantaviral, phleboviral or nairoviral genomes. The advantage to characterization of an amplicon in a highly conserved region is that there is a low probability that the region will evolve past the point of primer recognition, in which case, the amplification step would fail. Such a primer set is thus useful as a broad range survey-type primer. In another embodiment of the present invention, the intelligent primers produce bioagent identifying amplicons in a region which evolves more quickly than the stable region described above. The advantage of characterization bioagent identifying amplicon corresponding to an evolving genomic region is that it is useful for distinguishing emerging strain variants.

The present invention also has significant advantages as a platform for identification of diseases caused by emerging viruses. The present invention eliminates the need for prior knowledge of bioagent sequence to generate hybridization probes. Thus, in another embodiment, the present invention provides a means of determining the etiology of a virus infection when the process of identification of viruses is carried out in a clinical setting and, even when the virus is a new species never observed before. This is possible because the methods are not confounded by naturally occurring evolutionary variations (a major concern for characterization of viruses which evolve rapidly) occurring in the sequence acting as the template for production of the bioagent identifying amplicon. Measurement of molecular mass and determination of base composition is accomplished in an unbiased manner without sequence prejudice.

Another embodiment of the present invention also provides a means of tracking the spread of any species or strain of virus when a plurality of samples obtained from different locations are analyzed by the methods described above in an epidemiological setting. In one embodiment, a plurality of samples from a plurality of different locations are analyzed with primers which produce bioagent identifying amplicons, a subset of which contain a specific virus. The corresponding locations of the members of the virus-containing subset indicate the spread of the specific virus to the corresponding locations.

The present invention also provides kits for carrying out the methods described herein. In some embodiments, the kit may comprise a sufficient quantity of one or more primer pairs to perform an amplification reaction on a target polynucleotide from a bioagent to form a bioagent identifying amplicon. In some embodiments, the kit may comprise from one to fifty primer pairs, from one to twenty primer pairs, from one to ten primer pairs, or from two to five primer pairs. In some embodiments, the kit may comprise one or more primer pairs recited in Tables 4-7.

In some embodiments, the kit may comprise one or more broad range survey primer(s), division wide primer(s), or drill-down primer(s), or any combination thereof. A kit may be designed so as to comprise particular primer pairs for identification of a particular bioagent. For example, a broad range survey primer kit may be used initially to identify an unknown bioagent as a member of the filovirus genus. Another example of a division-wide kit may be used to distinguish Zaire Ebola virus, Sudan Ebola virus and Marburg virus from each other. A drill-down kit may be used, for example, to distinguish different subtypes of Zaire Ebola virus, or to identify genetically engineered filoviruses. In some embodiments, any of these kits may be combined to comprise a combination of broad range survey primers and division-wide primers so as to be able to identify the species of an unknown bioagent.

In some embodiments, the kit may contain standardized calibration polynucleotides for use as internal amplification calibrants. Internal calibrants are described in commonly owned U.S. Patent Application Ser. No. 60/545,425 which is incorporated herein by reference in its entirety.

In some embodiments, the kit may also comprise a sufficient quantity of reverse transcriptase (if an RNA virus is to be identified for example), a DNA polymerase, suitable nucleoside triphosphates (including any of those described above), a DNA ligase, and/or reaction buffer, or any combination thereof, for the amplification processes described above. A kit may further include instructions pertinent for the particular embodiment of the kit, such instructions describing the primer pairs and amplification conditions for operation of the method. A kit may also comprise amplification reaction containers such as microcentrifuge tubes and the like. A kit may also comprise reagents or other materials for isolating bioagent nucleic acid or bioagent identifying amplicons from amplification, including, for example, detergents, solvents, or ion exchange resins which may be linked to magnetic beads. A kit may also comprise a table of measured or calculated molecular masses and/or base compositions of bioagents using the primer pairs of the kit.

While the present invention has been described with specificity in accordance with certain of its embodiments, the following examples serve only to illustrate the invention and are not intended to limit the same. In order that the invention disclosed herein may be more efficiently understood, examples are provided below. It should be understood that these examples are for illustrative purposes only and are not to be construed as limiting the invention in any manner.

EXAMPLES

Example 1

Selection of Primers that Define Bioagent Identifying Amplicons for VHF Viruses

For design of primers that define viral hemorrhagic fever virus bioagent identifying amplicons, relevant sequences from, for example, GenBank were obtained, aligned and scanned for regions where pairs of PCR primers would amplify products of about 45 to about 200 nucleotides in length and distinguish species and/or sub-species from each other by their molecular masses or base compositions. A typical process shown in FIG. 1 is employed.

A database of expected base compositions for each primer region is generated using an in silico PCR search algorithm, such as (ePCR). An existing RNA structure search algorithm (Macke et al., Nucl. Acids Res., 2001, 29, 4724-4735, which is incorporated herein by reference in its entirety) has been modified to include PCR parameters such as hybridization conditions, mismatches, and thermodynamic calculations (SantaLucia, Proc. Natl. Acad. Sci. U.S.A., 1998, 95, 1460-1465, which is incorporated herein by reference in its entirety). This also provides information on primer specificity of the selected primer pairs.

Tables 4-7 represent collections of primers (sorted by forward primer name) designed to identify, flaviviruses (Table 4), filoviruses (Table 5), bunyaviruses (Table 6) and arenaviruses (Table 7) using the methods described herein. Primer sites were identified on essential filoviral, flaviviral, hantaviral, phleboviral, nairoviral and arenaviral genes, such as, for example, RNA-dependent RNA polymerase and nucleocapsid genes. The forward or reverse primer name shown in Tables 4-7 indicates the gene region of the viral genome to which the primer hybridizes relative to a reference sequence. In Table 4, for example, the forward primer name FLAV_NC_001474_10032_10056_F indicates that the forward primer hybridizes to residues 10032-10056 of a flavivirus reference sequence represented by GenBank Accession No. NC_001474 (SEQ ID NO: 1). In Tables 4-7, $T^a$=5-propynyluracil; $C^a$=5-propynylcytosine; I=inosine. The primer pair number is an in-house database index number.

TABLE 4

Primer Pairs for Identification of Flaviviruses

| Primer Pair Number | For. Primer Name | For. Primer Sequence | For. SEQ ID NO: | Rev. Primer Name | Rev. Primer Sequence | Rev. SEQ ID NO: |
|---|---|---|---|---|---|---|
| 2194 | FLAV_NC_001474_10032_10056_F | TGCAGAGTGGGCCAAGAACATCTGG | 2 | FLAV_NC_001474_10138_10159_R | TGCTCTCCAGTTTGAGCTCCCAGTG | 62 |

TABLE 4-continued

Primer Pairs for Identification of Flaviviruses

| Primer Pair Number | For. Primer Name | For. Primer Sequence | For. SEQ ID NO: | Rev. Primer Name | Rev. Primer Sequence | Rev. SEQ ID NO: |
|---|---|---|---|---|---|---|
| 2243 | FLAV_NC_001474_2084_2108_F | TAGGAGACACAGCTTGGGACTTTGG | 3 | FLAV_NC_001474_2185_2208_R | TTGCGTGATCCAGGACATTCCTCC | 63 |
| 2242 | FLAV_NC_001474_2389_2411_F | TGGAGAGAGGTCTCAGAGTGGTA | 4 | FLAV_NC_001474_2518_2536_R | TGCTCCTCACATGGCCAT | 64 |
| 2241 | FLAV_NC_001474_2658_2679_F | TGAAATTGGCTGGAAGGCCTGG | 5 | FLAV_NC_001474_2731_2754_R | TCATTCCTTGGTCTCCGGTCCATC | 65 |
| 2240 | FLAV_NC_001474_2805_2829_F | TGGAATGTTCACGACCAACATATGG | 6 | FLAV_NC_001474_2914_2937_R | TCTCTCTATCCAGTAACCCATGTC | 66 |
| 2239 | FLAV_NC_001474_2860_2879_F | TGTGACACAGGAGTCATGGG | 7 | FLAV_NC_001474_2908_2932_R | TCATCCAGAGACTCTGATCTGTGTG | 67 |
| 2238 | FLAV_NC_001474_2910_2933_F | TGCTGACATGGGTTACTGGATAGA | 8 | FLAV_NC_001474_3019_3038_R | TCCAGCACTCCATTGCTCCA | 68 |
| 2237 | FLAV_NC_001474_3214_3239_F | TCTGTGAGGAGCACCACAGAGAGTGG | 9 | FLAV_NC_001474_3313_3339_R | TACCGGCCTTATTTCCATGGCATACCA | 69 |
| 2246 | FLAV_NC_001474_33_56_F | TGCTGTCAATATGCTGAAACGCGG | 10 | FLAV_NC_001474_143_166_R | TCCTGAAGAACGCGAAAAGAGCCA | 70 |
| 2236 | FLAV_NC_001474_3306_3335_F | TGGCTGCTGGTATGGAATGGAGATTAGACC | 11 | FLAV_NC_001474_3412_3436_R | TGGCCAGGAACATGACCAGAAGGCC | 71 |
| 2235 | FLAV_NC_001474_4561_4583_F | TTCCACACTCTATGGCACACAAC | 12 | FLAV_NC_001474_4627_4649_R | TCCTCTTTCACACTGCCCCAGTA | 72 |
| 2234 | FLAV_NC_001474_5270_5297_F | TCATGGATGAAGCACATTTCACAGATCC | 13 | FLAV_NC_001474_5341_5365_R | TGAAGATCGCAGCTGCCTCTCCCAT | 73 |
| 2233 | FLAV_NC_001474_5273_5300_F | TGGATGAAGCTCATTTCACCGATCCAGC | 14 | FLAV_NC_001474_5365_5385_R | TCCCGGCGGGGTGGCTGTCAT | 74 |
| 2232 | FLAV_NC_001474_5287_5309_F | TGGACTGATCCCCACAGCATAGC | 15 | FLAV_NC_001474_5401_5421_R | TATGGCTCCGTTGGACTCCGG | 75 |
| 2231 | FLAV_NC_001474_5514_5540_F | TAGCGTGAAAATGGGGAATGAGATTGC | 16 | FLAV_NC_001474_5629_5653_R | TGTCAGTTGTGATGACAAAGTCCCA | 76 |
| 2230 | FLAV_NC_001474_6050_6071_F | TCACACCGTGGCTGGCATGGCA | 17 | FLAV_NC_001474_6109_6131_R | TCCTCTGGGCCTTCCCATGTCCA | 77 |
| 2229 | FLAV_NC_001474_6947_6968_F | TGGGTCTTGGCAAAGGATGGCC | 18 | FLAV_NC_001474_7069_7092_R | TCCTGGGCCTATTATGGCATAATG | 78 |
| 2228 | FLAV_NC_001474_7271_7295_F | TGAGGACAACATGGGCCTTGTGTGA | 19 | FLAV_NC_001474_7357_7381_R | TGGACACGGCTATGGTGGTGTTCCA | 79 |
| 2245 | FLAV_NC_001474_749_773_F | TGGCGGCTGTTCTTGGTTGGATGCT | 20 | FLAV_NC_001474_835_862_R | TGCTCATTCCCAGGCAGTTAAAGCTGTA | 80 |
| 2227 | FLAV_NC_001474_7703_7727_F | TCGGCTGTGGAAGAGGAGGCTGGTC | 21 | FLAV_NC_001474_7777_7803_R | TGGTTCTTCATGTCCTGGTCCTCCTTT | 81 |
| 2226 | FLAV_NC_001474_7713_7736_F | TAGAGGCGGCTGGTCCTACTATGC | 22 | FLAV_NC_001474_7808_7831_R | TGTTCCAACCGAGGCTTGTTACCA | 82 |
| 2244 | FLAV_NC_001474_835_858_F | TACAGCTTCAACTGTCTGGGAATG | 23 | FLAV_NC_001474_889_910_R | TCAAATCCACCCAAGTGGCTCC | 83 |
| 2225 | FLAV_NC_001474_8358_8382_F | TCCATACAGGACATGGCAGTACTGG | 24 | FLAV_NC_001474_8452_8474_R | TCTTCCCGTGCATTCCATGGCCA | 84 |

TABLE 4-continued

Primer Pairs for Identification of Flaviviruses

| Primer Pair Number | For. Primer Name | For. Primer Sequence | For. SEQ ID NO: | Rev. Primer Name | Rev. Primer Sequence | Rev. SEQ ID NO: |
|---|---|---|---|---|---|---|
| 2224 | FLAV_NC_001474_8377_8400_F | TACCACGGAAGTTATGAGGTGAAG | 25 | FLAV_NC_001474_8479_8498_R | TCAGTCATGGCCATGGTGGT | 85 |
| 2223 | FLAV_NC_001474_8528_8555_F | TCAAAGAGAAGGTTGACACGAAAGCTCC | 26 | FLAV_NC_001474_8593_8615_R | TAGGCCCACAACCAGTTGGTGGT | 86 |
| 2222 | FLAV_NC_001474_8803_8831_F | TGTCACACGTGTGTCTACAACATGATGGG | 27 | FLAV_NC_001474_8887_8907_R | TGCTCCCAGCCACATGTACCA | 87 |
| 2221 | FLAV_NC_001474_8807_8831_2_F | TCACCTGCATCTACAACATGATGGG | 28 | FLAV_NC_001474_8926_8951_R | TGGTCTTCATTGAGGAATCCCAGAGC | 88 |
| 2220 | FLAV_NC_001474_8807_8831_F | TCCATTGCGTGTACAACATGATGGG | 29 | FLAV_NC_001474_8887_8908_R | TACTCCCCAGCCACATGTACCA | 89 |
| 2219 | FLAV_NC_001474_8808_8831_F | TACTTGCGTCTACAACATGATGGG | 30 | FLAV_NC_001474_8887_8907_R | TGCTCCCAGCCACATGTACCA | 87 |
| 2218 | FLAV_NC_001474_8812_8840_2_F | TGTGTGTACAACATGATGGGGAAGAGAGA | 31 | FLAV_NC_001474_8881_8905_R | TGCCCAGCCACATGTACCAGATGGC | 90 |
| 2217 | FLAV_NC_001474_8812_8840_F | TGTGTCTACAACATGATGGGAAAGAGAGA | 32 | FLAV_NC_001474_8887_8907_R | TGCTCCCAGCCACATGTACCA | 87 |
| 2216 | FLAV_NC_001474_8865_8885_F | TGCCAAGGGAAGCAGGGCCAT | 33 | FLAV_NC_001474_8926_8951_R | TGGTCTTCATTGAGGAATCCCAGAGC | 88 |
| 2215 | FLAV_NC_001474_8874_8898_F | TAGCCGAGCCATCTGGTACATGTGG | 34 | FLAV_NC_001474_8941_8966_R | TCTCTGGAAAGCCAGTGGTCTTCATT | 91 |
| 2213 | FLAV_NC_001474_8880_8903_F | TGCCATCTGGTACATGTGGCTGGG | 35 | FLAV_NC_001474_8971_8992_R | TTCCCTCAACTCCAGCTCCACT | 92 |
| 2214 | FLAV_NC_001474_8880_8903_F | TGCCATCTGGTACATGTGGCTGGG | 35 | FLAV_NC_001474_8941_8966_R | TCTCTGGAAAGCCAGTGGTCTTCATT | 91 |
| 2211 | FLAV_NC_001474_8885_8906_2_F | TCTGGTTCATGTGGCTGGGAGC | 36 | FLAV_NC_001474_8941_8964_R | TCTGCCCAGCCAGTGGTCTTCATT | 93 |
| 2210 | FLAV_NC_001474_8885_8906_F | TCTGGTACATGTGGCTGGGAGC | 37 | FLAV_NC_001474_8977_9002_R | TGCAGACCTTCTCCTTCCACTCCACT | 94 |
| 2212 | FLAV_NC_001474_8885_8906_F | TCTGGTACATGTGGCTGGGAGC | 37 | FLAV_NC_001474_8941_8964_R | TCTGCCCAGCCAGTGGTCTTCATT | 93 |
| 2209 | FLAV_NC_001474_8930_8955_F | TGGGATTCCTGAATGAAGACCACTGG | 38 | FLAV_NC_001474_9061_9084_R | TGTGTCCCAGCCGGCTGTGTCATC | 95 |
| 2208 | FLAV_NC_001474_8971_8996_F | TCATTGAGTGGAGTGGAAGGAGAAGG | 39 | FLAV_NC_001474_9061_9080_2_R | TCCCAGCCGGCTGTGTCATC | 96 |
| 2207 | FLAV_NC_001474_8984_9011_2_F | TGGAAGGCATTGGCTTACAATACCTAGG | 40 | FLAV_NC_001474_9061_9080_R | TCCCATCCAGCGGTGTCATC | 97 |
| 2206 | FLAV_NC_001474_8984_9011_F | TGGAGGGAATCAGCCTGAACTACCTGG | 41 | FLAV_NC_001474_9064_9085_R | TCGTGTCCCAGCCAGCTGTGTC | 98 |
| 2205 | FLAV_NC_001474_8999_9026_F | TCCAGAAGCTGGGATACATCCTGCGTGA | 42 | FLAV_NC_001474_9112_9135_R | TAGCAACTCCAGCACCTTAGCTTC | 99 |
| 2204 | FLAV_NC_001474_9239_9263_F | TCATAAGTCGACGAGACCAGAGAGG | 43 | FLAV_NC_001474_9313_9339_R | TGCTTCTGCCATTCTGATCAATTGGAC | 100 |

TABLE 4-continued

Primer Pairs for Identification of Flaviviruses

| Primer Pair Number | For. Primer Name | For. Primer Sequence | For. SEQ ID NO: | Rev. Primer Name | Rev. Primer Sequence | Rev. SEQ ID NO: |
|---|---|---|---|---|---|---|
| 2203 | FLAV_NC_001474_9259_9281_F | TGAGGCTCAGGTCAGGTTGTGAC | 44 | FLAV_NC_001474_9328_9351_R | TATGACACCCTCCCCCTCCATCAT | 101 |
| 2202 | FLAV_NC_001474_9437_9458_F | TGGCGGTGAGTGGAGACGACTG | 45 | FLAV_NC_001474_9501_9526_R | TAACCTTGGACATGGCGTTGAGATGG | 102 |
| 2201 | FLAV_NC_001474_9439_9461_F | TCTGTCAGCGGAGATGACTGTGT | 46 | FLAV_NC_001474_9514_9539_R | TGGATGTCTTTTCGGACCTTTGACAT | 103 |
| 2200 | FLAV_NC_001474_9492_9518_F | TGCCCTTTACTTCCTGAATGACATGGC | 47 | FLAV_NC_001474_9571_9596_R | TGTGAGCAGAAGGGGACCTCTTCCCA | 104 |
| 2199 | FLAV_NC_001474_9729_9752_F | TAAGGCCTACGGACAGATGTGGCT | 48 | FLAV_NC_001474_9847_9870_R | TGCACCACTGGCATGGATGCTCCA | 105 |
| 2198 | FLAV_NC_001474_9746_9767_F | TGTGGCTGCTGCTGTACTTCCA | 49 | FLAV_NC_001474_9864_9889_R | TGTCTTCTGTTGTCATCCACTCTCCT | 106 |
| 2197 | FLAV_NC_001474_9827_9851_F | TCCCAACAAGCCGAACAACCTGGTC | 50 | FLAV_NC_001474_9871_9894_R | TAGCATGTCTTCCGTGGTCATCCA | 107 |
| 2196 | FLAV_NC_001474_9871_9891_F | TGGATGACGACGGAAGACATG | 51 | FLAV_NC_001474_9901_9923_R | TCCTCAATCCAGACCCTGTTCCA | 108 |
| 2195 | FLAV_NC_001474_9909_9936_F | TGTCTGGATTGAGGAGAATGAATGGATG | 52 | FLAV_NC_001474_9994_10015_R | TGAGGCTTCCACACCAGATGTC | 109 |
| 526 | FLAV_NC001474_5201_5216P_F | TGAT[a]GT[a]GTC[a]ATGC[a]CAC | 53 | FLAV_NC001474_5272_5288P_R | TAATGGGCTT[a]C[a]AT[a]C[a]C[a]AT | 110 |
| 524 | FLAV_NC001474_8812_8831P_F | TGTATGT[a]ACAACAT[a]GAT[a]GGG | 54 | FLAV_NC001474_8887_8904P_R | TCCCAGCCACATGTAC[a]C[a]A | 111 |
| 525 | FLAV_NC001474_8818_8831P_F | T[a]ACAACAT[a]GAT[a]GGG | 55 | FLAV_NC001474_8887_8901P_R | TAGCCACATGTAC[a]C[a]A | 112 |
| 523 | FLAV_NC001474_8818_8840_2P_F | T[a]ACAAC[a]AT[a]GAT[a]GGGGAAGIGIGA | 56 | FLAV_NC001474_8887_8904P_R | TCCCAGCCACATGTAC[a]C[a]A | 111 |
| 522 | FLAV_NC001474_8818_8840P_F | T[a]ACAAC[a]AT[a]GAT[a]GGGAAAGAGAGA | 57 | FLAV_NC001474_8887_8904P_R | TCCCAGCCACATGTAC[a]C[a]A | 111 |
| 569 | FLAV_NC001474_8887_8903P_F | TGGTACAT[a]GT[a]GGC[a]TGGG | 58 | FLAV_NC001474_8941_8956P_R | TC[a]C[a]AGTGGTCTT[a]C[a]AT[a]T | 113 |
| 528 | FLAV_NC001474_8939_8955_2P_F | T[a]GAATGAAGATC[a]ACT[a]GG | 59 | FLAV_NC001474_9061_9080P_R | TC[a]C[a]C[a]AICCIGCIGTGTCITC | 114 |
| 530 | FLAV_NC001474_8939_8955_2P_F | T[a]GAATGAAGATC[a]ACT[a]GG | 59 | FLAV_NC001474_9061_9080P_R | TC[a]C[a]C[a]AICCIGCIGTGTCITC | 114 |
| 566 | FLAV_NC001474_8939_8955_3P_F | T[a]GAATGAAGATC[a]ACT[a]GG | 59 | FLAV_NC001474_9061_9080_2P_R | TC[a]C[a]C[a]AICCIGCIGTGTCATC | 115 |
| 567 | FLAV_NC001474_8939_8955_4P_F | T[a]GAATGAAGACC[a]ATT[a]GG | 60 | FLAV_NC001474_9061_9080_3_R | TCCCAICCIGCIGTGTCATC | 116 |
| 529 | FLAV_NC001474_8939_8955P_F | T[a]GAATGAAGACC[a]ATT[a]GG | 60 | FLAV_NC001474_9061_9080_R | TCCCAICCIGCIGTGTCITC | 117 |
| 527 | FLAV_NC001474_8939_8955P_F | T[a]GAATGAAGACC[a]ATT[a]GG | 60 | FLAV_NC001474_9061_9080_R | TCCCAICCIGCIGTGTCITC | 117 |
| 568 | FLAV_NC001474_9736_9750P_F | T[a]ACGCGCAGAT[a]GT[a]GG | 61 | FLAV_NC001474_9871_9889P_R | TGTCTTCTGTTGTCAT[a]C[a]C[a]A | 118 |

Reference Sequence NC_001474 (SEQ ID NO: 1) represents the genome of the Dendue virus.

TABLE 5

Primer Pairs for Identification of Filoviruses

| Primer pair number | For. primer name | For. sequence | For. SEQ ID NO: | Rev. primer name | Rev. sequence | Rev. SEQ ID NO: |
|---|---|---|---|---|---|---|
| 504 | FILO_NC002549_1051_1072P_F | TGGAC$^a$AC$^a$AU$^a$GATGGT$^a$AAT$^a$TT$^a$T$^a$C | 119 | FILO_NC002549_1131_1151_2P_R | TGGCAT$^a$C$^a$ATGACCAGCCAC$^a$C$^a$A | 152 |
| 503 | FILO_NC002549_1051_1072P_F | TGGAC$^a$AC$^a$AT$^a$GATGGT$^a$AAT$^a$TT$^a$T$^a$C | 120 | FILO_NC002549_1131_1151P_R | TGGCAT$^a$C$^a$ATGGCCGGCCAC$^a$C$^a$A | 153 |
| 747 | FILO_NC002549_13309_13331_F | TGTGAAGCTCTGTTAGCAGATGG | 121 | FILO_NC002549_13399_13418_R | TGGTGCCATGATGCCTGATG | 154 |
| 508 | FILO_NC002549_13311_13331P_F | TGAAGCTC$^a$T$^a$GTT$^a$AGC$^a$AGAT$^a$GG | 122 | FILO_NC002549_13351_13374_2P_R | TT$^a$C$^a$AGT$^a$GAC$^a$TAC$^a$C$^a$AT$^a$C$^a$ATAT$^a$T$^a$GCT | 155 |
| 825 | FILO_NC002549_13311_13331P_F | TGAAGCTC$^a$T$^a$GTT$^a$AGC$^a$AGAT$^a$GG | 122 | FILO_NC002549_13351_13374_2P_R | TT$^a$C$^a$AGT$^a$GAC$^a$TAC$^a$C$^a$AT$^a$C$^a$ATAT$^a$T$^a$GCT | 155 |
| 825 | FILO_NC002549_13311_13331P_F | TGAAGCTC$^a$T$^a$GTT$^a$AGC$^a$AGAT$^a$GG | 122 | FILO_NC002549_13351_13374P_R | TT$^a$C$^a$AGT$^a$GAC$^a$TAC$^a$C$^a$AT$^a$C$^a$ATGT$^a$T$^a$ACT | 156 |
| 507 | FILO_NC002549_13311_13331P_F | TGAAGCTC$^a$T$^a$GTT$^a$AGC$^a$AGAT$^a$GG | 122 | FILO_NC002549_13351_13374P_R | TT$^a$C$^a$AGT$^a$GAC$^a$TAC$^a$C$^a$AT$^a$C$^a$ATGT$^a$T$^a$ACT | 156 |
| 509 | FILO_NC002549_13311_13331P_F | TGAAGCTC$^a$T$^a$GTT$^a$AGC$^a$AGAT$^a$GG | 122 | FILO_NC002549_13357_13377P_R | TCGTT$^a$C$^a$AGT$^a$GAC$^a$TAC$^a$C$^a$AT$^a$C$^a$AT | 157 |
| 859 | FILO_NC002549_13397_13418_2_F | TGCATCAGGCATCTTGGCACCA | 123 | FILO_NC002549_13465_13498_R | TGGCGAGATTGTATTTCTCTAGATCAGTGACAAA | 158 |
| 858 | FILO_NC002549_13397_13418_F | TTCATCAGGCATCATGGCACCA | 124 | FILO_NC002549_13471_13499_R | TCGGCGAGGTTGTATTTCTCTAGATCAGT | 159 |
| 746 | FILO_NC002549_13401_13420_F | TCAGGCATCATGGCACCACA | 125 | FILO_NC002549_13471_13497_R | TGCAAGGTTGTATTTCTCTAGATCAGT | 160 |
| 510 | FILO_NC002549_13401_13420P_F | TC$^a$AGGCTT$^a$C$^a$ATGGCAC$^a$C$^a$ACA | 126 | FILO_NC002549_13471_13494P_R | TAGAT$^a$T$^a$GT$^a$ATT$^a$T$^a$C$^a$T$^a$C$^a$TAGAT$^a$C$^a$AGT | 161 |
| 857 | FILO_NC002549_13461_13490_F | TAGCCCTGTCACTGATCTAGAGAAATACAA | 127 | FILO_NC002549_13594_13621_3_R | TGCGGTAATCACTGACATGCATATAACA | 162 |
| 852 | FILO_NC002549_13546_13577_F | TATGGTGTGAGGAATGTCTTTGATTGGATGCA | 128 | FILO_NC002549_13594_13621_2_R | TGCAAAAATCACTGACATGCATGTAACA | 163 |
| 853 | FILO_NC002549_13546_13577P_F | TAT$^a$GGT$^a$GT$^a$IIIIAATGTCTTTGATTGGATGCA | 129 | FILO_NC002549_13594_13624P_R | TGC$^a$T$^a$AT$^a$AAIIITCACTGACATGCATGTAACA | 164 |
| 850 | FILO_NC002549_13551_13577_F | TGTGCGGAATGTCTTTGATTGGATGCA | 130 | FILO_NC002549_13594_13621_R | TATGCCAATCACTGACATGCATGTAACA | 165 |
| 851 | FILO_NC002549_13551_13577P_F | TGTGCGGAATGTCT$^a$T$^a$TGAT$^a$T$^a$GGAT$^a$GC$^a$A | 130 | FILO_NC002549_13594_13621P_R | TATGCCAAT$^a$C$^a$AC$^a$T$^a$GAC$^a$AT$^a$GC$^a$ATGTAACA | 165 |

TABLE 5-continued

Primer Pairs for Identification of Filoviruses

| Primer pair number | For. primer name | For. sequence | For. SEQ ID NO: | Rev. primer name | Rev. sequence | Rev. SEQ ID NO: |
|---|---|---|---|---|---|---|
| 511 | FILO_NC002549_13557_13579P_F | TAATaGTCTaTaTaGATaTaGGATaGCaATT | 131 | FILO_NC002549_13594_13614P_R | TTaCaACaTaGACaATaGCaATaATaAACaA | 166 |
| 855 | FILO_NC002549_13591_13621_F | TIICGTTACATGCATGTCAGTGACTATTATA | 132 | FILO_NC002549_13726_13750_R | TTTGIGCACAGGAIATGCTTGTCCA | 167 |
| 854 | FILO_NC002549_13591_13621P_F | TIICGTaACATaGCaATaGTCAGTGACTATTATA | 132 | FILO_NC002549_13726_13750P_R | TTTaGIGCaACaAGGAIATGCTTGTCCA | 167 |
| 565 | FILO_NC002549_13594_13613P_F | TGTaTaACATaGCaATaGTCAGTGA | 133 | FILO_NC002549_13696_13715P_R | TGTAGTCCCTCTATCCCaTaCaC | 168 |
| 856 | FILO_NC002549_13594_13621_F | TGCCGCATGCATGTCAGTGATTATTATA | 134 | FILO_NC002549_13726_13750_2_R | TTTGAGCACAGGATATGCTTGTCCA | 169 |
| 866 | FILO_NC002549_13722_13745_2_F | TCTGTGGACAAGTATATCATGTGC | 135 | FILO_NC002549_13795_13816_2_R | TACACTGATTGTCACCCATGAC | 170 |
| 745 | FILO_NC002549_13722_13745_F | TCTGTGGACAAGTATATCATGTGC | 135 | FILO_NC002549_13795_13816_R | TACACTGATTGTCACCCATCAC | 171 |
| 865 | FILO_NC002549_13722_13745P_F | TCTGTGGACaAAGTATaATaCaATaGTaGC | 135 | FILO_NC002549_13795_13816P_R | TACACTGATaTaGTaCaACaCaCaATGAC | 170 |
| 861 | FILO_NC002549_13722_13751_2P_F | TCCGTGGACaAAGTATaATaCaATaGTaGCTCAAAT | 136 | FILO_NC002549_13795_13823_2P_R | TCTGTGATACACTGATaTaGTaCaACaCaCaATGAC | 172 |
| 862 | FILO_NC002549_13722_13751_F | TCCGTGGACAAGTATATCATGTGCTCAAAT | 136 | FILO_NC002549_13795_13823_R | TCTGTGATACACTGATTGTCACCCATGAC | 172 |
| 860 | FILO_NC002549_13722_13751P_F | TCCGTaGGACAAGTATaATaCATGTaGCTCAAAT | 136 | FILO_NC002549_13795_13823P_R | TCTGTGATACACTGATaTGTCACCaCaATGAC | 172 |
| 512 | FILO_NC002549_13726_13745P_F | TGGACaAAGTATaATaCaATaGTaGC | 137 | FILO_NC002549_13799_13817P_R | TTACACTGATaTaGTaCaACaCaCaA | 173 |
| 864 | FILO_NC002549_13726_13751_F | TGGACAAGTATATCATGTGCTCAAAT | 138 | FILO_NC002549_13798_13823_R | TCTGTGATACACTGATTGTCACCCAT | 174 |
| 863 | FILO_NC002549_13726_13751P_F | TGGACaAAGTATaATaCaATaGTaGCTCAAAT | 138 | FILO_NC002549_13798_13823P_R | TCTGTGATACACTGATaTaGTaCaACaCaCaAT | 174 |
| 506 | FILO_NC002549_1432_1449P_F | TGGAGTGGCaCACaAGCaACA | 139 | FILO_NC002549_1466_1487P_R | TCTaGTTaCaTCaCaAACaATaTaGACTCC | 175 |
| 505 | FILO_NC002549_1432_1449P_F | TGGAGTGGCaCACaAGCaACA | 139 | FILO_NC002549_1472_1492P_R | TTGATACTaGTTaCaTCaCaAACaATT | 176 |
| 514 | FILO_NC002549_14644_14666P_F | TCaATaCaAAAATCaCaATaGTaTATaGAGTCG | 140 | FILO_NC002549_14720_14736P_R | TCCaTaTaCaAAGGTATCaCaTaA | 177 |
| 513 | FILO_NC002549_14652_14672P_F | TCaCaTaGTaAATaGAGTCaGCTaTaTaGC | 141 | FILO_NC002549_14720_14739P_R | TGTTCCaTaTaCaAAGATATCaCaTaA | 178 |

TABLE 5-continued

Primer Pairs for Identification of Filoviruses

| Primer pair number | For. primer name | For. sequence | For. SEQ ID NO: | Rev. primer name | Rev. sequence | Rev. SEQ ID NO: |
|---|---|---|---|---|---|---|
| 867 | FILO_NC002549_890_909_F | GAGACAACGGAAGCTAATGC | 142 | FILO_NC002549_1057_1076_R | AACGGAAGATCACCATCATG | 179 |
| 868 | FILO_NC002549_911_930_F | GGTCAGTTTCTATCCTTTGC | 143 | FILO_NC002549_1041_1060_R | CATGTGTCCAACTGATTGCC | 180 |
| 871 | FILO_NC002549_938_963_2_F | TTTCTACCCAAACTTGTCGTTGGGGA | 144 | FILO_NC002549_1055_1080_2_R | TTCAAACGGAAGATCACCATCATGTG | 181 |
| 870 | FILO_NC002549_938_963_F | TTCCTTCCCAAACTGGTCGTTGGAGA | 145 | FILO_NC002549_1052_1078_R | TAGGCGGAAAATTACCATCATGTGTCC | 182 |
| 869 | FILO_NC002549_938_963_F | TTCCTTCCCAAACTGGTCGTTGGAGA | 145 | FILO_NC002549_1055_1080_R | TGCAACCGGAAAATTACCATCATGTG | 183 |
| 873 | FILO_NC002549_942_963_F | TCCCAAAACTTGTCGTCGGAGA | 146 | FILO_NC002549_1040_1062_R | TTCATGTGGCCTGTGGTAAGCCA | 184 |
| 501 | FILO_NC002549_943_963_2P_F | TC[a]C[a]GAAACTGGT[a]CGT[a]GGGAGA | 147 | FILO_NC002549_1052_1073_2P_R | TGAAAATTACCTT[a]C[a]AT[a]GT[a]GTCC | 185 |
| 502 | FILO_NC002549_943_963_3P_F | TC[a]C[a]GAAACTGGT[a]TGT[a]CGGAGA | 148 | FILO_NC002549_1052_1073_3P_R | TGAAAATTACTTT[a]C[a]AT[a]GT[a]GTCC | 186 |
| 748 | FILO_NC002549_943_963_F | TCCGAAACTGGTAGTGGGAGA | 149 | FILO_NC002549_1040_1061_R | TCATGTGTCCTACTGATTGCCA | 187 |
| 500 | FILO_NC002549_943_963P_F | TC[a]C[a]GAAACTGGT[a]CGT[a]AGGAGA | 150 | FILO_NC002549_1052_1073P_R | TGAAAATTACCAT[a]C[a]AT[a]GT[a]GTCC | 188 |
| 872 | FILO_NC002549_984_1011_F | TTCAGAGGCAAATTCAGGTACATGCAGA | 151 | FILO_NC002549_1040_1066_R | TACCATCATGTGTCCTACTGATTGCCA | 189 |

Reference sequence NC_002549 (SEQ ID NO: 268) represents the genome of Ebola Zaire virus.

TABLE 6

Primer Pairs for Identification of Bunyaviruses

| Primer Pair Number | For. Primer Name | For. Primer Sequence | For. SEQ ID NO: | Rev. Primer Name | Rev. Primer Sequence | Rev. SEQ ID NO: |
|---|---|---|---|---|---|---|
| 592 | HVLGENE_X55901_1740_1760_F | TACAGCCACATGGTTCCAATA | 190 | HVLGENE_X55901_1849_1871P_R | TCAAAGATTGCACATAGTTT[a]C[a]AT | 216 |
| 591 | HVLGENE_X55901_2_23P_F | T[a]GGAGAAAT[a]ATAGAGAGATTCA | 191 | HVLGENE_X55901_125_144_R | TGACCAGTCATGCTTTATCA | 217 |
| 593 | HVLGENE_X55901_2077_2096_F | TCAACTGTCGGTGCAAGTGG | 192 | HVLGENE_X55901_2182_2201P_R | TTCCCATGCAGACCCT[a]T[a]TTC | 218 |
| 594 | HVLGENE_X55901_2820_2840_F | TAAGGCACTCAGATGGGCATC | 193 | HVLGENE_X55901_2899_2920P_R | TGGCAT[a]C[a]TGCACTAACATACAT | 219 |
| 373 | HVLGENE_X55901_2897_2918_F | TCATGTATGTTAGTGCTGATGC | 194 | HVLGENE_X55901_2926_2946_R | TGAATTATCTCCTGGTGACCA | 220 |
| 374 | HVLGENE_X55901_2897_2918_F | TCATGTATGTTAGTGCTGATGC | 194 | HVLGENE_X55901_2928_2949_R | TGCTGAATTATCTCCTGGTGAC | 221 |
| 595 | HVLGENE_X55901_3279_3299P_F | TGCTCATCATT[a]C[a]AGATGATGC | 195 | HVLGENE_X55901_3331_3351_R | TAAC[a]C[a]AATCAGTTC[a]C[a]ATCATC | 222 |

TABLE 6-continued

Primer Pairs for Identification of Bunyaviruses

| Primer Pair Number | For. Primer Name | For. Primer Sequence | For. SEQ ID NO: | Rev. Primer Name | Rev. Primer Sequence | Rev. SEQ ID NO: |
|---|---|---|---|---|---|---|
| 596 | HVLGENE_X55901_3279_3299P_F | TGCTCATCATT$^a$C$^a$AGATGATGC | 195 | HVLGENE_X55901_3412_3431P_R | TTAAACATGCTCT$^a$T$^a$C$^a$C$^a$ACAT | 223 |
| 370 | HVLGENE_X55901_3329_3350_F | TAGATGATGGAACTGACTGGTT | 196 | HVLGENE_X55901_3412_3435_R | TAGATTAAACATGCTTTTCCACAT | 224 |
| 371 | HVLGENE_X55901_3408_3430_F | TGAGATGTGGAAAAGCATGTTTA | 196 | HVLGENE_X55901_3526_3549_R | TATTGATACAGCACAACCTTCAAA | 225 |
| 372 | HVLGENE_X55901_4173_4195_F | TATTGTAACAGCTATGACCATGC | 197 | HVLGENE_X55901_4224_4244_R | TTCATGTGTTGCTTTGCTTGC | 226 |
| 597 | HVLGENE_X55901_4182_4202_F | TGCTATGACAATGCAGTCACC | 198 | HVLGENE_X55901_4267_4287_R | TACCTCCCTGAATGTTACCCA | 227 |
| 598 | HVLGENE_X55901_5329_5348P_F | T$^a$GTGGGAT$^a$GAGAT$^a$T$^a$AAAAC | 199 | HVLGENE_X55901_5401_5420P_R | TTAGGCTTTCC$^a$C$^a$CATTCAAA | 228 |
| 375 | HVSGENE_NC003466_1050_1070_F | TATGCGGAATACCATCATGGC | 200 | HVSGENE_NC003466_1153_1172_R | TGGTCCAGTTGTATTCCCAT | 229 |
| 599 | HVSGENE_NC003466_1143_1163_F | TACACAATCGATGGGAATACA | 201 | HVSGENE_NC003466_1234_1253_R | TCAGGATCCATATCATCACC | 230 |
| 605 | NAIRON_U88410_1169_1187_F | TGGCTCTACATGCACCCTG | 202 | NAIRON_U88410_1226_1246P_R | TACAGGGATAGTCC$^a$C$^a$AAAGCA | 231 |
| 601 | NAIRON_U88410_12_29_F | TACGTGCCGCTTTCGCCC | 203 | NAIRON_U88410_146_168_R | TCACAGAAGGAGGCGGAGTTTGT | 232 |
| 600 | NAIRON_U88410_3_20P_F | TCAAAGACACACGTGC$^a$CG | 204 | NAIRON_U88410_56_76_R | TGCCTCGATTTGGTTCTCCAT | 233 |
| 602 | NAIRON_U88410_438_456_F | TGGCTGCCCTAAAGTGGAG | 205 | NAIRON_U88410_518_537_R | TCGCCAGGGACTTTGTACTC | 234 |
| 603 | NAIRON_U88410_517_534P_F | TGAGT$^a$ACAAAGTCC$^a$C$^a$TGG | 206 | NAIRON_U88410_569_588P_R | TTCC$^a$T$^a$GCTCCTAATCATGTC | 235 |
| 604 | NAIRON_U88410_568_588P_F | TGACAT$^a$GAT$^a$TAGGAGCAGGAA | 207 | NAIRON_U88410_692_708P_R | TCC$^a$C$^a$AAGGAGGGTTGAA | 236 |
| 583 | PHLEBOL_NC002043_2769_2789P_F | TGGT$^a$C$^a$T$^a$GAGAGAGATCTATGT | 208 | PHLEBOL_NC002043_2899_2917_R | TGCCGTGTGTTTCAGGAAT | 237 |
| 584 | PHLEBOL_NC002043_2894_2915_F | TGACGATTCCTGAAACACATGG | 209 | PHLEBOL_NC002043_2965_2986_R | TCCACTTGCTAGCATCATCTGA | 238 |
| 585 | PHLEBOL_NC002043_2958_2975P_F | TGCGACAT$^a$C$^a$AGATGAT$^a$GC | 210 | PHLEBOL_NC002043_3058_3076P_R | TCGAGCATC$^a$C$^a$ATC$^a$T$^a$AAT$^a$GAT | 239 |
| 590 | PHLEBOL_NC002043_2965_2985_F | TCAGATGATGCTAGCAAGTGG | 211 | PHLEBOL_NC002043_3058_3080_R | TACATCGAGCATCCTCTAATGAT | 240 |
| 586 | PHLEBOL_NC002043_3243_3260P_F | TACTGGGAT$^a$GAT$^a$GC$^a$AGGG | 212 | PHLEBOL_NC002043_3386_3403P_R | TATCAT$^a$C$^a$T$^a$GAGC$^a$C$^a$CTGCA | 241 |
| 587 | PHLEBOL_NC002043_3287_3302P_F | TTCACAC$^a$C$^a$CTGCACCA | 213 | PHLEBOL_NC002043_3386_3403P_R | TATCAT$^a$C$^a$T$^a$GAGC$^a$C$^a$CTGCA | 241 |

TABLE 6-continued

Primer Pairs for Identification of Bunyaviruses

| Primer Pair Number | For. Primer Name | For. Primer Sequence | For. SEQ ID NO: | Rev. Primer Name | Rev. Primer Sequence | Rev. SEQ ID NO: |
|---|---|---|---|---|---|---|
| 588 | PHLEBOL_NC002043_3386_3401P_F | T[a]GC[a]AAGGCT[a]C[a]AGATGA | 214 | PHLEBOL_NC002043_3509_3525P_R | TGATGGGT[a]AAAT[a]GCC[a]AA | 242 |
| 589 | PHLEBOL_NC002043_4103_4122P_F | TGAACATAC[a]C[a]AGAGAAC[a]T[a]GG | 215 | PHLEBOL_NC002043_4201_4221P_R | TCCTGGACTATGGACCT[a]T[a]CTC | 243 |

Reference sequence X55901 (SEQ ID NO: 269) represents the L genome segment of the Hantaan virus. Reference sequence NC_004366 (SEQ ID NO: 270) represents the S genome segment of the Andes virus. Reference sequence U88410 (SEQ ID NO: 271) represents the sequence coding for the nucleoprotein gene of Crimean-Congo hemorrhagic fever virus. Reference sequence NC_002043 (SEQ ID NO: 272) represents the L genome segment of the Rift Valley fever virus.

TABLE 7

Primer Pairs for Identification of Arenaviruses

| Primer Pair Number | For. Primer Name | For. Primer Sequence | For. SEQ ID NO: | Rev. Primer Name | Rev. Primer Sequence | Rev. SEQ ID NO: |
|---|---|---|---|---|---|---|
| 576 | ARENAL_NC004297_3866_3884_2P_F | TTCTTGACAT[a]GGGTCAGGG | 244 | ARENAL_NC004297_3979_4000_2P_R | TCTGGTCAT[a]C[a]ACTAGAGGTATA | 257 |
| 575 | ARENAL_NC004297_3866_3884P_F | TTCTTGATAT[a]GGGCCAGGG | 245 | ARENAL_NC004297_3979_4000P_R | TCTGGTCAT[a]C[a]ACTAGAAGTGTA | 258 |
| 578 | ARENAL_NC004297_3869_3884_2P_F | T[a]TGACAT[a]GGGTC[a]AGGG | 246 | ARENAL_NC004297_3988_4005P_R | TGAGATCTGGTCAT[a]C[a]ACT | 259 |
| 577 | ARENAL_NC004297_3869_3884P_F | T[a]TGATAT[a]GGGCC[a]AGGG | 247 | ARENAL_NC004297_3988_4005P_R | TGAGATCTGGTCAT[a]C[a]ACT | 259 |
| 574 | ARENAL_NC004297_3976_3995P_F | TCTT[a]ACACCT[a]C[a]AAGTGAT[a]GA | 248 | ARENAL_NC004297_4099_4118P_R | TTAGGGC[a]T[a]AGACAAACT[a]T[a]GTT | 260 |
| 573 | ARENAL_NC004297_3979_4001P_F | TACACTT[a]C[a]ATAGTGAT[a]GATCAGAT | 249 | ARENAL_NC004297_4099_4118P_R | TTAGGGC[a]T[a]AGACAAACT[a]T[a]GTT | 260 |
| 570 | ARENAL_NC004297_4105_4124P_F | T[a]T[a]TGTCAGCC[a]C[a]TAAAAGTGT | 250 | ARENAL_NC004297_4216_4235P_R | TCT[a]T[a]T[a]GCACTTTACAT[a]T[a]GTG | 261 |
| 571 | ARENAL_NC004297_4105_4124P_F | T[a]T[a]TGTCAGCC[a]C[a]TAAAAGTGT | 251 | ARENAL_NC004297_4201_4219_R | TGTGTAGCGCTGCAGCAAC | 262 |
| 572 | ARENAL_NC004297_4812_4829P_F | TAACAAAT[a]C[a]AGCAT[a]T[a]CCA | 252 | ARENAL_NC004297_4841_4857P_R | TC[a]C[a]T[a]ATAAAGC[a]C[a]AGATG | 263 |
| 582 | ARENAN_NC002496_474_494_2_F | TGGTGTTGTGAGAGTCTGGGA | 253 | ARENAN_NC002496_520_540_2_R | TGGCATTGACCCAAACTGGTT | 264 |
| 581 | ARENAN_NC002496_474_494_F | TGGTGTTGTGAAGGTCTGGGA | 254 | ARENAN_NC002496_520_540_R | TGGCATTGACCCGAACTGATT | 265 |

TABLE 7-continued

Primer Pairs for Identification of Arenaviruses

| Primer Pair Number | For. Primer Name | For. Primer Sequence | For. SEQ ID NO: | Rev. Primer Name | Rev. Primer Sequence | Rev. SEQ ID NO: |
|---|---|---|---|---|---|---|
| 580 | ARENAN_NC004296_937_953_2P_F | T$^a$C$^a$AGGTGAAGGTT$^a$GGC$^a$C | 255 | ARENAN_NC002496_982_1002_2_R | TGTGTTGTCCCAAGCCCTTCC | 266 |
| 579 | ARENAN_NC004296_937_953P_F | T$^a$C$^a$AGGTGATGGAT$^a$GGC$^a$C | 256 | ARENAN_NC002496_982_1002_R | TGTGTTGTCCCAAGCTCTCCC | 267 |

Reference sequence NC_004297 (SEQ ID NO: 273) represents the L genome segment of the Lassa virus. Reference sequence NC_004296 (SEQ ID NO: 274) represents the S genome segment of the Lassa virus.

Example 2

One-Step RT-PCR of RNA Virus Samples

RNA was isolated from virus-containing samples according to methods well known in the art. To generate bioagent identifying amplicons for RNA viruses, a one-step RT-PCR protocol was developed. All RT-PCR reactions were assembled in 50 μl reactions in the 96 well microtiter plate format using a Packard MPII liquid handling robotic platform and MJ Dyad® thermocyclers (MJ research, Waltham, Mass.). The RT-PCR reaction consisted of 4 units of Amplitaq Gold®, 1.5× buffer II (Applied Biosystems, Foster City, Calif.), 1.5 mM $MgCl_2$, 0.4 M betaine, 10 mM DTT, 20 mM sorbitol, 50 ng random primers (Invitrogen, Carlsbad, Calif.), 1.2 units Superasin (Ambion, Austin, Tex.), 100 ng polyA DNA, 2 units Superscript III (Invitrogen, Carlsbad, Calif.), 400 ng T4 Gene 32 Protein (Roche Applied Science, Indianapolis, Ind.), 800 µM dNTP mix, and 250 nM of each primer.

The following RT-PCR conditions were used to amplify the sequences used for mass spectrometry analysis: 60° C. for 5 minutes, 4° C. for 10 minutes, 55° C. for 45 minutes, 95° C. for 10 minutes followed by 8 cycles of 95° C. for 30 seconds, 48° C. for 30 seconds, and 72° C. for 30 seconds, with the 48° C. annealing temperature increased 0.9° C. after each cycle. The PCR reaction was then continued for 37 additional cycles of 95° C. for 15 seconds, 56° C. for 20 seconds, and 72° C. for 20 seconds. The reaction concluded with 2 minutes at 72° C.

Example 3

Solution Capture Purification of PCR Products for Mass Spectrometry with Ion Exchange Resin-Magnetic Beads For solution capture of nucleic acids with ion exchange resin linked to magnetic beads, 25 µl of a 2.5 mg/mL suspension of BioClon amine terminated supraparamagnetic beads were added to 25 to 50 µl of a PCR (or RT-PCR) reaction containing approximately 10 pM of a typical PCR amplification product. The above suspension was mixed for approximately 5 minutes by vortexing or pipetting, after which the liquid was removed after using a magnetic separator. The beads containing bound PCR amplification product were then washed 3× with 50 mM ammonium bicarbonate/50% MeOH or 100 mM ammonium bicarbonate/50% MeOH, followed by three more washes with 50% MeOH. The bound PCR amplicon was eluted with 25 mM piperidine, 25 mM imidazole, 35% MeOH, plus peptide calibration standards.

Example 4

Mass Spectrometry and Base Composition Analysis

The ESI-FTICR mass spectrometer is based on a Bruker Daltonics (Billerica, Mass.) Apex II 70e electrospray ionization Fourier transform ion cyclotron resonance mass spectrometer that employs an actively shielded 7 Tesla superconducting magnet. The active shielding constrains the majority of the fringing magnetic field from the superconducting magnet to a relatively small volume. Thus, components that might be adversely affected by stray magnetic fields, such as CRT monitors, robotic components, and other electronics, can operate in close proximity to the FTICR spectrometer. All aspects of pulse sequence control and data acquisition were performed on a 600 MHz Pentium II data station running Bruker's Xmass software under Windows NT 4.0 operating system. Sample aliquots, typically 15 µl, were extracted directly from 96-well microtiter plates using a CTC HTS PAL autosampler (LEAP Technologies, Carrboro, N.C.) triggered by the FTICR data station. Samples were injected directly into a 10 µl sample loop integrated with a fluidics handling system that supplies the 100 µl/hr flow rate to the ESI source. Ions were formed via electrospray ionization in a modified Analytica (Branford, Conn.) source employing an off axis, grounded electrospray probe positioned approximately 1.5 cm from the metalized terminus of a glass desolvation capillary. The atmospheric pressure end of the glass capillary was biased at 6000 V relative to the ESI needle during data acquisition. A counter-current flow of dry $N_2$ was employed to assist in the desolvation process. Ions were accumulated in an external ion reservoir comprised of an rf-only hexapole, a skimmer cone, and an auxiliary gate electrode, prior to injection into the trapped ion cell where they were mass analyzed. Ionization duty cycles >99% were achieved by simultaneously accumulating ions in the external ion reservoir during ion detection. Each detection event consisted of 1M data points digitized over 2.3 s. To improve the signal-to-noise ratio (S/N), 32 scans were co-added for a total data acquisition time of 74 s.

The ESI-TOF mass spectrometer is based on a Bruker Daltonics MicroTOF™. Ions from the ESI source undergo orthogonal ion extraction and are focused in a reflectron prior to detection. The TOF and FTICR are equipped with the same automated sample handling and fluidics described above. Ions are formed in the standard MicroTOF™ ESI source which is equipped with the same off-axis sprayer and glass capillary as the FTICR ESI source. Consequently, source conditions were the same as those described above. External ion accumulation was also employed to improve ionization duty cycle during data acquisition. Each detection event on the TOF was comprised of 75,000 data points digitized over 75 µs.

The sample delivery scheme allows sample aliquots to be rapidly injected into the electrospray source at high flow rate and subsequently be electrosprayed at a much lower flow rate for improved ESI sensitivity. Prior to injecting a sample, a bolus of buffer was injected at a high flow rate to rinse the transfer line and spray needle to avoid sample contamination/carryover. Following the rinse step, the autosampler injected the next sample and the flow rate was switched to low flow. Following a brief equilibration delay, data acquisition commenced. As spectra were co-added, the autosampler continued rinsing the syringe and picking up buffer to rinse the injector and sample transfer line. In general, two syringe rinses and one injector rinse were required to minimize sample carryover. During a routine screening protocol a new sample mixture was injected every 106 seconds. More recently a fast wash station for the syringe needle has been implemented which, when combined with shorter acquisition times, facilitates the acquisition of mass spectra at a rate of just under one spectrum/minute.

Raw mass spectra were post-calibrated with an internal mass standard and deconvoluted to monoisotopic molecular masses. Unambiguous base compositions were derived from the exact mass measurements of the complementary single-stranded oligonucleotides. Quantitative results are obtained by comparing the peak heights with an internal PCR calibration standard present in every PCR well at 500 molecules per well. Calibration methods are commonly owned and disclosed in U.S. Provisional Patent Application Ser. No. 60/545,425 which is incorporated herein by reference in entirety.

Example 5

De Novo Determination of Base Composition of Amplification Products Using Molecular Mass Modified Deoxynucleotide Triphosphates Because the molecular masses of the four natural nucleobases have a relatively narrow molecular mass range (A=313.058, G=329.052, C=289.046, T=304.046—See Table 8), a persistent source of ambiguity in assignment of base composition can occur as follows: two nucleic acid strands having different base composition may have a difference of about 1 Da when the base composition difference between the two strands is G⇌A (−15.994) combined with C⇌T (+15.000). For example, one 99-mer nucleic acid strand having a base composition of $A_{27}G_{30}C_{21}T_{21}$ has a theoretical molecular mass of 30779.058 while another 99-mer nucleic acid strand having a base composition of $A_{26}G_{31}C_{22}T_{20}$ has a theoretical molecular mass of 30780.052. A 1 Da difference in molecular mass may be within the experimental error of a molecular mass measurement and thus, the relatively narrow molecular mass range of the four natural nucleobases imposes an uncertainty factor.

The present invention provides for a means for removing this theoretical 1 Da uncertainty factor through amplification of a nucleic acid with one mass-tagged nucleobase and three natural nucleobases. The term "nucleobase" as used herein is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

Addition of significant mass to one of the 4 nucleobases (dNTPs) in an amplification reaction, or in the primers themselves, will result in a significant difference in mass of the resulting amplification product (significantly greater than 1 Da) arising from ambiguities arising from the G⇌A combined with C⇌T event (Table 8). Thus, the same the G⇌A (−15.994) event combined with 5-Iodo-C⇌T (−110.900) event would result in a molecular mass difference of 126.894. If the molecular mass of the base composition $A_{27}G_{30}$5-Iodo-$C_{21}T_{21}$ (33422.958) is compared with $A_{26}G_{31}$5-Iodo-$C_{22}T_{20}$, (33549.852) the theoretical molecular mass difference is +126.894. The experimental error of a molecular mass measurement is not significant with regard to this molecular mass difference. Furthermore, the only base composition consistent with a measured molecular mass of the 99-mer nucleic acid is $A_{27}G_{30}$5-Iodo-$C_{21}T_{21}$. In contrast, the analogous amplification without the mass tag has 18 possible base compositions.

TABLE 8

Molecular Masses of Natural Nucleobases and the Mass-Modified Nucleobase 5-Iodo-C and Molecular Mass Differences Resulting from Transitions

| Nucleobase | Molecular Mass | Transition | Δ Molecular Mass |
|---|---|---|---|
| A | 313.058 | A-->T | −9.012 |
| A | 313.058 | A-->C | −24.012 |
| A | 313.058 | A-->5-Iodo-C | 101.888 |
| A | 313.058 | A-->G | 15.994 |
| T | 304.046 | T-->A | 9.012 |
| T | 304.046 | T-->C | −15.000 |
| T | 304.046 | T-->5-Iodo-C | 110.900 |
| T | 304.046 | T-->G | 25.006 |
| C | 289.046 | C-->A | 24.012 |
| C | 289.046 | C-->T | 15.000 |
| C | 289.046 | C-->G | 40.006 |
| 5-Iodo-C | 414.946 | 5-Iodo-C-->A | −101.888 |
| 5-Iodo-C | 414.946 | 5-Iodo-C-->T | −110.900 |
| 5-Iodo-C | 414.946 | 5-Iodo-C-->G | −85.894 |
| G | 329.052 | G-->A | −15.994 |
| G | 329.052 | G-->T | −25.006 |
| G | 329.052 | G-->C | −40.006 |
| G | 329.052 | G-->5-Iodo-C | 85.894 |

Example 6

Data Processing

Mass spectra of bioagent-identifying amplicons are analyzed independently using e.g., a maximum-likelihood processor, such as is widely used in radar signal processing. This processor, referred to as GenX, first makes maximum likelihood estimates of the input to the mass spectrometer for each primer by running matched filters for each base composition aggregate on the input data. This includes the GenX response to a calibrant for each primer.

The algorithm emphasizes performance predictions culminating in probability-of-detection versus probability-of-false-alarm plots for conditions involving complex backgrounds of naturally occurring organisms and environmental contaminants. Matched filters consist of a priori expectations of signal values given the set of primers used for each of the bioagents. A genomic sequence database is used to define the mass base count matched filters. The database contains the sequences of known bacterial bioagents and includes threat organisms as well as benign background organisms. The latter is used to estimate and subtract the spectral signature produced by the background organisms. A maximum likelihood detection of known background organisms is implemented using matched filters and a running-sum estimate of the noise covariance. Background signal strengths are estimated and used along with the matched filters to form signatures which are then subtracted the maximum likelihood process is applied to this "cleaned up" data in a similar manner employing matched filters for the organisms and a running-sum estimate of the noise-covariance for the cleaned up data.

The amplitudes of all base compositions of bioagent-identifying amplicons for each primer are calibrated and a final maximum likelihood amplitude estimate per organism is made based upon the multiple single primer estimates. Models of all system noise are factored into this two-stage maximum likelihood calculation. The processor reports the number of molecules of each base composition contained in the spectra. The quantity of amplification product corresponding to the appropriate primer set is reported as well as the quantities of primers remaining upon completion of the amplification reaction.

Base count blurring can be carried out as follows. "Electronic PCR" can be conducted on nucleotide sequences of the desired bioagents to obtain the different expected base counts that could be obtained for each primer pair. See, world wide web at, for example, ncbi.nlm.nih.gov/sutils/e-pcr/; Schuler, Genome Res. 7:541-50, 1997. In one illustrative embodiment, one or more spreadsheets, such as Microsoft Excel workbooks contains a plurality of worksheets. First in this example, there is a worksheet with a name similar to the workbook name; this worksheet contains the raw electronic PCR data. Second, there is a worksheet named "filtered bioagents base count" that contains bioagent name and base count; there is a separate record for each strain after removing sequences that are not identified with a genus and species and removing all sequences for bioagents with less than 10 strains. Third, there is a worksheet, "Sheet1" that contains the frequency of substitutions, insertions, or deletions for this primer pair. This data is generated by first creating a pivot table from the data in the "filtered bioagents base count" worksheet and then executing an Excel VBA macro. The macro creates a table of differences in base counts for bioagents of the same species, but different strains. One of ordinary skill in the art may understand additional pathways for obtaining similar table differences without undo experimentation.

Application of an exemplary script, involves the user defining a threshold that specifies the fraction of the strains that are represented by the reference set of base counts for each bioagent. The reference set of base counts for each bioagent may contain as many different base counts as are needed to meet or exceed the threshold. The set of reference base counts is defined by taking the most abundant strain's base type composition and adding it to the reference set and then the next most abundant strain's base type composition is added until the threshold is met or exceeded. The current set of data were obtained using a threshold of 55%, which was obtained empirically.

For each base count not included in the reference base count set for that bioagent, the script then proceeds to determine the manner in which the current base count differs from each of the base counts in the reference set. This difference may be represented as a combination of substitutions, Si=Xi, and insertions, Ii=Yi, or deletions, Di=Zi. If there is more than one reference base count, then the reported difference is chosen using rules that aim to minimize the number of changes and, in instances with the same number of changes, minimize the number of insertions or deletions. Therefore, the primary rule is to identify the difference with the minimum sum (Xi+Yi) or (Xi+Zi), e.g., one insertion rather than two substitutions. If there are two or more differences with the minimum sum, then the one that will be reported is the one that contains the most substitutions.

Differences between a base count and a reference composition are categorized as either one, two, or more substitutions, one, two, or more insertions, one, two, or more deletions, and combinations of substitutions and insertions or deletions. The different types of changes and their probabilities of occurrence have been delineated in U.S. Patent Application Publication No. 2004209260 (U.S. application Ser. No. 10/418,514) which is incorporated herein by reference in entirety.

Example 7

Identification of Five Different Strains of Filoviruses

Four primer pairs from Table 5—primer pair nos. 853 (SEQ ID NOs: 129:164), 856 (SEQ ID NOs: 134:169), 858 (SEQ ID NOs: 124:159) and 864 (SEQ ID NOs: 138:174) were selected as candidate primer pairs for providing broad coverage of all known viral bioagents in the filoviridae family after amplification tests of 24 primer pairs wherein efficiency of primer pair amplification was assessed by gel electrophoresis. Each of these four primer pairs targets the L polymerase gene region. Samples of isolates of Zaire Ebola virus (Mayinga strain), Sudan Ebola virus (Boniface strain), Reston Ebola virus (Reston strain), and two isolates of Marburg virus (M/Kenya/Kitum/Cave/1987/Ravn strain and Voege strain) were obtained from the Center for Disease Control (CDC). RNA was isolated and reverse transcribed from these isolate samples according to Example 2. For each different reaction wherein a different primer pair used (primer pair numbers 853, 856, 858 and 864), the resulting cDNA was diluted by a factor of $10^{-3}$ to $10^{-6}$ and 100 copies of a calibration polynucleotide (SEQ ID NO: 275) contained within the pCR Blunt® vector (Invitrogen, Carlsbad, Calif.) was spiked into the sample. The calibration polynucleotide is based upon a portion of sequence of the Zaire Ebola virus (Mayinga) genome (SEQ ID NO: 268) and contains a series of deletions 5 nucleobases in length which, for each amplification product produced by primer pair numbers 853, 856, 858 and 864, provide enough of a difference in molecular mass to distinguish each calibration amplicon from the corresponding filovirus identifying amplicon. The 5 nucleobase deletions are located at the following coordinates with respect to the reference sequence (SEQ ID NO: 268): 15339-15343, 15441-15445, 15583-15587, 15641-15645, and 15772-15776.

The viral isolate cDNA and the calibrant were amplified and amplification products were purified by magnetic solution capture according to Example 3 followed by mass spectrometric analysis according to Example 4. Base compositions were deconvolved from the molecular masses of the filovirus identifying amplicons and are shown in Table 9 along with the expected base compositions based on known sequence information. It should be noted that primer pair number 858 was not expected to prime the Sudan Ebola virus and, as expected, an amplification product was not observed.

This example indicates that the four primer pairs investigated are functional in their intended purpose for producing filovirus identifying amplicons with base compositions that can identify different filovirus strains.

TABLE 9

Expected and Observed Base Compositions of Filovirus Identifying Amplicons Produced with Primer Pair Nos: 853 (SEQ ID NOs: 129:164), 856 (SEQ ID NOs: 134:169), 858 (SEQ ID NOs: 124:159) and 864 (SEQ ID NOs: 138:174)

| Virus | Strain | Sequence Available | Primer Pair | Expected Base Composition [A G C T] | Observed Base Composition [A G C T] |
|---|---|---|---|---|---|
| Zaire Ebola virus | Mayinga | Yes | 853 | [20 19 14 26] | [20 19 14 26] |
| Sudan Ebola virus | Boniface | Yes | 853 | [18 19 15 27] | [18 19 15 27] |
| Reston Ebola virus | Reston | Yes | 853 | [18 20 13 28] | [18 20 13 28] |
| Marburg virus | M/Kenya/Kitum/Cave/1987/Ravn | No | 853 | — | [19 18 13 29] |
| Marburg virus | Voege | No | 853 | — | [19 18 13 29] |
| Calibrant | Based on Ebola Virus Zaire | Yes | 853 | [17 19 13 25] | [17 19 13 25] |
| Zaire Ebola virus | Mayinga | Yes | 856 | [50 35 40 32] | [50 35 40 32] |
| Sudan Ebola virus | Boniface | Yes | 856 | [47 36 34 40] | [47 36 34 40] |
| Reston Ebola virus | Reston | Yes | 856 | [48 35 36 38] | [48 35 36 38] |
| Marburg virus | M/Kenya/Kitum/Cave/1987/Ravn | No | 856 | — | [41 35 30 51] |
| Marburg virus | Voege | No | 856 | — | [50 33 34 40] |
| Calibrant | Based on Ebola Virus Zaire | Yes | 856 | [49 34 38 31] | [49 34 38 31] |
| Zaire Ebola virus | Mayinga | Yes | 858 | [32 24 22 25] | [32 24 22 25] |
| Sudan Ebola virus | Boniface | Yes | 858 | Amplification not expected | Amplification not observed |
| Reston Ebola virus | Reston | Yes | 858 | [30 25 22 26] | [30 25 22 26] |
| Marburg virus | M/Kenya/Kitum/Cave/1987/Ravn | No | 858 | — | [34 24 20 25] |
| Marburg virus | Voege | No | 858 | — | [34 24 22 23] |
| Calibrant | Based on Ebola Virus Zaire | Yes | 858 | [30 23 21 24] | [30 23 21 24] |
| Zaire Ebola virus | Mayinga | Yes | 864 | [29 22 14 33] | [29 22 14 33] |
| Sudan Ebola virus | Boniface | Yes | 864 | [32 23 17 26] | [32 23 17 26] |
| Reston Ebola virus | Reston | Yes | 864 | [31 22 16 29] | [31 22 16 29] |
| Marburg virus | M/Kenya/Kitum/Cave/1987/Ravn | No | 864 | — | [36 20 16 26] |
| Marburg virus | Voege | No | 864 | — | [38 17 15 28] |
| Calibrant | Based on Ebola Virus Zaire | Yes | 864 | [28 20 13 32] | [28 20 13 32] |

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, internet web sites, and the like) cited in the present application is incorporated herein by reference in its entirety. Those skilled in the art will appreciate that numerous changes and modifications may be made to the embodiments of the invention and that such changes and modifications may be made without departing from the spirit of the invention. It is therefore intended that the appended claims cover all such equivalent variations as fall within the true spirit and scope of the invention.

What is claimed is:

1. An oligonucleotide primer 23 to 35 nucleobases in length comprising at least 70% sequence identity with SEQ ID NO: 129.

2. A composition comprising the primer of claim 1.

3. The composition of claim 2 further comprising an oligonucleotide primer 22 to 35 nucleobases in length comprising at least 70% sequence identity with SEQ ID NO: 164.

4. The composition of claim 3 wherein either or both of said primers comprises at least one modified nucleobase.

5. The composition of claim 4 wherein said modified nucleobase is 5-propynyluracil or 5-propynylcytosine.

6. The composition of claim 3 wherein either or both of said primers comprises at least one universal nucleobase.

7. The composition of claim 6 wherein said universal nucleobase is inosine.

8. The composition of claim 3 wherein either or both of said primers further comprises a non-templated T residue on the 5'-end.

9. The composition of claim 3 wherein either or both of said primers comprises at least one non-template tag.

10. The composition of claim 3 wherein either or both of said primers comprises at least one molecular mass modifying tag.

11. A kit comprising the composition of claim 3.

12. The kit of claim 11 further comprising at least one calibration polynucleotide.

13. The kit of claim 11 further comprising at least one ion exchange resin linked to magnetic beads.

14. A method for identification of an unknown filovirus comprising:
   amplifying nucleic acid from said filovirus using the composition of claim 4 to obtain an amplification product;
   determining the molecular mass of said amplification product;
   optionally, determining the base composition of said amplification product from said molecular mass; and
   comparing said molecular mass or base composition with a plurality of molecular masses or base compositions of known filoviral bioagent identifying amplicons, wherein a match between said molecular mass or base composition and a member of said plurality of molecular masses or base compositions identifies said unknown filovirus.

15. The method of claim 14 wherein said molecular mass is determined by mass spectrometry.

16. A method of determining the presence or absence of a filovirus in a sample comprising:
   amplifying nucleic acid from said sample using the composition of claim 4 to obtain an amplification product;
   determining the molecular mass of said amplification product;
   optionally, determining the base composition of said amplification product from said molecular mass; and
   comparing said molecular mass or base composition of said amplification product with the known molecular masses or base compositions of one or more known filoviral bioagent identifying amplicons, wherein a match between said molecular mass or base composition of said amplification product and the molecular mass or base composition of one or more known filoviral bioagent identifying amplicons indicates the presence of said filovirus in said sample.

17. The method of claim 16 wherein said molecular mass is determined by mass spectrometry.

18. A method for determination of the quantity of an unknown filovirus in a sample comprising:
   contacting said sample with the composition of claim 4 and a known quantity of a calibration polynucleotide comprising a calibration sequence;
   concurrently amplifying nucleic acid from said unknown filovirus and nucleic acid from said calibration polynucleotide in said sample with the composition of claim 4 to obtain a first amplification product comprising an filoviral bioagent identifying amplicon and a second amplification product comprising a calibration amplicon;
   determining the molecular mass and abundance for said filoviral bioagent identifying amplicon and said calibration amplicon; and
   distinguishing said filoviral bioagent identifying amplicon from said calibration amplicon based on molecular mass, wherein comparison of filoviral bioagent identifying amplicon abundance and calibration amplicon abundance indicates the quantity of filovirus in said sample.

19. The method of claim 18 further comprising determining the base composition of said filoviral bioagent identifying amplicon.

20. An oligonucleotide primer 22 to 35 nucleobases in length comprising at least 70% sequence identity with SEQ ID NO: 164.

* * * * *